(12) United States Patent
Yanagi et al.

(10) Patent No.: US 7,084,266 B1
(45) Date of Patent: Aug. 1, 2006

(54) CLONED GENOME OF INFECTIOUS HEPATITUS C VIRUS OF GENOTYPE 2A AND USES THEREOF

(75) Inventors: Masayuki Yanagi, Kanazawa (JP); Jens Bukh, Bethesda, MD (US); Suzanne U. Emerson, Gaithersburg, MD (US); Robert H. Purcell, Gaithersburg, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/980,559

(22) PCT Filed: Feb. 6, 2000

(86) PCT No.: PCT/US00/15446

§ 371 (c)(1),
(2), (4) Date: May 14, 2002

(87) PCT Pub. No.: WO00/75338

PCT Pub. Date: Dec. 14, 2000

Related U.S. Application Data

(60) Provisional application No. 60/137,693, filed on Jun. 4, 1999.

(51) Int. Cl.
*C12N 7/00* (2006.01)
*A61K 39/12* (2006.01)
*A61K 39/29* (2006.01)

(52) U.S. Cl. ............... 536/23.7; 536/23.72; 536/23.1; 435/235.1; 435/325; 435/239; 514/44; 424/189.1; 424/204.1; 424/228.1

(58) Field of Classification Search ............ 536/23.7, 536/23.1, 23.71; 435/325, 235.1, 239; 524/44; 424/189.1, 204.1, 228.1
See application file for complete search history.

(56) References Cited

U.S. PATENT DOCUMENTS 5,428,145 A * 6/1995 Okamoto et al. ........ 536/23.72
5,874,565 A * 2/1999 Rice et al. ................. 536/24.1

FOREIGN PATENT DOCUMENTS

| EP | 532167 A2 * | 7/1992 |
| EP | 0532 167 | 3/1993 |
| WO | WO 91/15575 | 10/1991 |
| WO | WO 00/26418 | 5/2000 |

OTHER PUBLICATIONS

Yoo et al. J. Virol. 1995, vol. 69, No. 1, pp. 32-38.*
Sequence conparision data sheets.*
Okamoto, H. et al. "Nucleotide sequence of genomic RNA of hepatitis C virus isolated from a human carrier: comparison with reported isolates for conserved and divergent region." Journal of General Virology, 72 (pp. 2697-2704 ) 1991.
Han J. H. et al, "Group specific sequences and conserved secondary structure at the 3' end of HCV genome and its implication for viral replication." Nucleic Acids Research , Oxford University Press, 20:13. (p. 3520) Apr. 1992.
Yanagi, M. et al, "Transcripts of a chimeric cDNA clone of Hepatitis C virus genotype 1b are infectious in vivo." Virology 244 (pp. 161-172) 1998.
Ohno, T. et al, "New hepatitis C virus (HCV) genotyping system that allows for identification of HCV genotypes 1a, 1b, 2a, 2b, 3a, 3b, 4, 5a, and 6a," Journal of Clinical Microbiology 35:1 (pp. 201-207) 1997.
Hashimoto, M. et al. "Typing six major hepatitis C virus genotypes by polymerase chain reaction using primers derived from nucleotide sequences of the NS5 region." International Hepatology Communications 4:5 (pp. 263-267) 1996.
Yong Yuan Zhang et al, "Greater diversity of hepatitis C virus genotypes found in Hong Kong than in Mainland China." Journal of Clinical Microbiology 33:11 (pp. 2931-2934) 1995.
Fox, S. et al., "Rapid genotyping of hepatitis C virus isolates by dideoxy fingerprinting." Journal of Virology Methods 53:1 (pp. 1-9) May 1995.

(Continued)

*Primary Examiner*—James Housel
*Assistant Examiner*—Bao Qun Li
(74) *Attorney, Agent, or Firm*—Knobbe, Martens, Olson & Bear, LLP

(57) ABSTRACT

The present invention discloses nucleic acid sequence which encodes infectious hepatitis C virus of strain HC-J6$_{CH}$, gentotype 2a, and the use of the sequence, and polypeptides encoded by all or part of the sequence, in the development of vaccines and diagnostics for HCV and in the development of screening assays for the identification of antiviral agents for HCV.

11 Claims, 22 Drawing Sheets

OTHER PUBLICATIONS

Yanagi, M. et al, "Hepatitis C Virus: An infectious molecular clone of a second major genotype (2a) and lack of viability of intertypic 1a and 2a chimeras." Virology 262 (pp. 250-263) 1999.

De Francesco, R. et al, "A zinc binding site in viral serine proteinases." Biochemistry 35:41 (pp. 13282-13287) 1996.

Stempniak, M. et al, "The NS3 proteinase domain of hepatitis C virus is a zinc-containing enzyme." Journal of Virology 71:4 (pp. 2881-2886) 1997.

Park, Y.M. et al, "Monitoring antibody titers to recombinant core-NS3 fusion polypeptide is useful for evaluating hepatitis C virus infection and responses to interferon-alpha therapy," J. Korean Medicine Sci. 14 (pp. 165-170) Apr. 1999.

Mison, L.M. et al. "Prevalence of hepatitis C virus and geneotype distribution in an Australian volunteer blood donor population," Transfusion 37 (pp. 73-78) Jan. 1997.

Wright-Minogue, J. et al. "Cross-genotypic interaction between hepatitis C virus NS3 protease domains and NS4A cofactors," Journal of Hepatology 32:3 (pp. 497-504) 2000.

Martin, J. et al. "In vitro effect of amantadine and interferon. alpha.—2a on hepatitis C virus makers in cultured peripheral blood mononuclear cells from hepatitis C virus-infected patients," Antiviral Research 42:1 (pp. 59-70) 1999.

Urushihara, A. et al. "Changes in antibody titers to hepatitis C virus following interferon therapy for chronic infection." Journal of Medical Virology 42:4 (pp. 348-356) 1994.

Sali, D.L. et al. "Serine protease of Hepatitis C virus expressed in insect cells as the NS3/4A complex." Biochemistry 37:10 (pp. 3392-3401) 1998.

Calvo, P.L. et al. "Hepatitis C virus heteroduplex tracking assay for genotype determination reveals diverging Genotype 2 isolates in Italian hemodialysis patients." J. of Clinical Microbiology 36:1 (pp. 227-233) Jan. 1998.

Bukh, J. et al. "At least 12 genotypes of hepatitis C virus predicted by sequence analysis of the putative E1 gene of isolates collected worldwide." Proceedings of the NAS of the USA, US, NAS 90 (pp. 8234-8238) Sep. 1994.

Simmonds. P. et al. "Identification of genotypes of hepatitis C virus by sequence comparisons in the core, E1 and NS-5 regions." J. of General Virology 75 (pp. 1053-1061) 1994.

Van Doorn, I.J., et al. "Sequence analysis of hepatitis C virus genotypes 1 to 5 reveals multiple novel subtypes in the Benelux countries." J. of General Virology 76 (pp. 1871-1876) 1995.

Chaodong, Wu et al, "Antibody response to E2 glycoprotein induced in mice by immunization with plasmid DNA containing sequence derived from a chinese genotype III/2a isolate of hepatitis C virus." Chinese Medical Journal 112:2 (pp. 166-168) Feb. 1999.

Yuki, N. et al. "Quantitative analysis of antibody to Hepatitis C virus Envelope 2 Glycoprotein in patients with chronic Hepatitis C virus infection." Hepatology 23:5 (pp. 947-952) May 1996.

Longombardo, G. et al, Immune response to an epitope of the NS4 protein of Hepatitis C virus in HCV-related disorders.

Fabrizi, F. et al, "Hepatitis C virus genotypes in chronic dialysis patients." Nephrol. Dial. Transplant. 11 (pp. 679-683) 1996.

Lin, H-H. et al. "Serotypes, genotypes and levels of Hepatitis C Viremia in pregnant women in Taiwan." J. Formos. Medl. Assoc. 95:6 (pp. 429-434) 1996.

Devesa, M. et al, "Reduced antibody reactivity to Hepatitis C virus antigen in Hemodialysis patients coinfected with hepatits B virus." Clinical and Diagnostic Laboratory Immunology 4:6 (pp. 639-642) Nov. 1997.

Yuki, N. et al, "Hepatitis C virus replicative levels and efficiency of genotyping by specific PCR and antibody assay." J. of Clinical Microbiology 35:5 (pp. 1184-1189) May 1997.

Zhang, Z-X et al, "Evaluation of the multiple peptide assay for typing of antibodies to the Hepatitis C Virus: Relation to genomic typing by the Polymerase Chain Reaction." J. of Medical Virology 45 (pp. 50-55) 1995.

Nomura, H. et al, "Interferon therapy and Hepatitis C virus." Journal of Gastroenterology and Hepatology 14:1 (pp. 85-89) Jan. 1999.

Furusyo, N. et al, "Differences between interferon-alpha and -beta treatrment for patients with chronic hepatitis C virus infection." Digestive Diseases and Sciences 44:3 (pp. 608-617) Mar. 1999.

Yao, G.B. et al, "Long-term efficacy of recombinant interferon alpha 2a in the treatment of chronic Hepatitis C: A randomized prospective study comparing two dose schedules in Chinese patients." Hepato-Gastroenterology 46 (pp. 1059-1064) Apr. 1999.

Martinot-Peignoux, M et al, "Predictors of sustained response to alpha interferon therapy in chronic hepatitis C," Journal of Hepatology 29:2 (pp. 214-223) Aug. 1998.

Lee, W.M., "Therapy of Hepatitis C: Interferon Alfa-2a trials." Hepatology 26 (pp. 89S-95S) 1997.

Linsay, K.L., "Therapy of Hepatitis C: Overview" Hepatology 26 (pp. 71S-77S) 1997.

Marakami, T. et al, "Mutations in Nonstructural protein 5A gene and response to interferon in Hepatitis C virus genotype 2 infection." Hepatology 30 (pp. 1045-1053) Oct. 1999.

* cited by examiner

FIG. 5A

5' Untranslated Region

```
             1                                                                          90
H77C         GCCAGCCCCC TGATGGGGGC GACACTCCAC CATGAATCAC TCCCCTGTGA GGAACTACTG TCTTCACGCA GAAAGCGTCT AGCCATGGCG
H77CV-J6S    .......... .......... .......... .......... .......... .......... .......... .......... ..........
H77(p7)CV-J6S .......... .......... .......... .......... .......... .......... .......... .......... ..........
H77-J6S      .......... .......... .......... .......... .......... .......... .......... .......... ..........
H77(p7)-J6S  .......... .......... .......... .......... .......... .......... .......... .......... ..........
J6CF         A..C...... ..A..A.... .......... .......... ....G..... .......... .......... .......... ..........

91                                                                         180
H77C         TTAGTATGAG TGTCGTGCAG CCTCCAGGAC CCCCCCTCCC GGGAGAGCCA TAGTGGTCTG CGGAACCGGT GAGTACACCG GAATTGCCAG
H77CV-J6S    .......... .......... .......... .......... .......... .......... .......... .......... .........G
H77(p7)CV-J6S .......... .......... .......... .......... .......... .......... .......... .......... .........G
H77-J6S      .......... .......... .......... .......... .......... .......... .......... .......... ..........
H77(p7)-J6S  .......... .......... ......A... .......... ......C... .......... .......... .......... ..........
J6CF         ...A..T... .......... .......... .......... .......... .......... .......... .......... .........G
                                                                              ─────────
                                                                                 AgeI 181                                                                        270
H77C         GACGACCGGG TCCTTTCTTG GATAAACCCG CTCAATGCCT GGAGATTTGG GCGTGCCCCC GCAAGACTGC TAGCCGAGTA GTGTTGGGTC
H77CV-J6S    ..A..T.... .......... .......... ...T...... ...CC..... .......... .......... .......... .........C
H77(p7)CV-J6S ..A..T.... .......... .......... ...T...... ...CC..... .......... .......... .......... .........C
H77-J6S      .......... .......... .......... .......... .......... .......... .......... .......... ..........
H77(p7)-J6S  ..A..T.... .......... .......... ...T...... ...CC..... .......... .......... .......... .........T
J6CF         .......... .......... .......... .......... .......... .......... .......... .......... .........T 271                                                                        360
H77C         GCGAAAGGCC TTGTGGTACT GCCTGATAGG GTGCTTGCGA GTGCCCCGGG AGGTCTCGTA GACCGTGCAC CATGAGCACG AATCCTAAAC
H77CV-J6S    .......... .......... .......... .......... .......... .......... .......... .......... ..........
H77(p7)CV-J6S .......... .......... .......... .......... .......... .......... .......... .......... ........A
H77-J6S      .......... .......... .......... .......... .......... .......... .......... .......... ........A
H77(p7)-J6S  .......... .......... .......... .......... .......... .......... .......... .......... ........A
J6CF         .......... .......... .......... .......... .......... .......... .......... .......... ........A
```

FIG. 5B

3' Untranslated Region

```
              9375                                                                                              9518
H77C          TGAAGGTTGG GGTAAACACT CCGGCCTCTT AGCCATTTC AAGCCATTC CTG (Polypyrimidine tract)81  AATGGTGGCT CCATCTTAGC
H77CV-J6S     ..........                                           (Polypyrimidine tract)81     ..........  ..........
H77(p7)CV-J6S ..........                                           (Polypyrimidine tract)81     ..........  ..........
H77-J6S       ..........                                           (Polypyrimidine tract)81     ..........  ..........
H77(p7)-J6S   ..........                                           (Polypyrimidine tract)81     ..........  ..........
J6CF          .AG..CGGCA CAC.TTAG.. A.ACT.CA.A GCTAAC.G..  .C-      (Polypyrimidine tract)132    ----------  ..........

9519                                                                                              9599
H77C          CCTAGTCACG GCTAGCTGTG AAAGGTCCGT GAGCCGCATG ACTGCAGAGA GTGCTGATAC TGGCCTCTCT GCAGATCATG T
H77CV-J6S     .......... .......... .......... .......... .......... .......... .......... .......... .
H77(p7)CV-J6S .......... .......... .......... .......... .......... .......... .......... .......... .
H77-J6S       .......... .......... .......... .......... .......... .......... .......... .......... .
H77(p7)-J6S   .......... .......... .......... .......... .......... .......... ...C.TA... ....T..... .
J6CF          .......... .......... .......... .......... .......... .......... ...C.TA... ....T..... .
```

E2/p7/NS2 Region

```
                         E2/p7↓                                                 p7                         p7/NS2↓                             825
              730
H77C          RVCSCLWMMLLISQAEA ALENLVILNAASLAGTHGLVSFLVFFCFAWYLKGRWVPGAVYALYGMWPLLLLLLALPQRAYA LDTEVAASCGGVVLVG
H77CV-J6S     ...A......LI.LG... ....K....H..A.SCN.FLY.VI..VA...I...V..L.T.S.T.L.SFS.........Q. ................
H77(p7)CV-J6S ...A......LI.LG... ....K....H..A.SCN.FLY.VI..VA...I...V..L.T.S.T.L.SFS............ ................
H77-J6S       ...A......LI.LG... ....K....H..A.SCN.FLY.VI..VA...I...V..L.T.S.T.L.SFS.........Q. ................
H77(p7)-J6S   ...A......LI.LG... ....K....H..A.SCN.FLY.VI..VA...I...V..L.T.S.T.L.SFS............ ................
J6CF          ...A......LI.LG... ....K....H..A.SCN.FLY.VI..VA...I...V..L.T.S.T.L.SFS.........Q. Y.AS.HGQI.AAL..M
```

H77C

```
          10         20         30         40         50
1234567890 1234567890 1234567890 1234567890 1234567890
GCCAGCCCCC TGATGGGGGC GACACTCCAC CATGAATCAC TCCCCTGTGA   50
GGAACTACTG TCTTCACGCA GAAAGCGTCT AGCCATGGCG TTAGTATGAG  100
TGTCGTGCAG CCTCCAGGAC CCCCCCTCCC GGAGAGCCA TAGTGGTCTG  150
CGGAACCGGT GAGTACACCG GAATTGCCAG GACGACCGGG TCCTTTCTTG  200
GATAAACCCG CTCAATGCCT GGAGATTTGG GCGTGCCCCC GCAAGACTGC  250
TAGCCGAGTA GTGTTGGGTC GCGAAAGGCC TTGTGGTACT GCCTGATAGG  300
GTGCTTGCGA GTGCCCCGGG AGGTCTCGTA GACCGTGCAC CATGAGCACG  350
AATCCTAAAC CTCAAAGAAA AACCAAACGT AACACCAACC GTCGCCCACA  400
GGACGTCAAG TTCCCGGGTG GCGGTCAGAT CGTTGGTGGA GTTTACTTGT  450
TGCCGCGCAG GGGCCCTAGA TTGGGTGTGC GCGCGACGAG GAAGACTTCC  500
GAGCGGTCGC AACCTCGAGG TAGACGTCAG CCTATCCCCA AGGCACGTCG  550
GCCCGAGGGC AGGACCTGGG CTCAGCCCGG GTACCCTTGG CCCCTCTATG  600
GCAATGAGGG TTGCGGGTGG GCGGGATGGC TCCTGTCTCC CCGTGGCTCT  650
CGGCCTAGCT GGGGCCCCAC AGACCCCCGG CGTAGGTCGC GCAATTTGGG  700
TAAGGTCATC GATACCCTTA CGTGCGGCTT CGCCGACCTC ATGGGGTACA  750
TACCGCTCGT CGGCGCCCCT CTTGGAGGCG CTGCCAGGGC CCTGGCGCAT  800
GGCGTCCGGG TTCTGGAAGA CGGCGTGAAC TATGCAACAG GAACCTTCC  850
TGGTTGCTCT TTCTCTATCT TCCTTCTGGC CCTGCTCTCT TGCCTGACTG  900
TGCCCGCTTC AGCCTACCAA GTGCGCAATT CCTCGGGGCT TTACCATGTC  950
ACCAATGATT GCCCTAACTC GAGTATTGTG TACGAGGCGG CCGATGCCAT 1000
CCTGCACACT CCGGGGTGTG TCCCTTGCGT TCGCGAGGGT AACGCCTCGA 1050
GGTGTTGGGT GGCGGTGACC CCCACGGTGG CCACCAGGGA CGGCAAACTC 1100
CCCACAACGC AGCTTCGACG TCATATCGAT CTGCTTGTCG GGAGCGCCAC 1150
CCTCTGCTCG GCCCTCTACG TGGGGGACCT GTGCGGGTCT GTCTTTCTTG 1200
TTGGTCAACT GTTACCTTC TCTCCAGGC GCCACTGGAC GACGCAAGAC 1250
TGCAATTGTT CTATCTATCC CGGCCATATA ACGGGTCATC GCATGGCATG 1300
GGATATGATG ATGAACTGGT CCCCTACGGC AGCGTTGGTG GTAGCTCAGC 1350
TGCTCCGGAT CCCACAAGCC ATCATGGACA TGATCGCTGG TGCTCACTGG 1400
GGAGTCCTGG CGGGCATAGC GTATTTCTCC ATGGTGGGA ACTGGGCGAA 1450
GGTCCTGGTA GTGCTGCTGC TATTGCCCGG CGTCGACGCG GAAACCCACG 1500
TCACCGGGG AAATGCCGGC CGCACCACGG CTGGCTTGT TGGTCTCCTT 1550
ACACCAGGCG CCAAGCAGAA CATCCAACTG ATCAACACCA ACGGCAGTTG 1600
GCACATCAAT AGCACGGCCT TGAATTGCAA TGAAAGCCTT AACACCGGCT 1650
GGTTAGCAGG GCTCTTCTAT CAACACAAAT TCAACTCTTC AGGCTGTCCT 1700
GAGAGGTTGG CCAGCTGCCG ACGCCTTACC GATTTGCCC AGGGCTGGGG 1750
TCCTATCAGT TATGCCAACG GAAGCGGCCT CGACGAACGC CCCTACTGCT 1800
GGCACTACCC TCCAAGACCT TGTGGCATTG TGCCCGCAAA GAGCGTGTGT 1850
GGCCCGGTAT ATTGCTTCAC TCCCAGCCCC GTGGTGGTGG AACGACCGA 1900
```

```
         10         20         30         40         50
1234567890 1234567890 1234567890 1234567890 1234567890
CAGGTCGGGC GCGCCTACCT ACAGCTGGGG TGCAAATGAT ACGGATGTCT   1950
TCGTCCTTAA CAACACCAGG CCACCGCTGG GCAATTGGTT CGGTTGTACC   2000
TGGATGAACT CAACTGGATT CACCAAAGTG TGCGGAGCGC CCCCTTGTGT   2050
CATCCGAGGG GTGGGCAACA ACACCTTGCT CTGCCCCACT GATTGCTTCC   2100
GCAAACATCC GGAAGCCACA TACTCTCGGT GCGGCTCCGG TCCCTGGATT   2150
ACACCCAGGT GCATGGTCGA CTACCCGTAT AGGCTTTGGC ACTATCCTTG   2200
TACCATCAAT TACACCATAT TCAAAGTCAG GATGTACGTG GGAGGGGTCG   2250
AGCACAGGCT GGAAGCGGCC TGCAACTGGA CGCGGGGCGA ACGCTGTGAT   2300
CTGGAAGACA GGGACAGGTC CGAGCTCAGC CCGTTGCTGC TGTCCACCAC   2350
ACAGTGGCAG GTCCTTCCGT GTTCTTTCAC GACCCTGCCA GCCTTGTCCA   2400
CCGGCCTCAT CCACCTCCAC CAGAACATTG TGGACGTGCA GTACTTGTAC   2450
GGGGTAGGGT CAAGCATCGC GTCCTGGGCC ATTAAGTGGG AGTACGTCGT   2500
TCTCCTGTTC CTTCTGCTTG CAGACGCGCG CGTCTGCTCC TGCTTGTGGA   2550
TGATGTTACT CATATCCCAA GCGGAGGCGG CTTTGGAGAA CCTCGTAATA   2600
CTCAATGCAG CATCCCTGCC CGGACGCAC GGTCTTGTGT CCTTCCTCGT    2650
GTTCTTCTGC TTTGCGTGGT ATCTGAAGGG TAGGTGGGTG CCCGGAGCGG   2700
TCTACGCCCT CTACGGGATG TGGCCTCTCC TCCTGCTCCT GCTGGCGTTG   2750
CCTCAGCGGG CATACGCACT GGACACGGAG GTGGCCGCGT CGTGTGGCGG   2800
CGTTGTTCTT GTCGGGTTAA TGGCGCTGAC TCTGTCGCCA TATTACAAGC   2850
GCTATATCAG CTGGTGCATG TGGTGGCTTC AGTATTTTCT GACCAGAGTA   2900
GAAGCGCAAC TGCACGTGTG GGTTCCCCCC CTCAACGTCC GGGGGGGGCG   2950
CGATGCCGTC ATCTTACTCA TGTGTGTAGT ACACCCGACC CTGGTATTTG   3000
ACATCACCAA ACTACTCCTG GCCATCTTCG GACCCCTTTG GATTCTTCAA   3050
GCCAGTTTGC TTAAAGTCCC CTACTTCGTG CGCGTTCAAG GCCTTCTCCG   3100
GATCTGCGCG CTAGCGCGGA AGATAGCCGG AGGTCATTAC GTGCAAATGG   3150
CCATCATCAA GTTAGGGGCG CTTACTGGCA CCTATGTGTA TAACCATCTC   3200
ACCCCTCTTC GAGACTGGGC GCACAACGGC CTGCGAGATC TGGCCGTGGC   3250
TGTGGAACCA GTCGTCTTCT CCCGAATGGA GACCAAGCTC ATCACGTGGG   3300
GGCAGATAC CGCCGCGTGC GGTGACATCA TCAACGGCTT GCCCGTCTCT   3350
GCCCGTAGGG GCCAGGAGAT ACTGCTTGGG CCAGCCGACG GAATGGTCTC   3400
CAAGGGGTGG AGGTTGCTGG CGCCCATCAC GGCGTACGCC CAGCAGACGA   3450
GAGGCCTCCT AGGGTGTATA ATCACCAGCC TGACTGGCCG GGACAAAAAC   3500
CAAGTGGAGG GTGAGGTCCA GATCGTGTCA ACTGCTACCC AAACCTTCCT   3550
GGCAACGTGC ATCAATGGG TATGCTGGAC TGTCTACCAC GGGGCCGGAA    3600
CGAGGACCAT CGCATCACCC AAGGGTCCTG TCATCCAGAT GTATACCAAT   3650
GTGGACCAAG ACCTTGTGGG CTGGCCCGCT CCTCAAGGTT CCCGCTCATT   3700
GACACCCTGT ACCTGCGGCT CCTCGGACCT TTACCTGGTC ACGAGGCACG   3750
CCGATGTCAT TCCCGTGCGC CGGCGAGGTG ATAGCAGGGG TAGCCTGCTT   3800
```

|  | 10 | 20 | 30 | 40 | 50 |  |
|---|---|---|---|---|---|---|
|  | 1234567890 | 1234567890 | 1234567890 | 1234567890 | 1234567890 |  |
|  | TGCCCCGGC | CCATTTCCTA | CTTGAAAGGC | TCCTCGGGG | GTCCGCTGTT | 3850 |
|  | GTGCCCGCG | GGACACGGCG | TGGGCTATT | CAGGGCGGCG | GTGTGCACCC | 3900 |
|  | GTGGAGTGGC | TAAAGCGGTG | GACTTTATCC | CTGTGGAGAA | CCTAGGGACA | 3950 |
|  | ACCATGAGAT | CCCCGGTGTT | CACGGACAAC | TCCTCTCCAC | CAGCAGTGCC | 4000 |
|  | CCAGAGCTTC | CAGGTGGCCC | ACCTGCATGC | TCCCACGGGC | AGCGGTAAGA | 4050 |
|  | GCACCAAGGT | CCCGGCTGCG | TACGCAGCCC | AGGGCTACAA | GGTGTTGGTG | 4100 |
|  | CTCAACCCCT | CTGTTGCTGC | AACGCTGGGC | TTTGGTGCTT | ACATGTCCAA | 4150 |
|  | GGCCCATGGG | GTTGATCCTA | ATATCAGGAC | CGGGGTGAGA | ACAATTACCA | 4200 |
|  | CTGGCAGCCC | CATCACGTAC | TCCACCTACG | GCAAGTTCCT | TGCCGACGGC | 4250 |
|  | GGGTGCTCAG | GAGGTGCTTA | TGACATAATA | ATTTGTGACG | AGTGCCACTC | 4300 |
|  | CACGGATGCC | ACATCCATCT | TGGGCATCGG | CACTGTCCTT | GACCAAGCAG | 4350 |
|  | AGACTGCGGG | GGCGAGACTG | GTTGTGCTCG | CCACTGCTAC | CCCTCCGGGC | 4400 |
|  | TCCGTCACTG | TGTCCCATCC | TAACATCGAG | GAGGTTGCTC | TGTCCACCAC | 4450 |
|  | CGGAGAGATC | CCCTTTTACG | GCAAGGCTAT | CCCCCTCGAG | GTGATCAAGG | 4500 |
|  | GGGAAGACA | TCTCATCTTC | TGCCACTCAA | AGAAGAAGTG | CGACGAGCTC | 4550 |
|  | GCCGCGAAGC | TGGTCGCATT | GGGCATCAAT | GCCGTGGCCT | ACTACCGCGG | 4600 |
|  | TCTTGACGTG | TCTGTCATCC | CGACCAGCGG | CGATGTTGTC | GTCGTGTCGA | 4650 |
|  | CCGATGCTCT | CATGACTGGC | TTTACCGGCG | ACTTCGACTC | TGTGATAGAC | 4700 |
|  | TGCAACACGT | GTGTCACTCA | GACAGTCGAT | TTCAGCCTTG | ACCCTACCTT | 4750 |
|  | TACCATTGAG | ACAACCACGC | TCCCCCAGGA | TGCTGTCTCC | AGGACTCAAC | 4800 |
|  | GCCGGGGCAG | GACTGGCAGG | GGAAGCCAG | GCATCTATAG | ATTTGTGGCA | 4850 |
|  | CCGGGGGAGC | GCCCCTCCGG | CATGTTCGAC | TCGTCCGTCC | TCTGTGAGTG | 4900 |
|  | CTATGACGCG | GGCTGTGCTT | GGTATGAGCT | CACGCCCGCC | GAGACTACAG | 4950 |
|  | TTAGGCTACG | AGCGTACATG | AACACCCCGG | GGCTTCCCGT | GTGCCAGGAC | 5000 |
|  | CATCTTGAAT | TTTGGGAGGG | CGTCTTTACG | GGCCTCACTC | ATATAGATGC | 5050 |
|  | CCACTTTTTA | TCCCAGACAA | AGCAGAGTGG | GGAGAACTTT | CCTTACCTGG | 5100 |
|  | TAGCGTACCA | AGCCACCGTG | TGCGCTAGGG | CTCAAGCCCC | TCCCCCATCG | 5150 |
|  | TGGGACCAGA | TGTGGAAGTG | TTTGATCCGC | CTTAAACCCA | CCCTCCATGG | 5200 |
|  | GCCAACACCC | CTGCTATACA | GACTGGGCGC | TGTTCAGAAT | GAAGTCACCC | 5250 |
|  | TGACGCACCC | AATCACCAAA | TACATCATGA | CATGCATGTC | GGCCGACCTG | 5300 |
|  | GAGGTCGTCA | CGAGCACCTG | GGTGCTCGTT | GGGGGCGTCC | TGGCTGCTCT | 5350 |
|  | GGCCGCGTAT | TGCCTGTCAA | CAGGCTGCGT | GGTCATAGTG | GCAGGATCG | 5400 |
|  | TCTTGTCCGG | GAAGCCGGCA | ATTATACCTG | ACAGGGAGGT | TCTCTACCAG | 5450 |
|  | GAGTTCGATG | AGATGGAAGA | GTGCTCTCAG | CACTTACCGT | ACATCGAGCA | 5500 |
|  | AGGGATGATG | CTCGCTGAGC | AGTTCAAGCA | GAAGGCCCTC | GGCCTCCTGC | 5550 |
|  | AGACCGCGTC | CCGCCATGCA | GAGGTTATCA | CCCCTGCTGT | CCAGACCAAC | 5600 |
|  | TGGCAGAAAC | TCGAGGTCTT | TTGGGCGAAG | CACATGTGGA | ATTTCATCAG | 5650 |
|  | TGGATACAA | TACTTGGCGG | GCCTGTCAAC | GCTGCCTGGT | AACCCCGCCA | 5700 |

| 10 | 20 | 30 | 40 | 50 | |
|---|---|---|---|---|---|
| 1234567890 | 1234567890 | 1234567890 | 1234567890 | 1234567890 | |
| TTGCTTCATT | GATGGCTTTT | ACAGCTGCCG | TCACCAGCCC | ACTAACCACT | 5750 |
| GGCCAAACCC | TCCTCTTCAA | CATATTGGGG | GGGTGGGTGG | CTGCCCAGCT | 5800 |
| CGCCGCCCCC | GGTGCCGCTA | CTGCCTTTGT | GGGTGCTGGC | CTAGCTGGCG | 5850 |
| CCGCCATCGG | CAGCGTTGGA | CTGGGGAAGG | TCCTCGTCGA | CATTCTTGCA | 5900 |
| GGGTATGGCG | CGGCGTGGC | GGGAGCTCTT | GTAGCATTCA | AGATCATGAG | 5950 |
| CGGTGAGGTC | CCCTCCACGG | AGGACCTGGT | CAATCTGCTG | CCCGCCATCC | 6000 |
| TCTCGGCTGG | AGCCCTTGTA | GTCGGTGTGG | TCTGCGCAGC | AATACTGCGC | 6050 |
| CGGCACGTTG | GCCCGGCGA | GGGGCAGTG | CAATGGATGA | ACCGGCTAAT | 6100 |
| AGCCTTCGCC | TCCCGGGGA | ACCATGTTTC | CCCCACGCAC | TACGTGCCGG | 6150 |
| AGAGCGATGC | AGCCGCCCGC | GTCACTGCCA | TACTCAGCAG | CCTCACTGTA | 6200 |
| ACCAGCTCC | TGAGGCGACT | GCATCAGTGG | ATAAGCTCGG | AGTGTACCAC | 6250 |
| TCCATGCTCC | GGTTCCTGGC | TAAGGGACAT | CTGGGACTGG | ATATGCGAGG | 6300 |
| TGCTGAGCCA | CTTTAAGACC | TGGCTGAAAG | CCAAGCTCAT | GCCACAACTG | 6350 |
| CCTGGGATTC | CCTTTGTGTC | CTGCCAGCGC | GGGTATAGGG | GGGTCTGGCG | 6400 |
| AGGAGACGGC | ATTATGCACA | CTCGCTGCCA | CTGTGGAGCT | GAGATCACTG | 6900 |
| GACATGTCAA | AAACGGACG | ATGAGGATCG | TCGGTCCTAG | GACCTGCAGG | 6950 |
| AACATGTGGA | GTGGGACGTT | CCCCATTAAC | GCCTACACCA | CGGGCCCCTG | 6550 |
| TACTCCCCTT | CCTGCGCCGA | ACTATAAGTT | CGCGCTGTGG | AGGGTGTCTG | 6600 |
| CAGAGGAATA | CGTGGAGATA | AGGCGGGTGG | GGGACTTCCA | CTACGTATCG | 6650 |
| GGTATGACTA | CTGACAATCT | TAAATGCCCG | TGCCAGATCC | CATCGCCCGA | 6700 |
| ATTTTTCACA | GAATTGGACG | GGGTGCGCCT | ACACAGGTTT | GCGCCCCCTT | 6750 |
| GCAAGCCCTT | GCTGCGGGAG | GAGGTATCAT | TCAGAGTAGG | ACTCCACGAG | 6800 |
| TACCCGGTGG | GGTCGCAATT | ACCTTGCGAG | CCCGAACCGG | ACGTAGCCGT | 6850 |
| GTTGACGTCC | ATGCTCACTG | ATCCCTCCA | TATAACAGCA | GAGGCGGCCG | 6900 |
| GGAGAAGGTT | GCCGAGAGGG | TCACCCCCTT | CTATGGCCAG | CTCCTCGGCT | 6950 |
| AGCCAGCTGT | CCGCTCCATC | TCTCAAGGCA | ACTTGCACCG | CCAACCATGA | 7000 |
| CTCCCCTGAC | GCCGAGCTCA | TAGAGGCTAA | CCTCCTGTGG | AGGCAGGAGA | 7050 |
| TGGGCGGCAA | CATCACCAGG | GTTGAGTCAG | AGAACAAAGT | GGTGATTCTG | 7100 |
| GACTCCTTCG | ATCCGCTTGT | GGCAGAGGAG | GATGAGCGGG | AGGTCTCCGT | 7150 |
| ACCTGCAGAA | ATTCTGCGGA | AGTCTCGGAG | ATTCGCCCGG | GCCCTGCCCG | 7200 |
| TCTGGGCGCG | GCCGGACTAC | AACCCCCCGC | TAGTAGAGAC | GTGGAAAAAG | 7250 |
| CCTGACTACG | AACCACCTGT | GGTCCATGGC | TGCCCGCTAC | CACCTCCACG | 7300 |
| GTCCCCTCCT | GTGCCTCCGC | CTCGGAAAAA | GCGTACGGTG | GTCCTCACCG | 7350 |
| AATCAACCCT | ATCTACTGCC | TTGGCCGAGC | TTGCCACCAA | AAGTTTGGC | 7400 |
| AGCTCCTCAA | CTTCCGCAT | TACGGGCGAC | AATACGACAA | CATCCTCTGA | 7450 |
| GCCCGCCCCT | TCTGGCTGCC | CCCCCGACTC | CGACGTTGAG | TCCTATTCTT | 7500 |
| CCATGCCCCC | CCTGGAGGG | GAGCCTGGGG | ATCCGGATCT | CAGCGACGGG | 7550 |
| TCATGGTCGA | CCGTCAGTAG | TGGGCCGAC | ACGGAAGATG | TCGTGTGCTG | 7600 |

| 10 | 20 | 30 | 40 | 50 | |
|---|---|---|---|---|---|
| 1234567890 | 1234567890 | 1234567890 | 1234567890 | 1234567890 | |
| CTCAATGTCT | TATTCCTGGA | CAGGCGCACT | CGTCACCCCG | TGCGCTGCGG | 7650 |
| AAGAACAAAA | ACTGCCCATC | AACGCACTGA | GCAACTGGTT | GCTACGCCAT | 7700 |
| CACAATCTGG | TGTATTCCAC | CACTTCACGC | AGTGCTTGCC | AAAGGCAGAA | 7750 |
| GAAAGTCACA | TTTGACAGAC | TGCAAGTTCT | GGACAGCCAT | TACCAGGACG | 7800 |
| TGCTCAAGGA | GGTCAAAGCA | GCGGCGTCAA | AAGTGAAGGC | TAACTTGCTA | 7850 |
| TCCGTAGAGG | AAGCTTGCAG | CCTGACGCCC | CCACATTCAG | CCAAATCCAA | 7900 |
| GTTTGGCTAT | GGGCAAAAG | ACGTCCGTTG | CCATCCAGA | AAGGCCGTAG | 7950 |
| CCCACATCAA | CTCCGTGTGG | AAAGACCTTC | TGGAAGACAG | TGTAACACCA | 8000 |
| ATAGACACTA | CCATCATGGC | CAAGAACGAG | GTTTTCTGCG | TTCAGCCTGA | 8050 |
| GAAGGGGGGT | CGTAAGCCAG | CTCGTCTCAT | CGTGTTCCCC | GACCTGGGCG | 8100 |
| TGCGCGTGTG | CGAGAAGATG | GCCCTGTACG | ACGTGGTTAG | CAAGCTCCCC | 8150 |
| CTGGCCGTGA | TGGAAGCTC | CTACGGATTC | CAATACTCAC | CAGGACAGCG | 8200 |
| GGTTGAATTC | CTCGTGCAAG | CGTGGAAGTC | CAAGAAGACC | CCGATGGGGT | 8250 |
| TCTCGTATGA | TACCCGCTGT | TTTGACTCCA | CAGTCACTGA | GAGCGACATC | 8300 |
| CGTACGGAGG | AGGCAATTTA | CCAATGTTGT | GACCTGGACC | CCCAAGCCCG | 8350 |
| CGTGGCCATC | AAGTCCCTCA | CTGAGAGGCT | TTATGTTGGG | GGCCCTCTTA | 8400 |
| CCAATTCAAG | GGGGAAAAC | TGCGGCTACC | GCAGGTGCCG | CGCGAGCGGC | 8450 |
| GTACTGACAA | CTAGCTGTGG | TAACACCCTC | ACTTGCTACA | TCAAGGCCCG | 8500 |
| GGCAGCCTGT | CGAGCCGCAG | GGCTCCAGGA | CTGCACCATG | CTCGTGTGTG | 8550 |
| GCGACGACTT | AGTCGTTATC | TGTGAAAGTG | CGGGGGTCCA | GGAGGACGCG | 8600 |
| GCGAGCCTGA | GAGCCTTCAC | GGAGGCTATG | ACCAGGTACT | CCGCCCCCCC | 8650 |
| CGGGGACCCC | CCACAACCAG | AATACGACTT | GGAGCTTATA | ACATCATGCT | 8700 |
| CCTCCAACGT | GTCAGTCGCC | CACGACGGCG | CTGGAAAGAG | GGTCTACTAC | 8750 |
| CTTACCCGTG | ACCCTACAAC | CCCCCTCGCG | AGAGCCGCGT | GGGAGACAGC | 8800 |
| AAGACACACT | CCAGTCAATT | CCTGGCTAGG | CAACATAATC | ATGTTTGCCC | 8850 |
| CCACACTGTG | GGCGAGGATG | ATACTGATGA | CCCATTTCTT | TAGCGTCCTC | 8900 |
| ATAGCCAGGG | ATCAGCTTGA | ACAGGCTCTT | AACTGTGAGA | TCTACGGAGC | 8950 |
| CTGCTACTCC | ATAGAACCAC | TGGATCTACC | TCCAATCATT | CAAAGACTCC | 9000 |
| ATGGCCTCAG | CGCATTTTCA | CTCCACAGTT | ACTCTCCAGG | TGAAATCAAT | 9050 |
| AGGGTGGCCG | CATGCCTCAG | AAAACTTGGG | GTCCCGCCCT | TGCGAGCTTG | 9100 |
| GAGACACCGG | GCCCGGAGCG | TCCGCGCTAG | GCTTCTGTCC | AGAGGAGGCA | 9150 |
| GGCTGCCAT | ATGTGGCAAG | TACCTCTTCA | ACTGGGCAGT | AAGAACAAAG | 9200 |
| CTCAAACTCA | CTCCAATAGC | GGCCGCTGGC | CGGCTGGACT | TGTCCGGTTG | 9250 |
| GTTCACGGCT | GGCTACAGCG | GGGAGACAT | TTATCACAGC | GTGTCTCATG | 9300 |
| CCCGGCCCCG | CTGGTTCTGG | TTTGCCTAC | TCCTGCTCGC | TGCAGGGGTA | 9350 |
| GGCATCTACC | TCCTCCCCAA | CCGATGAAGG | TTGGGGTAAA | CACTCCGGCC | 9400 |
| TCTTAAGCCA | TTTCCTGTTT | TTTTTTTTTT | TTTTTTTTTT | TTTTTCTTTT | 9450 |
| TTTTTTTCTT | TCCTTTCCTT | CTTTTTTTCC | TTTCTTTTTC | CCTTCTTTAA | 9500 |

```
         10         20         30         40         50
1234567890 1234567890 1234567890 1234567890 1234567890
TGGTGGCTCC ATCTTAGCCC TAGTCACGGC TAGCTGTGAA AGGTCCGTGA    9550
GCCGCATGAC TGCAGAGAGT GCTGATACTG GCCTCTCTGC AGATCATGT     9599
```

```
         10         20         30         40         50
1234567890 1234567890 1234567890 1234567890 1234567890
MSTNPKPQRK TKRNTNRRPQ DVKFPGGGQI VGGVYLLPRR GPRLGVRATR   50
KTSERSQPRG RRQPIPKARR PEGRTWAQPG YPWPLYGNEG CGWAGWLLSP  100
RGSRPSWGPT DPRRRSRNLG KVIDTLTCGF ADLMGYIPLV GAPLGGAARA  150
LAHGVRVLED GVNYATGNLP GCSFSIFLLA LLSCLTVPAS AYQVRNSSGL  200
YHVTNDCPNS SIVYEAADAI LHTPGCVPCV REGNASRCWV AVTPTVATRD  250
GKLPTTQLRR HIDLLVGSAT LCSALYVGDL CGSVFLVGQL FTFSPRRHWT  300
TQDCNCSIYP GHITGHRMAW DMMMNWSPTA ALVVAQLLRI PQAIMDMIAG  350
AHWGVLAGIA YFSMVGNWAK VLVVLLLFAG VDAETHVTGG NAGRTTAGLV  400
GLLTPGAKQN IQLINTNGSW HINSTALNCN ESLNTGWLAG LFYQHKFNSS  450
GCPERLASCR RLTDFAQGWG PISYANGSGL DERPYCWHYP PRPCGIVPAK  500
SVCGPVYCFT PSPVVVGTTD RSGAPTYSWG ANDIDVFVLN NTRPPLGNWF  550
GCTWMNSTGF TKVCGAPPCV IGGVGNNTLL CPTDCFRKHP EATYSRCGSG  600
PWITPRCMVD YPYRLWHYPC TINYTIFKVR MYVGGVEHRL EAACNWTRGE  650
RCDLEDRDRS ELSPLLLSTT QWQVLPCSFT TLPALSTGLI HLHQNIVDVQ  700
YLYGVGSSIA SWAIKWEYVV LLFLLLADAR VCSCLWMMLL ISQAEAALEN  750
LVILNAASLA GTHGLVSFLV FFCFAWYLKG RWVPGAVYAL YGMWPLLLLL  800
LALPQRAYAL DTEVAASCGG VVLVGLMALT LSPYYKRYIS WCMWWLQYFL  850
TRVEAQLHVW VPPLNVRGGR DAVILLMCVV HPTLVFDITK LLLAIFGPLW  900
ILQASLLKVP YFVRVQGLLR ICALARKIAG GHYVQMAIIK LGALTGTYVY  950
NHLTPLRDWA HNGLRDLAVA VEPVVFSRME TKLITWGADT AACGDIINGL 1000
PVSARRGQEI LLGPADGMVS KGWRLLAPIT AYAQQTRGLL GCIITSLTGR 1050
DKNQVEGEVQ IVSTATQTFL ATCINGVCWT VYHGAGTRTI ASPKGPVIQM 1100
YTNVDQDLVG WPAPQGSRSL TPCTCGSSDL YLVTRHADVI PVRRRGDSRG 1150
SLLSPRPISY LKGSSGGPLL CPAGHAVGLF RAAVCTRGVA KAVDFIPVEN 1200
LGTTMRSPVF TDNSSPPAVP QSFQVAHLHA PTGSGKSTKV PAAYAAQGYK 1250
VLVLNPSVAA TLGFGAYMSK AHGVDPNIRT GVRTITTGSP ITYSTYGKFL 1300
ADGGCSGGAY DIIICDECHS TDATSILGIG TVLDQAETAG ARLVVLATAT 1350
PPGSVTVSHP NIEEVALSTT GEIPFYGKAI PLEVIKGGRH LIFCHSKKKC 1400
DELAAKLVAL GINAVAYYRG LDVSVIPTSG DVVVVSTDAL MTGFTGDFDS 1450
VIDCNTCVTQ TVDFSLDPTF TIETTTLPQD AVSRTQRRGR TGRGKPGIYR 1500
FVAPGERPSG MFDSSVLCEC YDAGCAWYEL TPAETTVRLR AYMNTPGLPV 1550
CQDHLEFWEG VFTGLTHIDA HFLSQTKQSG ENFPYLVAYQ ATVCARAQAP 1600
PPSWDQMWKC LIRLKPTLHG PTPLLYRLGA VQNEVTLTHP ITKYIMTCMS 1650
ADLEVVTSTW VLVGGVLAAL AAYCLSTGCV VIVGRIVLSG KPAIIPDREV 1700
LYQEFDEMEE CSQHLPYIEQ GMMLAEQFKQ KALGLLQTAS RHAEVITPAV 1750
QTNWQKLEVF WAKHMWNFIS GIQYLAGLST LPGNPAIASL MAFTAAVTSP 1800
LTTGQTLLFN ILGGWVAAQL AAPGAATAFV GAGLAGAAIG SVGLGKVLVD 1850
ILAGYGAGVA GALVAFKIMS GEVPSTEDLV NLLPAILSPG ALVVGVVCAA 1900
```

```
         10         20         30         40         50
1234567890 1234567890 1234567890 1234567890 1234567890
ILRRHVGPGE GAVQWMNRLI AFASRGNHVS PTHYVPESDA AARVTAILSS   1950
LTVTQLLRRL HQWISSECTT PCSGSWLRDI WDWICEVLSD FKTWLKAKLM   2000
PQLPGIPFVS CQRGYRGVWR GDGIMHTRCH CGAETTGHVK NGTMRIVGPR   2050
TCRNMWSGTF PINAYTTGPC TPLPAPNYKF ALWRVSAEEY VEIRRVGDFH   2100
YVSGMTTDNL KCPCQIPSPE FFTELDGVRL HRFAPPCKPL LREEVSFRVG   2150
LHEYPVGSQL PCEPEPDVAV LTSMLTDPSH ITAEAAGRRL ARGSPPSMAS   2200
SSASQLSAPS LKATCTANHD SPDAELIEAN LLWRQEMGGN ITRVESENKV   2250
VILDSFDPLV AEEDEREVSV PAEILRKSRR FARALPVWAR PDYNPPLVET   2300
WKKPDYEPPV VHGCPLPPPR SPPVPPPRKK RTVVLTESTL STALAELATK   2350
SFGSSSTSGI TGDNTTTSSE PAPSGCPPDS DVESYSSMPP LEGEPGDPDL   2400
SDGSWSTVSS GADTEDVVCC SMSYSWTGAL VTPCAAEEQK LPINALSNSL   2450
LRHHNLVYST TSRSACQRQK KVTFDRLQVL DSHYQDVLKE VKAAASKVKA   2500
NLLSVEEACS LTPPHSAKSK FGYGAKDVRC HARKAVAHIN SVWKDLLEDS   2550
VTPIDTTIMA KNEVFCVQPE KGGRKPARLI VFPDLGVRVC EKMALYDVVS   2600
KLPLAVMGSS YGFQYSPGQR VEFLVQAWKS KKTPMGFSYD TRCFDSTVTE   2650
SDIRTEEAIY QCCDLDPQAR VAIKSLTERL YVGGPLTNSR GENCGYRRCR   2700
ASGVLTTSCG NTLTCYIKAR AACRAAGLQD CTMLVCGDDL VVICESAGVQ   2750
EDAASLRAFT EAMTRYSAPP GDPPQPEYDL ELITSCSSNV SVAHDGAGKR   2800
VYYLTRDPTT PLARAAWETA RHTPVNSWLG NIIMFAPTLW ARMILMTHFF   2850
SVLIARDQLE QALNCEIYGA CYSIEPLDLP PIIQRLHGLS AFSLHSYSPG   2900
EINRVAACLR KLGVPPLRAW RHRARSVRAR LLSRGGRAAI CGKYLFNWAV   2950
RTKLKLTPIA AAGRLDLSGW FTAGYSGGDI YHSVSHARPR WFWFCLLLLA   3000
AGVGIYLLPN R                                            3011
```

```
         10         20         30         40         50
1234567890 1234567890 1234567890 1234567890 1234567890
GCCAGCCCCC TGATGGGGC  GACACTCCAC CATGAATCAC TCCCTGTGA    50
GGAACTACTG TCTTCACGCA GAAAGCGTCT AGCCATGGCG TTAGTATGAG  100
TGTCGTGCAG CCTCCAGGAC CCCCCCTCCC GGGAGAGCCA TAGTGGTCTG  150
CGGAACCGGT GAGTACACCG GAATTGCCAG GACGACCGGG TCCTTTCTTG  200
GATCAACCCG CTCAATGCCT GGAGATTTGG GCGTGCCCCC GCGAGACTGC  250
TAGCCGAGTA GTGTTGGGTC GCGAAAGGCC TTGTGGTACT GCCTGATAGG  300
GTGCTTGCGA GTGCCCCGGG AGGTCTCGTA GACCGTGCAC CATGAGCACG  350
AATCCTAAAC CTCAAAGAAA AACCAAACGT AACACCAACC GCCGCCCACA  400
GGACGTCAAG TTCCCGGGCG GTGGTCAGAT CGTTGGTGGA GTTTACCTGT  450
TGCCGCGCAG GGGCCCCAGG TTGGGTGTGC GCGCGACTAG GAAGGCTTCC  500
GAGCGGTCGC AACCTCGTGG AAGGCGACAA CCTATCCCAA AGGCTCGCCG  550
ACCCGAGGGC AGGGCCTGGG CTCAGCCCGG GTACCCTTGG CCCTCTATG   600
GCAATGAGGG CCTGGGGTGG GCAGGATGGC TCCTGTCACC CCGCGGCTCC  650
CGGCCTAGTT GGGGCCCCAC GGACCCCCGG CGTAGGTCGC GTAACTTGGG  700
TAAGGTCATC GATACCCTTA CATGCGGCTT CGCCGATCTC ATGGGGTACA  750
TTCCGCTCGT CGGCGCCCCC CTAGGGGCG  CTGCCAGGGC CTTGGCACAC  800
GGTGTCCGGG TTCTGGAGGA CGGCGTGAAC TATGCAACAG GGAACTTGCC  850
CGGTTGCTCT TTCTCTATCT TCCTCTTGGC TCTGCTGTCC TGTTTGACCA  900
TCCCAGCTTC CGCTTATGAA GTGCGCAACG TGTCCGGGAT ATACCATGTC  950
ACGAACGACT GCTCCAACTC AAGCATTGTG TATGAGGCAG CGGACGTGAT 1000
CATGCATACT CCCGGGTGCG TGCCCTGTGT TCAGGAGGGT AACAGCTCCC 1050
GTTGCTGGGT AGCGCTCACT CCCACGCTCG CGGCCAGGAA TGCCAGCGTC 1100
CCCACTACGA CAATACGACG CCACGTCGAC TTGCTCGTTG GGACGGCTGC 1150
TTTCTGCTCC GCTATGTACG TGGGGGATCT CTGCGGATCT ATTTTCCTCG 1200
TCTCCCAGCT GTTCACCTTC TCGCCTCGCC GGCATGAGAC AGTGCAGGAC 1250
TGCAACTGCT CAATCTATCC CGGCCATGTA TCAGGTCACC GCATGGCTTG 1300
GGATATGATG ATGAACTGGT CACCTACAAC AGCCCTAGTG GTGTCGCAGT 1350
TGCTCCGGAT CCCACAAGCT GTCGTGGACA TGGTGGCGGG GGCCCACTGG 1400
GGAGTCCTGG CGGGCCTTGC CTACTATTCC ATGGTAGGA  ACTGGGCTAA 1450
GGTTCTGATT GTGGCGCTAC TCTTTGCCGG CGTTGACGGG GAGACCCACA 1500
CGACGGGGAG GGTGGCCGGC CACACCACCT CCGGGTTCAC GTCCCTTTTC 1550
TCATCTGGGG CGTCTCAGAA AATCCAGCTT GTGAATACCA ACGGCAGCTG 1600
GCACATCAAC AGGACTGCCC TAAATTGCAA TGACTCCCTC CAAACTGGGT 1650
TCTTTGCCGC GCTGTTTTAC GCACACAAGT TCAACTCGTC CGGGTGCCCG 1700
GAGCGCATGG CCAGCTGCCG CCCCATTGAC TGGTTCGCCC AGGGGTGGGG 1750
CCCCATCACC TATACTAAGC CTAACAGCTC GGATCAGAGG CCTTATTGCT 1800
GGCATTACGC GCCTCGACCG TGTGGTGTCG TACCCGCGTC GCAGGTGTGT 1850
GGTCCAGTGT ATTGTTTCAC CCCAAGCCCT GTTGTGGTGG GGACCACCGA 1900
```

```
          10         20         30         40         50
 1234567890 1234567890 1234567890 1234567890 1234567890
 TCGTTCCGGT GTCCCTACGT ATAGCTGGGG GGAGAATGAG ACAGACGTGA  1950
 TGCTCCTCAA CAACACGCGT CCGCCACAAG GCAACTGGTT CGGCTGTACA  2000
 TGGATGAATA GTACTGGGTT CACTAAGACG TGCGGAGGTC CCCCGTGTAA  2050
 CATCGGGGGG GTCGGTAACC GCACCTTGAT CTGCCCCACG GACTGCTTCC  2100
 GGAAGCACCC CGAGGCTACT TACACAAAAT GTGGCTCGGG GCCCTGGTTG  2150
 ACACCTAGGT GCCTAGTAGA CTACCCATAC AGGCTTTGGC ACTACCCCTG  2200
 CACTCTCAAT TTTTCCATCT TTAAGGTTAG GATGTATGTG GGGGCGTGG   2250
 AGCACAGGCT CAATGCCGCA TGCAATTGGA CTCGAGGAGA GCGCTGTAAC  2300
 TTGGAGGACA GGGATAGGTC AGAACTCAGC CCGCTGCTGC TGTCTACAAC  2350
 AGAGTGGCAG ATACTGCCCT GTGCTTTCAC CACCCTACCG GCTTTATCCA  2400
 CTGGTTTGAT CCATCTCCAT CAGAACATCG TGGACGTGCA ATACCTGTAC  2450
 GGTGTAGGGT CAGCGTTTGT CTCCTTTGCA ATCAAATGGG AGTACATCCT  2500
 GTTGCTTTTC CTTCTCCTGG CAGACGCGCG CGTGTGTGCC TGCTTGTGGA  2550
 TGATGCTGCT GATAGCCCAG GCTGAGGCCG CCTTAGAGAA CTTGGTGGTC  2600
 CTCAATGCGG CGTCCGTGGC CGGAGCGCAT GGTATTCTCT CCTTTCTTGT  2650
 GTTCTTCTGC GCCGCCTGGT ACATTAAGGG CAGGCTGGCT CCTGGCGCGG  2700
 CGTATGCTTT TTATGGCGTA TGCCCGCTGC TCCTGCTCCT ACTGGCGTTA  2750
 CCACCACGAG CTTACGCCTT GGACCGGGAG ATGGCTGCAT CGTGCGGGG   2800
 TGCGGTTCTT GTAGGTCTGG TATTCTTGAC CTTGTCACCA TACTACAAAG  2850
 TGTTTCTCAC TAGGCTCATA TGGTGGTTAC AATACTTTAT CACCAGAGCC  2900
 GAGGCGCACA TGCAAGTGTG GGTCCCCCCC CTCAACGTTC GGGAGGCCG   2950
 CGATGCCATC ATCCTCCTCA CGTGTGCGGT TCATCCAGAG TTAATTTTTG  3000
 ACATCACCAA ACTCCTGCTC GCCATACTCG GCCCGCTCAT GGTGCTCCAG  3050
 GCTGGCATAA CGAGAGTGCC GTACTTCGTG CGCGCTCAAG GCTCATTCG   3100
 TGCATGCATG TTAGTGCGAA AAGTCGCCGG GGTCATTAT GTCCAAATGG   3150
 TCTTCATGAA GCTGGGCGCG CTGACAGGTA CGTACGTTTA TAACCATCTT  3200
 ACCCCACTGC GGGACTGGGC CCACGCGGGC CTACGAGACC TTGCGGTGGC  3250
 GGTAGAGCCC GTCGTCTTCT CCGCCATGGA GACCAAGGTC ATCACCTGGG  3300
 GAGCAGACAC CGCTGCGTGT GGGACATCA TCTTGGGTCT ACCCGTCTCC   3350
 GCCCGAAGGG GGAAGGAGAT ATTTTTGGGA CCGGCTGATA GTCTCGAAGG  3400
 GCAAGGGTGG CGACTCCTTG CGCCCATCAC GGCTACTCC CAACAAACGC   3450
 GGGGCGTACT TGGTTGCATC ATCACTAGCC TCACAGGCCG GACAAGAAC   3500
 CAGGTCGAAG GGGAGGTTCA AGTGGTTTCT ACCGCAACAC AATCTTTCCT  3550
 GGCGACCTGC ATCAACGGCG TGTGCTGGAC TGTCTACCAT GGCGCTGGCT  3600
 CGAAGACCCT AGCCGGTCCA AAAGGTCCAA TCACCCAAAT GTACACCAAT  3650
 GTAGACCTGG ACCTCGTCGG CTGGCAGGCG CCCCCCGGGG CGCGCTCCAT  3700
 GACACCATGC AGCTGTGGCA GCTCGGACCT TTACTTGGTC ACGAGACATG  3750
 CTGATGTCAT TCCGGTGCGC CGGCGAGGCG ACAGCAGGGG AAGTCTACTC  3800
```

```
            10         20         30         40         50
    1234567890 1234567890 1234567890 1234567890 1234567890
    TCCCCCAGGC CCGTCTCCTA CCTGAAAGGC TCCTCGGGTG GTCCATTGCT   3850
    TTGCCCTTCG GGCACGTCG  TGGGCGTCTT CCGGGCTGCT GTGTGCACCC   3900
    GGGGGGTCGC GAAGGCGGTG GACTTCATAC CCGTTGAGTC TATGGAAACT   3950
    ACCATGCGGT CTCCGGTCTT CACAGACAAC TCAACCCCCC CGGCTGTACC   4000
    GCAGACATTC CAAGTGGCAC ATCTGCACGC TCCTACTGGC AGCGGCAAGA   4050
    GCACCAAAGT GCCGGCTGCG TATGCAGCCC AAGGGTACAA GGTGCTCGTC   4100
    CTGAACCCGT CCGTTGCCGC CACCTTAGGG TTTGGGCCGT ATATGTCCAA   4150
    GGCACACGGT ATCGACCCTA ACATCAGAAC TGGGGTAAGG ACCATTACCA   4200
    CGGGCGGCTC CATTACGTAC TCCACCTATG GCAAGTTCCT TGCCGACGGT   4250
    GGCTGTTCTG GGGCGCCTA  TGACATCATA ATATGTGATG AGTGCCACTC   4300
    AACTGACTCG ACTACCATCT TGGGCATCGG CACAGTCCTG GACCAAGCGG   4350
    AGACGGCTGG AGCGCGGCTC GTCGTGCTCG CCACCGCTAC ACCTCCGGA    4400
    TCGGTTACCG TGCCACACCC CAATATCGAG GAAATAGGCC TGTCCAACAA   4450
    TGGAGAGATC CCCTTCTATG GCAAAGCCAT CCCCATTGAG GCCATCAAGG   4500
    GGGGAGGCA  TCTCATTTTC TGCCATTCCA AGAAGAAATG TGACGAGCTC   4550
    GCCGCAAAGC TGACAGGCCT CGGACTGAAC GCTGTAGCAT ATTACCGGGG   4600
    CCTTGATGTG TCCGTCATAC CGCCTATCGG AGACGTCGTT GTCGTGGCAA   4650
    CAGACGCTCT AATGACGGGT TTCACCGGCG ATTTGACTC  AGTGATCGAC   4700
    TGCAATACAT GTGTCACCCA GACAGTCGAC TTCAGCTTGG ATCCCACCTT   4750
    CACCATTGAG ACGACGACCG TGCCCCAAGA CGCGGTGTCG CGCTCGCAAC   4800
    GGCGAGGTAG AACTGGCAGG GGTAGGAGTG GCATCTACAG GTTTGTGACT   4850
    CCAGGAGAAC GGCCCTCGGG CATGTTCGAT TCTTCGGTCC TGTGTGAGTG   4900
    CTATGACGCG GGCTGTGCTT GGTATGAGCT CACGCCCGCT GAGACCTCGG   4950
    TTAGGTTGCG GGCTTACCTA AATACACCAG GGTTGCCCGT CTGCCAGGAC   5000
    CATCTGGAGT TCTGGGAGAG CGTCTTCACA GGCCTCACCC ACATAGATGC   5050
    CCACTTCCTG TCCAGACTA  AACAGGCAGG AGACAACTTT CCTTACCTGG   5100
    TGGCATATCA AGCTACAGTG TGCGCCAGGG CTCAAGCTCC ACCTCCATCG   5150
    TGGGACCAAA TGTGGAAGTG TCTCATACGG CTGAAACCTA CACTGCACGG   5200
    GCCAACACCC CTGCTGTATA GGCTAGGAGC CGTCCAAAAT GAGGTCATCC   5250
    TCACACACCC CATAACTAAA TACATCATGG CATGCATGTC GGCTGACCTG   5300
    GAGGTCGTCA CTAGCACCTG GGTGCTGGTA GGCGGAGTCC TTGCAGCTTT   5350
    GGCCGCATAC TGCCTGACGA CAGGCAGTGT GGTCATTGTG GGCAGGATCA   5400
    TCTTGTCCGG GAAGCCAGCT GTCGTTCCCG ACAGGGAAGT CCTCTACCAG   5450
    GAGTTCGATG AGATGGAAGA GTGTGCCTCA CAACTTCCTT ACATCGAGCA   5500
    GGGAATGCAG CTCGCCGAGC AATTCAAGCA AAAGGCGCTC GGGTTGTTGC   5550
    AAACGGCCAC CAAGCAAGCG GAGGCTGCTG CTCCCGTGGT GGAGTCCAAG   5600
    TGGCGAGCCC TTGAGACCTT CTGGGCGAAG CACATGTGGA ATTTCATCAG   5650
    CGGAATACAG TACCTAGCAG GCTTATCCAC TCTGCCTGGA AACCCCGCGA   5700
```

|  10 | 20 | 30 | 40 | 50 | |
|---|---|---|---|---|---|
| 1234567890 | 1234567890 | 1234567890 | 1234567890 | 1234567890 | |
| TAGCATCATT | GATGGCATTT | ACAGCTTCTA | TCACTAGCCC | GCTCACCACC | 5750 |
| CAAAACACCC | TCCTGTTTAA | CATCTTGGGG | GGATGGGTGG | CTGCCCAACT | 5800 |
| CGCTCCTCCC | AGCGCTGCGT | CAGCTTTCGT | GGGCGCCGGC | ATCGCCGGAG | 5850 |
| CGGCTGTTGG | CAGCATAGGC | CTTGGGAAGG | TGCTCGTGGA | CATCTTGGCG | 5900 |
| GGCTATGGGG | CAGGGGTAGC | CGGCGCACTC | GTGGCCTTTA | AGGTCATGAG | 5950 |
| CGGCGAGGTG | CCCTCCACCG | AGGACCTGGT | CAACTTACTC | CCTGCCATCC | 6000 |
| TCTCTCCTGG | TGCCCTGGTC | GTCGGGGTCG | TGTGCGCAGC | AATACTGCGT | 6050 |
| CGGCACGTGG | GCCCGGGAGA | GGGGCTGTG  | CAGTGGATGA | ACCGGCTGAT | 6100 |
| AGCGTTCGCT | TGCGGGGTA  | ACCACGTCTC | CCCTACGCAC | TATGTGCCTG | 6150 |
| AGAGCGACGC | TGCAGCACGT | GTCACTCAGA | TCCTCTCTAG | CCTTACCATC | 6200 |
| ACTCAACTGC | TGAAGCGGCT | CCACCAGTGG | ATTAATGAGG | ACTGCTCTAC | 6250 |
| GCCATGCTCC | GGCTCGTGGC | TAAGGGATGT | TTGGATTGG  | ATATGCACGG | 6300 |
| TGTTGACTGA | CTTCAAGACC | TGGCTCCAGT | CCAAACTCCT | GCCGCGGTTA | 6350 |
| CCGGGAGTCC | CTTTCCTGTC | ATGCCAACGC | GGGTACAAGG | GAGTCTGGCG | 6400 |
| GGGGACGGC  | ATCATGCAAA | CCACCTGCCC | ATGCGGAGCA | CAGATCGCCG | 6450 |
| GACATGTCAA | AAACGGTTCC | ATGAGGATCG | TAGGGCCTAG | AACCTGCAGC | 6500 |
| AACACGTGGC | ACGGAACGTT | CCCCATCAAC | GCATACACCA | CGGGACCTTG | 6550 |
| CACACCCTCC | CCGGCGCCCA | ACTATTCCAG | GGCGCTATGG | CGGGTGGCTG | 6600 |
| CTGAGGAGTA | CGTGGAGGTT | ACGCGTGTGG | GGGATTTCCA | CTACGTGACG | 6650 |
| GGCATGACCA | CTGACAACGT | AAAGTGCCCA | TGCCAGGTTC | CGGCCCCCGA | 6700 |
| ATTCTTCACG | GAGGTGGATG | GAGTGCGGTT | GCACAGGTAC | GCTCCGGCGT | 6750 |
| GCAAACCTCT | TCTACGGGAG | GACGTCACGT | TCCAGGTCGG | GCTCAACCAA | 6800 |
| TACTTGGTCG | GGTCGCAGCT | CCCATGCGAG | CCCGAACCGG | ACGTAACAGT | 6850 |
| GCTTACTTCC | ATGCTCACCG | ATCCCTCCCA | CATTACAGCA | GAGACGGCTA | 6900 |
| AGCGTAGGCT | GGCTAGAGGG | TCTCCCCCCT | CTTTAGCCAG | CTCATCAGCT | 6950 |
| AGCCAGTTGT | CTGCGCCTTC | TTTGAAGGCG | ACATGCACTA | CCCACCATGA | 7000 |
| CTCCCCGGAC | GCTGACCTCA | TCGAGGCCAA | CCTCTTGTGG | CGGCAGGAGA | 7050 |
| TGGGCGGAAA | CATCACTCGC | GTGGAGTCAG | AGAATAAGGT | AGTAATTCTG | 7100 |
| GACTCTTTCG | AACCGCTTCA | CGCGGAGGGG | GATGAGAGGG | AGATATCCGT | 7150 |
| CGCGGCGGAG | ATCCTGCGAA | AATCCAGGAA | GTTCCCCTCA | GCGTTGCCCA | 7200 |
| TATGGGCACG | CCCGGACTAC | AATCCTCCAC | TGCTAGAGTC | CTGGAAGGAC | 7250 |
| CCGGACTACG | TCCCTCCGGT | GGTACACGGA | TGCCCATTGC | CACCTACCAA | 7300 |
| GGCTCCTCCA | ATACCACCTC | CACGGAGAAA | GAGGACGGTT | GTCCTGACAG | 7350 |
| AATCCAATGT | GTCTTCTGCC | TTGGCGGAGC | TCGCCACTAA | GACCTTCGGT | 7400 |
| AGCTCCGGAT | CGTCGGCCGT | TGATAGCGGC | ACGGCGACCG | CCCTTCCTGA | 7450 |
| CCTGGCCTCC | GACGACGGTG | ACAAAGGATC | CGACGTTGAG | TGTACTCCT  | 7500 |
| CCATGCCCCC | CCTTGAAGGG | GAGCCGGGGG | ACCCCGATCT | CAGCGACGGG | 7550 |
| TCTTGGTCTA | CCGTGAGTGA | GGAGGCTAGT | GAGGATGTCG | TCTGCTGCTC | 7600 |

```
          10         20         30         40         50
    1234567890 1234567890 1234567890 1234567890 1234567890
    AATGTCCTAT ACGTGGACAG GCGCCCTGAT CACGCCATGC GCTGCGGAGG    7650
    AAAGTAAGCT GCCCATCAAC CCGTTGAGCA ACTCTTTGCT GCGTCACCAC    7700
    AACATGGTCT ACGCCACAAC ATCCCGCAGC GCAAGCCTCC GGCAGAAGAA    7750
    GGTCACCTTT GACAGATTGC AAGTCCTGGA TGATCATTAC CGGGACGTAC    7800
    TCAAGGAGAT GAAGGCGAAG GCGTCCACAG TTAAGGCTAA GCTTCTATCT    7850
    ATAGAGGAGG CCTGCAAGCT GACGCCCCA CATTCGGCCA AATCCAAATT     7900
    TGGCTATGGG GCAAAGGACG TCCGGAACCT ATCCAGCAGG GCCGTTAACC    7950
    ACATCCGCTC CGTGTGGGAG GACTTGCTGG AAGACACTGA AACACCAATT    8000
    GACACCACCA TCATGGCAAA AAGTGAGGTT TTCTGCGTCC AACCAGAGAA    8050
    GGGAGGCCGC AAGCCAGCTC GCCTTATCGT ATTCCCAGAC CTGGAGTTC     8100
    GTGTATGCGA GAAGATGGCC CTTTACGACG TGGTCTCCAC CCTTCCTCAG    8150
    GCCGTGATGG GCTCCTCATA CGGATTTCAA TACTCCCCA AGCAGCGGGT     8200
    CGAGTTCCTG GTGAATACCT GGAAATCAAA GAAATGCCCT ATGGGCTTCT    8250
    CATATGACAC CCGCTGTTTT GACTCAACGG TCACTGAGAG TGACATTCGT    8300
    GTTGAGGAGT CAATTTACCA ATGTTGTGAC TTGGCCCCCG AGGCCAGACA    8350
    GGCCATAAGG TCGCTCACAG AGCGGCTTTA CATCGGGGGT CCCCTGACTA    8400
    ACTCAAAAGG GCAGAACTGC GGTTATCGCC GGTGCCGCGC AAGTGGCGTG    8450
    CTGACGACTA GCTGCGGTAA TACCCTCACA TGTTACTTGA AGGCCACTGC    8500
    AGCCTGTCGA GCTGCAAAGC TCCAGGACTG CACGATGCTC GTGAACGGAG    8550
    ACGACCTTGT CGTTATCTGT GAAAGCGCGG GAACCCAGGA GGATGCGGCG    8600
    GCCCTACGAG CCTTCACGGA GGCTATGACT AGGTATTCCG CCCCCCCCGG    8650
    GGATCCGCCC CAACCAGAAT ACGACCTGGA GCTGATAACA TCATGTTCCT    8700
    CCAATGTGTC AGTCGCGCAC GATGCATCTG GCAAAAGGGT ATACTACCTC    8750
    ACCCGTGACC CCACCACCCC CCTTGCACGG GCTGCGTGGG AGACAGCTAG    8800
    ACACACTCCA ATCAACTCTT GGCTAGGCAA TATCATCATG TATGCGCCCA    8850
    CCCTATGGGC AAGGATGATT CTGATGACTC ACTTTTTCTC CATCCTTCTA    8900
    GCTCAAGAGC AACTTGAAAA AGCCCTGGAT TGTCAGATCT ACGGGGCTTG    8950
    CTACTCCATT GAGCCACTTG ACCTACCTCA GATCATTGAA CGACTCCATG    9000
    GTCTTAGCGC ATTTACACTC CACAGTTACT CTCCAGGTGA GATCAATAGG    9050
    GTGGCTTCAT GCCTCAGGAA ACTTGGGGTA CCACCCTTGC GAACCTGGAG    9100
    ACATCGGGCC AGAAGTGTCC GCGCTAAGCT ACTGTCCAG GGGGGAGGG     9150
    CCGCCACTTG TGCAGATAC CTCTTTAACT GGGCAGTAAG GACCAAGCTT    9200
    AAACTCACTC CAATCCCGGC CGCGTCCAG CTGGACTTGT CTGGCTGGTT     9250
    CGTCGCTGGT TACAGCGGGG GAGACATATA TCACAGCCTG TCTCGTGCCC    9300
    GACCCCGCTG GTTTCCGTTG TGCCTACTCC TACTTTCTGT AGGGGTAGGC    9350
    ATTTACCTGC TCCCCAACCG ATGAACGGGG AGCTAACCAC TCCAGGCCTT    9400
    AAGCCATTTC CTGTTTTTTT TTTTTTTTTT TTTTTTTTTT TCTTTTTTTT    9450
    TTTCTTTCCT TTCCTTCTTT TTTTCCTTTC TTTTTCCCTT CTTTAATGGT    9500
```

FIG. 7E

```
         10         20         30         40         50
1234567890 1234567890 1234567890 1234567890 1234567890
GGCTCCATCT TAGCCCTAGT CACGGCTAGC TGTGAAAGGT CCGTGAGCCG   9550
CATGACTGCA GAGAGTGCTG ATACTGGCCT CTCTGCAGAT CATGT        9595
```

FIG. 7F

```
          10         20         30         40         50
 1234567890 1234567890 1234567890 1234567890 1234567890
 MSTNPKPQRK TKRNINRRPQ DVKFPGGGQI VGGVYLLPRR GPRLGVRATR   50
 KASERSQPRG RRQPIPKARR PEGRAWAQPG YPWPLYGNEG LGWAGWLLSP  100
 RGSRPSWGPT DPRRRSRNLG KVIDILTCGF ADLMGYIPLV GAPLGGAARA  150
 LAHGVRVLED GVNYATGNLP GCSFSIFLLA LLSCLTIPAS AYEVRNVSGI  200
 YHVINDCSNS SIVYEAADVI MHTPGCVPCV QEGNSSRCWV ALTPILAARN  250
 ASVPTTTIRR HVDLLVGIAA FCSAMYVGDL CGSIFLVSQL FTFSPRRHET  300
 VQDCNCSTYP GHVSGHRMAW DMMMNWSPTT ALVVSQLLRI PQAVVDMVAG  350
 AHWGVLAGLA YYSMVGNWAK VLIVALLFAG VDGETHTTGR VAGHTTSGFT  400
 SLFSSGASQK IQLVNINGSW HINRTALNCN DSLQTGFFAA LFYAHKFNSS  450
 GCPERMASCR PIDWFAQGWG PITYTKPNSS DQRPYCWHYA PRPCGVVPAS  500
 QVCGPVYCFT PSPVVVGTTD RSGVPTYSWG ENEIDVMLLN NIRPPQGNWF  550
 GCTWMNSTGF TKTCGGPPCN IGGVGNRILI CPTDCFRKHP EATYTKCGSG  600
 PWLTPRCLVD YPYRLWHYPC TLNFSIFKVR MYVGGVEHRL NAACWIRGE   650
 RCNLEDRDRS ELSPLLLSTT EWQILPCAFT TLPALSTGLI HLHQNIVDVQ  700
 YLYGVGSAFV SFAIKWEYIL LLFLLLADAR VCACLWMMLL IAQAEAALEN  750
 LVVLNAASVA GAHGILSFLV FFCAAWYIKG RLAPGAAYAF YGVWPLLLLL  800
 LALPPRAYAL DREMAASCGG AVLVGLVFLT LSPYYKVFLT RLIWWLQYFI  850
 TRAEAHMQWW VPPLNVRGGR DAIILLTCAV HPELIFDITK LLLAILGPLM  900
 VLQAGTIRVP YFVRAQGLIR ACMLVRKVAG GHYVQMVFMK LGALTGTYVY  950
 NHLTPLRDWA HAGLRDLAVA VEPVVFSAME TKVTIWGADT AACGDIILGL 1000
 PVSARRGKEI FLGPADSLEG QGWRLLAPIT AYSQQTRGVL GCIITSLTGR 1050
 DKNQVEGEVQ VVSTATQSFL ATCINGVCWT VYHGAGSKTL AGPKGPITQM 1100
 YTNVDLDLVG WQAPPGARSM TPCSCGSSDL YLVTRHADVI PVRRRGDSRG 1150
 SLLSPRPVSY LKGSSGGPLL CPSGHVVGVF RAAVCTRGVA KAVDFIPVES 1200
 METTMRSPVF TLNSTPPAVP QTFQVAHLHA PTGSGKSTKV PAAYAAQGYK 1250
 VLVLNPSVAA TLGFGAYMSK AHGIDPNIRT GVRTTTTGGS ITYSTYGKFL 1300
 ADGGCSGGAY DIIICDECHS TDSTTILGIG TVLDQAETAG ARLVVLATAT 1350
 PPGSVTVPHP NIEEIGLSNN GEIPFYGKAI PIEAIKGGRH LIFCHSKKKC 1400
 DELAAKLTGL GLNAVAYYRG LDVSVIPPIG DVVVVATDAL MIGFTGDFDS 1450
 VIDCNTCVTQ TVDFSLDPTF TIETTTVPQD AVSRSQRRGR TGRGRSGIYR 1500
 FVTPGERPSG MFDSSVLCEC YDAGCAWYEL TPAETSVRLR AYLNTPGLPV 1550
 CQDHLEFWES VFTGLTHIDA HFLSQIKQAG DNFPYLVAYQ ATVCARAQAP 1600
 PPSWDQMWKC LIRLKPTLHG PTPLLYRLGA VQNEVILTHP ITKYIMACMS 1650
 ADLEVVTSTW VLVGGVLAAL AAYCLTTGSV VIVGRIILSG KPAVVPDREV 1700
 LYQEFDEMEE CASQLPYIEQ GMQLAEQFKQ KALGLLQTAT KQAEAAAPVV 1750
 ESKWRALETF WAKHMWNFIS GIQYLAGLST LPGNPAIASL MAFTASITSP 1800
 LTTQNILLFN ILGGWVAAQL APPSAASAFV GAGIAGAAVG SIGLGKVLVD 1850
 ILAGYGAGVA GALVAFKVMS GEVPSTEDLV NLLPAILSPG ALVVGVVCAA 1900
```

FIG. 7G

|          10         20         30         40         50         |      |
|------------------------------------------------------------------|------|
| 1234567890 1234567890 1234567890 1234567890 1234567890           |      |
| ILRRHVGPGE GAVQWMNRLI AFASRGNHVS PIHYVPESDA AARVTQILSS            | 1950 |
| LTTTQLLKRL HQWINEDCST PCSGSWLRDV WDWICTVLTD FKTWLQSKLL            | 2000 |
| PRLPGVPFLS CQRGYKGVWR GDGIMQTTCP CGAQIAGHVK NGSMRIVGPR            | 2050 |
| TCSNIWHGIF PINAYTTGPC TPSPAPNYSR ALWRVAAEEY VEVIRVGDFH            | 2100 |
| YVTGMTTDW KCPCQVPAPE FFTEVDGVRL HRYAPACKPL LREDVIFQVG             | 2150 |
| LNQYLWGSQL PCEPEPDVIV LTSMLTDPSH ITAETAKRRL ARGSPPSLAS            | 2200 |
| SSASQLSAPS LKATCTIHHD SPDADLIEAN LLWRQEMGGN ITRVESENKV            | 2250 |
| VILDSFEPLH AEGDEREISV AAEILRKSRK FPSALPIWAR PDYNPPLLES            | 2300 |
| WKDPDYVPPV VHGCPLPPIK APPIPPPRRK RTVVLTESNV SSALAELATK            | 2350 |
| TFGSSGSSAV DSGTATALPD LASDDGDKGS DVESYSSMPP LEGEPGDPDL            | 2400 |
| SDGSWSIVSE EASEDVVCCS MSYTWTGALI TPCAAEESKL PINPLSNSLL            | 2450 |
| RHHNMVYATT SRSASLRQKK VTFDRLQVLD DHYRDVLKEM KAKASTVKAK            | 2500 |
| LLSIEEACKL TPPHSAKSKF GYGAKDVRNL SSRAVNHIRS VWEDLLEDTE            | 2550 |
| TPIDTTIMAK SEVFCVQPEK GGRKPARLIV FPDLGVRVCE KMALYDVVST            | 2600 |
| LPQAVMGSSY GFQYSPKQRV EFLVNIWKSK KCPMGFSYDT RCFDSTVIES            | 2650 |
| DIRVEESTYQ CCDLAPEARQ AIRSLTERLY IGGPLINSKG QNCGYRRCRA            | 2700 |
| SGVLTTSCGN TLTCYLKATA ACRAAKLQDC TMLVNGDDLV VICESAGTQE            | 2750 |
| DAAALRAFTE AMIRYSAPPG DPPQPEYDLE LITSCSSNVS VAHDASGKRV            | 2800 |
| YYLTRDPTTP LARAAWETAR HTPINSWLGN IIMYAPTLWA RMILMIHFFS            | 2850 |
| ILLAQEQLEK ALDCQIYGAC YSIEPLDLPQ IIERLHGLSA FILHSYSPGE            | 2900 |
| INRVASCLRK LGVPPLRIWR HRARSVRAKL LSQGGRAATC GRYLFNWAVR            | 2950 |
| TKLKLTPIPA ASQLDLSGWF VAGYSGGDIY HSLSRARPRW FPLCLLLLSV            | 3000 |
| GVGIYLLPNR                                                       | 3010 |

FIG. 7H

CLONED GENOME OF INFECTIOUS HEPATITUS C VIRUS OF GENOTYPE 2A AND USES THEREOF

RELATED APPLICATIONS

This application is the National Stage of International Application No. PCT/US00/15446, filed 2 Jun. 2000, designating the United States of America and published in English on 14 Dec. 2000 as WO 00/75338, which claims the benefit of priority of U.S. Provisional Application No. 60/137,693 filed 4 Jun. 1999.

FIELD OF INVENTION

The present invention relates to molecular approaches to the production of nucleic acid sequence which comprises the genome of infectious hepatitis C virus. In particular, the invention provides a nucleic acid sequence which comprises the genome of an infectious hepatitis C virus of genotype 2a. The invention therefore relates to the use of the nucleic acid sequence and polypeptides encoded by all or part of the sequence in the development of vaccines and diagnostic assays for HCV and in the development of screening assays for the identification of antiviral agents for HCV.

BACKGROUND OF INVENTION

Hepatitis C virus (HCV) has a positive-sense single-strand RNA genome and is a member of the genus *Hepacivirus* within the Flaviviridae family of viruses (Rice, 1996). As for all positive-stranded RNA viruses, the genome of HCV functions as mRNA from which all viral proteins necessary for propagation are translated.

The viral genome of HCV is approximately 9600 nucleotides (nts) in length and consists of a highly conserved 5' untranslated region (UTR), a single long open reading frame (ORF) of approximately 9,000 nts and a complex 3' UTR. The 5' UTR contains an internal ribosomal entry site (Tsukiyama-Kohara et al., 1992; Honda et al., 1996). The 3' UTR consists of a short variable region, a polypyrimidine tract of variable length and, at the 3' end, a highly conserved region of approximately 100 nucleotides (Kolykhalov et al., 1996; Tanaka et al., 1995; Tanaka et al., 1996; Yamada et al., 1996). The last 46 nucleotides of this conserved region were predicted to form a stable stem-loop structure thought to be critical for viral replication (Blight and Rice, 1997; Ito and Lai, 1997; Tsuchihara et al., 1997). The ORF encodes a large polypeptide precursor that is cleaved into at least 10 proteins by host and viral proteinases (Rice, 1996). The predicted envelope proteins contain several conserved N-linked glycosylation sites and cysteine residues (Okamoto et al., 1992a). The NS3 gene encodes a serine protease and an RNA helicase and the NS5B gene encodes an RNA-dependent RNA polymerase.

A remarkable characteristic of HCV is its genetic heterogeneity, which is manifested throughout the genome (Bukh et al., 1995). The most heterogeneous regions of the genome are found in the envelope genes, in particular the hypervariable region 1 (HVR1) at the N-terminus of E2 (Hijikata et al., 1991; Weiner et al., 1991). HCV circulates as a quasispecies of closely related genomes in an infected individual. Globally, six major HCV genotypes (genotypes 1–6) and multiple subtypes (a, b, c, etc.) have been identified (Bukh et al., 1993; Simmonds et al., 1993).

The nucleotide and deduced amino acid sequences among isolates within a quasispecies generally differ by <2%, whereas those between isolates of different genotypes vary by as much as 35%. Genotypes 1, 2 and 3 are found worldwide and constitute more than 90% of the HCV infections in North and South America, Europe, Russia, China, Japan and Australia (Forns and Bukh, 1998). Throughout these regions genotype 1 accounts for the majority of HCV infections but genotypes 2 and 3 each account for 5–15%.

At present, more than 80% of individuals infected with HCV become chronically infected and these chronically infected individuals have a relatively high risk of developing chronic hepatitis, liver cirrhosis and hepatocellular carcinoma (Hoofnagle, 1997). The only effective therapy for chronic hepatitis C, interferon (IFN), alone or in combination with ribavirin, induces a sustained response in less than 50% of treated patients (Davis et al., 1998; McHutchinson et al., 1998). Consequently, HCV is currently the most common cause of end stage liver failure and the reason for about 30% of liver transplants performed in the U.S. (Hoofnagle, 1997). In addition, a number of recent studies suggested that the severity of liver disease and the outcome of therapy may be genotype-dependent (reviewed in Bukh et al., 1997). In particular, these studies suggested that infection with HCV genotype 1b was associated with more severe liver disease (Brechot, 1997) and a poorer response to IFN therapy (Fried and Hoofnagle, 1995). As a result of the inability to develop a universally effective therapy against HCV infection, it is estimated that there are still more than 25,000 new infections yearly in the U.S. (Alter 1997) Moreover, since there is no vaccine for HCV, HCV remains a serious public health problem.

Despite the intense interest in the development of vaccines and therapies for HCV, progress has been hindered by the absence of a useful cell culture system and the lack of any small animal model for laboratory study. For example, while replication of HCV in several cell lines has been reported, such observations have turned out not to be highly reproducible. In addition, the chimpanzee is the only animal model, other than man, for this disease. Consequently, HCV has been studied only by using clinical materials obtained from patients or experimentally infected chimpanzees, an animal model whose availability is very limited.

However, several researchers have recently reported the construction of infectious cDNA clones of HCV, the identification of which would permit a more effective search for susceptible cell lines and facilitate molecular analysis of the viral genes and their function. For example, Yoo et al., and Dash et al., (1997) (1995) reported that RNA transcripts from cDNA clones of HCV-1 (genotype 1a) and HCV-N (genotype 1b), respectively, resulted in viral replication after transfection into human hepatoma cell lines. Unfortunately, the viability of these clones was not tested in vivo and concerns were raised about the infectivity of these cDNA clones in vitro (Fausto, 1997). In addition, both clones did not contain the terminal 98 conserved nucleotides at the very 3' end of the UTR.

Kolykhalov et al., (1997) and Yanagi et al. (1997, 1998) reported the derivation from HCV strains H77 (genotype 1a) and HC-J4 (genotype 1b) of cDNA clones of HCV that are infectious for chimpanzees. However, while these infectious clones will aid in studying HCV replication and pathogenesis and will provide an important tool for development of in vitro replication and propagation systems, it is important to have infectious clones of more than one genotype, given the extensive genetic heterogeneity of HCV and the potential impact of such heterogeneity on the development of effective therapies and vaccines for HCV.

In addition, synthetic chimeric viruses can be used to map the functional regions of viruses with different phenotypes. In flaviviruses and pestiviruses, infectious chimeric viruses have been successfully engineered to express different functional units of related viruses (Bray and Lai, 1991; Pletnev et al., 1992, 1998; Vassilev et al., 1997) and in some cases it has been possible to make chimeras between non-related or distantly related viruses. For instance, the IRES element of poliovirus or bovine viral diarrhea virus has been replaced with IRES sequences from HCV (Frolov et al., 1998; Lu and Wimmer, 1996; Zhao et al., 1999). Recently, the construction of an infectious chimera of two closely related HCV subtypes has been reported. The chimera contained the complete ORF of a genotype 1b strain but had the 5' and 3' termini of a genotype 1a strain (Yanagi et al., 1998).

It is important to determine whether chimeras constructed from more divergent HCV strains are infectious because such chimeras could be used to define the functions of viral units and to dissect the immune response.

SUMMARY OF THE INVENTION

The present invention relates to nucleic acid sequence which comprises the genome of infectious hepatitis C virus and in particular, nucleic acid sequence which comprises the genome of infectious hepatitis C virus of genotype 2a. It is therefore an object of the invention to provide nucleic acid sequence which encodes infectious hepatitis C virus. Such nucleic acid sequence is referred to throughout the application as "infectious nucleic acid sequence".

For the purposes of this application, nucleic acid sequence refers to RNA, DNA, cDNA or any variant thereof capable of directing host organism synthesis of a hepatitis C virus polypeptide. It is understood that nucleic acid sequence encompasses nucleic acid sequences, which due to degeneracy, encode the same polypeptide sequence as the nucleic acid sequences described herein.

The invention also relates to the use of the infectious nucleic acid sequences to produce chimeric genomes consisting of portions of the open reading frames of nucleic acid sequences of other genotypes (including, but not limited to, genotypes 1, 2, 3, 4, 5 and 6) and subtypes (including, but not limited to, subtypes 1a, 1b, 2a, 2b, 2c, 3a, 4a–4f, 5a and 6a) of HCV. For example, infectious nucleic acid sequence of the 2a strain HC-J6, described herein can be used to produce chimeras with sequences from the genomes of other strains of HCV from different genotypes or subtypes. Nucleic acid sequences which comprise sequences from two or more HCV genotypes or subtypes are designated "chimeric nucleic acid sequences".

The invention further relates to mutations of the infectious nucleic acid sequence of the invention where mutation includes, but is not limited to, point mutations, deletions and insertions. In one embodiment, a gene or fragment thereof can be deleted to determine the effect of the deleted gene or genes on the properties of the encoded virus such as its virulence and its ability to replicate. In an alternative embodiment, a mutation may be introduced into the infectious nucleic acid sequences to examine the effect of the mutation on the properties of the virus.

The invention also relates to the introduction of mutations or deletions into the infectious nucleic acid sequence in order to produce an attenuated hepatitis C virus suitable for vaccine development.

The invention further relates to the use of the infectious nucleic acid sequence to produce attenuated viruses via passage in vitro or in vivo of the viruses produced by transfection of a host cell with the infectious nucleic acid sequence.

The present invention also relates to the use of the nucleic acid sequence of the invention or fragments thereof in the production of polypeptides where "nucleic acid sequence of the invention" refers to infectious nucleic acid sequence, mutations of infectious nucleic acid sequence, chimeric nucleic acid sequence and sequences which comprise the genome of attenuated viruses produced from the infectious nucleic acid sequence of the invention. In one embodiment, said polypeptide or polypeptides are fully or partially purified from hepatitis C virus produced by cells transfected with nucleic acid sequence of the invention. In another embodiment, the polypeptide or polypeptides are produced recombinantly from a fragment of the nucleic acid sequences of the invention. In yet another embodiment, the polypeptides are chemically synthesized.

The polypeptides of the invention, especially structural polypeptides, can serve as immunogens in the development of vaccines or as antigens in the development of diagnostic assays for detecting the presence of HCV in biological samples.

The invention therefore also relates to vaccines for use in immunizing mammals especially humans against hepatitis C. In one embodiment, the vaccine comprises one or more polypeptides made from the nucleic acid sequence of the invention or fragment thereof. In a second embodiment, the vaccine comprises a hepatitis C virus produced by transfection of host cells with the nucleic acid sequences of the invention.

The present invention therefore relates to methods for preventing hepatitis C in a mammal. In one embodiment the method comprises administering to a mammal a polypeptide or polypeptides encoded by the nucleic acid sequence of the invention in an amount effective to induce protective immunity to hepatitis C. In another embodiment, the method of prevention comprises administering to a mammal a hepatitis C virus of the invention in an amount effective to induce protective immunity against hepatitis C.

In yet another embodiment, the method of protection comprises administering to a mammal the nucleic acid sequence of the invention or a fragment thereof in an amount effective to induce protective immunity against hepatitis C.

The invention also relates to hepatitis C viruses produced by host cells transfected with the nucleic acid sequence of the present invention.

The invention therefore also provides pharmaceutical compositions comprising the nucleic acid sequence of the invention and/or the encoded hepatitis C viruses. The invention further provides pharmaceutical compositions comprising polypeptides encoded by the nucleic acid sequence of the invention or fragments thereof. The pharmaceutical compositions of the invention may be used prophylactically or therapeutically.

The invention also relates to antibodies to the hepatitis C virus of the invention or their encoded polypeptides and to pharmaceutical compositions comprising these antibodies.

The invention also relates to the use of the nucleic acid sequences of the invention to identify cell lines capable of supporting the replication of HCV in vitro.

The invention further relates to the use of the nucleic acid sequences of the invention or their encoded viral enzymes (e.g. NS3 serine protease, NS3 helicase, NS5B RNA polymerase) to develop screening assays to identify antiviral agents for HCV.

BRIEF DESCRIPTION OF FIGURES

FIGS. 5A and 5B show the alignment of the nucleotide sequences of the 5' (H77CV-J6S-SEQ ID NO: 50; H77(p7) CV-J6S-SEQ ID NO: 51; H77-J6S-SEQ ID NO: 52; H77 (p7)-J6S-SEQ ID NO: 53) (FIG. 5A) and 3' UTRs (H77C-SEQ ID NO: 55; H77CV-J6S-SEQ ID NO: 56; H77(p7)CV-J6S-SEQ ID NO: 57: H77-J6S-SEQ ID NO: 58; H77(p7)-J6S-SEQ ID NO: 59; J6CF-SEQ ID NO: 60) (FIG. 5B) and the amino acid sequences of E2/p7/NS2 junctions (H77C-SEQ ID NO: 61; H77CV-J6S-SEQ ID NO: 62; H77(p7)CV-J6S-SEQ ID NO: 63; H77-J6S-SEQ ID NO: 64; H77(p7)-J6S-SEQ ID NO: 65; J6CF-SEQ ID NO: 66) (FIG. 5B) in the intertypic 1a, 2a chimeric cDNA clones. In the 5' UTR alignment, the first 39 nts of core believed to be important for the IRES function were included (Lemon and Honda, 1997). Top line: the sequence of the infectious genotype 1a clone pCV-H77C (Yanagi et al., 1997) (SEQ ID NO: 49). Bottom line: the sequence of the infectious genotype 2a clone pJ6CF (SEQ ID NO: 54). Dot: identity with the sequence of H77C. Capital. letter: different from the sequence of H77C. Dash: deletion. Bold face: initiation or stop codon of the ORF. Underlined: AgeI cleavage site. Arrow: putative sites in the HCV polyprotein cleaved by host signal peptidases. Numbering corresponds to the sequence of pCV-H77C.

FIGS. 6A–6F show the nucleotide sequence of the infectious hepatitis C virus clone of genotype 1a strain H77C (SEQ ID NO: 67) and FIGS. 6G–6H show the amino acid sequence encoded by the clone (SEQ ID NO: 68).

FIGS. 7A–7F show the nucleotide sequence of the infectious hepatitis C virus clone of genotype 1b strain HC-J4 (SEQ ID NO: 69) and FIGS. 7G-H show the amino acid sequence encoded by the clone (SEQ ID NO: 70).

DESCRIPTION OF THE INVENTION

Figure 1:
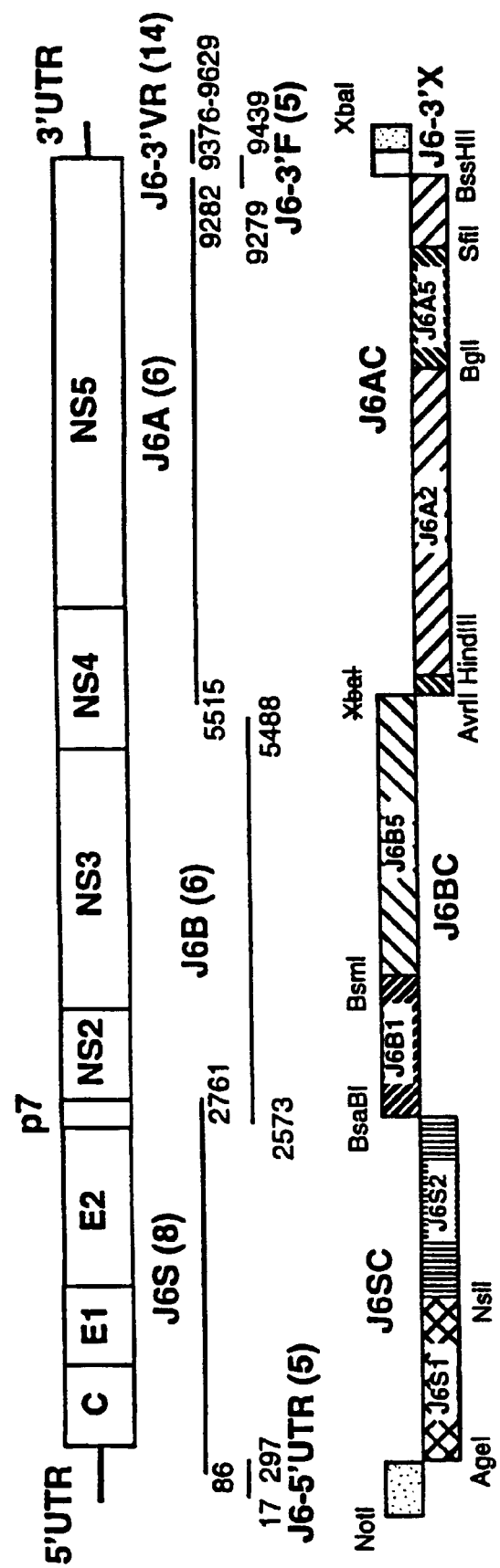
FIG. 1 shows the amplification and cloning of hepatitis C virus genotype 2a (strain HC-J6$_{Ch}$). The nucleotide positions correspond to the sequence of PJ6CF, a full length cDNA clone of hepatitis C virus, genotype 2a, strain HC-J6$_{CH}$. Products from polymerase chain reaction are also shown. The names of the clones obtained from these products are indicated (number of clones sequenced are shown in parenthesis). The composition of the full-length cDNA clone is shown at the bottom. The restriction enzymes used for cloning are indicated. An XbaI site in HC-J6$_{CH}$ was eliminated by a silent substitution at position 5494.

The present invention relates to nucleic acid sequence which comprises the genome of an infectious hepatitis C virus. More specifically, the invention relates to nucleic acid sequence which encodes infectious hepatitis C virus of strain HC-J6$_{CH}$, genotype 2a. The infectious nucleic acid sequence of the invention is shown in SEQ ID NO:1 and is contained in a plasmid construct deposited with the American Type Culture Collection (ATCC) on May 28, 1999 and having ATCC accession number PTA-153.

The invention also relates to "chimeric nucleic acid sequences" where the chimeric nucleic acid sequences consist of open-reading frame sequences and/or 5' and/or 3' untranslated sequences taken from nucleic acid sequences of hepatitis C viruses of different genotypes or subtypes.

In one embodiment, the chimeric nucleic acid sequence consists of sequence from the genome of infectious HCV of genotype 2a which encodes structural polypeptides and sequence from the genome of a HCV of a different genotype or subtype which encodes nonstructural polypeptides.

Alternatively, the nonstructural region of infectious HCV of genotype 2a and structural region of a HCV of a different genotype or subtype may be combined. This will result in a chimeric nucleic acid sequence consisting of sequence from the genome of infectious HCV of genotype 2a which encodes nonstructural polypeptides and sequence from the genome of a HCV of a another genotype or subtype which encodes structural polypeptides.

Preferably, the nucleic acid sequence from the genome of the infectious HCV clone of genotype 1a (deposited with the ATCC on Jun. 2, 1999; FIGS. 6A–6F), or the nucleic acid sequence from the genome of the infectious HCV clone of genotype 1b (ATCC accession number 209596; FIGS. 7A–7F) is used to construct the chimeric nucleic acid sequence with the HCV of genotype 2a of the invention.

It is believed that the construction of such chimeric nucleic acid sequences will be of importance in studying the growth and virulence properties of hepatitis C virus and in the production of candidate hepatitis C virus vaccines suitable to confer protection against multiple genotypes of HCV. For example, one might produce a "multivalent" vaccine by putting epitopes from several genotypes or subtypes into one clone. Alternatively one might replace just a single gene from an infectious sequence with the corresponding gene from the genomic sequence of a strain from another genotype or subtype or create a chimeric gene which contains portions of a gene from two genotypes or subtypes. Examples of genes which could be replaced or which could be made chimeric, include, but are not limited to, the E1, E2 and NS4 genes.

The invention further relates to mutations of the infectious nucleic acid sequences where "mutations" include, but are not limited to, point mutations, deletions and insertions. Of course, one of ordinary skill in the art would recognize that the size of the insertions would be limited by the ability of the resultant nucleic acid sequence to be properly packaged within the virion. Such mutations could be produced by techniques known to those of skill in the art such as site-directed mutagenesis, fusion PCR, and restriction digestion followed by religation.

In one embodiment, mutagenesis might be undertaken to determine sequences that are important for viral properties such as replication or virulence. For example, one may introduce a mutation into the infectious nucleic acid sequence which eliminates the cleavage site between the NS4A and NS4B polypeptides to examine the effects on viral replication and processing of the polypeptide.

Alternatively, one may delete all or part of a gene or of the 5' or 3' nontranslated region contained in an infectious nucleic acid sequence and then transfect a host cell (animal or cell culture) with the mutated sequence and measure viral replication in the host by methods known in the art such as RT-PCR. Preferred genes include, but are not limited to, the P7, NS4B and NS5A genes. Of course, those of ordinary skill in the art will understand that deletion of part of a gene, preferably the central portion of the gene, may be preferable to deletion of the entire gene in order to conserve the cleavage site boundaries which exist between proteins in the HCV polyprotein and which are necessary for proper processing of the polyprotein.

In the alternative, if the transfection is into a host animal such as a chimpanzee, one can monitor the virulence phenotype of the virus produced by transfection of the mutated infectious nucleic acid sequence by methods known in the art such as measurement of liver enzyme levels (alanine aminotransferase (ALT) or isocitrate dehydrogenase (ICD)) or by histopathology of liver biopsies. Thus, mutations of the infectious nucleic acid sequences may be useful in the production of attenuated HCV strains suitable for vaccine use.

The invention also relates to the use of the infectious nucleic acid sequence of the present invention to produce attenuated viral strains via passage in vitro or in vivo of the virus produced by transfection with the infectious nucleic acid sequence.

The present invention therefore relates to the use of the nucleic acid sequence of the invention to identify cell lines capable of supporting the replication of HCV.

In particular, it is contemplated that the mutations of the infectious nucleic acid sequence of the invention and the production of chimeric sequences as discussed above may be useful in identifying sequences critical for cell culture adaptation of HCV and hence, may be useful in identifying cell lines capable of supporting HCV replication.

Transfection of tissue culture cells with the nucleic acid sequences of the invention may be done by methods of transfection known in the art such as electroporation, precipitation with DEAE-Dextran or calcium phosphate or liposomes.

In one such embodiment, the method comprises the growing of animal cells, especially human cells, in vitro and transfecting the cells with the nucleic acid of the invention, then determining if the cells show indicia of HCV infection. Such indicia include the detection of viral antigens in the cell, for example, by immunofluorescence procedures well known in the art; the detection of viral polypeptides by Western blotting using antibodies specific therefor; and the detection of newly transcribed viral RNA within the cells via methods such as RT-PCR. The presence of live, infectious virus particles following such tests may also be shown by injection of cell culture medium or cell lysates into healthy, susceptible animals, with subsequent exhibition of the signs and symptoms of HCV infection.

Suitable cells or cell lines for culturing HCV include, but are not limited to, lymphocyte and hepatocyte cell lines known in the art.

Alternatively, primary hepatocytes can be cultured, and then infected with HCV; or, the hepatocyte cultures could be derived from the livers of infected chimpanzees. In addition, various immortalization methods known to those of ordinary skill in the art can be used to obtain cell lines derived from hepatocyte cultures. For example, primary hepatocyte cultures may be fused to a variety of cells to maintain stability.

The present invention further relates to the in vitro and in vivo production of hepatitis C viruses from the nucleic acid sequences of the invention.

In one embodiment, the sequences of the invention can be inserted into an expression vector that functions in eukaryotic cells. Eukaryotic expression vectors suitable for producing high efficiency gene transfer in vivo are well known to those of ordinary skill in the art and include, but are not limited to, plasmids, vaccinia viruses, retroviruses, adenoviruses and adeno-associated viruses.

In another embodiment, the sequences contained in the recombinant expression vector can be transcribed in vitro by methods known to those of ordinary skill in the art in order to produce RNA transcripts which encode the hepatitis C viruses of the invention. The hepatitis C viruses of the invention may then be produced by transfecting cells by methods known to those of ordinary skill in the art with either the in vitro transcription mixture containing the RNA transcripts or with the recombinant expression vectors containing the nucleic acid sequences described herein.

The hepatitis C viruses produced from the sequences of the invention may be purified or partially purified from the transfected cells by methods known to those of ordinary skill in the art. In a preferred embodiment, the viruses are partially purified prior to their use as immunogens in the pharmaceutical compositions and vaccines of the present invention.

The present invention therefore relates to the use of the hepatitis C viruses produced from the nucleic acid sequences of the invention as immunogens in live or killed (e.g., formalin inactivated) vaccines to prevent hepatitis C in a mammal.

In an alternative embodiment, the immunogen of the present invention may be an infectious nucleic acid sequence, a chimeric nucleic acid sequence, or a mutated infectious nucleic acid sequence which encodes a hepatitis C virus. Where the sequence is a cDNA sequence, the cDNAs and their RNA transcripts may be used to transfect a mammal by direct injection into the liver tissue of the mammal as described in the Examples.

Alternatively, direct gene transfer may be accomplished via administration of a eukaryotic expression vector containing a nucleic acid sequence of the invention.

In yet another embodiment, the immunogen may be a polypeptide encoded by the nucleic acid sequences of the invention. The present invention therefore also relates to polypeptides produced from the nucleic acid sequences of the invention or fragments thereof. In one embodiment, polypeptides of the present invention can be recombinantly produced by synthesis from the nucleic acid sequences of the invention or isolated fragments thereof, and purified, or partially purified, from transfected cells using methods already known in the art. In an alternative embodiment, the polypeptides may be purified or partially purified from viral particles produced via transfection of a host cell with the nucleic acid sequences of the invention. Such polypeptides might, for example, include either capsid or envelope polypeptides prepared from the sequences of the present invention.

When used as immunogens, the nucleic acid sequences of the invention, or the polypeptides or viruses produced therefrom, are preferably partially purified prior to use as immunogens in pharmaceutical compositions and vaccines of the present invention. When used as a vaccine, the sequences and the polypeptide and virus products thereof, can be administered alone or in a suitable diluent, including, but not limited to, water, saline, or some type of buffered medium. The vaccine according to the present invention may be administered to an animal, especially a mammal, and most especially a human, by a variety of routes, including, but not limited to, intradermally, intramuscularly, subcutaneously, or in any combination thereof.

Suitable amounts of material to administer for prophylactic and therapeutic purposes will vary depending on the route selected and the immunogen (nucleic acid, virus, polypeptide) administered. One skilled in the art will appreciate that the amounts to be administered for any particular treatment protocol can be readily determined without undue experimentation. The vaccines of the present invention may be administered once or periodically until a suitable titer of anti-HCV antibodies appear in the blood. For an immunogen consisting of a nucleic acid sequence, a suitable amount of nucleic acid sequence to be used for prophylactic purposes might be expected to fall in the range of from about 100 µg to about 5 mg and most preferably in the range of from about 500 µg to about 2 mg. For a polypeptide, a suitable amount to use for prophylactic purposes is preferably 100 ng to 100 µg and for a virus $10^2$ to $10^6$ infectious doses. Such administration will, of course, occur prior to any sign of HCV infection.

A vaccine of the present invention may be employed in such forms as capsules, liquid solutions, suspensions or elixirs for oral administration, or sterile liquid forms such as solutions or suspensions. An inert carrier is preferably used, such as saline or phosphate-buffered saline, or any such carrier in which the HCV of the present invention can be suitably suspended. The vaccines may be in the form of single dose preparations or in multi-dose flasks which can be utilized for mass-vaccination programs of both animals and humans. For purposes of using the vaccines of the present invention reference is made to Remington's *Pharmaceutical Sciences*, Mack Publishing Co., Easton, Pa., Osol (Ed.) (1980); and *New Trends and Developments in Vaccines*, Voller et al. (Eds.), University Park Press, Baltimore, Md. (1978), both of which provide much useful information for preparing and using vaccines. Of course, the polypeptides of the present invention, when used as vaccines, can include, as part of the composition or emulsion, a suitable adjuvant, such as alum (or aluminum hydroxide) when humans are to be vaccinated, to further stimulate production of antibodies by immune cells. When nucleic acids, viruses or polypeptides are used for vaccination purposes, other specific adjuvants such as CpG motifs (Krieg, A. K. et al. (1995) and (1996)), may prove useful.

When the nucleic acids, viruses and polypeptides of the present invention are used as vaccines or inocula, they will normally exist as physically discrete units suitable as a unitary dosage for animals, especially mammals, and most especially humans, wherein each unit will contain a predetermined quantity of active material calculated to produce the desired immunogenic effect in association with the required diluent. The dose of said vaccine or inoculum according to the present invention is administered at least once. In order to increase the antibody level, a second or booster dose may be administered at some time after the initial dose. The need for, and timing of, such booster dose will, of course, be determined within the sound judgment of the administrator of such vaccine or inoculum and according to sound principles well known in the art. For example, such booster dose could reasonably be expected to be advantageous at some time between about 2 weeks to about 6 months following the initial vaccination. Subsequent doses may be administered as indicated.

The nucleic acid sequences, viruses and polypeptides of the present invention can also be administered for purposes of therapy, where a mammal, especially a primate, and most especially a human, is already infected, as shown by well known diagnostic measures. When the nucleic acid sequences, viruses or polypeptides of the present invention are used for such therapeutic purposes, much of the same criteria will apply as when it is used as a vaccine, except that inoculation will occur post-infection. Thus, when the nucleic acid sequences, viruses or polypeptides of the present invention are used as therapeutic agents in the treatment of infection, the therapeutic agent comprises a pharmaceutical composition containing a sufficient amount of said nucleic acid sequences, viruses or polypeptides so as to elicit a therapeutically effective response in the organism to be treated. Of course, the amount of pharmaceutical composition to be administered will, as for vaccines, vary depending on the immunogen contained therein (nucleic acid, polypeptide, virus) and on the route of administration.

The therapeutic agent according to the present invention can thus be administered by subcutaneous, intramuscular or intradermal routes. One skilled in the art will certainly appreciate that the amounts to be administered for any particular treatment protocol can be readily determined without undue experimentation. Of course, the actual amounts will vary depending on the route of administration as well as the sex, age, and clinical status of the subject which, in the case of human patients, is to be determined with the sound judgment of the clinician.

The therapeutic agent of the present invention can be employed in such forms as capsules, liquid solutions, suspensions or elixirs, or sterile liquid forms such as solutions or suspensions. An inert carrier is preferably used, such as saline, phosphate-buffered saline, or any such carrier in which the HCV of the present invention can be suitably suspended. The therapeutic agents may be in the form of single dose preparations or in the multi-dose flasks which can be utilized for mass-treatment programs of both animals and humans. Of course, when the nucleic acid sequences, viruses or polypeptides of the present invention are used as therapeutic agents they may be administered as a single dose or as a series of doses, depending on the situation as determined by the person conducting the treatment.

The nucleic acids, polypeptides and viruses of the present invention can also be utilized in the production of antibodies against HCV. The term "antibody" is herein used to refer to immunoglobulin molecules and immunologically active portions of immunoglobulin molecules. Examples of antibody molecules are intact immunoglobulin molecules, substantially intact immunoglobulin molecules and portions of an immunoglobulin molecule, including those portions known in the art as Fab, F(ab')$_2$ and F(v) as well as chimeric antibody molecules.

Thus, the polypeptides, viruses and nucleic acid sequences of the present invention can be used in the generation of antibodies that immunoreact (i.e., specific binding between an antigenic determinant-containing molecule and a molecule containing an antibody combining site such as a whole antibody molecule or an active portion thereof) with antigenic determinants on the surface of hepatitis C virus particles.

The present invention therefore also relates to antibodies produced following immunization with the nucleic acid sequences, viruses or polypeptides of the present invention. These antibodies are typically produced by immunizing a mammal with an immunogen or vaccine to induce antibody molecules having immunospecificity for polypeptides or viruses produced in response to infection with the nucleic acid sequences of the present invention. When used in generating such antibodies, the nucleic acid sequences, viruses, or polypeptides of the present invention may be linked to some type of carrier molecule. The resulting antibody molecules are then collected from said mammal. Antibodies produced according to the present invention have the unique advantage of being generated in response to authentic, functional polypeptides produced according to the actual cloned HCV genome.

The antibody molecules of the present invention may be polyclonal or monoclonal. Monoclonal antibodies are readily produced by methods well known in the art. Portions of immunoglobin molecules, such as Fabs, as well as chimeric antibodies, may also be produced by methods well known to those of ordinary skill in the art of generating such antibodies.

The antibodies according to the present invention may also be contained in blood, plasma, serum, hybridoma supernatants, and the like. Alternatively, the antibody of the present invention is isolated to the extent desired by well known techniques such as, for example, using DEAE Sephadex. The antibodies produced according to the present invention may be further purified so as to obtain specific classes or subclasses of antibody such as IgM, IgG, IgA, and the like. Antibodies of the IgG class are preferred for purposes of passive protection.

The antibodies of the present invention are useful in the prevention and treatment of diseases caused by hepatitis C virus in animals, especially mammals, and most especially humans.

In providing the antibodies of the present invention to a recipient mammal, preferably a human, the dosage of administered antibodies will vary depending on such factors as the mammal's age, weight, height, sex, general medical condition, previous medical history, and the like.

In general, it will be advantageous to provide the recipient mammal with a dosage of antibodies in the range of from about 1 mg/kg body weight to about 10 mg/kg body weight of the mammal, although a lower or higher dose may be administered if found desirable. Such antibodies will normally be administered by intravenous or intramuscular route as an inoculum. The antibodies of the present invention are intended to be provided to the recipient subject in an amount sufficient to prevent, lessen or attenuate the severity, extent or duration of any existing infection.

The antibodies prepared by use of the nucleic acid sequences, viruses or polypeptides of the present invention are also highly useful for diagnostic purposes. For example, the antibodies can be used as in vitro diagnostic agents to test for the presence of HCV in biological samples taken from animals, especially humans. Such assays include, but are not limited to, radioimmunoassays, EIA, fluorescence, Western blot analysis and ELISAs. In one such embodiment, the biological sample is contacted with antibodies of the present invention and a labeled second antibody is used to detect the presence of HCV to which the antibodies are bound.

Such assays may be, for example, direct where the labeled first antibody is immunoreactive with the antigen, such as, for example, a polypeptide on the surface of the virus; indirect where a labeled second antibody is reactive with the first antibody; a competitive protocol such as would involve the addition of a labeled antigen; or sandwich where both labeled and unlabeled antibody are used, as well as other protocols well known and described in the art.

In one embodiment, an immunoassay method would utilize an antibody specific for HCV envelope determinants and would further comprise the steps of contacting a biological sample with the HCV-specific antibody and then detecting the presence of HCV material in the test sample using one of the types of assay protocols as described above. Polypeptides and antibodies produced according to the present invention may also be supplied in the form of a kit, either present in vials as purified material, or present in compositions and suspended in suitable diluents as previously described.

In a preferred embodiment, such a diagnostic test kit for detection of HCV antigens in a test sample comprises in combination a series of containers, each container a reagent needed for such assay. Thus, one such container would contain a specific amount of HCV-specific antibody as already described, a second container would contain a diluent for suspension of the sample to be tested, a third container would contain a positive control and an additional container would contain a negative control. An additional container could contain a blank.

For all prophylactic, therapeutic and diagnostic uses, the antibodies of the invention and other reagents, plus appropriate devices and accessories, may be provided in the form of a kit so as to facilitate ready availability and ease of use.

The present invention also relates to the use of nucleic acid sequences and polypeptides of the present invention to screen potential antiviral agents for antiviral activity against HCV. Such screening methods are known by those of skill in the art. Generally, the antiviral agents are tested at a variety of concentrations, for their effect on preventing viral replication in cell culture systems which support viral replication, and then for an inhibition of infectivity or of viral pathogenicity (and a low level of toxicity) in an animal model system.

In one embodiment, animal cells (especially human cells) transfected with the nucleic acid sequences of the invention are cultured in vitro and the cells are treated with a candidate antiviral agent (a chemical, peptide etc.) by adding the candidate agent to the medium. The treated cells are then exposed, possibly under transfecting or fusing conditions known in the art, to the nucleic acid sequences of the present invention. A sufficient period of time would then be allowed to pass for infection to occur, following which the presence or absence of viral replication would be determined versus untreated control cells by methods known to those of ordinary skill in the art. Such methods include, but are not limited to, the detection of viral antigens in the cell, for example, by immunofluorescence procedures well known in the art; the detection of viral polypeptides by Western blotting using antibodies specific therefor; the detection of newly transcribed viral RNA within the cells by PT-PCR; and the detection of the presence of live, infectious virus particles by injection of cell culture medium or cell lysates into healthy, susceptible animals, with subsequent exhibition of the signs and symptoms of HCV infection. A comparison of results obtained for control cells (treated only with nucleic acid sequence) with those obtained for treated cells (nucleic acid sequence and antiviral agent) would indicate, the degree, if any, of antiviral activity of the candidate antiviral agent. Of course, one of ordinary skill in the art would readily understand that such cells can be treated with the candidate antiviral agent either before or after exposure to the nucleic acid sequence of the present invention so as to determine what stage, or stages, of viral infection and replication said agent is effective against.

In an alternative embodiment, viral enzyme such as NS3 protease, NS2–NS3 protease, NS3 helicase or NS5B RNA polymerase may be produced from a nucleic acid sequence of the invention and used to screen for inhibitors which may act as antiviral agents. The structural and nonstructural regions of the HCV genome, including nucleotide and amino acid locations, have been determined, for example, as depicted in Houghton, M. (1996), FIG. 1; and Major, M. E. et al. (1997), Table 2.

Such above-mentioned protease inhibitors may take the form of chemical compounds or peptides which mimic the known cleavage sites of the protease and may be screened using methods known to those of skill in the art (Houghton, M. (1996) and Major, M. E. et al. (1997)). For example, a substrate may be employed which mimics the protease's natural substrate, but which provides a detectable signal (e.g. by fluorimetric or colorimetric methods) when cleaved. This substrate is then incubated with the protease and the candidate protease inhibitor under conditions of suitable pH, temperature etc. to detect protease activity. The proteolytic activities of the protease in the presence or absence of the candidate inhibitor are then determined.

In yet another embodiment, a candidate antiviral agent (such as a protease inhibitor) may be directly assayed in vivo for antiviral activity by administering the candidate antiviral agent to a chimpanzee transfected with a nucleic acid sequence of the invention or infected with a virus of the invention and then measuring viral replication in vivo via methods such as RT-PCR. Of course, the chimpanzee may be treated with the candidate agent either before or after transfection with the infectious nucleic acid sequence or infected with a virus of the invention so as to determine what stage, or stages, of viral infection and replication the agent is effective against.

The invention also provides that the nucleic acid sequences, viruses and polypeptides of the invention may be supplied in the form of a kit, alone or in the form of a pharmaceutical composition.

All scientific publication and/or patents cited herein are specifically incorporated by reference. The following examples illustrate various aspects of the invention but are in no way intended to limit the scope thereof.

EXAMPLES

Materials and Methods

Source of HCV

An infectious plasma pool of HCV genotype 2a (HC-J6$_{CH}$) prepared from acute phase plasma of a chimpanzee experimentally inoculated with plasma from a Japanese patient infected with strain HC-J6 (Okamoto et al., 1991) was used for cloning. An infectious cDNA clone of HCV strain H77, genotype 1a was also used (pCV-H77C; Yanagi et al., 1997).

Amplification, Cloning and Sequence Analysis

Viral RNA was extracted from 100 µl aliquots of the HC-J6$_{CH}$ plasma pool with the TRIzol system (GIBCO/BRL) (Yanagi et al., 1997). Primers used in cDNA synthesis and PCR amplification were based on the genomic sequence of strain HC-J6 (Okamoto et al., 1991) and from the conserved region (3'X) of the 3' UTR of HCV genotype 2a (Tanaka et al., 1996) (Table 1). The RNA was denatured at 65° C. for 2 min, and cDNA was synthesized at 42° C. for 1 hour with Superscript II reverse transcriptase (GIBCO/BRL) and specific reverse primers in 20 µl reaction volumes. The cDNA mixtures were treated with RNase H and RNase T1 (GIBCO/BRL) at 37° C. for 20 min.

TABLE 1

Oligonucleotides used for amplification and cloning of strain HC-J6$_{CH}$, genotype 2a

| Designation | Sequence (5' → 3')[a] |
|---|---|
| 2427S-H77 | ACTGGACACGGAGGTGGCCGCGTC |
| 2426S-H77 | TTGTTCTTGTCGGGTTAATGGCGC |
| 2645R-H77 | GGGTGTACTACACACATGAGTAAG |
| 2832R-H77 | AAGCGCCCCTAACTGATGATG |
| H2751SII | CGTCATCGATACCTCAGCGGGCATATGCA CTGGACACGGA |
| H2786R | GTCCAGTGCATATGCCCGCTGAGG |
| H2870R | CATGCACCAGCTGATATAGCGCTTGTAATATG |
| H7851S | TCCGTAGAGGAAGCTTGCAGCCTGACGCCC |
| H9140S (M) | CAGAGGAGGCAGGGTGCTATATGTGGCAAGTAC |
| H9173R (M) | GTACTTGCCACATATAGCAGCCCTGCCTCCTCTG |
| H9471R | CGTCTCTAGACAGGAAATGGCTTAAGAGGCCGGAGTGT TACC |
| J6-H2556S | TTATGGATGCTCATCTTGTTGGGCCAGGCCGAAGCA GCTTTGGAGAACCTCGTAATACTCAATGC |
| 356RF-J6H | AGGATTTGTGCTCATGGTGCACGGTCTACGAG |
| 1S-J6F[b] | TTTTTTTTGCGGCCGCTAATACGACTCACTATAGAC CCGCCCCTAATAGG |
| 333S-J6 | CCGTGCACCATGAGCACAAATCCTAAACCTC |
| 753R-J6 | GGATGTACCCCATGAGGTCGGCAAAG |
| 2543S-J6F | GTTTGCGCCTGCTTATGGATGCTCATCTTG |
| 2787R-J6(26) | GCGTCATAAGCATATGCCTGTTGGGG |
| 3329R-J6 | CCCTCAGCACTGGAGTACATCTG |
| 5487-J6F | CGTCATGCATACCCCTAGGGCGGCTCTCATTGAAG AGGG |
| 5518R-J6F | CGTCCCCTCTTCAATGAGAGCCGCTCTAGA |
| 9251S-J6F | GCGGTGAAGACCAAGCTCAAACTCACTC |
| 9305R-J6F | AATCTAGAAGGCGCGCTTCCGGCAATGGAGTGAGT TGAGC |
| 9310R-J6F | CGTCTCTAGAGGATAAATCCAGGAGGCGCGCTTCC GGC |
| 9399S-J6F | TACTTTTTGTAGGGGTAGGCCTTTTCC |

TABLE 1-continued

Oligonucleotides used for amplification and cloning
of strain HC-J6$_{CH}$, genotype 2a

| Designation | Sequence (5' → 3')[a] |
|---|---|
| 9464-J6F | CGTCTCTAGAGTGTAGCTAATGTGTGCCGCTCTA |
| 9470(24)-J6 | CTATGGAGTGTAGCTAATGTGTGC |
| J6- 3' XR | CGTC TCTAGACATGATCTGCAGAGAGACCAGTTACGGCAC TCTCTGFCAGTCATGCGGCTCACGGACCTTTCACAG CTAGCCGTGACTAGGGCTAAGATGGAGCCACC |

[a]HCV-specific sequences are shown in plain text, non HCV-specific sequences are shown in bold face, and cleavage sites used for cDNA cloning are underlined.
[b]The core sequence of the T7 promotor is shown in italics.

The strategy used to amplify and clone the full-length HC-J6$_{CH}$ sequence is shown in FIG. 1. Nucleotide positions correspond to those of the 2a infectious clone (pJ6CF) that is described herein. The 5' end of HC-J6$_{CH}$(nts. 17–297, excluding primer sequences) was amplified from 2 µl of cDNA synthesized with primer a-2 (Yanagi et al., 1996). PCR was performed with AmpliTaq Gold DNA polymerase (Perkin-Elmer) as described previously (Yanagi et al., 1996) using primers 1S-J6F and a-2. After purification, the amplified products were cloned into pGEM-T Easy vector (Promega) using standard procedures and 5 clones (pJ6-5'UTR) were sequenced.

The 3' end of HC-J6$_{CH}$ was amplified in 3 overlapping pieces. RT-PCR of a short fragment of NS5B (nts. 9279–9439) was performed with primers 9251S-J6F and 9464R-J6F as described above. The PCR products were cloned into pGEM-T Easy vector and sequence analysis was performed from 5 pJ6-3'F clones. A second region spanning from NS5B to the conserved region of the 3' UTR (nts. 9376–9629) was amplified in RT-nested PCR (external primers H9261F and H3'X58R, internal primers H9282F and H3'X45R) (Yanagi et al., 1997). The amplified products were cloned into pGEM-9zf(−) by using HindIII and XbaI sites and 14 pJ6-3'VR clones were sequenced. The third fragment, which included the 3' terminal sequence was amplified with primers 9399S-J6F and J6-3'XR from one of the pJ6-3'VR clones, and cloned into one of the pJ6-3'F clones by using StuI and XbaI sites (pJ6-3'X).

The ORF of HCV HC-J6$_{CH}$ was amplified by long RT-PCR in 3 overlapping pieces. The amplification was performed on 2 µl of the cDNA mixtures with the Advantage cDNA polymerase mix (Clontech) (Yanagi et al., 1997). The J6S fragment (nts. 86–2761) was amplified with primers a-1 (Yanagi et al., 1996) and J6-2787R from cDNA synthesized with primer J6-3329R. A single PCR round was performed in a Robocycler thermal cycler (Stratagene), and consisted of denaturation at 99° C. for 35 sec, annealing at 67° C. for 30 sec and elongation at 68° C. for 4 min 30 sec during the first 5 cycles, 5 min during the next 10 cycles, 5 min 30 sec during the following 10 cycles and 6 min during the last 10 cycles. The J6B fragment (nts. 2573–5488) was amplified with primers 2543S-J6F and 5518R-J6F from cDNA synthesized with primer 5518R-J6F. Finally, the J6A fragment (nts. 5515–9282) was amplified with primers 5487S-J6F and 9310R-J6F from cDNA synthesized with primer 9470R(24)-J6F. PCR amplifications of fragments J6B and J6A consisted of denaturation at 99° C. for 35 sec, annealing at 67° C. for 30 sec and elongation at 68° C. for 6 min during the first 5 cycles, 7 min during the next 10 cycles, 8 min during the following 10 cycles and 9 min during the last 10 cycles.

After purification of the long PCR products with QIAquick PCR purification kit (QIAGEN), A-tailing reactions were performed with AmpliTaq DNA polymerase (Perkin Elmer) at 72° C. for 1 hour. The gel-purified A-tailed PCR products were cloned into pCR2.1 vector (Invitrogen) or pGEM-T Easy vector (Promega). DH5-alpha competent cells (GIBCO BRL) were transformed and selected on LB agar plates containing 100 µg/ml ampicillin (SIGMA) and amplified in LB liquid cultures at 30° C. for 18–20 hrs (Yanagi et al., 1997). Midiprep was performed using Wizard Plus Midipreps DNA Purification System (Promega). Multiple clones of the J6S, J6A and the J6B fragments were sequenced.

The consensus sequence of strain HC-J6$_{CH}$(nts. 17–9629) was determined by direct sequencing of PCR products (nts. 297–3004 and nts. 4893–5762) and by sequence analysis of the TA clones (nts. 17–5488 and nts. 5515–9629)(FIG. 1). Both strands of DNA were sequenced in all cases. Analyses of genomic sequences, including multiple sequence alignments and tree analyses, were performed with GeneWorks (Oxford Molecular Group) (Bukh et al., 1995).

Construction of Chimeric cDNA Clones of Genotypes 1a & 2a

Figure 4:
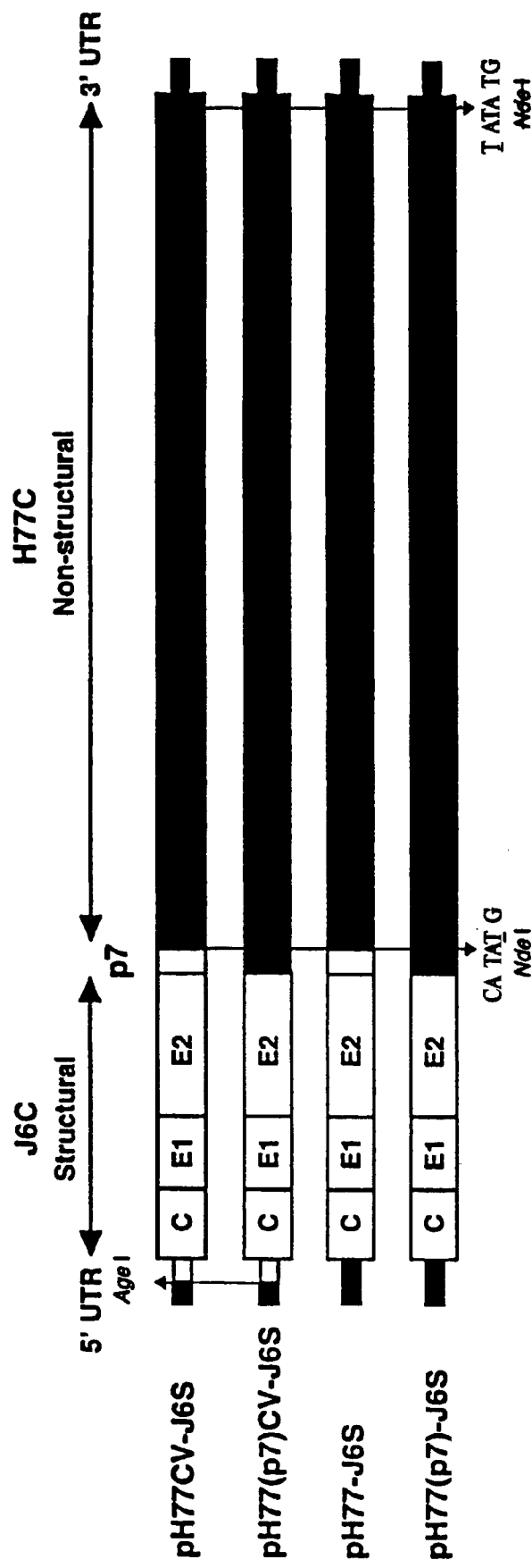
FIG. 4 shows the construction of four intertypic chimeric cDNA clones. White boxes are sequences derived from genotype 2a clone pJ6CF, and black boxes are sequences derived from genotype 1a clone pCV-H77C (Yanagi et al., 1997). An NdeI site (mutation at position 9158 of pCV-H77C) was eliminated and an artificial NdeI site (mutation at position 2765 of pCV-H77C) was created by site-directed mutagenesis; silent mutations are underlined.

Four full-length intertypic chimeric cDNA clones were constructed (FIGS. 4, 5A, 5B). In each clone the C, E1 and E2 genes encoded the consensus amino acid sequence of HC-J6$_{CH}$. The p7 protein was encoded either by the HC-J6$_{CH}$ or pCV-H77C consensus sequence, and the NS proteins were all encoded by pCV-H77C genes. To engineer these cDNA clones, an NdeI site from pCV-H77C was first eliminated by a silent substitution (C to T) at position 9158. In brief, two fragments were amplified from pCV-H77C with primers H7851S and H9173R(M) and with primers H9140S(M) and H9417R (Table 3), gel-purified and used for fusion PCR with primers H7851S and H9417R. The fusion PCR products were cloned into pCV-H77C by using HindIII and AflII sites. A new artificial NdeI site was introduced by a silent substitution (C to T) at position 2765. PCR products, which were amplified from pCV-H77C with primer H2751SII containing artificial ClaI and NdeI sites and primer H2870R, were cloned into the modified pCV-H77C by using ClaI and Eco47III sites. The final construct (pH77CV) was used as a cassette vector to construct the intertypic chimeric HCV cDNA clones.

The four chimeric cDNA clones were constructed as follows. pH77CV-J6S (nucleotide sequence shown in SEQ ID No:3 and amino acid sequence shown in SEQ ID No:4): The AgeI/BsmI fragment of clone J6S2 and the BsmI/NdeI fragment of clone J6S1, were cloned into pH77CV by using AgeI and NdeI sites; pH77 (p7)CV-J6S (nucleotide sequence shown in SEQ ID No:5 and amino acid sequence shown in SEQ ID No:6): A fragment of pH77CV-J6S was replaced with a fragment amplified from pCV-H77C with primers J6-H2556S and H2786R by using BsaBI and NdeI sites; J6S (nucleotide sequence shown in SEQ ID No:7 and amino acid sequence shown in SEQ ID No:8): A fragment amplified from pH77 pCV-H77C with primers a-1 and 356RF-J6H77 and another fragment amplified from pH77CV-J6S with primers 333S-J6 and 753R-J6 were gel-purified and a fusion-PCR was performed with primers a-1 and 753R-J6. The AgeI/ClaI fragment of the subcloned fusion PCR products and the ClaI/NdeI fragment of pH77CV-J6S were cloned into pH77CV-J6S by using AgeI and NdeI sites; pH77(p7)-J6S (nucleotide sequence shown in SEQ ID No:9 and amino acid sequence shown in SEQ ID No:10): The AgeI/ClaI fragment of J6S and the ClaI/NdeI fragment of (p7)CV-J6S were cloned into pH77(p7)CV-J6S by using AgeI and NdeI sites.

Each intertypic chimeric cDNA clone was retransformed to select a single clone, and large-scale preparation of plasmid DNA was performed with a QIAGEN plasmid Maxi kit as described previously (Yanagi et al., 1997). Each of the four cDNA clones was completely sequenced before inoculation. Each clone was genetically stable since the digestion pattern was as expected following retransformation and the complete sequence was the expected one.

Construction of Full-Length cDNA Clone HC-J6$_{CH}$

An overview of the full-length HC-J6$_{CH}$ clone is presented in FIG. 1. In the final construct pJ6CF, which encodes the consensus polyprotein of HC-J6$_{CH}$, an XbaI site was eliminated by a silent substitution (A to G) at position 5494. Digested fragments containing the consensus sequence were purified from the appropriate subclones and ligated using the sites indicated. The full-length cDNA clone (pJ6CF) was retransformed to select a single clone, and large-scale preparation of plasmid DNA followed by the complete sequence analysis was performed. Clone pJ6CF was genetically stable.

Intrahepatic Transfection of Chimpanzee with Transcribed RNA

In duplicate 100 µl reactions, RNA was transcribed in vitro with T7 RNA polymerase (Promega) from 10 µg of template plasmid linearized with XbaI (Promega) as described previously (Yanagi et al., 1997). The integrity of the RNA was checked by electrophoresis through agarose gel stained with ethidium bromide (Yanagi et al., 1997). Each transcription mixture was diluted with 400 µl of ice-cold phosphate-buffered saline without calcium or magnesium and then immediately frozen on dry ice and stored at −80° C. Within 24 hours, both transcription mixtures were injected into the same chimpanzee by percutaneous intrahepatic injection guided by ultrasound (Yanagi et al., 1998, 1999). If the chimpanzee did not become infected, the same transfection was repeated once. After two negative results, the next clone was inoculated into the same chimpanzee following the same protocol. Injections were performed at weeks 0 and 2 with pH77CV-J6S, at weeks 5 and 8 with pH77(p7)CV-J6S, at weeks 14 and 16 with pH77-J6S, at weeks 19 and 23 with pH77(p7)-J6S, at week 28 with pJ6CF, and finally at week 34 with pCV-H77C. The chimpanzee was maintained under conditions that met or exceeded all requirements for its use in an approved facility.

Serum samples were collected weekly from the chimpanzee and monitored for liver enzyme levels by standard procedures, anti-HCV antibodies by the second-generation ELISA (Abbott) and HCV RNA by a sensitive RT-nested PCR assay with AmpliTaq Gold DNA polymerase using primers from the 5' UTR (Yanagi et al., 1996). Samples were scored as negative for HCV RNA if two independent tests on 100 µl of serum were negative. The genome equivalent (GE) titer of HCV in positive samples was determined by RT-nested PCR on 10-fold serial dilutions of the extracted RNA (Bukh et al., 1998). The consensus sequence of the complete ORF from the chimpanzee infected with RNA transcripts of pJ6CF was determined by direct sequencing of overlapping PCR products obtained by long RT-nested PCR as previously described (Yanagi et al., 1997) with HC-J6 specific primers. After the intrahepatic transfection with RNA transcripts of pCV-H77C, we performed H77(genotype 1a)-specific RT-nested PCR with primers 2427S-H77 and 2832R-H77 for the 1st round and with primers 2462S-H77 and 2645R-H77 for the 2nd round (Table 3). The sensitivity of this assay was equivalent to that of the assay using 5' UTR primers when testing serum containing only H77, genotype 1a. The genome titer of genotype 1a was determined by using this specific RT-nested PCR on 10-fold serial dilutions of the extracted RNA.

Example 1

Sequence Analysis of HCV Strain HC-J6$_{CH}$

As minor deviations from the consensus amino acid sequence were found previously to render full-length HCV cDNA clones noninfectious (Yanagi et al., 1997, 1998), the consensus sequence of the cloning source of genotype 2a (strain HC-J6$_{CH}$) was determined prior to constructing any full-length clones. In brief, a plasma pool containing strain HC-J6$_{CH}$ was prepared from acute phase plasmapheresis units collected from a chimpanzee experimentally infected with HC-J6 (Okamoto et al., 1991). The HCV genome titer of this pool was $10^{5.4}$ genome equivalents (GE)/ml (Quantiplex HCV RNA bDNA 2.0, Chiron) and the infectivity titer was $10^4$ chimpanzee infectious doses/ml.

The consensus sequence of the 5' UTR of HC-J6$_{CH}$ (nts. 17–340) was deduced from 5 clones containing nts. 17–297 and 8 clones containing nts. 86–340. The 5' UTR of the various clones was highly conserved, but the consensus sequence of HC-J6$_{CH}$ differed by 2 nucleotides from that published previously for HC-J6 (Okamoto et al., 1991: C to T at position 36 and T to C at position 222).

The consensus sequence of 14 clones of the 3' UTR of HC-J6$_{CH}$ indicated that the 39 nucleotide long variable region was highly conserved in this strain and was identical to that previously published for HC-J6 (Okamoto et al., 1991). The polypyrimidine tract varied greatly in length (84–164 nucleotides), and contained some conserved A residues. In the conserved region, the proximal 16 nucleotides were identical to those previously published for isolates of different HCV genotypes (Kolykhalov et al., 1996; Tanaka et al., 1996; Yamada et al., 1996). The remaining 82 nucleotides of the conserved region were determined for other genotype 2a strains (Tanaka et al., 1996) but not for HC-J6 or HC-J6$_{CH}$.

Figure 2:
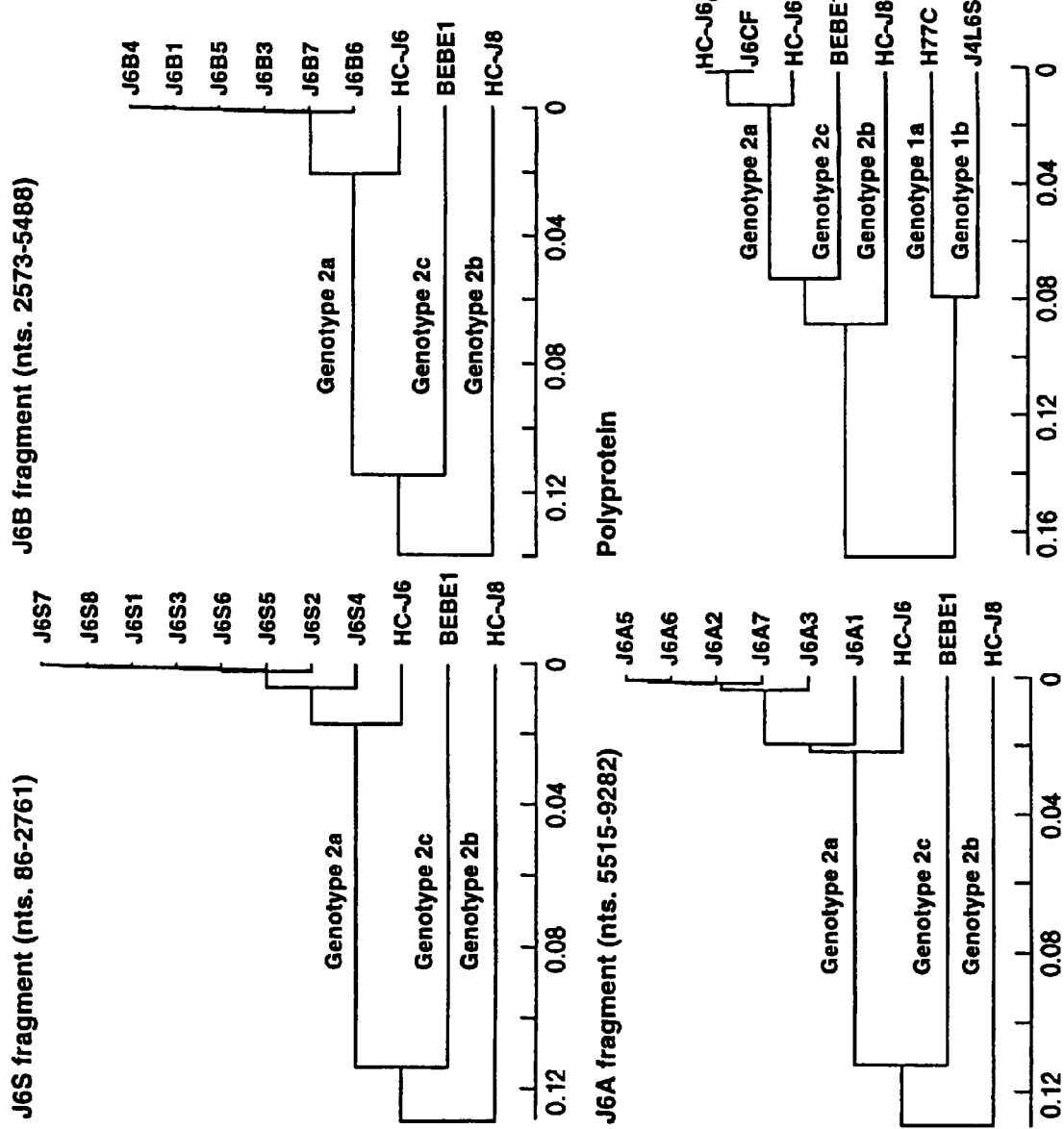
FIG. 2 shows tree analysis of clones amplified from an infectious acute phase plasma pool generated in a chimpanzee inoculated with human plasma containing strain HC-J6 (Okamoto et al., 1991) as well as a tree of the predicted polyprotein sequence of HC-J6$_{CH}$ and the infectious HC-J6$_{CH}$cDNA clone (pJ6CF). The nucleotide positions with deletions or insertions were stripped in the analysis of the clones. Multiple sequence alignments and tree analyses were performed with GeneWorks (Oxford Molecular Group) (Bukh et al., 1995). Genotype designations are indicated. Other sequences included in the analysis are HC-J8 (Okamoto et al., 1992), genotype 1a infectious clone BEBE1 (Nakao et al., 1996), H77C (Yanagi et al., 1997); genotype 1b infectious clone J4L6S (Yanagi et al., 1998). The scale in each tree indicates the calculated genetic distance.

The ORF of HC-J6$_{CH}$ was amplified in 3 fragments by RT-PCR (FIG. 1). Eight clones of the J6S fragment (nts. 86–2761), 6 clones of the J6B fragment (nts. 2573–5488) and 6 clones of the J6A fragment (nts. 5515–9298) were sequenced. PCR fragments containing nts. 5489–5514 were sequenced directly. A quasispecies was found at 243 nucleotide (2.7%) and 69 amino acid (2.3%) positions, scattered throughout the 9099 nts (3033 aa) of the ORF. However, the majority, 231 nucleotide substitutions, were detected only once and 71.6% of these represented silent mutations. The 12 remaining nucleotide substitutions were each restricted to 2 clones and only 4 of these resulted in amino acid changes. The nucleotide difference among the J6S clones ranged from 0.1–1.3%, among the J6B clones it ranged from 0.1–0.3%, and it ranged from 0.2–4.0% among the J6A clones (FIG. 2). Three of 8 J6S clones, 4 of 6 J6B clones, and all 6 J6A clones had defective polyproteins due to nucleotide deletions, insertions or substitutions.

Figure 3:
FIG. 3 shows the alignment of the hypervariable region 1 sequences from 8 J6S clones of strain HC-J6$_{CH}$(J6S1-SEQ ID NO: 39: J6S2-SEQ ID NO: 40: J6S3-SEQ ID NO: 41; J6S5-SEQ ID NO: 42; J6S6-SEQ ID NO: 43; J6S7-SEQ ID NO: 44; J6S8-SEQ ID NO: 45; J6S4-SEQ ID NO: 46). HC-J6$_{CH}$(SEQ ID NO: 47) represents the consensus amino acid sequence of the infectious plasma pool from an experimentally infected chimpanzee. HC-J6 (SEQ ID NO: 48) is the published amino acid sequence of the original inoculum (Okamoto et al., 1991).

The sequences of clones of strain HC-J6$_{CH}$ were relatively homogeneous. This was highlighted by the high degree of conservation among clones of the HVR1 (FIG. 3), a region frequently used to study the quasispecies of HCV (Bukh et al., 1995). An exception was the sequence of clone J6A1, which differed by about 4% from the other clones of this region (FIG. 2). Importantly, the consensus sequence of strain HC-J6$_{CH}$(nts. 17–9629) could be determined with no ambiguity at the nucleotide or deduced amino acid level. The difference between the consensus ORF sequence of HC-J6$_{CH}$ from the experimentally infected chimpanzee and that of HC-J6 of the inoculum (Okamoto et al., 1991) was 4.1% and 2.2% at the nucleotide and deduced amino acid levels, respectively (FIG. 2, Table 2). Moreover, we found that 12 (44.4%) of the 27 amino acids constituting HVR1 differed between HC-J6$_{CH}$ and HC-J6 (FIG. 3). Such diversities are greater than the <2% generally considered to comprise a quasispecies. In fact, these differences are equivalent to those found between the two prototype strains of HCV genotype 1a [strains HCV-1 (Choo et al., 1991) and H77 (Yanagi et al., 1997)]. These results indicated that HC-J6$_{CH}$, which represented the major species in the experimentally infected chimpanzee, was a minor species in the original inoculum.

TABLE 2

Percent difference of nucleotide and predicted amino acid sequences between strain HC-J6 (Okamoto et al., 1991) and strain HC-J6$_{CH}$ from acute phase plasma pool of a chimpanzee inoculated with HC-J6

| Genome Region | nt. position[a] | % nt. difference | % a.a. difference |
|---|---|---|---|
| ORF | 341–9439 | 4.1 (373/9099)[b] | 2.2 (66/3033)[b] |
| 5' UTR | 17–340 | 0.6 (2/324) | |
| Core | 341–913 | 0.5 (3/573) | 0 (0/191) |
| E1 | 914–1489 | 4.3 (25/576) | 2.1 (4/192) |
| HVR1 | 1490–1570 | 24.7 (20/81) | 44.4 (12/27) |
| E2-$_{HVR1}$ | 1571–2590 | 3.9 (40/1020) | 3.2 (11/340) |
| p7 | 2591–2779 | 3.7 (7/189) | 3.2 (2/63) |
| NS2 | 2780–3430 | 4.0 (26/651) | 2.8 (6/217) |
| NS3 | 3431–5323 | 4.0 (76/1893) | 0.8 (5/631) |
| NS4A | 5324–5485 | 4.3 (7/162) | 1.9 (1/54) |
| NS4B | 5486–6268 | 3.7 (29/783) | 0.4 (1/261) |
| NS5A | 6269–7666 | 5.4 (75/1398) | 3.4 (16/466) |
| NS5B | 7667–9439 | 3.7 (65/1773) | 1.4 (8/591) |
| 3' UTR | 9440–9481 | 0 (0/42) | |

[a]The nucleotide positions correspond to those of the infectious full-length genotype 2a clone (pJ6CF).
[b]The numbers in parenthesis indicate the nucleotide or amino acid differences for each region.

Example 2

Chimeric Molecular Clones

As chimeric flaviviruses with substituted structural genes have been useful in defining the biological function of viral sequences or proteins, in analyzing immune responses and in generating attenuated vaccine candidates (Bray and Lai, 1991; Chambers et al., 1999; Pletnev et al., 1992, 1993, 1998). The consensus sequence of the 2a structural genes and surrounding region was substituted for that of the infectious 1a cDNA clone. In the genotype 1a backbone, two silent mutations were introduced for cloning purposes [at positions 2765 (p7) and 9158 (NS5B) of pCV-H77C] (FIG. 4). The complete sequence of each chimera was verified. Infectivity of RNA transcripts from four different intertypic chimeric clones (FIGS. 4, 5A, 5B) was evaluated by consecutive intrahepatic transfections of a chimpanzee. Clones were considered not to be viable if viral RNA was not detected in the serum within two weeks of the repeat transfection. All chimeric clones contained the C, E1 and E2 genes of genotype 2a. The two chimeric clones tested initially differed from each other in that one had the p7 gene of 2a (pH77CV-J6S) and the other [pH77(p7)CV-J6S] the p7 gene of 1a. They differed from the two other clones in that the 186 nucleotides of the 5' UTR just upstream of the initiation codon were from the 2a genotype. Since neither clone containing the chimeric 5' UTR was infectious, the chimeric 5' UTR was replaced with the consensus genotype 1a 5' UTR to generate the two p7 varieties [pH77-J6S and pH77(p7)-J6S]. After consecutive transfection of the four clones, no HCV RNA, anti-HCV or ALT elevation was detected in the chimpanzee during 28 weeks of follow-up, suggesting that RNA transcripts from these intertypic chimeric clones were not viable in vivo.

This finding that the intertypic clones between genotypes 1a and 2a were not viable was surprising since flavivirus chimeras containing the structural region of dengue virus type 1 or 2 or of tick-borne encephalitis virus and the nonstructural region of an infectious dengue type 4 virus were viable (Bray and Lai, 1991; Pletnev et al., 1992, 1993). While considerable sequence variation exists between the infectious genotype 1a and 2a clones of HCV (Table 3), these viruses exhibit a higher degree of genetic heterogeneity than do the major genotypes of HCV. For other flaviviruses, however, it was possible to obtain infectious chimeric clones only if the capsid region was derived from the backbone cDNA clone (Chambers et al., 1999; Pletnev and Men, 1998).

TABLE 3

Percent difference of the amino acid sequences between the infectious clone of genotype 1a (pCV-H77C; Yanagi et al., 1997) and the infectious clone of genotype 2a (pJ6CF) of hepatitis C virus

| Genome Region[a] | % difference |
|---|---|
| Polyprotein | 27.9 (839/3007)[b] |
| Core | 8.9 (17/191) |
| E1 | 37.0 (71/192) |
| HVR1 | 59.3 (16/27) |
| E2-$_{HVR1}$ | 27.1 (91/336) |
| p7 | 38.1 (24/63) |
| NS2 | 41.9 (91/217) |
| NS3 | 19.2 (121/631) |
| NS4A | 33.3 (18/54) |
| NS4B | 26.8 (70/261) |
| NS5A | 38.5 (171/444) |
| NS5B | 25.2 (149/591) |

[a]Genome regions defined as in Table 1.
[b]The numbers in parenthesis indicate the amino acid differences for each region.
Positions with deletions or insertions in E2 (4 aa positions) and NS5A (26 aa positions) were not considered.

Trivial explanations may account for the lack of viability of these intertypic chimeras. First, the two silent mutations introduced in the genotype 1a backbone (one in p7 and one in NS5B) for cloning purposes could potentially eliminate infectivity. This is, however, very unlikely since mutations at these positions exist among field isolates of HCV including strain HC-J6$_{CH}$(Bukh et al., 1998). Also, it is noteworthy that the three previously published infectious clones of strain H77 had numerous silent nucleotide differences (Hong et al., 1999; Kolykhalov et al., 1997; Yanagi et al., 1997). Second, signal peptidases might not cleave the chimeric E2/p7 or p7/NS2 junction. This seems unlikely, however, since eukaryotic signal peptidases typically recognize the amino acid sequences upstream of the cleavage site [the (−3, −1) rule] (Nielsen et al., 1997) and the amino acids at these two sites are conserved between genotypes 1a and 2a (FIG. 5B). Finally, the E2/p7 and/or p7/NS2 gene junctions could differ between genotypes 1a and 2a. The junctions determined for genotypes 1a and 1b were used (Lin et al., 1994; Mizushima et al., 1994; Selby et al., 1994) because those for genotype 2a have not been identified. In the latter two cases, further analyses of genotype 2a should eventually provide sufficient data to overcome such potential problems and it would most likely be possible to construct a viable chimera.

More complicated explanations for the lack of viability of the chimeras might be required if critical genotype-specific interactions occur as regards the structural proteins, the nonstructural proteins and the genomic RNA. For instance, one cannot rule out that the chimeras were not viable because the IRES function was compromised. In in vitro studies the IRES activity depended on RNA sequences not only in the 5' UTR but also extending 3' of the translation initiation site (Hahm et al., 1998; Lemon and Honda, 1997; Reynolds et al., 1995). Although the 3' border of the HCV IRES is still controversial it is believed to involve at most the first 39 nts of the core gene (Lemon and Honda, 1997). The 5' UTR of the intertypic chimeras was either a chimera of genotype 1a and 2a sequences or the entire 5' UTR was derived from the 1a clone (FIGS. 4, 5A). Importantly, the 5' end of core is conserved among genotypes 1a and 2a (FIG. 5A). Thus, the predicted IRES-like secondary structure is maintained in these chimeras, suggesting that the IRES activity most likely was maintained.

Possible interactions between the structural proteins and the nonstructural proteins and/or the genomic RNA, which involve RNA packaging, replication or translation are conceivable. In poliovirus, which is another positive-sense RNA virus, functional coupling of RNA packaging to RNA replication and of RNA replication to translation have been suggested (Novak and Kirkegaard, 1994; Nugent et al., 1999). Similar to other viruses of the Flaviviridae family, a membrane-associated replicase complex is thought to initiate replication at the 3' end of HCV and to synthesize a complementary negative-strand RNA (Rice, 1996). The putative cis-acting elements at the 5' and 3' termini which are believed to be important for viral genome replication (Rice 1996; Frolov et al., 1998) should be maintained in the intertypic HCV chimeras at least in the two constructs with the authentic 1a 5'UTR. However, it is conceivable that the viral packaging system was interrupted (Frolov et al., 1998). Studies using a Kunjin flavivirus replicon system and providing the structural proteins in trans suggested that the essential encapsidation signals did not reside in the structural region of the genome (Khromykh et al., 1997, 1998). The location of the packaging signals of HCV is not known. However, if the structural proteins encapsidate viral RNA via genotype-specific sequences outside of the structural region, the chimeras would be unable to package the RNA and it might be extremely difficult to construct viable chimeras between highly divergent strains.

Example 3

A Consensus Molecular Clone of Genotype 2a is Infectious In Vivo

In order to prove that the genotype 2a portion used in the 4 intertypic chimeric cDNA clones indeed represented the infectious sequence, a consensus full-length cDNA clone of HC-J6$_{CH}$(pJ6CF) was constructed. The core sequence of the T7 promoter, a 5' guanosine residue and the full-length sequence of HC-J6$_{CH}$(9711 nts) were cloned into pGEM-9Zf vector using NotI/XbaI sites. Within the HCV sequence there were no deduced amino acid differences and only 4 nucleotide differences (at nucleotide positions 1822, 5494, 9247 and 9289) from the consensus sequence of HC-J6$_{CH}$ as determined in the present study. The silent mutation at position 1822 was within the structural region and so was also present in the four intertypic chimeras. The 5' terminal 16 nts and the 3' terminal 82 nts were deduced from previously published HCV genotype 2a sequences (Okamoto et al., 1991, Tanaka et al., 1996). The full-length cDNA clone of genotype 2a contained a 5' UTR of 340 nts, an ORF of 9099 nts encoding 3033 amino acids and a 3' UTR consisting of a variable region of 39 nts followed by a 132 nucleotide-long polypyrimidine tract interrupted with 3 A residues and the 3' terminal conserved region of 98 nts.

RNA transcripts from pJ6CF were injected into the same chimpanzee used for injection of the 4 intertypic chimeras. The chimpanzee became infected at the first attempt with an HCV titer of $10^2$ GE/ml at week 1 post inoculation (p.i.), and $10^3$–$10^4$ GE/ml during weeks 2 to 6 p.i. The consensus sequence of PCR products of the complete ORF, amplified from serum obtained during week 5 p.i., was identical to the sequence of pJ6CF and there was no evidence of a quasispecies. Since RNA transcripts of this infectious genotype 2a clone were infectious in vivo, and it shared an exact sequence with the non-infectious intertypic chimeric clones, their failure to replicate must have been the result of incompatibilities between the genotype 1a and 2a sequences.

To confirm that the chimpanzee used was susceptible also to infection by genotype 1a, which comprised most of the intertypic chimeras, the chimpanzee was subsequently inoculated with RNA transcripts from the infectious genotype 1a clone (pCV-H77C). Serum samples were tested in an H77-specific RT-PCR assay to identify super-infection with genotype 1a. At week 1 p.i. the total HCV genome titer was $10^4$ GE/ml and the H77-specific (1a) genome titer was $10^2$ GE/ml. The H77-specific genome titer increased to $10^3$ GE/ml at week 2 p.i., and reached $10^4$ GE/ml during weeks 3–6 p.i. The consensus sequence of PCR products amplified with H77-specific primers at weeks 1–6 p.i. were found to be identical to that of pCV-H77C. However, the direct sequences of PCR products amplified with the 5' UTR primers at weeks 1–2 after inoculation of pCV-H77C were identical to that of pJ6CF indicating that the 2a genotype was still present and represented the majority species. These experiments confirmed that the inability of the intertypic 1a, 2a cDNA clones to infect the chimpanzee was not the result of protective immune responses in the chimpanzee but represented deficiencies intrinsic to the chimeras.

Discussion

The published infectious cDNA clones of HCV represent the two most important subtypes of genotype 1 (Hong et al., 1999; Kolykhalov et al., 1997; Yanagi et al., 1997, 1998). However, 5 more major genotypes of HCV are recognized. In the above Examples, the infectivity of a cDNA clone of a second major HCV genotype was demonstrated. As in previous studies, the infectivity of RNA transcripts was demonstrated in vivo by intrahepatic transfection of a chimpanzee. This new infectious clone (pJ6CF) encodes the consensus polyprotein of HCV strain HC-J6$_{CH}$, genotype 2a. Its encoded polyprotein differs from those of the infectious clones of genotypes 1a and 1b by approximately 30% (Table 2). Genotype 2 strains, in particular subtypes 2a and 2b, have a worldwide distribution and important differences between genotypes 1 and 2 with respect to pathogenesis and treatment were indicated in previous studies. The availability of an infectious clone representing a second major genotype of HCV should permit new ways of studying the molecular biology and immunopathology of this important and genetically quite different human pathogen.

The 5' and 3' UTRs of HCV are believed to be critical for viral replication, translation and viral packaging (Rice, 1996). The 5' 203 terminal nucleotides and the 3' 101 terminal nucleotides of the published infectious clones of genotypes 1a and 1b were identical. However, the sequences of UTRs of the genotype 2a clone differ from those of the genotype 1 clones. Overall, the 5' UTR of the genotype 2a clone has 17 nt differences and a single nucleotide deletion compared with the infectious clones of genotype 1a (FIG. 5A). Five of these differences and the deletion are within the first 30 nucleotides, whereas the remainder are found within the predicted IRES structure. Differences also exist between the 3' UTR of the genotype 2a clone and the clones of genotype 1a (FIG. 5B). The sequences of the variable region are very different. Recent study has shown this region is not critical for infectivity in vivo (Yanagi et al., 1999). Within the regions which are critical for infectivity in vivo (Yanagi et al., 1999), the 132 nucleotide-long polypyrimidine tract of the genotype 2a clone has 3 unique A residues interspersed and the 3' terminal conserved region of 98 nts has 4 nt differences within the 3' terminal stable stem-loop structure (FIG. 5B) (Kolykhalov et al., 1996; Tanaka et al., 1996). Since the 2a clone was infectious these sequence differences are apparently real and are compatible with infectivity. Further studies are required to determine whether these represent critical genotype-specific sequences.

REFERENCES

1. Alter, M. J. (1997). Hepatology 26, 62S–65S.
2. Blight, K. J. and Rice, C. M. (1997). J. Virol. 71, 7345–7352.
3. Brechot, C. (1997). Hepatology 25, 772–774.
4. Bray, M. and Lai, C.-J. (1991). Construction of intertypic chimeric dengue viruses by substitution of structural protein genes. *Proc. Natl. Acad. Sci. USA* 88, 10342–10346.
5. Bukh, J., Apgar, C. L., Engle, R., Govindarajan, S., Hegerich, P. A., Tellier, R., Wong, D. C., Elkins, R. & Kew, M. C. (1998). Experimental infection of chimpanzees with hepatitis C virus of genotype 5a: genetic analysis of the virus and generation of a standardized challenge pool. *J. Infect. Dis.* 178, 1193–1197.
6. Bukh, J., Emerson, S. U. and Purcell, R. H. (1997). Genetic heterogeneity of hepatitis C virus and related viruses. In "Viral Hepatitis and Liver Disease, Proceedings of IX Triennial International Symposium on Viral Hepatitis and Liver Disease, Rome, Italy, 1996" (M. Rizzetto, R. H. Purcell, J. L. Gerin and G. Verme, Eds.), pp. 167–175. Edizioni Minerva Medica, Turin.
7. Bukh, J., Miller, R. H. and Purcell, R. H. (1995). Genetic heterogeneity of hepatitis C virus: quasispecies and genotypes. *Semin. Liver Dis.* 15, 41–63.
8. Bukh, J., Purcell, R. H. and Miller, R. H. (1993). At least 12 genotypes of hepatitis C virus predicted by sequence analysis of the putative E1 gene of isolates collected worldwide. *Proc. Natl. Acad. Sci. USA* 90, 8234–8238.
9. Choo, Q.-L., Richman, K. H., Han, J. H., Berger, K., Lee, C., Dong, C., Gallegos, C., Coit, D., Medina-Selby, A., Barr, P. J., Weiner, A. J., Bradley, D. W., Kuo, G. and Houghton M. (1991). Genetic organization and diversity of the hepatitis C virus. *Proc. Natl. Acad. Sci. USA* 88, 2451–2455.
10. Chambers T. J., Nestorowicz A., Mason P. W. and Rice C. M. (1999). Yellow Fever/Japanese Encephalitis Chimeric Viruses: Construction and Biological Properties. *J. Virol.* 73: 3095–3101.
11. Dash, S., et al. (1997). Am. J. Pathol. 151, 363–373.
12. Davis, G. L., Esteban-Mur, R., Rustgi, V., Hoefs, J., Gordon, S. C., Trepo, C., Shiffman, M. L., Zeuzem, S., Craxi, A., Ling, M.-H. and Albrecht, J., for the international hepatitis interventional therapy group. (1998). Interferon alfa-2b alone or in combination with ribavirin for the treatment of relapse of chronic hepatitis C. *N. Engl. J. Med.* 339, 1493–1499.
13. Fausto, N. (1997). Am. J. Pathol. 151, 361.
14. Forns, X., Bukh, J., Purcell, R. H., Emerson, S. U. (1997). How *Escherichia coli* can bias the results of molecular cloning: preferential selection of defective genomes of hepatitis C virus during the cloning procedure. *Proc. Natl. Acad. Sci. USA* 94, 13909–13914.
15. Forns, X. and Bukh, J. (1998). Methods for determining the hepatitis C virus genotype. *Viral Hepatitis Reviews* 4, 1–19.
16. Fried, M. W. and Hoofnagle, J. H. (1995). Semin. Liver Dis. 15, 82–91.
17. Frolov, I., McBride, M. S. and Rice, C. M. (1998). Cis-acting RNA elements required for replication of bovine viral diarrhea virus-hepatits C virus 5' nontranslated region chimeras. *RNA* 4, 1418–1435.
18. Hahm, B., Kim, Y. K., Kim, J. H., Kim, T. Y. and Jang, S. K. (1998). Heterogeneous nuclear ribonucleoprotein L interacts with the 3' border of the internal ribosomal entry site of hepatits C virus. *J. Virol.* 72, 8782–8788.
19. Hijikata, M., Kato, N., Ootsuyama, Y., Nakagawa, M., Ohkoshi, S. and Shimotohno, K. (1991). Hypervariable regions in the putative glycoprotein of hepatitis C virus. *Biochem. Biophys. Res. Commun.* 175, 220–228.
20. Honda, M., et al. (1996). RNA 2, 955–968.
21. Hong, Z., Beaudet-Miller, M., Lanford, R. E., Guerra, B., Wright-Minogue, J., Skelton, A., Baroudy, B. M., Reyes, G. R. and Lau, J. Y. N. (1999). Generation of transmissible hepatitis C virions from a molecular clone in chimpanzees. *Virology* 256, 36–44.
22. Hoofnagle, J. H. (1997). Hepatitis C: the clinical spectrum of disease. *Hepatology* 26, 15S–20S.
23. Houghton, M. (1996). Hepatitis C viruses. In "Fields Virology" (B. N. Fields, D. M. Knipe, P. M. Howley, et al., Eds.), Third ed., pp. 1035–1058. Lippincott-Raven Publishers, Philadelphia.
24. Khromykh, A. A. and Westaway, E. G. (1997). Subgenomic replicons of the flavivirus Kunjin: construction and applications. *J. Virol.* 71, 1497–1505.
25. Ito, T. and Lai, M. M. C. (1997). J. Virol. 71, 8698–8706.
26. Khromykh, A. A., Varnavski, A. N. and Westaway, E. G. (1998). Encapsidation of the flavivirus Kunjin replicon RNA by using a complementation system providing Kunjin virus structural proteins in *trans. J. Virol.* 72, 5967–5977.
27. Kolykhalov, A. A., Feinstone, S. M. and Rice, C. M. (1996). Identification of a highly conserved sequence element at the 3' terminus of hepatitis C virus genome RNA. *J. Virol.* 70, 3363–3371.
28. Kolykhalov, A. A., Agapov, E. V., Blight, K. J., Mihalik, K., Feinstone, S. M. and Rice, C. M. (1997). Transmission of hepatitis C by intrahepatic inoculation with transcribed RNA. *Science* 277, 570–574.
29. Lemon, S. M. and Honda, M. (1997). Internal ribosome entry sites within the RNA genomes of hepatits C virus and other flaviviruses. *Semin. Virol.* 8, 274–288.

30. Lin, C., Lindenbach, B. D., Pragai, B. M., McCourt, D. W. and Rice, C. M. (1994). Processing in the hepatitis C virus E2-NS2 region: identification of p7 and two distinct E2-specific products with different C termini. *J. Virol.* 68, 5063–5073.
31. Lu, H.-H. and Wimmer, E. (1996). Poliovirus chimeras replicating under the translational control of genetic elements of hepatitis C virus reveal unusual properties of the internal ribosomal entry site of hepatitis C virus. *Proc. Natl. Acad. Sci. USA* 93, 1412–1417.
32. McHutchison, J. G., Gordon, S. C., Schiff, E. R., Shiffman, M. L., Lee, W. M., Rustgi, V. K., Goodman, Z. D., Ling, M.-H., Cort, S. and Albrecht, J. K., for the hepatits interventional therapy group. (1998). Interferon alfa-2b alone or in combination with ribavirin as initial treatment for chronic hepatitis C. *N. Engl. J. Med.* 339, 1485–1492.
33. Mizushima, H., Hijikata, M., Asabe, S.-I., Hirota, M., Kimura, K. and Shimotohno, K. (1994). Two hepatitis C virus glycoprotein E2 products with different C termini. *J. Virol.* 68, 6215–6222.
34. Nakao, H., Okamoto, H., Tokita, H., Inoue, T., Iizuka, H., Pozzato, G. and Mishiro, S. (1996). Full-length genomic sequence of a hepatitis C virus genotype 2c isolate (BEBE1) and the 2c-specific PCR primers. *Arch. Virol.* 141, 701–704.
35. Nielsen, H., Engelbrecht, J., Brunak, S. and von Heijne, G. (1997). Identification of prokaryotic and eukaryotic signal peptides and prediction of their cleavage sites. *Protein Eng.* 10, 1–6.
36. Novak, J. E. and Kirkegaard, K. (1994). Coupling between genome translation and replication in an RNA virus. *Genes Dev.* 8, 1726–1737.
37. Nugent, C. I., Johnson, K. L., Sarnow, P. and Kirkegaard, K. (1999). Functional coupling between replication and packaging of poliovirus replicon RNA. *J. Virol.* 73, 427–435.
38. Okamoto, H., Kurai, K., Okada, S. I., Yamamoto, K., Iizuka, H., Tanaka, T., Fukuda, S., Tsuda, F. and Mishiro, S. (1992). Full-length sequence of hepatitis C virus genome having poor homology to reported isolates: comparative study of four distinct genotypes. *Virology* 188, 331–341.
39. Okamoto, H., Okada, S., Sugiyama, Y., Kurai, K., Iizuka, H., Machida, A., Miyakawa, Y. and
40. Mayumi, M. (1991). Nucleotide sequence of the genomic RNA of hepatitis C virus isolated from a human carrier: comparison with reported isolates for conserved and divergent regions. *J. Gen. Virol.* 72, 2697–2704.
41. Pletnev, A. G., Bray, M., Huggins, J. and Lai, C.-J. (1992). Construction and characterization of chimeric tick-borne encephalitis/dengue type 4 viruses. *Proc. Natl. Acad. Sci. USA* 89, 10532–10536.
42. Pletnev, A. G., Bray, M. and Lai, C.-J. (1993). Chimeric tick-borne encephalitis and dengue type 4 viruses: Effects of mutations on neurovirulence in mice. *J. Virol.* 67, 4956–4963.
43. Pletnev, A. G. and Men, R. (1998). Attenuation of the Langat tick-borne flavivirus by chimerization with mosquito-borne flavivirus dengue type 4. *Proc. Natl. Acad. Sci. USA* 95, 1746–1751.
44. Reynolds, J. E., Kaminski, A., Kettinen, H. J., Grace, K., Clarke, B. E., Carroll, A. R., Rowlands, D. J. and Jackson, R. J. (1995). Unique features of internal initiation of hepatitis C virus RNA translation. *EMBO J.* 14, 6010–6020.

45. Rice, C. M. (1996). Flaviviridae: The viruses and their replication, In "Fields Virology". (B. N. Fields, D. M. Knipe, P. M. Howley, et al., Eds.), Third ed., pp. 931–959. Lippincott-Raven Publishers, Philadelphia.
46. Robertson, B., Myers, G., Howard, C., Brettin, T., Bukh, J., Gaschen, B., Gojobori, T., Maertens, G., Mizokami, M., Nainan, O., Netesov, S., Nishioka, K., Shin-i, T., Simmonds, P., Smith, D., Stuyver, L. and Weiner, A. (1998). Classification, nomenclature, and database development for hepatitis C virus (HCV) and related viruses: proposals for standardization. *Arch. Virol.* 143, 2493–2503.
47. Selby, M. J., Glazer, E., Masiarz, F. and Houghton, M. (1994). Complex processing and protein:protein interactions in the E2:NS2 region of HCV. *Virology* 204, 114–122.
48. Simmonds, P., Holmes, E. C., Cha, T.-A., Chan, S.-W., McOmish, F., Irvine, B., Beall, E., Yap, P. L., Kolberg, J. and Urdea, M. S. (1993). Classification of hepatitis C virus into six major genotypes and a series of subtypes by phylogenetic analysis of the NS-5 region. *J. Gen. Virol.* 74, 2391–2399.
49. Tanaka, T., Kato, N., Cho, M.-J. and Shimotohno, K. (1995). A novel sequence found at the 3' terminus of hepatitis C virus genome. *Biochem. Biophys. Res. Commun.* 215, 744–749.
50. Tanaka, T., Kato, N., Cho, M.-J., Sugiyama, K. and Shimotohno, K. (1996). Structure of the 3' terminus of the hepatitis C virus genome. *J. Virol.* 70, 3307–3312.
51. Tsuchihara, K., et al. (1997) *J. Virol.* 71, 6720–6726.
52. Tsukiyama-Kohara, K., et al. (1992) *J. Virol.* 66, 1476–1483.
53. Vassilev, V. B., Collett, M. S. and Donis, R. O. (1997). Authentic and chimeric full-length genomic cDNA clones of bovine viral diarrhea virus that yield infectious transcripts. *J. Virol.* 71, 471–478.
54. Weiner, A. J., Brauer, M. J., Rosenblatt, J., Richman, K. H., Tung, J., Crawford, K., Bonino, F., Saracco, G., Choo, Q.-L., Houghton, M. and Han, J. H. (1991). Variable and hypervariable domains are found in the regions of HCV corresponding to the Flavivirus envelope and NS1 proteins and the Pestivirus envelope glycoproteins. *Virology* 180, 842–848.
55. World Health Organization (1997). Hepatitis C. *Weekly Epidemiol. Rec.* 72, 65–72.
56. Yamada, N., Tanihara, K., Takada, A., Yorihuzi, T., Tsutsumi, M., Shimomura, H., Tsuji, T. and Date, T. (1996). Genetic organization and diversity of the 3' noncoding region of the hepatitis C virus genome. *Virology* 223, 255–261.
57. Yanagi, M., Bukh, J., Emerson, S. U. and Purcell, R. H. (1996). Contamination of commercially available fetal bovine sera with bovine viral diarrhea virus genomes: implications for the study of hepatitis C virus in cell cultures. *J. Infect. Dis.* 174, 1324–1327.
58. Yanagi, M., Purcell, R. H., Emerson, S. U. and Bukh, J. (1997). Transcripts from a single full-length cDNA clone of hepatitis C virus are infectious when directly transfected into the liver of a chimpanzee. *Proc. Natl. Acad. Sci. USA* 94, 8738–8743.
59. Yanagi, M., St. Claire, M., Shapiro, M., Emerson, S. U., Purcell, R. H. and Bukh, J. (1998). Transcripts of a chimeric cDNA clone of hepatitis C virus genotype 1b are infectious in vivo. *Virology* 244, 161–172.

60. Yanagi, M., St. Claire, M., Emerson, S. U., Purcell, R. H. and Bukh, J. (1999). In vivo analysis of the 3' untranslated region of hepatitis C virus after in vitro mutagenesis of an infectious cDNA clone. *Proc. Natl. Acad. Sci. USA* 96, 2291–2295.

61. Yoo, B. J., et al. (1995). *J. Virol.* 69, 32–38.

62. Zhao, W. D., Wimmer, E. and Lahser, F. C. (1999). Poliovirus/hepatitis C virus (internal ribosomal entry site-core) chimeric viruses: improved growth properties through modification of a proteolytic cleavage site and requirement for core RNA sequences but not for core-related polypeptides. *J. Virol.* 73, 1546–1554.

What is claimed is:

1. A purified and isolated nucleic acid molecule which encodes human hepatitis C virus of genotype 2a, said molecule capable of expressing said virus when transfected into cells and further capable of infectivity in vivo, wherein said molecule encodes the amino acid sequence of SEQ ID NO: 2.

2. The nucleic acid molecule of claim 1, wherein said molecule comprises the nucleic acid sequence of SEQ ID NO: 1.

3. A DNA construct comprising a nucleic acid molecule according to claim 1.

4. A DNA construct comprising a nucleic acid molecule according to claim 2.

5. An RNA transcript of the DNA construct of claim 3.

6. An RNA transcript of the DNA construct of claim 4.

7. An in vitro cell transfected with the DNA construct of claim 3.

8. An in vitro cell transfected with the DNA construct of claim 4.

9. An in vitro cell transfected with the RNA transcript of claim 5.

10. An in vitro cell transfected with the RNA transcript of claim 6.

11. A composition comprising a nucleic acid molecule of claim 1 or 2 suspended in a suitable amount of a pharmaceutically acceptable diluent or excipient.

* * * * *

SEQUENCE LISTING

<160> NUMBER OF SEQ ID NOS: 70

<210> SEQ ID NO 1
<211> LENGTH: 9711
<212> TYPE: DNA
<213> ORGANISM: Hepatitis C virus

<400> SEQUENCE: 1

```
acccgcccct aatagggggcg acactccgcc atgaatcact ccctgtgag gaactactgt      60 cttcacgcag aaagcgtcta gccatggcgt tagtatgagt gtcgtacagc ctccaggccc     120 cccctcccg ggagagccat agtggtctgc ggaaccggtg agtacaccgg aattgccggg     180
aagactgggt cctttcttgg ataaacccac tctatgcccg gccatttggg cgtgcccccg     240
caagactgct agccgagtag cgttgggttg cgaaaggcct tgtggtactg cctgatagggg    300 tgcttgcgag tgccccggga ggtctcgtag accgtgcacc atgagcacaa atcctaaacc     360
tcaaagaaaa accaaaagaa acaccaaccg tcgcccacaa gacgttaagt tcccggggcgg    420 cggccagatc gttggcggag tatacttgtt gccgcgcagg ggcccaggt tgggtgtgcg     480 cgcgacaagg aagacttcgg agcggtccca gccacgtgga aggcgccagc ccatccctaa     540
agatcggcgc tccactggca atcctgggg aaaaccagga taccctggc ccctatacgg     600 gaatgaggga ctcggctggg caggatggct cctgtccccc cgaggttccc gtccctcttg     660 gggcccccaat gaccccggc ataggtcgcg caacgtgggt aaggtcatcg atacccctaac    720 gtgcggcttt gccgacctca tggggtacat ccctgtcgtg ggcgccccgc tcggcggcgt     780
cgccagagct ctcgcgcatg gcgtgagagt cctggaggac ggggttaatt ttgcaacagg     840
gaacttaccc ggttgctcct ttctatctt cttgctggcc ctgctgtcct gcatcaccac     900
cccggtctcc gctgccgaag tgaagaacat cagtaccggc tacatggtga ctaacgactg     960
caccaatgac agcattacct ggcagctcca ggctgctgtc ctccacgtcc ccgggtgcgt    1020
cccgtgcgag aaagtgggga atgcatctca gtgctggata ccggtctcac cgaatgtggc    1080
cgtgcagcgg cccggcgccc tcacgcaggg cttgcggacg cacatcgaca tggttgtgat    1140
gtccgccacg ctctgctctg ccctctacgt gggggacctc tgcggtgggg tgatgctcgc    1200
agcccaaatg ttcattgtct cgccgcagca ccactggttt gtccaagact gcaattgctc    1260
catctaccct ggtaccatca ctggacaccg catggcatgg gacatgatga tgaactggtc    1320
gcccacggct accatgatct ggcgtacgc gatgcgtgtc cccgaggtca ttatagacat    1380
cattagcggg gctcattggg gcgtcatgtt cggcttggcc tacttctcta tgcagggagc    1440
gtgggcgaaa gtcgttgtca tccttctgtt ggccgccggg gtggacgcgc gcacccatac    1500
tgttgggggt tctgccgcgc agaccaccgg gcgcctcacc agcttatttg acatgggccc    1560
caggcagaaa atccagctcg ttaacaccaa tggcagctgg cacatcaacc gcaccgccct    1620
gaactgcaat gactccttgc acaccggctt tatcgcgtct ctgttctaca cccacagctt    1680
caactcgtca ggatgtcccg aacgcatgtc cgcctgcgc agtatcgagg ccttccgggt    1740
```

```
gggatggggc gccttgcaat atgaggataa tgtcaccaat ccagaggata tgagacccta    1800
ttgctggcac tacccaccaa ggcagtgtgg cgtggtctcc gcgaagactg tgtgtggccc    1860
agtgtactgt ttcacccca gcccagtggt agtgggcacg accgacaggc ttggagcgcc     1920
cacttacacg tggggggaga atgagacaga tgtcttccta ttgaacagca ctcgaccacc    1980 gctgggtca tggttcggct gcacgtggat gaactcttct ggctacacca agacttgcgg     2040
cgcaccaccc tgccgtacta gagctgactt caacgccagc acggacctgt tgtgcccac     2100 ggactgtttt aggaagcatc ctgataccac ttacctcaaa tgcggctctg ggccctggct    2160
cacgccaagg tgcctgatcg actaccccta caggctctgg cattaccct gcacagttaa     2220 ctataccatc ttcaaaataa ggatgtatgt gggaggggtt gagcacaggc tcacggctgc    2280
atgcaatttc actcgtgggg atcgttgcaa cttggaggac agagacagaa gtcaactgtc    2340
tcctttgttg cactccacca cggaatgggc cattttacct tgctcttact cggacctgcc    2400
cgccttgtcg actggtcttc tccacctcca ccaaaacatc gtggacgtac aattcatgta    2460
tggcctatca cctgccctca caaaatacat cgtccgatgg gagtgggtaa tactcttatt    2520
cctgctctta gcggacgcca gggttttgcgc ctgcttatgg atgctcatct tgttgggcca   2580
ggccgaagca gcactagaga agctggtcat cttgcacgct gcgagcgcag ctagctgcaa    2640
tggcttccta tattttgtca tcttttttcgt ggctgcttgg tacatcaagg gtcgggtagt   2700 cccccttagct acctattccc tcactggcct gtggtccttt agcctactgc tcctagcatt   2760
gccccaacag gcttatgctt atgacgcatc tgtgcatggc cagataggag cggctctgct    2820
ggtaatgatc actctctta ctctcacccc cgggtataag acccttctca gccggttttt     2880
gtggtggttg tgctatcttc tgaccctggg ggaagctatg gtccaggagt gggcaccacc    2940
tatgcaggtg cgcggtggcc gtgatggcat catatgggcc gtcgccatat tctacccagg    3000
tgtggtgttt gacataacca agtggctctt ggcggtgctt gggcctgctt acctcctaaa    3060
aggtgctttg acgcgcgtgc cgtacttcgt cagggctcac gctctactga ggatgtgcac    3120
catggcaagg catctcgcgg ggggcaggta cgtccagatg cgctactag cccttggcag     3180 gtggactggc acttacatct atgaccacct caccctatg tcggattggg ctgctagtgg     3240
cctgcgggac ctggcggtcg ccgttgagcc tatcatcttc agtccgatgg agaagaaagt    3300
cattgtctgg ggagcggaga cagctgcttg tggggacatt ttacacggac ttcccgtgtc    3360
cgcccgactt ggtcgggagg tcctccttgg cccagctgat ggctatacct ccaaggggtg    3420
gagtcttctc gccccccatca ctgcttacgc ccagcagaca cgtggccttt tgggcaccat   3480
agtggtgagc atgacggggc gcgacaagac agaacaggct gggaaattc aggtcctgtc     3540 cacagtcact cagtccttcc tcggaacatc catctcgggg gttttgtgga ctgtctacca    3600
tggagctggc aacaagactc tggccggctc acggggtccg gtcacgcaga tgtactccag    3660
tgctgagggg gacttagtag ggtggcccag ccccctggg actaaatctt ggagccgtg      3720 cacgtgtgga gcggtcgacc tgtacctggt cacgcggaac gctgatgtca tcccggctcg    3780
aagacgcggg gacaaacggg gagcgctact ctccccgaga cctctttcca ccttgaaggg    3840
gtcctcagga ggcccggtgc tatgcccag gggccacgct gtcggagtct ccgggcagc      3900 tgtgtgctct cggggcgtgg ctaagtccat agatttcatc cccgttgaga cactcgacat    3960
cgtcacgcgg tccccaccct ttagtgacaa cagcacacca cctgctgtgc cccagaccta    4020
tcaggtcggg tacttgcatg ccccgactgg cagtggaaag agcaccaaag ttcctgtcgc    4080
atatgctgct caggggtata aagtgctagt gcttaatccc tcagtggctg ccaccctggg    4140
```

```
gtttggggcg tacttgtcta aggcacatgg catcaatccc aacattagga ctggagtcag    4200
gactgtgacg accggggcgc ccatcacgta ctccacatat ggcaaattcc tcgccgatgg    4260
gggctgtgcg gcggcgcct acgacatcat catatgtgat gaatgccatg ccgtggactc     4320
taccaccatc cttggcatcg aacagtcct tgatcaagca gagacagctg gggtcagact     4380
aactgtgctg gctacagcta cgcccctgg gtcagtgaca accccccacc ccaacataga    4440
ggaggtggcc cttgggcagg agggcgagat ccccttctat ggggagggcga ttccctgtc    4500 ttacatcaag ggaggaagac atctgatctt ctgccattca agaaaaagt gtgacgagct     4560 cgcggcggcc cttcggggta tgggcttgaa ctcagtggca tactacagag ggttggacgt    4620
ctccgtaata ccaactcagg gagacgtagt ggtcgtcgcc accgacgccc tcatgacagg    4680
gtatactggg gactttgact ccgtgatcga ctgcaacgta gcggtcactc aagttgtaga    4740 cttcagtttta gaccccacat tcaccataac cacacagatt gtccctcaag acgctgtctc    4800
acgtagccag cgccggggtc gcacgggtag gggaagactg ggcatttata ggtatgtttc    4860
cactggtgag cgagcctcag gaatgtttga cagtgtagtg ctctgtgagt gctacgacgc   4920
aggggccgca tggtatgagc tcacaccatc ggagaccacc gtcaggctca gggcgtattt    4980
caacacgccc ggtttgcctg tgtgccaaga ccatcttgag ttttgggagg cagttttcac    5040
cggcctcaca cacatagatg cccacttcct ttcccaaaca aagcaatcgg gggaaaattt     5100
cgcatactta acagcctacc aggctacagt gtgcgctagg gccaaagccc ccccccgtc     5160 ctgggacgtc atgtggaagt gtttgactcg actcaagccc acactcgtgg gccccacacc    5220
tctcctgtac cgcttgggct ctgttaccaa cgaggtcacc ctcacacatc ccgtgacgaa    5280
atacatcgcc acctgcatgc aagccgacct tgaggtcatg accagcacat gggtcttggc    5340 aggggagtc ttggcggccg tcgccgcgta ttgcctggcg accgggtgtg tttgcatcat     5400
cggccgcttg cacattaacc agcgagccgt cgttgcgccg gacaaggagg tcctctatga    5460
ggcttttgat gagatggagg aatgtgcctc tagggcggct ctcattgaag aggggcagcg    5520
gatagccgag atgctgaagt ccaagatcca aggcttattg cagcaagctt ccaaacaagc    5580
tcaagacata caacccactg tgcaggcttc atggcccaag gtagaacaat tctgggccaa    5640
acacatgtgg aacttcatta gcggcatcca atacctcgca ggactatcaa cactgccagg    5700
gaaccctgca gtagcttcca tgatggcgtt cagtgccgcc ctcaccagtc cgctgtcaac    5760
aagcaccact atccttctca acatttgggg ggctggcta gcatcccaaa ttgcaccacc    5820
cgcgggggcc actggcttcg ttgtcagtgg cctagtggga ctgccgtag gcagtatagg    5880 cttaggtaag gtgctagtgg acatcctggc agggtatggt gcgggcattt cggggggctct    5940 cgtcgcattc aagatcatgt ctggcgagaa gccctccatg gaggatgtcg tcaacttgct    6000
gcctggaatt ctgtctccgg gtgccttggt agtgggagtc atctgcgcgg ccattctgcg    6060
ccgacacgtg ggaccggggg aaggcgccgt ccaatggatg aatagactca ttgccttttgc   6120 ttccagagga aatcacgtcg ccccccacca ctacgtgacg gagtcggatg cgtcgcagcg    6180
tgtgacccaa ctacttggct cccttaccat aaccagcctg ctcagaagac tccacaactg    6240
gattactgag gactgcccca tcccatgcgg cggctcgtgg ctccgcgatg tgtgggactg    6300
ggtttgcacc atcctaacag actttaaaaa ttggctgacc tccaaattat tcccaaagat    6360
gcccggcctc cccttttgtct cctgtcaaaa ggggtacaag ggcgtgtggg ccggcactgg    6420
catcatgacc acacggtgtc cttgcggcgc caatatctct ggcaatgtcc gcttgggctc    6480
```

```
catgagaatc acggggccta agacctgcat gaatatctgg caggggacct ttcctatcaa    6540
ttgttacacg gagggccagt gcgtgccgaa acccgcgcca aactttaagg tcgccatctg    6600
gagggtggcg gcctcagagt acgcggaggt gacgcagcac gggtcatacc actacataac    6660
aggactcacc actgataact tgaaagtccc ctgccaacta ccctctcccg agttcttttc    6720
ctgggtggac ggagtgcaga tccataggtt tgccccaca ccgaagccgt ttttccggga    6780
tgaggtctcg ttctgcgttg ggcttaattc atttgtcgtc gggtcccagc ttccttgcga    6840
ccctgaaccc gacacagacg tattgatgtc catgctaaca gatccatctc atatcacggc    6900
ggagactgca gcgcggcgtt tagcgcgggg gtcaccccca tccgaggcaa gctcctcggc    6960
gagccagcta tcggcaccat cgctgcgagc cacctgcacc acccacggca agcctatga    7020 tgtggacatg gtggatgcta acctgttcat gggggcgat gtgactcgga tagagtctgg    7080
gtccaaagtg gtcgttctgg actctctcga cccaatggtc gaagaaagga gcgaccttga    7140
gccttcgata ccatcagaat acatgctccc caagaagagg ttcccaccag ctttaccggc    7200
ctgggcacgg cctgattaca acccaccgct tgtggaatcg tggaaaaggc cagattacca    7260
accgccacct gttgcgggct gtgctctccc tcctcctagg aaaacccga cgcctccccc    7320 aaggaggcgc cggacagtgg gcctaagtga ggactccata ggagatgccc ttcaacagct    7380
ggccattaag tcctttggcc agccccccc aagcggcgat tcaggccttt ccacgggggc    7440
gggcgctgcc gattccggca gtcagacgcc tcctgatgag ttggcccttt cggagacagg    7500
ttccatctct tccatgcccc ccctcgaggg ggagcttgga gatccagacc tggagcctga    7560
gcaggtagag ccccaacccc cccccaggg ggggtggca gctcccggct cggactcggg    7620
gtcctggtct acttgctccg aggaggacga ctccgtcgtg tgctgctcca tgtcatactc    7680
ctggaccggg gctctaataa ctccttgtag tcccgaagag gagaagttac cgattaaccc    7740
cttgagcaac tccctgttgc gatatcacaa caaggtgtac tgtaccacaa caaagagcgc    7800
ctcactaagg gctaaaaagg taactttttga taggatgcaa gtgctcgact cctactacga    7860
ctcagtctta aaggacatta agctagcggc ctccaaggtc accgcaaggc tcctcaccat    7920
ggaggaggct tgccagttaa ccccacccca ttctgcaaga tctaaatatg ggtttggggc    7980
taaggaggtc cgcagcttgt ccgggagggc cgttaaccac atcaagtccg tgtggaagga    8040
cctcctggag gactcagaaa caccaattcc cacaaccatt atggccaaaa atgaggtgtt    8100
ctgcgtggac cccaccaagg ggggcaagaa agcagctcgc cttatcgttt accctgacct    8160
cggcgtcagg gtctgcgaga agatggccct ttatgacatt acacaaaaac ttcctcaggc    8220
ggtgatgggg gcttcttatg gattccagta ttcccccgct cagcgggtag agtttctctt    8280
gaaagcatgg gcggaaaaga aggaccctat gggttttttcg tatgataccc gatgctttga    8340
ctcaaccgtc actgagagag acatcaggac tgaggagtcc atatatcggg cctgctcctt    8400
gcccgaggag gcccacactg ccatacactc gctaactgag agactttacg tgggagggcc    8460
tatgttcaac agcaagggcc aaacctgcgg gtacaggcgt tgccgcgcca gcggggtgct    8520
caccactagc atggggaaca ccatcacatg ctacgtgaaa gccttagcgg cttgtaaagc    8580
tgcagggata atcgcgccca caatgctggt atgcggcgat gacttggttg tcatctcaga    8640
aagccagggg accgaggagg acgagcgaa cctgagagcc ttcacggagg ctatgaccag    8700
gtattctgcc cctcctggtg accccccag accggagtat gatctggagc tgataacatc    8760
ttgctcctca aatgtgtctg tggcgctggg cccacaaggc cgccgcagat actacctgac    8820
cagagaccct accactccaa tcgcccgggc tgcctgggaa acagttagac actcccctgt    8880
```

-continued

```
caattcatgg ctgggaaaca tcatccagta cgccccgacc atatgggctc gcatggtcct    8940
gatgacacac ttcttctcca ttctcatggc tcaagacacg ctggaccaga acctcaactt    9000
tgagatgtac ggagcggtgt actccgtgag tcccttggac ctcccagcta taattgaaag    9060
gttacatggg cttgacgctt tttctctgca cacatacact ccccacgaac tgacacgggt    9120
ggcttcagcc ctcagaaaac ttggggcgcc acccctcaga gcgtggaaga gccgggcacg    9180
tgcagtcagg gcgtccctca tctcccgtgg ggggagagcg gccgtttgcg gtcgatatct    9240
cttcaattgg gcggtgaaga ccaagctcaa actcactcca ttgccggaag cgcgcctcct    9300
ggatttatcc agctggttca ccgtcggcgc cggcggggc gacatttatc acagcgtgtc      9360
gcgtgcccga ccccgcttat tgctctttgg cctactccta cttttgtag ggtaggcct       9420 tttcctactc cccgctcggt agagcggcac acattagcta cactccatag ctaactgtcc    9480
cttttttttt tttttttttt tttttttttt tttttttttt tttttttttt tttttttttt    9540
tttttttttt tttttttttt tttttctttt tttctctttt ccttctttct taccttattt    9600
tactttcttt cctggtggct ccatcttagc cctagtcacg gctagctgtg aaaggtccgt    9660
gagccgcatg actgcagaga gtgccgtaac tggtctctct gcagatcatg t              9711
```

<210> SEQ ID NO 2
<211> LENGTH: 3033
<212> TYPE: PRT
<213> ORGANISM: Hepatitis C virus

<400> SEQUENCE: 2

```
Met Ser Thr Asn Pro Lys Pro Gln Arg Lys Thr Lys Arg Asn Thr Asn
 1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Asn Asp Pro
            100                 105                 110

Arg His Arg Ser Arg Asn Val Gly Lys Val Ile Asp Thr Leu Thr Cys
        115                 120                 125

Gly Phe Ala Asp Leu Met Gly Tyr Ile Pro Val Val Gly Ala Pro Leu
    130                 135                 140

Gly Gly Val Ala Arg Ala Leu Ala His Gly Val Arg Val Leu Glu Asp
145                 150                 155                 160

Gly Val Asn Phe Ala Thr Gly Asn Leu Pro Gly Cys Ser Phe Ser Ile
                165                 170                 175

Phe Leu Leu Ala Leu Leu Ser Cys Ile Thr Thr Pro Val Ser Ala Ala
            180                 185                 190

Glu Val Lys Asn Ile Ser Thr Gly Tyr Met Val Thr Asn Asp Cys Thr
        195                 200                 205

Asn Asp Ser Ile Thr Trp Gln Leu Gln Ala Ala Val Leu His Val Pro
    210                 215                 220
```

-continued

```
Gly Cys Val Pro Cys Glu Lys Val Gly Asn Ala Ser Gln Cys Trp Ile
225                 230                 235                 240

Pro Val Ser Pro Asn Val Ala Val Gln Arg Pro Gly Ala Leu Thr Gln
            245                 250                 255

Gly Leu Arg Thr His Ile Asp Met Val Met Ser Ala Thr Leu Cys
        260                 265                 270

Ser Ala Leu Tyr Val Gly Asp Leu Cys Gly Val Met Leu Ala Ala
        275                 280                 285

Gln Met Phe Ile Val Ser Pro Gln His His Trp Phe Val Gln Asp Cys
    290                 295                 300

Asn Cys Ser Ile Tyr Pro Gly Thr Ile Thr Gly His Arg Met Ala Trp
305                 310                 315                 320

Asp Met Met Met Asn Trp Ser Pro Thr Ala Thr Met Ile Leu Ala Tyr
                325                 330                 335

Ala Met Arg Val Pro Glu Val Ile Ile Asp Ile Ile Ser Gly Ala His
        340                 345                 350

Trp Gly Val Met Phe Gly Leu Ala Tyr Phe Ser Met Gln Gly Ala Trp
        355                 360                 365

Ala Lys Val Val Val Ile Leu Leu Leu Ala Ala Gly Val Asp Ala Arg
    370                 375                 380

Thr His Thr Val Gly Gly Ser Ala Ala Gln Thr Thr Gly Arg Leu Thr
385                 390                 395                 400

Ser Leu Phe Asp Met Gly Pro Arg Gln Lys Ile Gln Leu Val Asn Thr
            405                 410                 415

Asn Gly Ser Trp His Ile Asn Arg Thr Ala Leu Asn Cys Asn Asp Ser
            420                 425                 430

Leu His Thr Gly Phe Ile Ala Ser Leu Phe Tyr Thr His Ser Phe Asn
        435                 440                 445

Ser Ser Gly Cys Pro Glu Arg Met Ser Ala Cys Arg Ser Ile Glu Ala
450                 455                 460

Phe Arg Val Gly Trp Gly Ala Leu Gln Tyr Glu Asp Asn Val Thr Asn
465                 470                 475                 480

Pro Glu Asp Met Arg Pro Tyr Cys Trp His Tyr Pro Arg Gln Cys
            485                 490                 495

Gly Val Val Ser Ala Lys Thr Val Cys Gly Pro Val Tyr Cys Phe Thr
            500                 505                 510

Pro Ser Pro Val Val Val Gly Thr Thr Asp Arg Leu Gly Ala Pro Thr
        515                 520                 525

Tyr Thr Trp Gly Glu Asn Glu Thr Asp Val Phe Leu Leu Asn Ser Thr
        530                 535                 540

Arg Pro Pro Leu Gly Ser Trp Phe Gly Cys Thr Trp Met Asn Ser Ser
545                 550                 555                 560

Gly Tyr Thr Lys Thr Cys Gly Ala Pro Pro Cys Arg Thr Arg Ala Asp
            565                 570                 575

Phe Asn Ala Ser Thr Asp Leu Leu Cys Pro Thr Asp Cys Phe Arg Lys
            580                 585                 590

His Pro Asp Thr Thr Tyr Leu Lys Cys Gly Ser Gly Pro Trp Leu Thr
            595                 600                 605

Pro Arg Cys Leu Ile Asp Tyr Pro Tyr Arg Leu Trp His Tyr Pro Cys
        610                 615                 620

Thr Val Asn Tyr Thr Ile Phe Lys Ile Arg Met Tyr Val Gly Gly Val
625                 630                 635                 640

Glu His Arg Leu Thr Ala Ala Cys Asn Phe Thr Arg Gly Asp Arg Cys
```

-continued

```
                645                 650                 655
Asn Leu Glu Asp Arg Asp Arg Ser Gln Leu Ser Pro Leu Leu His Ser
            660                 665                 670
Thr Thr Glu Trp Ala Ile Leu Pro Cys Ser Tyr Ser Asp Leu Pro Ala
        675                 680                 685
Leu Ser Thr Gly Leu Leu His Leu His Gln Asn Ile Val Asp Val Gln
    690                 695                 700
Phe Met Tyr Gly Leu Ser Pro Ala Leu Thr Lys Tyr Ile Val Arg Trp
705                 710                 715                 720
Glu Trp Val Ile Leu Leu Phe Leu Leu Ala Asp Ala Arg Val Cys
                725                 730                 735
Ala Cys Leu Trp Met Leu Ile Leu Leu Gly Gln Ala Glu Ala Leu
            740                 745                 750
Glu Lys Leu Val Ile Leu His Ala Ala Ser Ala Ala Ser Cys Asn Gly
        755                 760                 765
Phe Leu Tyr Phe Val Ile Phe Val Ala Ala Trp Tyr Ile Lys Gly
    770                 775                 780
Arg Val Val Pro Leu Ala Thr Tyr Ser Leu Thr Gly Leu Trp Ser Phe
785                 790                 795                 800
Ser Leu Leu Leu Ala Leu Pro Gln Gln Ala Tyr Ala Tyr Asp Ala
                805                 810                 815
Ser Val His Gly Gln Ile Gly Ala Ala Leu Leu Val Met Ile Thr Leu
            820                 825                 830
Phe Thr Leu Thr Pro Gly Tyr Lys Thr Leu Leu Ser Arg Phe Leu Trp
        835                 840                 845
Trp Leu Cys Tyr Leu Leu Thr Leu Gly Glu Ala Met Val Gln Glu Trp
    850                 855                 860
Ala Pro Pro Met Gln Val Arg Gly Gly Arg Asp Gly Ile Ile Trp Ala
865                 870                 875                 880
Val Ala Ile Phe Tyr Pro Gly Val Val Phe Asp Ile Thr Lys Trp Leu
                885                 890                 895
Leu Ala Val Leu Gly Pro Ala Tyr Leu Leu Lys Gly Ala Leu Thr Arg
            900                 905                 910
Val Pro Tyr Phe Val Arg Ala His Ala Leu Leu Arg Met Cys Thr Met
        915                 920                 925
Ala Arg His Leu Ala Gly Gly Arg Tyr Val Gln Met Ala Leu Leu Ala
    930                 935                 940
Leu Gly Arg Trp Thr Gly Thr Tyr Ile Tyr Asp His Leu Thr Pro Met
945                 950                 955                 960
Ser Asp Trp Ala Ala Ser Gly Leu Arg Asp Leu Ala Val Ala Val Glu
                965                 970                 975
Pro Ile Ile Phe Ser Pro Met Glu Lys Lys Val Ile Val Trp Gly Ala
            980                 985                 990
Glu Thr Ala Ala Cys Gly Asp Ile Leu His Gly Leu Pro Val Ser Ala
        995                 1000                1005
Arg Leu Gly Arg Glu Val Leu Leu Gly Pro Ala Asp Gly Tyr Thr Ser
    1010                1015                1020
Lys Gly Trp Ser Leu Leu Ala Pro Ile Thr Ala Tyr Ala Gln Gln Thr
1025                1030                1035                1040
Arg Gly Leu Leu Gly Thr Ile Val Ser Met Thr Gly Arg Asp Lys
                1045                1050                1055
Thr Glu Gln Ala Gly Glu Ile Gln Val Leu Ser Thr Val Thr Gln Ser
            1060                1065                1070
```

-continued

Phe Leu Gly Thr Ser Ile Ser Gly Val Leu Trp Thr Val Tyr His Gly
        1075                1080                1085

Ala Gly Asn Lys Thr Leu Ala Gly Ser Arg Gly Pro Val Thr Gln Met
        1090                1095                1100

Tyr Ser Ser Ala Glu Gly Asp Leu Val Gly Trp Pro Ser Pro Pro Gly
1105                1110                1115                1120

Thr Lys Ser Leu Glu Pro Cys Thr Cys Gly Ala Val Asp Leu Tyr Leu
                1125                1130                1135

Val Thr Arg Asn Ala Asp Val Ile Pro Ala Arg Arg Gly Asp Lys
        1140                1145                1150

Arg Gly Ala Leu Leu Ser Pro Arg Pro Leu Ser Thr Leu Lys Gly Ser
        1155                1160                1165

Ser Gly Gly Pro Val Leu Cys Pro Arg Gly His Ala Val Gly Val Phe
        1170                1175                1180

Arg Ala Ala Val Cys Ser Arg Gly Val Ala Lys Ser Ile Asp Phe Ile
1185                1190                1195                1200

Pro Val Glu Thr Leu Asp Ile Val Thr Arg Ser Pro Thr Phe Ser Asp
                1205                1210                1215

Asn Ser Thr Pro Pro Ala Val Pro Gln Thr Tyr Gln Val Gly Tyr Leu
        1220                1225                1230

His Ala Pro Thr Gly Ser Gly Lys Ser Thr Lys Val Pro Val Ala Tyr
        1235                1240                1245

Ala Ala Gln Gly Tyr Lys Val Leu Val Leu Asn Pro Ser Val Ala Ala
        1250                1255                1260

Thr Leu Gly Phe Gly Ala Tyr Leu Ser Lys Ala His Gly Ile Asn Pro
1265                1270                1275                1280

Asn Ile Arg Thr Gly Val Arg Thr Val Thr Thr Gly Ala Pro Ile Thr
                1285                1290                1295

Tyr Ser Thr Tyr Gly Lys Phe Leu Ala Asp Gly Gly Cys Ala Gly Gly
        1300                1305                1310

Ala Tyr Asp Ile Ile Ile Cys Asp Glu Cys His Ala Val Asp Ser Thr
        1315                1320                1325

Thr Ile Leu Gly Ile Gly Thr Val Leu Asp Gln Ala Glu Thr Ala Gly
        1330                1335                1340

Val Arg Leu Thr Val Leu Ala Thr Ala Thr Pro Pro Gly Ser Val Thr
1345                1350                1355                1360

Thr Pro His Pro Asn Ile Glu Glu Val Ala Leu Gly Gln Glu Gly Glu
                1365                1370                1375

Ile Pro Phe Tyr Gly Arg Ala Ile Pro Leu Ser Tyr Ile Lys Gly Gly
        1380                1385                1390

Arg His Leu Ile Phe Cys His Ser Lys Lys Lys Cys Asp Glu Leu Ala
        1395                1400                1405

Ala Ala Leu Arg Gly Met Gly Leu Asn Ser Val Ala Tyr Tyr Arg Gly
        1410                1415                1420

Leu Asp Val Ser Val Ile Pro Thr Gln Gly Asp Val Val Val Ala
1425                1430                1435                1440

Thr Asp Ala Leu Met Thr Gly Tyr Thr Gly Asp Phe Asp Ser Val Ile
                1445                1450                1455

Asp Cys Asn Val Ala Val Thr Gln Val Val Asp Phe Ser Leu Asp Pro
        1460                1465                1470

Thr Phe Thr Ile Thr Thr Gln Ile Val Pro Gln Asp Ala Val Ser Arg
        1475                1480                1485

-continued

```
Ser Gln Arg Arg Gly Arg Thr Gly Arg Gly Arg Leu Gly Ile Tyr Arg
    1490                1495                1500
Tyr Val Ser Thr Gly Glu Arg Ala Ser Gly Met Phe Asp Ser Val Val
1505                1510                1515                1520
Leu Cys Glu Cys Tyr Asp Ala Gly Ala Ala Trp Tyr Glu Leu Thr Pro
            1525                1530                1535
Ser Glu Thr Thr Val Arg Leu Arg Ala Tyr Phe Asn Thr Pro Gly Leu
        1540                1545                1550
Pro Val Cys Gln Asp His Leu Glu Phe Trp Glu Ala Val Phe Thr Gly
    1555                1560                1565
Leu Thr His Ile Asp Ala His Phe Leu Ser Gln Thr Lys Gln Ser Gly
    1570                1575                1580
Glu Asn Phe Ala Tyr Leu Thr Ala Tyr Gln Ala Thr Val Cys Ala Arg
1585                1590                1595                1600
Ala Lys Ala Pro Pro Pro Ser Trp Asp Val Met Trp Lys Cys Leu Thr
            1605                1610                1615
Arg Leu Lys Pro Thr Leu Val Gly Pro Thr Pro Leu Leu Tyr Arg Leu
        1620                1625                1630
Gly Ser Val Thr Asn Glu Val Thr Leu Thr His Pro Val Thr Lys Tyr
    1635                1640                1645
Ile Ala Thr Cys Met Gln Ala Asp Leu Glu Val Met Thr Ser Thr Trp
    1650                1655                1660
Val Leu Ala Gly Gly Val Leu Ala Ala Val Ala Ala Tyr Cys Leu Ala
1665                1670                1675                1680
Thr Gly Cys Val Cys Ile Ile Gly Arg Leu His Ile Asn Gln Arg Ala
            1685                1690                1695
Val Val Ala Pro Asp Lys Glu Val Leu Tyr Glu Ala Phe Asp Glu Met
        1700                1705                1710
Glu Glu Cys Ala Ser Arg Ala Ala Leu Ile Glu Glu Gly Gln Arg Ile
    1715                1720                1725
Ala Glu Met Leu Lys Ser Lys Ile Gln Gly Leu Leu Gln Gln Ala Ser
    1730                1735                1740
Lys Gln Ala Gln Asp Ile Gln Pro Thr Val Gln Ala Ser Trp Pro Lys
1745                1750                1755                1760
Val Glu Gln Phe Trp Ala Lys His Met Trp Asn Phe Ile Ser Gly Ile
            1765                1770                1775
Gln Tyr Leu Ala Gly Leu Ser Thr Leu Pro Gly Asn Pro Ala Val Ala
        1780                1785                1790
Ser Met Met Ala Phe Ser Ala Ala Leu Thr Ser Pro Leu Ser Thr Ser
    1795                1800                1805
Thr Thr Ile Leu Leu Asn Ile Leu Gly Gly Trp Leu Ala Ser Gln Ile
    1810                1815                1820
Ala Pro Pro Ala Gly Ala Thr Gly Phe Val Val Ser Gly Leu Val Gly
1825                1830                1835                1840
Ala Ala Val Gly Ser Ile Gly Leu Gly Lys Val Leu Val Asp Ile Leu
            1845                1850                1855
Ala Gly Tyr Gly Ala Gly Ile Ser Gly Ala Leu Val Ala Phe Lys Ile
        1860                1865                1870
Met Ser Gly Glu Lys Pro Ser Met Glu Asp Val Val Asn Leu Leu Pro
    1875                1880                1885
Gly Ile Leu Ser Pro Gly Ala Leu Val Val Gly Val Ile Cys Ala Ala
    1890                1895                1900
Ile Leu Arg Arg His Val Gly Pro Gly Glu Gly Ala Val Gln Trp Met
```

-continued

```
            1905                1910                1915                1920
Asn Arg Leu Ile Ala Phe Ala Ser Arg Gly Asn His Val Ala Pro Thr
            1925                1930                1935
His Tyr Val Thr Glu Ser Asp Ala Ser Gln Arg Val Thr Gln Leu Leu
            1940                1945                1950
Gly Ser Leu Thr Ile Thr Ser Leu Leu Arg Arg Leu His Asn Trp Ile
            1955                1960                1965
Thr Glu Asp Cys Pro Ile Pro Cys Gly Gly Ser Trp Leu Arg Asp Val
            1970                1975                1980
Trp Asp Trp Val Cys Thr Ile Leu Thr Asp Phe Lys Asn Trp Leu Thr
1985                1990                1995                2000
Ser Lys Leu Phe Pro Lys Met Pro Gly Leu Pro Phe Val Ser Cys Gln
            2005                2010                2015
Lys Gly Tyr Lys Gly Val Trp Ala Gly Thr Gly Ile Met Thr Thr Arg
            2020                2025                2030
Cys Pro Cys Gly Ala Asn Ile Ser Gly Asn Val Arg Leu Gly Ser Met
            2035                2040                2045
Arg Ile Thr Gly Pro Lys Thr Cys Met Asn Ile Trp Gln Gly Thr Phe
            2050                2055                2060
Pro Ile Asn Cys Tyr Thr Glu Gly Gln Cys Val Pro Lys Pro Ala Pro
2065                2070                2075                2080
Asn Phe Lys Val Ala Ile Trp Arg Val Ala Ala Ser Glu Tyr Ala Glu
            2085                2090                2095
Val Thr Gln His Gly Ser Tyr His Tyr Ile Thr Gly Leu Thr Thr Asp
            2100                2105                2110
Asn Leu Lys Val Pro Cys Gln Leu Pro Ser Pro Glu Phe Phe Ser Trp
            2115                2120                2125
Val Asp Gly Val Gln Ile His Arg Phe Ala Pro Thr Pro Lys Pro Phe
            2130                2135                2140
Phe Arg Asp Glu Val Ser Phe Cys Val Gly Leu Asn Ser Phe Val Val
2145                2150                2155                2160
Gly Ser Gln Leu Pro Cys Asp Pro Glu Pro Asp Thr Asp Val Leu Met
            2165                2170                2175
Ser Met Leu Thr Asp Pro Ser His Ile Thr Ala Glu Thr Ala Ala Arg
            2180                2185                2190
Arg Leu Ala Arg Gly Ser Pro Pro Ser Glu Ala Ser Ser Ser Ala Ser
            2195                2200                2205
Gln Leu Ser Ala Pro Ser Leu Arg Ala Thr Cys Thr Thr His Gly Lys
            2210                2215                2220
Ala Tyr Asp Val Asp Met Val Asp Ala Asn Leu Phe Met Gly Gly Asp
2225                2230                2235                2240
Val Thr Arg Ile Glu Ser Gly Ser Lys Val Val Leu Asp Ser Leu
            2245                2250                2255
Asp Pro Met Val Glu Glu Arg Ser Asp Leu Glu Pro Ser Ile Pro Ser
            2260                2265                2270
Glu Tyr Met Leu Pro Lys Lys Arg Phe Pro Pro Ala Leu Pro Ala Trp
            2275                2280                2285
Ala Arg Pro Asp Tyr Asn Pro Pro Leu Val Glu Ser Trp Lys Arg Pro
            2290                2295                2300
Asp Tyr Gln Pro Ala Thr Val Ala Gly Cys Ala Leu Pro Pro Pro Arg
2305                2310                2315                2320
Lys Thr Pro Thr Pro Pro Arg Arg Arg Arg Thr Val Gly Leu Ser
            2325                2330                2335
```

-continued

```
Glu Asp Ser Ile Gly Asp Ala Leu Gln Gln Leu Ala Ile Lys Ser Phe
        2340                2345                2350
Gly Gln Pro Pro Ser Gly Asp Ser Gly Leu Ser Thr Gly Ala Gly
    2355                2360                2365
Ala Ala Asp Ser Gly Ser Gln Thr Pro Pro Asp Glu Leu Ala Leu Ser
    2370                2375                2380
Glu Thr Gly Ser Ile Ser Ser Met Pro Leu Glu Gly Glu Leu Gly
2385                2390                2395                2400
Asp Pro Asp Leu Glu Pro Glu Gln Val Glu Pro Gln Pro Pro Gln
            2405                2410                2415
Gly Gly Val Ala Ala Pro Gly Ser Asp Ser Gly Ser Trp Ser Thr Cys
        2420                2425                2430
Ser Glu Glu Asp Asp Ser Val Val Cys Cys Ser Met Ser Tyr Ser Trp
        2435                2440                2445
Thr Gly Ala Leu Ile Thr Pro Cys Ser Pro Glu Glu Lys Leu Pro
        2450                2455                2460
Ile Asn Pro Leu Ser Asn Ser Leu Leu Arg Tyr His Asn Lys Val Tyr
2465                2470                2475                2480
Cys Thr Thr Thr Lys Ser Ala Ser Leu Arg Ala Lys Lys Val Thr Phe
                2485                2490                2495
Asp Arg Met Gln Val Leu Asp Ser Tyr Tyr Asp Ser Val Leu Lys Asp
        2500                2505                2510
Ile Lys Leu Ala Ala Ser Lys Val Thr Ala Arg Leu Leu Thr Met Glu
            2515                2520                2525
Glu Ala Cys Gln Leu Thr Pro Pro His Ser Ala Arg Ser Lys Tyr Gly
        2530                2535                2540
Phe Gly Ala Lys Glu Val Arg Ser Leu Ser Gly Arg Ala Val Asn His
2545                2550                2555                2560
Ile Lys Ser Val Trp Lys Asp Leu Leu Glu Asp Ser Glu Thr Pro Ile
                2565                2570                2575
Pro Thr Thr Ile Met Ala Lys Asn Glu Val Phe Cys Val Asp Pro Thr
        2580                2585                2590
Lys Gly Gly Lys Lys Ala Ala Arg Leu Ile Val Tyr Pro Asp Leu Gly
    2595                2600                2605
Val Arg Val Cys Glu Lys Met Ala Leu Tyr Asp Ile Thr Gln Lys Leu
        2610                2615                2620
Pro Gln Ala Val Met Gly Ala Ser Tyr Gly Phe Gln Tyr Ser Pro Ala
2625                2630                2635                2640
Gln Arg Val Glu Phe Leu Leu Lys Ala Trp Ala Glu Lys Lys Asp Pro
            2645                2650                2655
Met Gly Phe Ser Tyr Asp Thr Arg Cys Phe Asp Ser Thr Val Thr Glu
        2660                2665                2670
Arg Asp Ile Arg Thr Glu Glu Ser Ile Tyr Arg Ala Cys Ser Leu Pro
        2675                2680                2685
Glu Glu Ala His Thr Ala Ile His Ser Leu Thr Glu Arg Leu Tyr Val
        2690                2695                2700
Gly Gly Pro Met Phe Asn Ser Lys Gly Gln Thr Cys Gly Tyr Arg Arg
2705                2710                2715                2720
Cys Arg Ala Ser Gly Val Leu Thr Thr Ser Met Gly Asn Thr Ile Thr
                2725                2730                2735
Cys Tyr Val Lys Ala Leu Ala Ala Cys Lys Ala Ala Gly Ile Ile Ala
                2740                2745                2750
```

| | | | | | | | | | | |
|---|---|---|---|---|---|---|---|---|---|---|
|Pro|Thr|Met|Leu|Val|Cys|Gly|Asp|Asp|Leu|Val|Val|Ile|Ser|Glu|Ser|

Pro Thr Met Leu Val Cys Gly Asp Asp Leu Val Val Ile Ser Glu Ser
        2755                      2760                  2765

Gln Gly Thr Glu Glu Asp Glu Arg Asn Leu Arg Ala Phe Thr Glu Ala
        2770                      2775                  2780

Met Thr Arg Tyr Ser Ala Pro Pro Gly Asp Pro Arg Pro Glu Tyr
2785                2790                   2795                 2800

Asp Leu Glu Leu Ile Thr Ser Cys Ser Ser Asn Val Ser Val Ala Leu
        2805                      2810                  2815

Gly Pro Gln Gly Arg Arg Arg Tyr Tyr Leu Thr Arg Asp Pro Thr Thr
        2820                      2825                  2830

Pro Ile Ala Arg Ala Ala Trp Glu Thr Val Arg His Ser Pro Val Asn
        2835                      2840                  2845

Ser Trp Leu Gly Asn Ile Ile Gln Tyr Ala Pro Thr Ile Trp Ala Arg
        2850                      2855                  2860

Met Val Leu Met Thr His Phe Phe Ser Ile Leu Met Ala Gln Asp Thr
2865                2870                 2875                 2880

Leu Asp Gln Asn Leu Asn Phe Glu Met Tyr Gly Ala Val Tyr Ser Val
        2885                      2890                  2895

Ser Pro Leu Asp Leu Pro Ala Ile Ile Glu Arg Leu His Gly Leu Asp
        2900                      2905                  2910

Ala Phe Ser Leu His Thr Tyr Thr Pro His Glu Leu Thr Arg Val Ala
        2915                      2920                  2925

Ser Ala Leu Arg Lys Leu Gly Ala Pro Pro Leu Arg Ala Trp Lys Ser
        2930                      2935                  2940

Arg Ala Arg Ala Val Arg Ala Ser Leu Ile Ser Arg Gly Gly Arg Ala
2945                2950                 2955                 2960

Ala Val Cys Gly Arg Tyr Leu Phe Asn Trp Ala Val Lys Thr Lys Leu
        2965                      2970                  2975

Lys Leu Thr Pro Leu Pro Glu Ala Arg Leu Leu Asp Leu Ser Ser Trp
        2980                      2985                  2990

Phe Thr Val Gly Ala Gly Gly Gly Asp Ile Tyr His Ser Val Ser Arg
        2995                      3000                  3005

Ala Arg Pro Arg Leu Leu Leu Phe Gly Leu Leu Leu Leu Phe Val Gly
        3010                      3015                  3020

Val Gly Leu Phe Leu Leu Pro Ala Arg
3025                3030

<210> SEQ ID NO 3
<211> LENGTH: 9611
<212> TYPE: DNA
<213> ORGANISM: Hepatitis C virus

<400> SEQUENCE: 3

| | | | | | |
|---|---|---|---|---|---|
|gccagccccc|tgatggggggc|gacactccac|catgaatcac|tcccctgtga|ggaactactg|60|
|tcttcacgca|gaaagcgtct|agccatggcg|ttagtatgag|tgtcgtgcag|cctccaggac|120|
|cccccctccc|gggagagcca|tagtggtctg|cggaaccggt|gagtacaccg|gaattgccag|180|
|gacgaccggg|tcctttcttg|gataaaccccg|ctcaatgcct|ggagatttgg|gcgtgccccc|240|
|gcaagactgc|tagccgagta|gtgttgggtc|gcgaaaggcc|ttgtggtact|gcctgatagg|300|
|gtgcttgcga|gtgccccggg|aggtctcgta|gaccgtgcac|catgagcaca|aatcctaaac|360|
|ctcaaagaaa|aaccaaaaga|aacaccaacc|gtcgcccaca|agacgttaag|tttccgggcg|420|
|gcggccagat|cgttggcgga|gtatacttgt|tgccgcgcag|gggccccagg|ttgggtgtgc|480|
|gcgcgacaag|gaagacttcg|gagcggtccc|agccacgtgg|aaggcgccag|ccatccccta|540|

```
aagatcggcg ctccactggc aaatcctggg gaaaaccagg ataccctgg cccctatacg    600 ggaatgaggg actcggctgg gcaggatggc tcctgtcccc ccgaggttcc cgtccctctt   660
ggggccccaa tgaccccgg cataggtcgc gcaacgtggg taaggtcatc gatacctaa     720 cgtgcggctt tgccgacctc atggggtaca tccctgtcgt gggcgccccg ctcggcggcg   780
tcgccagagc tctcgcgcat ggcgtgagag tcctggagga cggggttaat tttgcaacag   840
ggaacttacc cggttgctcc ttttctatct tcttgctggc cctgctgtcc tgcatcacca   900
ccccggtctc cgctgccgaa gtgaagaaca tcagtaccgg ctacatggtg actaacgact   960
gcaccaatga cagcattacc tggcagctcc aggctgctgt cctccacgtc cccgggtgcg  1020
tcccgtgcga gaaagtgggg aatgcatctc agtgctggat accggtctca ccgaatgtgg  1080
ccgtgcagcg gcccggcgcc ctcacgcagg gcttgcggac gcacatcgac atggttgtga  1140
tgtccgccac gctctgctct gccctctacg tggggacct ctgcgtggg gtgatgctcg    1200 cagcccaaat gttcattgtc tcgccgcagc accactggtt tgtccaagac tgcaattgct  1260
ccatctaccc tggtaccatc actgacacc gcatggcatg ggacatgatg atgaactggt   1320
cgcccacggc taccatgatc ttggcgtacg cgatgcgtgt ccccgaggtc attatagaca  1380
tcattagcgg ggctcattgg ggcgtcatgt tcggcttggc ctacttctct atgcagggag  1440
cgtgggcgaa agtcgttgtc atccttctgt tggccgccgg ggtggacgcg cgcacccata  1500
ctgttggggg ttctgccgcg cagaccaccg ggcgcctcac cagcttattt gacatgggcc  1560
ccaggcagaa aatccagctc gttaacacca atggcagctg gcacatcaac cgcaccgccc  1620
tgaactgcaa tgactccttg cacaccggct ttatcgcgtc tctgttctac acccacagct  1680
tcaactcgtc aggatgtccc gaacgcatgt ccgcctgccg cagtatcgag gccttccggg  1740
tgggatgggg cgccttgcaa tatgaggata tgtcaccaa tccagaggat atgagaccct   1800
attgctggca ctacccacca aggcagtgtg gcgtggtctc cgcgaagact gtgtgtggcc  1860
cagtgtactg tttcacccc agcccagtgg tagtgggcac gaccgacagg cttggagcgc   1920
ccacttacac gtgggggag aatgagacag atgtcttcct attgaacagc actcgaccac   1980
cgctggggtc atggttcggc tgcacgtgga tgaactcttc tggctacacc aagacttgcg  2040
gcgcaccacc ctgccgtact agagctgact caacgccag cacggacctg ttgtgcccca   2100
cggactgttt taggaagcat cctgatacca cttacctcaa atgcggctct gggccctggc  2160
tcacgccaag gtgcctgatc gactacccct acaggtctg gcattacccc tgcacagtta   2220
actataccat cttcaaaata aggatgtatg tgggagggt tgagcacagg ctcacggctg   2280
catgcaattt cactcgtggg gatcgttgca acttggagga cagagacaga agtcaactgt  2340 ctccttttgtt gcactccacc acggaatggg ccatttttacc ttgctcttac tcggacctgc 2400
ccgccttgtc gactggtctt ctccacctcc accaaaacat cgtggacgta caattcatgt  2460
atggcctatc acctgccctc acaaaataca tcgtccgatg ggagtgggta atactcttat   2520
tcctgctctt agcggacgcc agggtttgcg cctgcttatg gatgctcatc ttgttgggcc  2580
aggccgaagc agcactagag aagctggtca tcttgcacgc tgcgagcgca gctagctgca  2640
atggcttcct atattttgtc atcttttttcg tggctgcttg gtacatcaag ggtcgggtag  2700
tccccttagc tacctattcc ctcactggcc tgtggtcctt tagcctactg ctcctagcat  2760 tgcccaaca ggcatatgca ctggacacgg aggtggccgc gtcgtgtggc ggcgttgttc    2820 ttgtcgggt aatggcgctg actctgtcgc catattacaa gcgctatatc agctggtgca   2880
```

```
tgtggtggct tcagtatttt ctgaccagag tagaagcgca actgcacgtg tgggttcccc    2940
ccctcaacgt ccggggggggg cgcgatgccg tcatcttact catgtgtgta gtacacccga    3000
ccctggtatt tgacatcacc aaactactcc tggccatctt cggacccctt tggattcttc    3060
aagccagttt gcttaaagtc ccctacttcg tgcgcgttca aggccttctc cggatctgcg    3120
cgctagcgcg gaagatagcc ggaggtcatt acgtgcaaat ggccatcatc aagttagggg    3180
cgcttactgg cacctatgtg tataaccatc tcacccctct tcgagactgg gcgcacaacg    3240
gcctgcgaga tctggccgtg gctgtggaac cagtcgtctt ctcccgaatg gagaccaagc    3300
tcatcacgtg gggggcagat accgccgcgt gcggtgacat catcaacggc ttgcccgtct    3360
ctgcccgtag gggccaggag atactgcttg ggccagccga cggaatggtc tccaaggggt    3420
ggaggttgct ggcgcccatc acggcgtacg cccagcagac gagaggcctc ctaggtgta    3480 taatcaccag cctgactggc cgggacaaaa accaagtgga gggtgaggtc cagatcgtgt    3540
caactgctac ccaaaccttc ctgcaacgt gcatcaatgg ggtatgctgg actgtctacc    3600
acggggccgg aacgaggacc atcgcatcac ccaagggtcc tgtcatccag atgtatacca    3660
atgtggacca agaccttgtg ggctggcccg ctcctcaagg ttcccgctca ttgacaccct    3720
gtacctgcgg ctcctcggac ctttacctgg tcacgaggca cgccgatgtc attcccgtgc    3780
gccggcgagg tgatagcagg ggtagcctgc tttcgccccg gcccatttcc tacttgaaag    3840
gctcctcggg gggtccgctg ttgtgccccg cgggacacgc cgtgggccta ttcagggccg    3900
cggtgtgcac ccgtggagtg gctaaagcgg tggactttat ccctgtggag aacctaggga    3960
caaccatgag atccccggtg ttcacggaca actcctctcc accagcagtg ccccagagct    4020
tccaggtggc ccacctgcat gctcccaccg gcagcggtaa gagcaccaag gtcccggctg    4080
cgtacgcagc ccagggctac aaggtgttgg tgctcaaccc ctctgttgct gcaacgctgg    4140
gctttggtgc ttacatgtcc aaggcccatg ggttgatcc taatatcagg accggggtga    4200
gaacaattac cactggcagc cccatcacgt actccaccta cggcaagttc cttgccgacg    4260
gcgggtgctc aggaggtgct tatgacataa taatttgtga cgagtgccac tccacggatg    4320
ccacatccat cttgggcatc ggcactgtcc ttgaccaagc agagactgcg ggggcgagac    4380
tggttgtgct cgccactgct accctcgg gctccgtcac tgtgtcccat cctaacatcg    4440
aggaggttgc tctgtccacc accggagaga tcccctttta cggcaaggct atccccctcg    4500
aggtgatcaa ggggggaaga catctcatct tctgccactc aaagaagaag tgcgacgagc    4560
tcgccgcgaa gctggtcgca ttgggcatca atgccgtggc ctactaccgc ggtcttgacg    4620
tgtctgtcat cccgaccagc ggcgatgttg tcgtcgtgtc gaccgatgct ctcatgactg    4680
gctttaccgg cgacttcgac tctgtgatag actgcaacac gtgtgtcact cagacagtcg    4740
atttcagcct tgaccctacc tttaccattg agacaaccac gctcccccag gatgctgtct    4800
ccaggactca acgccggggc aggactggca ggggaagcc aggcatctat agatttgtgg    4860
caccggggga gcgcccctcc ggcatgttcg actcgtccgt cctctgtgag tgctatgacg    4920
cgggctgtgc ttggtatgag ctcacgcccg ccgagactac agttaggcta cgagcgtaca    4980
tgaacacccc ggggcttccc gtgtgccagg accatcttga attttgggag ggcgtctta    5040 cgggcctcac tcatatagat gcccactttt tatcccgac aaagcagagt ggggagaact    5100
ttccttacct ggtagcgtac caagccaccg tgtgcgctag ggctcaagcc cctcccccat    5160
cgtgggacca gatgtggaag tgtttgatcc gccttaaacc caccctccat gggccaaacac    5220 ccctgctata cagactgggc gctgttcaga atgaagtcac cctgacgcac ccaatcacca    5280
```

-continued

```
aatacatcat gacatgcatg tcggccgacc tggaggtcgt cacgagcacc tgggtgctcg    5340
ttggcggcgt cctggctgct ctggccgcgt attgcctgtc aacaggctgc gtggtcatag    5400
tgggcaggat cgtcttgtcc gggaagccgg caattatacc tgacagggag gttctctacc    5460
aggagttcga tgagatggaa gagtgctctc agcacttacc gtacatcgag caagggatga    5520
tgctcgctga gcagttcaag cagaaggccc tcggcctcct gcagaccgcg tcccgccatg    5580
cagaggttat caccctgct gtccagacca actggcagaa actcgaggtc ttttgggcga    5640
agcacatgtg gaatttcatc agtgggatac aatacttggc gggcctgtca acgctgcctg    5700 gtaacccgc cattgcttca ttgatggctt ttacagctgc cgtcaccagc ccactaacca    5760
ctggccaaac cctcctcttc aacatattgg ggggtgggt ggctgcccag ctcgccgccc    5820
ccggtgccgc tactgccttt gtgggtgctg gcctagctgg cgccgccatc ggcagcgttg    5880
gactggggaa ggtcctcgtg gacattcttg cagggtatgg cgcgggcgtg gcgggagctc    5940
ttgtagcatt caagatcatg agcggtgagg tccctccac ggaggacctg gtcaatctgc    6000
tgcccgccat cctctcgcct ggagcccttg tagtcggtgt ggtctgcgca gcaatactgc    6060
gccggcacgt tggcccgggc gagggggcag tgcaatggat gaaccggcta atagccttcg    6120
cctcccgggg gaaccatgtt tcccccacgc actacgtgcc ggagagcgat gcagccgccc    6180
gcgtcactgc catactcagc agcctcactg taacccagct cctgaggcga ctgcatcagt    6240
ggataagctc ggagtgtacc actccatgct ccggttcctg gctaagggac atctgggact    6300
ggatatgcga ggtgctgagc gactttaaga cctggctgaa agccaagctc atgccacaac    6360
tgcctgggat tccctttgtg tcctgccagc gcgggtatag ggggtctgg cgaggagacg    6420 gcattatgca cactcgctgc cactgtggag ctgagatcac tggacatgtc aaaaacggga    6480
cgatgaggat cgtcggtcct aggacctgca ggaacatgtg gagtgggacg ttccccatta    6540
acgcctacac cacgggcccc tgtactcccc ttcctgcgcc gaactataag ttcgcgctgt    6600
ggagggtgtc tgcagaggaa tacgtggaga taaggcgggt gggggacttc cactacgtat    6660
cgggtatgac tactgacaat cttaaatgcc cgtgccagat cccatcgccc gaattttca    6720 cagaattgga cggggtgcgc ctacacaggt ttgcgccccc ttgcaagccc ttgctgcggg    6780
aggaggtatc attcagagta ggactccacg agtaccggt ggggtcgcaa ttaccttgcg    6840
agcccgaacc ggacgtagcc gtgttgacgt ccatgctcac tgatccctcc catataacag    6900
cagaggcggc cggagaagg ttggcgagag ggtcaccccc ttctatggcc agctcctcgg    6960
ctagccagct gtccgctcca tctctcaagg caacttgcac cgccaaccat gactcccctg    7020
acgccgagct catagaggct aacctcctgt ggaggcagga gatgggcggc aacatcacca    7080
gggttgagtc agagaacaaa gtggtgattc tggactcctt cgatccgctt gtggcagagg    7140
aggatgagcg ggaggtctcc gtacctgcag aaattctgcg gaagtctcgg agattcgccc    7200
gggccctgcc cgtctgggcg cggccggact acaacccccc gctagtagag acgtggaaaa    7260
agcctgacta cgaaccacct gtggtccatg gctgccgct accacctcca cggtcccctc    7320
ctgtgcctcc gcctcggaaa aagcgtacgg tggtcctcac cgaatcaacc ctatctactg    7380
ccttggccga gcttgccacc aaaagttttg gcagctcctc aacttccggc attacgggcg    7440
acaatacgac aacatcctct gagcccgccc cttctggctg ccccccgac tccgacgttg    7500 agtcctattc ttccatgccc cccctggagg gggagcctgg ggatccggat ctcagcgacg    7560
ggtcatggtc gacggtcagt agtgggggccg acacggaaga tgtcgtgtgc tgctcaatgt    7620
```

-continued

| | | | | |
|---|---|---|---|---|
| cttattcctg | dacaggcgca | ctcgtcaccc | cgtgcgctgc | ggaagaacaa aaactgccca | 7680 |
| tcaacgcact | gagcaactcg | ttgctacgcc | atcacaatct | ggtgtattcc accacttcac | 7740 |
| gcagtgcttg | ccaaaggcag | aagaaagtca | catttgacag | actgcaagtt ctggacagcc | 7800 |
| attaccagga | cgtgctcaag | gaggtcaaag | cagcggcgtc | aaaagtgaag gctaacttgc | 7860 |
| tatccgtaga | ggaagcttgc | agcctgacgc | ccccacattc | agccaaatcc aagtttggct | 7920 |
| atggggcaaa | agacgtccgt | tgccatgcca | gaaaggccgt | agcccacatc aactccgtgt | 7980 |
| ggaaagacct | tctggaagac | agtgtaacac | aatagacac | taccatcatg gccaagaacg | 8040 |
| aggttttctg | cgttcagcct | gagaaggggg | gtcgtaagcc | agctcgtctc atcgtgttcc | 8100 |
| ccgacctggg | cgtgcgcgtg | tgcgagaaga | tggccctgta | cgacgtggtt agcaagctcc | 8160 |
| ccctggccgt | gatgggaagc | tcctacggat | tccaatactc | accaggacag cgggttgaat | 8220 |
| tcctcgtgca | agcgtggaag | tccaagaaga | ccccgatggg | gttctcgtat gatacccgct | 8280 |
| gttttgactc | cacagtcact | gagagcgaca | tccgtacgga | ggaggcaatt taccaatgtt | 8340 |
| gtgacctgga | cccccaagcc | cgcgtggcca | tcaagtccct | cactgagagg ctttatgttg | 8400 |
| ggggccctct | taccaattca | agggggaaa | actgcggcta | ccgcaggtgc cgcgcgagcg | 8460 |
| gcgtactgac | aactagctgt | ggtaacaccc | tcacttgcta | catcaaggcc cgggcagcct | 8520 |
| gtcgagccgc | agggctccag | gactgcacca | tgctcgtgtg | tggcgacgac ttagtcgtta | 8580 |
| tctgtgaaag | tgcgggggtc | caggaggacg | cggcgagcct | gagagccttc acggaggcta | 8640 |
| tgaccaggta | ctccgccccc | cccgggggacc | ccccacaacc | agaatacgac ttggagctta | 8700 |
| taacatcatg | ctcctccaac | gtgtcagtcg | cccacgacgg | cgctggaaag agggtctact | 8760 |
| accttacccg | tgaccctaca | acccccctcg | cgagagccgc | gtgggagaca gcaagacaca | 8820 |
| ctccagtcaa | ttcctggcta | ggcaacataa | tcatgtttgc | ccccacactg tgggcgagga | 8880 |
| tgatactgat | gacccatttc | tttagcgtcc | tcatagccag | ggatcagctt gaacaggctc | 8940 |
| ttaactgtga | gatctacgga | gcctgctact | ccatagaacc | actggatcta cctccaatca | 9000 |
| ttcaaagact | ccatggcctc | agcgcatttt | cactccacag | ttactctcca ggtgaaatca | 9060 |
| atagggtggc | cgcatgcctc | agaaaacttg | gggtcccgcc | cttgcgagct tggagacacc | 9120 |
| gggcccggag | cgtccgcgct | aggcttctgt | ccagaggagg | cagggctgct atatgtggca | 9180 |
| agtacctctt | caactgggca | gtaagaacaa | agctcaaact | cactccaata gcggccgctg | 9240 |
| gccggctgga | cttgtccggt | tggttcacgg | ctggctacag | cggggagac atttatcaca | 9300 |
| gcgtgtctca | tgcccggccc | cgctggttct | ggttttgcct | actcctgctc gctgcagggg | 9360 |
| taggcatcta | cctcctcccc | aaccgatgaa | ggttggggta | acactccgg cctcttaagc | 9420 |
| catttcctgt | tttttttttt | tttttttttt | tttttttctt | tttttttttc tttcctttcc | 9480 |
| ttctttttttt | cctttctttt | tcccttcttt | aatggtggct | ccatcttagc cctagtcacg | 9540 |
| gctagctgtg | aaaggtccgt | gagccgcatg | actgcagaga | gtgctgatac tggcctctct | 9600 |
| gcagatcatg | t | | | | 9611 |

<210> SEQ ID NO 4
<211> LENGTH: 3015
<212> TYPE: PRT
<213> ORGANISM: Hepatitis C virus

<400> SEQUENCE: 4

Met Ser Thr Asn Pro Lys Pro Gln Arg Lys Thr Lys Arg Asn Thr Asn
1               5                   10                  15

```
Arg Arg Pro Gln Asp Val Lys Phe Pro Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Asn Asp Pro
            100                 105                 110

Arg His Arg Ser Arg Asn Val Gly Lys Val Ile Asp Thr Leu Thr Cys
        115                 120                 125

Gly Phe Ala Asp Leu Met Gly Tyr Ile Pro Val Val Gly Ala Pro Leu
    130                 135                 140

Gly Gly Val Ala Arg Ala Leu Ala His Gly Val Arg Val Leu Glu Asp
145                 150                 155                 160

Gly Val Asn Phe Ala Thr Gly Asn Leu Pro Gly Cys Ser Phe Ser Ile
                165                 170                 175

Phe Leu Leu Ala Leu Leu Ser Cys Ile Thr Thr Pro Val Ser Ala Ala
            180                 185                 190

Glu Val Lys Asn Ile Ser Thr Gly Tyr Met Val Thr Asn Asp Cys Thr
        195                 200                 205

Asn Asp Ser Ile Thr Trp Gln Leu Gln Ala Ala Val Leu His Val Pro
    210                 215                 220

Gly Cys Val Pro Cys Glu Lys Val Gly Asn Ala Ser Gln Cys Trp Ile
225                 230                 235                 240

Pro Val Ser Pro Asn Val Ala Val Gln Arg Pro Gly Ala Leu Thr Gln
                245                 250                 255

Gly Leu Arg Thr His Ile Asp Met Val Val Met Ser Ala Thr Leu Cys
            260                 265                 270

Ser Ala Leu Tyr Val Gly Asp Leu Cys Gly Gly Val Met Leu Ala Ala
        275                 280                 285

Gln Met Phe Ile Val Ser Pro Gln His His Trp Phe Val Gln Asp Cys
    290                 295                 300

Asn Cys Ser Ile Tyr Pro Gly Thr Ile Thr Gly His Arg Met Ala Trp
305                 310                 315                 320

Asp Met Met Met Asn Trp Ser Pro Thr Ala Thr Met Ile Leu Ala Tyr
                325                 330                 335

Ala Met Arg Val Pro Glu Val Ile Ile Asp Ile Ser Gly Ala His
            340                 345                 350

Trp Gly Val Met Phe Gly Leu Ala Tyr Phe Ser Met Gln Gly Ala Trp
        355                 360                 365

Ala Lys Val Val Ile Leu Leu Leu Ala Ala Gly Val Asp Ala Arg
    370                 375                 380

Thr His Thr Val Gly Gly Ser Ala Ala Gln Thr Thr Gly Arg Leu Thr
385                 390                 395                 400

Ser Leu Phe Asp Met Gly Pro Arg Gln Lys Ile Gln Leu Val Asn Thr
                405                 410                 415

Asn Gly Ser Trp His Ile Asn Arg Thr Ala Leu Asn Cys Asn Asp Ser
            420                 425                 430

Leu His Thr Gly Phe Ile Ala Ser Leu Phe Tyr Thr His Ser Phe Asn
```

-continued

```
                435                 440                 445
Ser Ser Gly Cys Pro Glu Arg Met Ser Ala Cys Arg Ser Ile Glu Ala
450                 455                 460

Phe Arg Val Gly Trp Gly Ala Leu Gln Tyr Glu Asp Asn Val Thr Asn
465                 470                 475                 480

Pro Glu Asp Met Arg Pro Tyr Cys Trp His Tyr Pro Pro Arg Gln Cys
                485                 490                 495

Gly Val Val Ser Ala Lys Thr Val Cys Gly Pro Val Tyr Cys Phe Thr
                500                 505                 510

Pro Ser Pro Val Val Gly Thr Thr Asp Arg Leu Gly Ala Pro Thr
        515                 520                 525

Tyr Thr Trp Gly Glu Asn Glu Thr Asp Val Phe Leu Leu Asn Ser Thr
        530                 535                 540

Arg Pro Pro Leu Gly Ser Trp Phe Gly Cys Thr Trp Met Asn Ser Ser
545                 550                 555                 560

Gly Tyr Thr Lys Thr Cys Gly Ala Pro Pro Cys Arg Thr Arg Ala Asp
                565                 570                 575

Phe Asn Ala Ser Thr Asp Leu Leu Cys Pro Thr Asp Cys Phe Arg Lys
                580                 585                 590

His Pro Asp Thr Thr Tyr Leu Lys Cys Gly Ser Gly Pro Trp Leu Thr
                595                 600                 605

Pro Arg Cys Leu Ile Asp Tyr Pro Tyr Arg Leu Trp His Tyr Pro Cys
        610                 615                 620

Thr Val Asn Tyr Thr Ile Phe Lys Ile Arg Met Tyr Val Gly Gly Val
625                 630                 635                 640

Glu His Arg Leu Thr Ala Ala Cys Asn Phe Thr Arg Gly Asp Arg Cys
                645                 650                 655

Asn Leu Glu Asp Arg Asp Arg Ser Gln Leu Ser Pro Leu Leu His Ser
                660                 665                 670

Thr Thr Glu Trp Ala Ile Leu Pro Cys Ser Tyr Ser Asp Leu Pro Ala
        675                 680                 685

Leu Ser Thr Gly Leu Leu His Leu His Gln Asn Ile Val Asp Val Gln
690                 695                 700

Phe Met Tyr Gly Leu Ser Pro Ala Leu Thr Lys Tyr Ile Val Arg Trp
705                 710                 715                 720

Glu Trp Val Ile Leu Leu Phe Leu Leu Leu Ala Asp Ala Arg Val Cys
                725                 730                 735

Ala Cys Leu Trp Met Leu Ile Leu Leu Gly Gln Ala Glu Ala Ala Leu
                740                 745                 750

Glu Lys Leu Val Ile Leu His Ala Ala Ser Ala Ala Ser Cys Asn Gly
                755                 760                 765

Phe Leu Tyr Phe Val Ile Phe Phe Val Ala Ala Trp Tyr Ile Lys Gly
                770                 775                 780

Arg Val Val Pro Leu Ala Thr Tyr Ser Leu Thr Gly Leu Trp Ser Phe
785                 790                 795                 800

Ser Leu Leu Leu Leu Ala Leu Pro Gln Gln Ala Tyr Ala Leu Asp Thr
                805                 810                 815

Glu Val Ala Ala Ser Cys Gly Gly Val Val Leu Val Gly Leu Met Ala
                820                 825                 830

Leu Thr Leu Ser Pro Tyr Tyr Lys Arg Tyr Ile Ser Trp Cys Met Trp
        835                 840                 845

Trp Leu Gln Tyr Phe Leu Thr Arg Val Glu Ala Gln Leu His Val Trp
850                 855                 860
```

-continued

```
Val Pro Pro Leu Asn Val Arg Gly Arg Asp Ala Val Ile Leu Leu
865                 870                 875                 880

Met Cys Val Val His Pro Thr Leu Val Phe Asp Ile Thr Lys Leu Leu
                885                 890                 895

Leu Ala Ile Phe Gly Pro Leu Trp Ile Leu Gln Ala Ser Leu Leu Lys
            900                 905                 910

Val Pro Tyr Phe Val Arg Val Gln Gly Leu Leu Arg Ile Cys Ala Leu
        915                 920                 925

Ala Arg Lys Ile Ala Gly Gly His Tyr Val Gln Met Ala Ile Ile Lys
    930                 935                 940

Leu Gly Ala Leu Thr Gly Thr Tyr Val Tyr Asn His Leu Thr Pro Leu
945                 950                 955                 960

Arg Asp Trp Ala His Asn Gly Leu Arg Asp Leu Ala Val Ala Val Glu
                965                 970                 975

Pro Val Val Phe Ser Arg Met Glu Thr Lys Leu Ile Thr Trp Gly Ala
            980                 985                 990

Asp Thr Ala Ala Cys Gly Asp Ile Ile Asn Gly Leu Pro Val Ser Ala
        995                 1000                1005

Arg Arg Gly Gln Glu Ile Leu Leu Gly Pro Ala Asp Gly Met Val Ser
    1010                1015                1020

Lys Gly Trp Arg Leu Leu Ala Pro Ile Thr Ala Tyr Ala Gln Gln Thr
1025                1030                1035                1040

Arg Gly Leu Leu Gly Cys Ile Ile Thr Ser Leu Thr Gly Arg Asp Lys
                1045                1050                1055

Asn Gln Val Glu Gly Glu Val Gln Ile Val Ser Thr Ala Thr Gln Thr
            1060                1065                1070

Phe Leu Ala Thr Cys Ile Asn Gly Val Cys Trp Thr Val Tyr His Gly
        1075                1080                1085

Ala Gly Thr Arg Thr Ile Ala Ser Pro Lys Gly Pro Val Ile Gln Met
    1090                1095                1100

Tyr Thr Asn Val Asp Gln Asp Leu Val Gly Trp Pro Ala Pro Gln Gly
1105                1110                1115                1120

Ser Arg Ser Leu Thr Pro Cys Thr Cys Gly Ser Ser Asp Leu Tyr Leu
                1125                1130                1135

Val Thr Arg His Ala Asp Val Ile Pro Val Arg Arg Arg Gly Asp Ser
            1140                1145                1150

Arg Gly Ser Leu Leu Ser Pro Arg Pro Ile Ser Tyr Leu Lys Gly Ser
        1155                1160                1165

Ser Gly Gly Pro Leu Leu Cys Pro Ala Gly His Ala Val Gly Leu Phe
    1170                1175                1180

Arg Ala Ala Val Cys Thr Arg Gly Val Ala Lys Ala Val Asp Phe Ile
1185                1190                1195                1200

Pro Val Glu Asn Leu Gly Thr Thr Met Arg Ser Pro Val Phe Thr Asp
                1205                1210                1215

Asn Ser Ser Pro Pro Ala Val Pro Gln Ser Phe Gln Val Ala His Leu
            1220                1225                1230

His Ala Pro Thr Gly Ser Gly Lys Ser Thr Lys Val Pro Ala Ala Tyr
        1235                1240                1245

Ala Ala Gln Gly Tyr Lys Val Leu Val Leu Asn Pro Ser Val Ala Ala
    1250                1255                1260

Thr Leu Gly Phe Gly Ala Tyr Met Ser Lys Ala His Gly Val Asp Pro
1265                1270                1275                1280
```

```
Asn Ile Arg Thr Gly Val Arg Thr Ile Thr Thr Gly Ser Pro Ile Thr
            1285                1290                1295

Tyr Ser Thr Tyr Gly Lys Phe Leu Ala Asp Gly Gly Cys Ser Gly Gly
            1300                1305                1310

Ala Tyr Asp Ile Ile Ile Cys Asp Glu Cys His Ser Thr Asp Ala Thr
            1315                1320                1325

Ser Ile Leu Gly Ile Gly Thr Val Leu Asp Gln Ala Glu Thr Ala Gly
            1330                1335                1340

Ala Arg Leu Val Val Leu Ala Thr Ala Thr Pro Pro Gly Ser Val Thr
1345                1350                1355                1360

Val Ser His Pro Asn Ile Glu Glu Val Ala Leu Ser Thr Thr Gly Glu
            1365                1370                1375

Ile Pro Phe Tyr Gly Lys Ala Ile Pro Leu Glu Val Ile Lys Gly Gly
            1380                1385                1390

Arg His Leu Ile Phe Cys His Ser Lys Lys Lys Cys Asp Glu Leu Ala
            1395                1400                1405

Ala Lys Leu Val Ala Leu Gly Ile Asn Ala Val Ala Tyr Tyr Arg Gly
            1410                1415                1420

Leu Asp Val Ser Val Ile Pro Thr Ser Gly Asp Val Val Val Val Ser
1425                1430                1435                1440

Thr Asp Ala Leu Met Thr Gly Phe Thr Gly Asp Phe Asp Ser Val Ile
            1445                1450                1455

Asp Cys Asn Thr Cys Val Thr Gln Thr Val Asp Phe Ser Leu Asp Pro
            1460                1465                1470

Thr Phe Thr Ile Glu Thr Thr Thr Leu Pro Gln Asp Ala Val Ser Arg
            1475                1480                1485

Thr Gln Arg Arg Gly Arg Thr Gly Arg Gly Lys Pro Gly Ile Tyr Arg
            1490                1495                1500

Phe Val Ala Pro Gly Glu Arg Pro Ser Gly Met Phe Asp Ser Ser Val
1505                1510                1515                1520

Leu Cys Glu Cys Tyr Asp Ala Gly Cys Ala Trp Tyr Glu Leu Thr Pro
            1525                1530                1535

Ala Glu Thr Thr Val Arg Leu Arg Ala Tyr Met Asn Thr Pro Gly Leu
            1540                1545                1550

Pro Val Cys Gln Asp His Leu Glu Phe Trp Glu Gly Val Phe Thr Gly
            1555                1560                1565

Leu Thr His Ile Asp Ala His Phe Leu Ser Gln Thr Lys Gln Ser Gly
            1570                1575                1580

Glu Asn Phe Pro Tyr Leu Val Ala Tyr Gln Ala Thr Val Cys Ala Arg
1585                1590                1595                1600

Ala Gln Ala Pro Pro Ser Trp Asp Gln Met Trp Lys Cys Leu Ile
            1605                1610                1615

Arg Leu Lys Pro Thr Leu His Gly Pro Thr Pro Leu Leu Tyr Arg Leu
            1620                1625                1630

Gly Ala Val Gln Asn Glu Val Thr Leu Thr His Pro Ile Thr Lys Tyr
            1635                1640                1645

Ile Met Thr Cys Met Ser Ala Asp Leu Glu Val Val Thr Ser Thr Trp
            1650                1655                1660

Val Leu Val Gly Gly Val Leu Ala Ala Leu Ala Ala Tyr Cys Leu Ser
1665                1670                1675                1680

Thr Gly Cys Val Val Ile Val Gly Arg Ile Val Leu Ser Gly Lys Pro
            1685                1690                1695

Ala Ile Ile Pro Asp Arg Glu Val Leu Tyr Gln Glu Phe Asp Glu Met
```

-continued

```
                1700                1705                1710
Glu Glu Cys Ser Gln His Leu Pro Tyr Ile Glu Gln Gly Met Met Leu
    1715                1720                1725

Ala Glu Gln Phe Lys Gln Lys Ala Leu Gly Leu Leu Gln Thr Ala Ser
    1730                1735                1740

Arg His Ala Glu Val Ile Thr Pro Ala Val Gln Thr Asn Trp Gln Lys
1745                1750                1755                1760

Leu Glu Val Phe Trp Ala Lys His Met Trp Asn Phe Ile Ser Gly Ile
        1765                1770                1775

Gln Tyr Leu Ala Gly Leu Ser Thr Leu Pro Gly Asn Pro Ala Ile Ala
        1780                1785                1790

Ser Leu Met Ala Phe Thr Ala Ala Val Thr Ser Pro Leu Thr Thr Gly
        1795                1800                1805

Gln Thr Leu Leu Phe Asn Ile Leu Gly Gly Trp Val Ala Ala Gln Leu
    1810                1815                1820

Ala Ala Pro Gly Ala Ala Thr Ala Phe Val Gly Ala Gly Leu Ala Gly
1825                1830                1835                1840

Ala Ala Ile Gly Ser Val Gly Leu Gly Lys Val Leu Val Asp Ile Leu
        1845                1850                1855

Ala Gly Tyr Gly Ala Gly Val Ala Gly Ala Leu Val Ala Phe Lys Ile
        1860                1865                1870

Met Ser Gly Glu Val Pro Ser Thr Glu Asp Leu Val Asn Leu Leu Pro
        1875                1880                1885

Ala Ile Leu Ser Pro Gly Ala Leu Val Val Gly Val Val Cys Ala Ala
        1890                1895                1900

Ile Leu Arg Arg His Val Gly Pro Gly Glu Gly Ala Val Gln Trp Met
1905                1910                1915                1920

Asn Arg Leu Ile Ala Phe Ala Ser Arg Gly Asn His Val Ser Pro Thr
            1925                1930                1935

His Tyr Val Pro Glu Ser Asp Ala Ala Ala Arg Val Thr Ala Ile Leu
        1940                1945                1950

Ser Ser Leu Thr Val Thr Gln Leu Leu Arg Arg Leu His Gln Trp Ile
        1955                1960                1965

Ser Ser Glu Cys Thr Thr Pro Cys Ser Gly Ser Trp Leu Arg Asp Ile
    1970                1975                1980

Trp Asp Trp Ile Cys Glu Val Leu Ser Asp Phe Lys Thr Trp Leu Lys
1985                1990                1995                2000

Ala Lys Leu Met Pro Gln Leu Pro Gly Ile Pro Phe Val Ser Cys Gln
            2005                2010                2015

Arg Gly Tyr Arg Gly Val Trp Arg Gly Asp Gly Ile Met His Thr Arg
            2020                2025                2030

Cys His Cys Gly Ala Glu Ile Thr Gly His Val Lys Asn Gly Thr Met
        2035                2040                2045

Arg Ile Val Gly Pro Arg Thr Cys Arg Asn Met Trp Ser Gly Thr Phe
    2050                2055                2060

Pro Ile Asn Ala Tyr Thr Thr Gly Pro Cys Thr Pro Leu Pro Ala Pro
2065                2070                2075                2080

Asn Tyr Lys Phe Ala Leu Trp Arg Val Ser Ala Glu Glu Tyr Val Glu
            2085                2090                2095

Ile Arg Arg Val Gly Asp Phe His Tyr Val Ser Gly Met Thr Thr Asp
            2100                2105                2110

Asn Leu Lys Cys Pro Cys Gln Ile Pro Ser Pro Glu Phe Phe Thr Glu
        2115                2120                2125
```

-continued

```
Leu Asp Gly Val Arg Leu His Arg Phe Ala Pro Pro Cys Lys Pro Leu
    2130                2135                2140
Leu Arg Glu Glu Val Ser Phe Arg Val Gly Leu His Glu Tyr Pro Val
2145                2150                2155                2160
Gly Ser Gln Leu Pro Cys Glu Pro Glu Pro Asp Val Ala Val Leu Thr
                2165                2170                2175
Ser Met Leu Thr Asp Pro Ser His Ile Thr Ala Glu Ala Ala Gly Arg
            2180                2185                2190
Arg Leu Ala Arg Gly Ser Pro Pro Ser Met Ala Ser Ser Ala Ser
            2195                2200                2205
Gln Leu Ser Ala Pro Ser Leu Lys Ala Thr Cys Thr Ala Asn His Asp
    2210                2215                2220
Ser Pro Asp Ala Glu Leu Ile Glu Ala Asn Leu Leu Trp Arg Gln Glu
2225                2230                2235                2240
Met Gly Gly Asn Ile Thr Arg Val Glu Ser Glu Asn Lys Val Val Ile
                2245                2250                2255
Leu Asp Ser Phe Asp Pro Leu Val Ala Glu Glu Asp Glu Arg Glu Val
            2260                2265                2270
Ser Val Pro Ala Glu Ile Leu Arg Lys Ser Arg Arg Phe Ala Arg Ala
    2275                2280                2285
Leu Pro Val Trp Ala Arg Pro Asp Tyr Asn Pro Pro Leu Val Glu Thr
    2290                2295                2300
Trp Lys Lys Pro Asp Tyr Glu Pro Pro Val Val His Gly Cys Pro Leu
2305                2310                2315                2320
Pro Pro Pro Arg Ser Pro Pro Val Pro Pro Pro Arg Lys Lys Arg Thr
                2325                2330                2335
Val Val Leu Thr Glu Ser Thr Leu Ser Thr Ala Leu Ala Glu Leu Ala
            2340                2345                2350
Thr Lys Ser Phe Gly Ser Ser Ser Thr Ser Gly Ile Thr Gly Asp Asn
    2355                2360                2365
Thr Thr Thr Ser Ser Glu Pro Ala Pro Ser Gly Cys Pro Pro Asp Ser
    2370                2375                2380
Asp Val Glu Ser Tyr Ser Ser Met Pro Pro Leu Glu Gly Glu Pro Gly
2385                2390                2395                2400
Asp Pro Asp Leu Ser Asp Gly Ser Trp Ser Thr Val Ser Ser Gly Ala
                2405                2410                2415
Asp Thr Glu Asp Val Val Cys Cys Ser Met Ser Tyr Ser Trp Thr Gly
            2420                2425                2430
Ala Leu Val Thr Pro Cys Ala Ala Glu Glu Gln Lys Leu Pro Ile Asn
    2435                2440                2445
Ala Leu Ser Asn Ser Leu Leu Arg His His Asn Leu Val Tyr Ser Thr
    2450                2455                2460
Thr Ser Arg Ser Ala Cys Gln Arg Gln Lys Lys Val Thr Phe Asp Arg
2465                2470                2475                2480
Leu Gln Val Leu Asp Ser His Tyr Gln Asp Val Leu Lys Glu Val Lys
                2485                2490                2495
Ala Ala Ala Ser Lys Val Lys Ala Asn Leu Leu Ser Val Glu Glu Ala
            2500                2505                2510
Cys Ser Leu Thr Pro Pro His Ser Ala Lys Ser Lys Phe Gly Tyr Gly
    2515                2520                2525
Ala Lys Asp Val Arg Cys His Ala Arg Lys Ala Val Ala His Ile Asn
    2530                2535                2540
```

```
Ser Val Trp Lys Asp Leu Leu Glu Asp Ser Val Thr Pro Ile Asp Thr
2545                2550                2555                2560

Thr Ile Met Ala Lys Asn Glu Val Phe Cys Val Gln Pro Glu Lys Gly
            2565                2570                2575

Gly Arg Lys Pro Ala Arg Leu Ile Val Phe Pro Asp Leu Gly Val Arg
        2580                2585                2590

Val Cys Glu Lys Met Ala Leu Tyr Asp Val Val Ser Lys Leu Pro Leu
    2595                2600                2605

Ala Val Met Gly Ser Ser Tyr Gly Phe Gln Tyr Ser Pro Gly Gln Arg
2610                2615                2620

Val Glu Phe Leu Val Gln Ala Trp Lys Ser Lys Lys Thr Pro Met Gly
2625                2630                2635                2640

Phe Ser Tyr Asp Thr Arg Cys Phe Asp Ser Thr Val Thr Glu Ser Asp
            2645                2650                2655

Ile Arg Thr Glu Glu Ala Ile Tyr Gln Cys Cys Asp Leu Asp Pro Gln
        2660                2665                2670

Ala Arg Val Ala Ile Lys Ser Leu Thr Glu Arg Leu Tyr Val Gly Gly
    2675                2680                2685

Pro Leu Thr Asn Ser Arg Gly Glu Asn Cys Gly Tyr Arg Arg Cys Arg
2690                2695                2700

Ala Ser Gly Val Leu Thr Thr Ser Cys Gly Asn Thr Leu Thr Cys Tyr
2705                2710                2715                2720

Ile Lys Ala Arg Ala Ala Cys Arg Ala Ala Gly Leu Gln Asp Cys Thr
            2725                2730                2735

Met Leu Val Cys Gly Asp Asp Leu Val Val Ile Cys Glu Ser Ala Gly
        2740                2745                2750

Val Gln Glu Asp Ala Ala Ser Leu Arg Ala Phe Thr Glu Ala Met Thr
    2755                2760                2765

Arg Tyr Ser Ala Pro Pro Gly Asp Pro Pro Gln Pro Glu Tyr Asp Leu
2770                2775                2780

Glu Leu Ile Thr Ser Cys Ser Ser Asn Val Ser Val Ala His Asp Gly
2785                2790                2795                2800

Ala Gly Lys Arg Val Tyr Tyr Leu Thr Arg Asp Pro Thr Thr Pro Leu
            2805                2810                2815

Ala Arg Ala Ala Trp Glu Thr Ala Arg His Thr Pro Val Asn Ser Trp
        2820                2825                2830

Leu Gly Asn Ile Ile Met Phe Ala Pro Thr Leu Trp Ala Arg Met Ile
    2835                2840                2845

Leu Met Thr His Phe Phe Ser Val Leu Ile Ala Arg Asp Gln Leu Glu
2850                2855                2860

Gln Ala Leu Asn Cys Glu Ile Tyr Gly Ala Cys Tyr Ser Ile Glu Pro
2865                2870                2875                2880

Leu Asp Leu Pro Pro Ile Ile Gln Arg Leu His Gly Leu Ser Ala Phe
            2885                2890                2895

Ser Leu His Ser Tyr Ser Pro Gly Glu Ile Asn Arg Val Ala Ala Cys
        2900                2905                2910

Leu Arg Lys Leu Gly Val Pro Pro Leu Arg Ala Trp Arg His Arg Ala
    2915                2920                2925

Arg Ser Val Arg Ala Arg Leu Leu Ser Arg Gly Gly Arg Ala Ala Ile
2930                2935                2940

Cys Gly Lys Tyr Leu Phe Asn Trp Ala Val Arg Thr Lys Leu Lys Leu
2945                2950                2955                2960

Thr Pro Ile Ala Ala Ala Gly Arg Leu Asp Leu Ser Gly Trp Phe Thr
```

-continued

```
                2965              2970              2975
Ala Gly Tyr Ser Gly Gly Asp Ile Tyr His Ser Val Ser His Ala Arg
           2980              2985              2990

Pro Arg Trp Phe Trp Phe Cys Leu Leu Leu Leu Ala Ala Gly Val Gly
      2995              3000              3005

Ile Tyr Leu Leu Pro Asn Arg
      3010              3015

<210> SEQ ID NO 5
<211> LENGTH: 9611
<212> TYPE: DNA
<213> ORGANISM: Hepatitis C virus

<400> SEQUENCE: 5
gccagccccc tgatgggggc gacactccac catgaatcac tcccctgtga ggaactactg      60
tcttcacgca gaaagcgtct agccatggcg ttagtatgag tgtcgtgcag cctccaggac     120 ccccctccc gggagagcca tagtggtctg cggaaccggt gagtacaccg gaattgccgg     180
gaagactggg tcctttcttg gataaaccca ctctatgccc ggccatttgg gcgtgccccc     240
gcaagactgc tagccgagta gcgttgggtt gcgaaaggcc ttgtggtact gcctgatagg     300
gtgcttgcga gtgccccggg aggtctcgta gaccgtgcac catgagcaca atcctaaac     360 ctcaaagaaa accaaaaga acaccaacc gtcgcccaca agacgttaag tttccgggcg     420
gcggccagat cgttggcgga gtatacttgt tgccgcgcag gggccccagg ttgggtgtgc     480
gcgcgacaag gaagacttcg gagcggtccc agccacgtgg aaggcgccag cccatcccta     540
aagatcggcg ctccactggc aaatcctggg gaaaaccagg atacccctgg cccctatacg     600
ggaatgaggg actcggctgg gcaggatggc tcctgtcccc ccgaggttcc cgtccctctt     660
ggggccccaa tgaccccgg cataggtcgc gcaacgtggg taaggtcatc gatacccta      720 cgtgcggctt gccgacctc atggggtaca tccctgtcgt gggcgccccg ctcggcggcg     780
tcgccagagc tctcgcgcat ggcgtgagag tcctggagga cggggttaat tttgcaacag     840
ggaacttacc cggttgctcc ttttctatct tcttgctggc cctgctgtcc tgcatcacca     900
ccccggtctc cgctgccgaa gtgaagaaca tcagtaccgg ctacatggtg actaacgact     960
gcaccaatga cagcattacc tggcagctcc aggctgctgt cctccacgtc ccgggtgcg    1020 tcccgtgcga gaaagtgggg aatgcatctc agtgctggat accggtctca ccgaatgtgg    1080
ccgtgcagcg gccccggcgcc ctcacgcagg gcttgcggac gcacatcgac atggttgtga    1140
tgtccgccac gctctgctct gccctctacg tggggacct ctgcggtggg gtgatgctcg    1200
cagcccaaat gttcattgtc tcgccgcagc accactggtt tgtccaagac tgcaattgct    1260
ccatctaccc tggtaccatc actggacacc gcatggcatg gacatgatg atgaactggt    1320 cgccacggc taccatgatc ttggcgtacg cgatgcgtgt ccccgaggtc attatagaca    1380
tcattagcgg ggctcattgg ggcgtcatgt tcggcttggc ctacttctct atgcagggag    1440
cgtgggcgaa agtcgttgtc atccttctgt tggccgccgg ggtggacgcg cgcacccata    1500
ctgttggggg ttctgccgcg cagaccaccg ggcgcctcac cagcttattt gacatgggcc    1560
ccaggcagaa aatccagctc gttaacacca atggcagctg gcacatcaac gcaccgccc    1620 tgaactgcaa tgactccttg cacaccggct ttatcgcgtc tctgttctac acccacagct    1680
tcaactcgtc aggatgtccc gaacgcatgt ccgcctgccg cagtatcgag gccttccggg    1740
tgggatgggg cgccttgcaa tatgaggata atgtcaccaa tccagaggat atgagaccct    1800
```

-continued

```
attgctggca ctacccacca aggcagtgtg gcgtggtctc cgcgaagact gtgtgtggcc    1860
cagtgtactg tttcaccccc agcccagtgg tagtgggcac gaccgacagg cttggagcgc    1920
ccacttacac gtgggggggag aatgagacag atgtcttcct attgaacagc actcgaccac   1980
cgctggggtc atggttcggc tgcacgtgga tgaactcttc tggctacacc aagacttgcg    2040
gcgcaccacc ctgccgtact agagctgact caacgccag cacggacctg ttgtgcccca     2100
cggactgttt taggaagcat cctgatacca cttacctcaa atgcggctct gggccctggc    2160
tcacgccaag gtgcctgatc gactacccct acaggctctg cattacccc tgcacagtta    2220 actataccat cttcaaaata aggatgtatg tgggaggggt tgagcacagg ctcacggctg    2280
catgcaattt cactcgtggg gatcgttgca acttggagga cagagacaga agtcaactgt    2340
ctcctttgtt gcactccacc acggaatggg ccattttacc ttgctcttac tcggacctgc    2400
ccgccttgtc gactggtctt ctccacctcc accaaaacat cgtggacgta caattcatgt    2460
atggcctatc acctgccctc acaaaataca tcgtccgatg ggagtgggta atactcttat    2520
tcctgctctt agcggacgcc agggtttgcg cctgcttatg gatgctcatc ttgttgggcc    2580
aggccgaagc agctttggag aacctcgtaa tactcaatgc agcatccctg ccgggacgc    2640 acggtcttgt gtccttcctc gtgttcttct gctttgcgtg gtatctgaag ggtaggtggg    2700
tgcccggagc ggtctacgcc ctctacggga tgtggcctct cctcctgctc ctgctggcgt    2760
tgcctcagcg ggcatatgca ctggacacgg aggtggccgc gtcgtgtggc ggcgttgttc    2820
ttgtcgggtt aatggcgctg actctgtcgc catattacaa gcgctatatc agctggtgca    2880
tgtggtggct tcagtatttt ctgaccagag tagaagcgca actgcacgtg tgggttcccc    2940
ccctcaacgt ccgggggggg gcgcgatgccg tcatcttact catgtgtgta gtacacccga    3000
ccctggtatt tgacatcacc aaactactcc tggccatctt cggacccctt tggattcttc    3060
aagccagttt gcttaaagtc ccctacttcg tgcgcgttca aggccttctc cggatctgcg    3120
cgctagcgcg gaagatagcc ggaggtcatt acgtgcaaat ggccatcatc aagttagggg    3180
cgcttactgg cacctatgtg tataaccatc tcacccctct tcgagactgg gcgcacaacg    3240
gcctgcgaga tctggccgtg gctgtggaac cagtcgtctt ctcccgaatg gagaccaagc    3300
tcatcacgtg gggggcagat accgccgcgt gcggtgacat catcaacggc ttgcccgtct    3360
ctgcccgtag gggccaggag atactgcttg gccagccga cggaatggtc tccaagggt    3420 ggaggttgct ggcgcccatc acggcgtacg cccagcagac gagaggcctc ctagggtgta    3480
taatcaccag cctgactggc cgggacaaaa ccaagtgga gggtgaggtc cagatcgtgt     3540
caactgctac ccaaaccttc ctggcaacgt gcatcaatgg ggtatgctgg actgtctacc    3600
acggggccgg aacgaggacc atcgcatcac ccaagggtcc tgtcatccag atgtatacca    3660
atgtggacca agaccttgtg ggctggcccg ctcctcaagg ttcccgctca ttgacaccct    3720
gtacctgcgg ctcctcggac ctttacctgg tcacgaggca cgccgatgtc attcccgtgc    3780
gccggcgagg tgatagcagg ggtagcctgc tttcgccccg gcccatttcc tacttgaaag    3840
gctcctcggg gggtccgctg ttgtgccccg cgggacacgc cgtgggccta ttcagggccg    3900
cggtgtgcac ccgtggagtg gctaaagcgg tggactttat ccctgtggag aacctaggga    3960
caaccatgag atccccggtg ttcacggaca actcctctcc accagcagtg ccccagagct    4020
tccaggtggc ccacctgcat gctcccaccg gcagcggtaa gagcaccaag gtcccggctg    4080
cgtacgcagc ccaggctac aaggtgttgg tgctcaaccc ctctgttgct gcaacgctgg     4140
gctttggtgc ttacatgtcc aaggcccatg gggttgatcc taatatcagg accggggtga    4200
```

```
gaacaattac cactggcagc cccatcacgt actccaccta cggcaagttc cttgccgacg    4260
gcgggtgctc aggaggtgct tatgacataa taatttgtga cgagtgccac tccacggatg    4320
ccacatccat cttgggcatc ggcactgtcc ttgaccaagc agagactgcg ggggcgagac    4380
tggttgtgct cgccactgct acccctccgg gctccgtcac tgtgtcccat cctaacatcg    4440
aggaggttgc tctgtccacc accggagaga tccccttttta cggcaaggct atccccctcg    4500
aggtgatcaa ggggggaaga catctcatct tctgccactc aaagaagaag tgcgacgagc    4560
tcgccgcgaa gctggtcgca ttgggcatca atgccgtggc ctactaccgc ggtcttgacg    4620
tgtctgtcat cccgaccagc ggcgatgttg tcgtcgtgtc gaccgatgct ctcatgactg    4680
gctttaccgg cgacttcgac tctgtgatag actgcaacac gtgtgtcact cagacagtcg    4740
atttcagcct tgaccctacc tttaccattg agacaaccac gctcccccag gatgctgtct    4800
ccaggactca acgccggggc aggactggca gggggaagcc aggcatctat agatttgtgg    4860
caccggggga gcgcccctcc ggcatgttcg actcgtccgt cctctgtgag tgctatgacg    4920
cgggctgtgc ttggtatgag ctcacgcccg ccgagactac agttaggcta cgagcgtaca    4980
tgaacacccc gggcttccc gtgtgccagg accatcttga atttgggag gcgtctttta    5040 cgggcctcac tcatatagat gcccacttt tatcccagac aaagcagagt ggggagaact    5100
ttccttacct ggtagcgtac caagccaccg tgtgcgctag ggctcaagcc cctcccccat    5160
cgtgggacca gatgtggaag tgtttgatcc gccttaaacc caccctccat gggccaacac    5220
ccctgctata cagactgggc gctgttcaga atgaagtcac cctgacgcac ccaatcacca    5280
aatacatcat gacatgcatg tcggccgacc tggaggtcgt cacgagcacc tgggtgctcg    5340
ttggcggcgt cctggctgct ctggccgcgt attgcctgtc aacaggctgc gtggtcatag    5400
tgggcaggat cgtcttgtcc gggaagccgg caattatacc tgacagggag gttctctacc    5460
aggagttcga tgagatggaa gagtgctctc agcacttacc gtacatcgag caagggatga    5520
tgctcgctga gcagttcaag cagaaggccc tcggcctcct gcagaccgcg tcccgccatg    5580
cagaggttat cacccctgct gtccagacca actggcagaa actcgaggtc ttttgggcga    5640
agcacatgtg gaatttcatc agtgggatac aatacttggc gggcctgtca acgctgcctg    5700 gtaacccgc cattgcttca ttgatggctt ttacagctgc cgtcaccagc ccactaacca    5760
ctggccaaac cctcctcttc aacatattgg ggggtgggt ggctgcccag ctcgccgccc    5820
ccggtgccgc tactgccttt gtgggtgctg gcctagctgg cgccgccatc ggcagcgttg    5880
gactggggaa ggtcctcgtg gacattcttg cagggtatgg cgcgggcgtg gcgggagctc    5940
ttgtagcatt caagatcatg agcggtgagg tcccctccac ggaggacctg gtcaatctgc    6000
tgcccgccat cctctcgcct ggagcccttg tagtcggtgt ggtctgcgca gcaatactgc    6060
gccggcacgt tggcccgggc gagggggcag tgcaatggat gaaccggcta atagccttcg    6120
cctcccgggg gaaccatgtt tcccccacgc actacgtgcc ggagagcgat gcagccgccc    6180
gcgtcactgc catactcagc agcctcactg taacccagct cctgaggcga ctgcatcagt    6240
ggataagctc ggagtgtacc actccatgct ccggttcctg ctaagggac atctgggact    6300 ggatatgcga ggtgctgagc gactttaaga cctggctgaa agccaagctc atgccacaac    6360
tgcctgggat tccctttgtg tcctgccagc gcgggtatag gggggtctgg cgaggagacg    6420
gcattatgca cactcgctgc cactgtggag ctgagatcac tggacatgtc aaaaacggga    6480
cgatgaggat cgtcggtcct aggacctgca ggaacatgtg gagtgggacg ttccccatta    6540
```

```
acgcctacac cacgggcccc tgtactcccc ttcctgcgcc gaactataag ttcgcgctgt   6600
ggagggtgtc tgcagaggaa tacgtggaga taaggcgggt gggggacttc cactacgtat   6660
cgggtatgac tactgacaat cttaaatgcc cgtgccagat cccatcgccc gaattttttca  6720 cagaattgga cggggtgcgc ctacacaggt ttgcgccccc ttgcaagccc ttgctgcggg   6780
aggaggtatc attcagagta ggactccacg agtacccgt ggggtcgcaa ttaccttgcg    6840
agcccgaacc ggacgtagcc gtgttgacgt ccatgctcac tgatccctcc catataacag   6900
cagaggcggc cggagaagg ttggcgagag ggtcaccccc ttctatggcc agctcctcgg    6960
ctagccagct gtccgctcca tctctcaagg caacttgcac cgccaaccat gactcccctg   7020
acgccgagct catagaggct aacctcctgt ggaggcagga gatgggcggc aacatcacca   7080
gggttgagtc agagaacaaa gtggtgattc tggactcctt cgatccgctt gtggcagagg   7140
aggatgagcg ggaggtctcc gtacctgcag aaattctgcg gaagtctcgg agattcgccc   7200 gggcctgcc cgtctgggcg cggccggact acaaccccc gctagtagag acgtggaaaa    7260
agcctgacta cgaaccacct gtggtccatg gctgcccgct accacctcca cggtcccctc   7320
ctgtgcctcc gcctcggaaa aagcgtacgg tggtcctcac cgaatcaacc ctatctactg   7380
ccttggccga gcttgccacc aaaagttttg gcagctcctc aacttccggc attacgggcg   7440
acaatacgac aacatcctct gagcccgccc cttctggctg cccccccgac tccgacgttg   7500
agtcctattc ttccatgccc ccctggagg gggagcctgg ggatccggat ctcagcgacg    7560
ggtcatggtc gacggtcagt agtggggccg acacggaaga tgtcgtgtgc tgctcaatgt   7620
cttattcctg gacaggcgca ctcgtcaccc cgtgcgctgc ggaagaacaa aaactgccca   7680
tcaacgcact gagcaactcg ttgctacgcc atcacaatct ggtgtattcc accacttcac   7740
gcagtgcttg ccaaaggcag aagaaagtca catttgacag actgcaagtt ctggacagcc   7800
attaccagga cgtgctcaag gaggtcaaag cagcggcgtc aaaagtgaag gctaacttgc   7860
tatccgtaga ggaagcttgc agcctgacgc ccccacattc agccaaatcc aagtttggct   7920
atggggcaaa agacgtccgt tgccatgcca gaaaggccgt agcccacatc aactccgtgt   7980
ggaaagacct tctggaagac agtgtaacac caatagacac taccatcatg gccaagaacg   8040
aggttttctg cgttcagcct gagaagggg gtcgtaagcc agctcgtctc atcgtgttcc    8100
ccgacctggg cgtgcgcgtg tgcgagaaga tggccctgta cgacgtggtt agcaagctcc   8160
ccctggccgt gatgggaagc tcctacggat tccaatactc accaggacag cgggttgaat   8220
tcctcgtgca agcgtggaag tccaagaaga ccccgatggg gttctcgtat gatacccgct   8280
gttttgactc cacagtcact gagagcgaca tccgtacgga ggaggcaatt taccaatgtt   8340
gtgacctgga cccccaagcc cgcgtggcca tcaagtccct cactgagagg ctttatgttg   8400
ggggccctct taccaattca agggggggaaa actgcggcta ccgcaggtgc cgcgcgagcg   8460
gcgtactgac aactagctgt ggtaacaccc tcacttgcta catcaaggcc cgggcagcct   8520
gtcgagccgc agggctccag gactgcacca tgctcgtgtg tggcgacgac ttagtcgtta   8580
tctgtgaaag tgcgggggtc caggaggacg cggcagcct gagagccttc acggaggcta    8640
tgaccaggta ctccgccccc cccggggacc cccacaacc agaatacgac ttggagctta   8700
taacatcatg ctcctccaac gtgtcagtcg cccacgacgg cgctggaaag agggtctact   8760
accttacccg tgaccctaca acccccctcg cgagagccgc gtgggagaca gcaagacaca   8820
ctccagtcaa ttcctggcta ggcaacataa tcatgtttgc ccccacactg tgggcgagga   8880
tgatactgat gacccatttc tttagcgtcc tcatagccag ggatcagctt gaacaggctc   8940
```

```
ttaactgtga gatctacgga gcctgctact ccatagaacc actggatcta cctccaatca    9000
ttcaaagact ccatggcctc agcgcatttt cactccacag ttactctcca ggtgaaatca    9060 ataggggtggc cgcatgcctc agaaaacttg gggtcccgcc cttgcgagct tggagacacc   9120
gggcccggag cgtccgcgct aggcttctgt ccagaggagg cagggctgct atatgtggca    9180
agtacctctt caactgggca gtaagaacaa agctcaaact cactccaata gcggccgctg    9240
gccggctgga cttgtccggt tggttcacgg ctggctacag cgggggagac atttatcaca    9300
gcgtgtctca tgcccggccc cgctggttct ggttttgcct actcctgctc gctgcagggg    9360
taggcatcta cctcctcccc aaccgatgaa ggttggggta acactccgg cctcttaagc     9420 catttcctgt tttttttttt tttttttttt tttttttctt tttttttttc tttccttttcc   9480 ttcttttttt cctttctttt tcccttcttt aatggtggcc ccatcttagc cctagtcacg    9540
gctagctgtg aaaggtccgt gagccgcatg actgcagaga gtgctgatac tggcctctct    9600
gcagatcatg t                                                         9611
```

<210> SEQ ID NO 6
<211> LENGTH: 3015
<212> TYPE: PRT
<213> ORGANISM: Hepatitis C virus

<400> SEQUENCE: 6

```
Met Ser Thr Asn Pro Lys Pro Gln Arg Lys Thr Lys Arg Asn Thr Asn
  1               5                  10                  15

Arg Arg Pro Gln Asp Val Lys Phe Pro Gly Gly Gly Gln Ile Val Gly
                 20                  25                  30

Gly Val Tyr Leu Leu Pro Arg Arg Gly Pro Arg Leu Gly Val Arg Ala
             35                  40                  45

Thr Arg Lys Thr Ser Glu Arg Ser Gln Pro Arg Gly Arg Arg Gln Pro
         50                  55                  60

Ile Pro Lys Asp Arg Arg Ser Thr Gly Lys Ser Trp Gly Lys Pro Gly
 65                  70                  75                  80

Tyr Pro Trp Pro Leu Tyr Gly Asn Glu Gly Leu Gly Trp Ala Gly Trp
                 85                  90                  95

Leu Leu Ser Pro Arg Gly Ser Arg Pro Ser Trp Gly Pro Asn Asp Pro
            100                 105                 110

Arg His Arg Ser Arg Asn Val Gly Lys Val Ile Asp Thr Leu Thr Cys
            115                 120                 125

Gly Phe Ala Asp Leu Met Gly Tyr Ile Pro Val Val Gly Ala Pro Leu
        130                 135                 140

Gly Gly Val Ala Arg Ala Leu Ala His Gly Val Arg Val Leu Glu Asp
145                 150                 155                 160

Gly Val Asn Phe Ala Thr Gly Asn Leu Pro Gly Cys Ser Phe Ser Ile
                165                 170                 175

Phe Leu Leu Ala Leu Leu Ser Cys Ile Thr Thr Pro Val Ser Ala Ala
            180                 185                 190

Glu Val Lys Asn Ile Ser Thr Gly Tyr Met Val Thr Asn Asp Cys Thr
            195                 200                 205

Asn Asp Ser Ile Thr Trp Gln Leu Gln Ala Ala Val Leu His Val Pro
        210                 215                 220

Gly Cys Val Pro Cys Glu Lys Val Gly Asn Ala Ser Gln Cys Trp Ile
225                 230                 235                 240

Pro Val Ser Pro Asn Val Ala Val Gln Arg Pro Gly Ala Leu Thr Gln
```

-continued

```
                245                 250                 255
Gly Leu Arg Thr His Ile Asp Met Val Met Ser Ala Thr Leu Cys
                260                 265                 270

Ser Ala Leu Tyr Val Gly Asp Leu Cys Gly Val Met Leu Ala Ala
                275                 280                 285

Gln Met Phe Ile Val Ser Pro Gln His His Trp Phe Val Gln Asp Cys
                290                 295                 300

Asn Cys Ser Ile Tyr Pro Gly Thr Ile Thr Gly His Arg Met Ala Trp
305                 310                 315                 320

Asp Met Met Met Asn Trp Ser Pro Thr Ala Thr Met Ile Leu Ala Tyr
                325                 330                 335

Ala Met Arg Val Pro Glu Val Ile Ile Asp Ile Ile Ser Gly Ala His
                340                 345                 350

Trp Gly Val Met Phe Gly Leu Ala Tyr Phe Ser Met Gln Gly Ala Trp
                355                 360                 365

Ala Lys Val Val Val Ile Leu Leu Ala Ala Gly Val Asp Ala Arg
                370                 375                 380

Thr His Thr Val Gly Gly Ser Ala Ala Gln Thr Thr Gly Arg Leu Thr
385                 390                 395                 400

Ser Leu Phe Asp Met Gly Pro Arg Gln Lys Ile Gln Leu Val Asn Thr
                405                 410                 415

Asn Gly Ser Trp His Ile Asn Arg Thr Ala Leu Asn Cys Asn Asp Ser
                420                 425                 430

Leu His Thr Gly Phe Ile Ala Ser Leu Phe Tyr Thr His Ser Phe Asn
                435                 440                 445

Ser Ser Gly Cys Pro Glu Arg Met Ser Ala Cys Arg Ser Ile Glu Ala
                450                 455                 460

Phe Arg Val Gly Trp Gly Ala Leu Gln Tyr Glu Asp Asn Val Thr Asn
465                 470                 475                 480

Pro Glu Asp Met Arg Pro Tyr Cys Trp His Tyr Pro Arg Gln Cys
                485                 490                 495

Gly Val Val Ser Ala Lys Thr Val Cys Gly Pro Val Tyr Cys Phe Thr
                500                 505                 510

Pro Ser Pro Val Val Val Gly Thr Thr Asp Arg Leu Gly Ala Pro Thr
                515                 520                 525

Tyr Thr Trp Gly Glu Asn Glu Thr Asp Val Phe Leu Leu Asn Ser Thr
                530                 535                 540

Arg Pro Pro Leu Gly Ser Trp Phe Gly Cys Thr Trp Met Asn Ser Ser
545                 550                 555                 560

Gly Tyr Thr Lys Thr Cys Gly Ala Pro Pro Cys Arg Thr Arg Ala Asp
                565                 570                 575

Phe Asn Ala Ser Thr Asp Leu Leu Cys Pro Thr Asp Cys Phe Arg Lys
                580                 585                 590

His Pro Asp Thr Thr Tyr Leu Lys Cys Gly Ser Gly Pro Trp Leu Thr
                595                 600                 605

Pro Arg Cys Leu Ile Asp Tyr Pro Tyr Arg Leu Trp His Tyr Pro Cys
                610                 615                 620

Thr Val Asn Tyr Thr Ile Phe Lys Ile Arg Met Tyr Val Gly Gly Val
625                 630                 635                 640

Glu His Arg Leu Thr Ala Ala Cys Asn Phe Thr Arg Gly Asp Arg Cys
                645                 650                 655

Asn Leu Glu Asp Arg Asp Arg Ser Gln Leu Ser Pro Leu Leu His Ser
                660                 665                 670
```

```
Thr Thr Glu Trp Ala Ile Leu Pro Cys Ser Tyr Ser Asp Leu Pro Ala
        675                 680                 685

Leu Ser Thr Gly Leu Leu His Leu His Gln Asn Ile Val Asp Val Gln
    690                 695                 700

Phe Met Tyr Gly Leu Ser Pro Ala Leu Thr Lys Tyr Ile Val Arg Trp
705                 710                 715                 720

Glu Trp Val Ile Leu Leu Phe Leu Leu Ala Asp Ala Arg Val Cys
                725                 730                 735

Ala Cys Leu Trp Met Leu Ile Leu Leu Gly Gln Ala Glu Ala Ala Leu
            740                 745                 750

Glu Asn Leu Val Ile Leu Asn Ala Ala Ser Leu Ala Gly Thr His Gly
            755                 760                 765

Leu Val Ser Phe Leu Val Phe Phe Cys Phe Ala Trp Tyr Leu Lys Gly
            770                 775                 780

Arg Trp Val Pro Gly Ala Val Tyr Ala Leu Tyr Gly Met Trp Pro Leu
785                 790                 795                 800

Leu Leu Leu Leu Leu Ala Leu Pro Gln Arg Ala Tyr Ala Leu Asp Thr
                805                 810                 815

Glu Val Ala Ala Ser Cys Gly Gly Val Val Leu Val Gly Leu Met Ala
                820                 825                 830

Leu Thr Leu Ser Pro Tyr Tyr Lys Arg Tyr Ile Ser Trp Cys Met Trp
        835                 840                 845

Trp Leu Gln Tyr Phe Leu Thr Arg Val Glu Ala Gln Leu His Val Trp
    850                 855                 860

Val Pro Pro Leu Asn Val Arg Gly Gly Arg Asp Ala Val Ile Leu Leu
865                 870                 875                 880

Met Cys Val Val His Pro Thr Leu Val Phe Asp Ile Thr Lys Leu Leu
                885                 890                 895

Leu Ala Ile Phe Gly Pro Leu Trp Ile Leu Gln Ala Ser Leu Leu Lys
                900                 905                 910

Val Pro Tyr Phe Val Arg Val Gln Gly Leu Leu Arg Ile Cys Ala Leu
            915                 920                 925

Ala Arg Lys Ile Ala Gly Gly His Tyr Val Gln Met Ala Ile Ile Lys
930                 935                 940

Leu Gly Ala Leu Thr Gly Thr Tyr Val Tyr Asn His Leu Thr Pro Leu
945                 950                 955                 960

Arg Asp Trp Ala His Asn Gly Leu Arg Asp Leu Ala Val Ala Val Glu
                965                 970                 975

Pro Val Val Phe Ser Arg Met Glu Thr Lys Leu Ile Thr Trp Gly Ala
            980                 985                 990

Asp Thr Ala Ala Cys Gly Asp Ile Ile Asn Gly Leu Pro Val Ser Ala
            995                 1000                1005

Arg Arg Gly Gln Glu Ile Leu Leu Gly Pro Ala Asp Gly Met Val Ser
    1010                1015                1020

Lys Gly Trp Arg Leu Leu Ala Pro Ile Thr Ala Tyr Ala Gln Gln Thr
1025                1030                1035                1040

Arg Gly Leu Leu Gly Cys Ile Ile Thr Ser Leu Thr Gly Arg Asp Lys
                1045                1050                1055

Asn Gln Val Glu Gly Glu Val Gln Ile Val Ser Thr Ala Thr Gln Thr
            1060                1065                1070

Phe Leu Ala Thr Cys Ile Asn Gly Val Cys Trp Thr Val Tyr His Gly
    1075                1080                1085
```

-continued

```
Ala Gly Thr Arg Thr Ile Ala Ser Pro Lys Gly Pro Val Ile Gln Met
    1090                1095                1100

Tyr Thr Asn Val Asp Gln Asp Leu Val Gly Trp Pro Ala Pro Gln Gly
1105                1110                1115                1120

Ser Arg Ser Leu Thr Pro Cys Thr Cys Gly Ser Ser Asp Leu Tyr Leu
                1125                1130                1135

Val Thr Arg His Ala Asp Val Ile Pro Val Arg Arg Gly Asp Ser
            1140                1145                1150

Arg Gly Ser Leu Leu Ser Pro Arg Pro Ile Ser Tyr Leu Lys Gly Ser
            1155                1160                1165

Ser Gly Gly Pro Leu Leu Cys Pro Ala Gly His Ala Val Gly Leu Phe
    1170                1175                1180

Arg Ala Ala Val Cys Thr Arg Gly Val Ala Lys Ala Val Asp Phe Ile
1185                1190                1195                1200

Pro Val Glu Asn Leu Gly Thr Thr Met Arg Ser Pro Val Phe Thr Asp
                1205                1210                1215

Asn Ser Ser Pro Pro Ala Val Pro Gln Ser Phe Gln Val Ala His Leu
                1220                1225                1230

His Ala Pro Thr Gly Ser Gly Lys Ser Thr Lys Val Pro Ala Ala Tyr
            1235                1240                1245

Ala Ala Gln Gly Tyr Lys Val Leu Val Leu Asn Pro Ser Val Ala Ala
                1250                1255                1260

Thr Leu Gly Phe Gly Ala Tyr Met Ser Lys Ala His Gly Val Asp Pro
1265                1270                1275                1280

Asn Ile Arg Thr Gly Val Arg Thr Ile Thr Thr Gly Ser Pro Ile Thr
                1285                1290                1295

Tyr Ser Thr Tyr Gly Lys Phe Leu Ala Asp Gly Gly Cys Ser Gly Gly
                1300                1305                1310

Ala Tyr Asp Ile Ile Ile Cys Asp Glu Cys His Ser Thr Asp Ala Thr
            1315                1320                1325

Ser Ile Leu Gly Ile Gly Thr Val Leu Asp Gln Ala Glu Thr Ala Gly
    1330                1335                1340

Ala Arg Leu Val Val Leu Ala Thr Ala Thr Pro Pro Gly Ser Val Thr
1345                1350                1355                1360

Val Ser His Pro Asn Ile Glu Glu Val Ala Leu Ser Thr Thr Gly Glu
                1365                1370                1375

Ile Pro Phe Tyr Gly Lys Ala Ile Pro Leu Glu Val Ile Lys Gly Gly
                1380                1385                1390

Arg His Leu Ile Phe Cys His Ser Lys Lys Lys Cys Asp Glu Leu Ala
            1395                1400                1405

Ala Lys Leu Val Ala Leu Gly Ile Asn Ala Val Ala Tyr Tyr Arg Gly
    1410                1415                1420

Leu Asp Val Ser Val Ile Pro Thr Ser Gly Asp Val Val Val Ser
1425                1430                1435                1440

Thr Asp Ala Leu Met Thr Gly Phe Thr Gly Asp Phe Asp Ser Val Ile
            1445                1450                1455

Asp Cys Asn Thr Cys Val Thr Gln Thr Val Asp Phe Ser Leu Asp Pro
            1460                1465                1470

Thr Phe Thr Ile Glu Thr Thr Thr Leu Pro Gln Asp Ala Val Ser Arg
            1475                1480                1485

Thr Gln Arg Arg Gly Arg Thr Gly Arg Gly Lys Pro Gly Ile Tyr Arg
    1490                1495                1500

Phe Val Ala Pro Gly Glu Arg Pro Ser Gly Met Phe Asp Ser Ser Val
```

```
                                    -continued
1505                1510                1515                1520

Leu Cys Glu Cys Tyr Asp Ala Gly Cys Ala Trp Tyr Glu Leu Thr Pro
            1525                1530                1535

Ala Glu Thr Thr Val Arg Leu Arg Ala Tyr Met Asn Thr Pro Gly Leu
        1540                1545                1550

Pro Val Cys Gln Asp His Leu Glu Phe Trp Glu Gly Val Phe Thr Gly
        1555                1560                1565

Leu Thr His Ile Asp Ala His Phe Leu Ser Gln Thr Lys Gln Ser Gly
        1570                1575                1580

Glu Asn Phe Pro Tyr Leu Val Ala Tyr Gln Ala Thr Val Cys Ala Arg
1585                1590                1595                1600

Ala Gln Ala Pro Pro Ser Trp Asp Gln Met Trp Lys Cys Leu Ile
            1605                1610                1615

Arg Leu Lys Pro Thr Leu His Gly Pro Thr Pro Leu Leu Tyr Arg Leu
            1620                1625                1630

Gly Ala Val Gln Asn Glu Val Thr Leu Thr His Pro Ile Thr Lys Tyr
            1635                1640                1645

Ile Met Thr Cys Met Ser Ala Asp Leu Glu Val Val Thr Ser Thr Trp
        1650                1655                1660

Val Leu Val Gly Gly Val Leu Ala Ala Leu Ala Ala Tyr Cys Leu Ser
1665                1670                1675                1680

Thr Gly Cys Val Val Ile Val Gly Arg Ile Val Leu Ser Gly Lys Pro
            1685                1690                1695

Ala Ile Ile Pro Asp Arg Glu Val Leu Tyr Gln Glu Phe Asp Glu Met
        1700                1705                1710

Glu Glu Cys Ser Gln His Leu Pro Tyr Ile Glu Gln Gly Met Met Leu
        1715                1720                1725

Ala Glu Gln Phe Lys Gln Lys Ala Leu Gly Leu Leu Gln Thr Ala Ser
        1730                1735                1740

Arg His Ala Glu Val Ile Thr Pro Ala Val Gln Thr Asn Trp Gln Lys
1745                1750                1755                1760

Leu Glu Val Phe Trp Ala Lys His Met Trp Asn Phe Ile Ser Gly Ile
            1765                1770                1775

Gln Tyr Leu Ala Gly Leu Ser Thr Leu Pro Gly Asn Pro Ala Ile Ala
            1780                1785                1790

Ser Leu Met Ala Phe Thr Ala Ala Val Thr Ser Pro Leu Thr Thr Gly
        1795                1800                1805

Gln Thr Leu Leu Phe Asn Ile Leu Gly Gly Trp Val Ala Ala Gln Leu
        1810                1815                1820

Ala Ala Pro Gly Ala Ala Thr Ala Phe Val Gly Ala Gly Leu Ala Gly
1825                1830                1835                1840

Ala Ala Ile Gly Ser Val Gly Leu Gly Lys Val Leu Val Asp Ile Leu
            1845                1850                1855

Ala Gly Tyr Gly Ala Gly Val Ala Gly Ala Leu Val Ala Phe Lys Ile
            1860                1865                1870

Met Ser Gly Glu Val Pro Ser Thr Glu Asp Leu Val Asn Leu Leu Pro
        1875                1880                1885

Ala Ile Leu Ser Pro Gly Ala Leu Val Val Gly Val Val Cys Ala Ala
        1890                1895                1900

Ile Leu Arg Arg His Val Gly Pro Gly Glu Gly Ala Val Gln Trp Met
1905                1910                1915                1920

Asn Arg Leu Ile Ala Phe Ala Ser Arg Gly Asn His Val Ser Pro Thr
            1925                1930                1935
```

-continued

His Tyr Val Pro Glu Ser Asp Ala Ala Ala Arg Val Thr Ala Ile Leu
            1940                1945                1950

Ser Ser Leu Thr Val Thr Gln Leu Leu Arg Arg Leu His Gln Trp Ile
            1955                1960                1965

Ser Ser Glu Cys Thr Thr Pro Cys Ser Gly Ser Trp Leu Arg Asp Ile
            1970                1975                1980

Trp Asp Trp Ile Cys Glu Val Leu Ser Asp Phe Lys Thr Trp Leu Lys
1985                1990                1995                2000

Ala Lys Leu Met Pro Gln Leu Pro Gly Ile Pro Phe Val Ser Cys Gln
            2005                2010                2015

Arg Gly Tyr Arg Gly Val Trp Arg Gly Asp Gly Ile Met His Thr Arg
            2020                2025                2030

Cys His Cys Gly Ala Glu Ile Thr Gly His Val Lys Asn Gly Thr Met
            2035                2040                2045

Arg Ile Val Gly Pro Arg Thr Cys Arg Asn Met Trp Ser Gly Thr Phe
            2050                2055                2060

Pro Ile Asn Ala Tyr Thr Thr Gly Pro Cys Thr Pro Leu Pro Ala Pro
2065                2070                2075                2080

Asn Tyr Lys Phe Ala Leu Trp Arg Val Ser Ala Glu Glu Tyr Val Glu
            2085                2090                2095

Ile Arg Arg Val Gly Asp Phe His Tyr Val Ser Gly Met Thr Thr Asp
            2100                2105                2110

Asn Leu Lys Cys Pro Cys Gln Ile Pro Ser Pro Glu Phe Phe Thr Glu
            2115                2120                2125

Leu Asp Gly Val Arg Leu His Arg Phe Ala Pro Pro Cys Lys Pro Leu
            2130                2135                2140

Leu Arg Glu Glu Val Ser Phe Arg Val Gly Leu His Glu Tyr Pro Val
2145                2150                2155                2160

Gly Ser Gln Leu Pro Cys Glu Pro Glu Pro Asp Val Ala Val Leu Thr
            2165                2170                2175

Ser Met Leu Thr Asp Pro Ser His Ile Thr Ala Glu Ala Ala Gly Arg
            2180                2185                2190

Arg Leu Ala Arg Gly Ser Pro Pro Ser Met Ala Ser Ser Ser Ala Ser
            2195                2200                2205

Gln Leu Ser Ala Pro Ser Leu Lys Ala Thr Cys Thr Ala Asn His Asp
            2210                2215                2220

Ser Pro Asp Ala Glu Leu Ile Glu Ala Asn Leu Leu Trp Arg Gln Glu
2225                2230                2235                2240

Met Gly Gly Asn Ile Thr Arg Val Glu Ser Glu Asn Lys Val Val Ile
            2245                2250                2255

Leu Asp Ser Phe Asp Pro Leu Val Ala Glu Glu Asp Glu Arg Glu Val
            2260                2265                2270

Ser Val Pro Ala Glu Ile Leu Arg Lys Ser Arg Arg Phe Ala Arg Ala
            2275                2280                2285

Leu Pro Val Trp Ala Arg Pro Asp Tyr Asn Pro Pro Leu Val Glu Thr
            2290                2295                2300

Trp Lys Lys Pro Asp Tyr Glu Pro Pro Val Val His Gly Cys Pro Leu
2305                2310                2315                2320

Pro Pro Pro Arg Ser Pro Pro Val Pro Pro Pro Arg Lys Lys Arg Thr
            2325                2330                2335

Val Val Leu Thr Glu Ser Thr Leu Ser Thr Ala Leu Ala Glu Leu Ala
            2340                2345                2350

```
Thr Lys Ser Phe Gly Ser Ser Thr Ser Gly Ile Thr Gly Asp Asn
        2355                2360                2365

Thr Thr Thr Ser Ser Glu Pro Ala Pro Ser Gly Cys Pro Pro Asp Ser
        2370                2375                2380

Asp Val Glu Ser Tyr Ser Ser Met Pro Leu Glu Gly Glu Pro Gly
2385                2390                2395                2400

Asp Pro Asp Leu Ser Asp Gly Ser Trp Ser Thr Val Ser Ser Gly Ala
            2405                2410                2415

Asp Thr Glu Asp Val Val Cys Cys Ser Met Ser Tyr Ser Trp Thr Gly
            2420                2425                2430

Ala Leu Val Thr Pro Cys Ala Glu Glu Gln Lys Leu Pro Ile Asn
        2435                2440                2445

Ala Leu Ser Asn Ser Leu Leu Arg His His Asn Leu Val Tyr Ser Thr
            2450                2455                2460

Thr Ser Arg Ser Ala Cys Gln Arg Gln Lys Lys Val Thr Phe Asp Arg
2465                2470                2475                2480

Leu Gln Val Leu Asp Ser His Tyr Gln Asp Val Leu Lys Glu Val Lys
            2485                2490                2495

Ala Ala Ala Ser Lys Val Lys Ala Asn Leu Leu Ser Val Glu Glu Ala
            2500                2505                2510

Cys Ser Leu Thr Pro Pro His Ser Ala Lys Ser Lys Phe Gly Tyr Gly
        2515                2520                2525

Ala Lys Asp Val Arg Cys His Ala Arg Lys Ala Val Ala His Ile Asn
        2530                2535                2540

Ser Val Trp Lys Asp Leu Leu Glu Asp Ser Val Thr Pro Ile Asp Thr
2545                2550                2555                2560

Thr Ile Met Ala Lys Asn Glu Val Phe Cys Val Gln Pro Glu Lys Gly
            2565                2570                2575

Gly Arg Lys Pro Ala Arg Leu Ile Val Phe Pro Asp Leu Gly Val Arg
            2580                2585                2590

Val Cys Glu Lys Met Ala Leu Tyr Asp Val Val Ser Lys Leu Pro Leu
        2595                2600                2605

Ala Val Met Gly Ser Ser Tyr Gly Phe Gln Tyr Ser Pro Gly Gln Arg
2610                2615                2620

Val Glu Phe Leu Val Gln Ala Trp Lys Ser Lys Lys Thr Pro Met Gly
2625                2630                2635                2640

Phe Ser Tyr Asp Thr Arg Cys Phe Asp Ser Thr Val Thr Glu Ser Asp
            2645                2650                2655

Ile Arg Thr Glu Glu Ala Ile Tyr Gln Cys Cys Asp Leu Asp Pro Gln
        2660                2665                2670

Ala Arg Val Ala Ile Lys Ser Leu Thr Glu Arg Leu Tyr Val Gly Gly
        2675                2680                2685

Pro Leu Thr Asn Ser Arg Gly Glu Asn Cys Gly Tyr Arg Arg Cys Arg
        2690                2695                2700

Ala Ser Gly Val Leu Thr Thr Ser Cys Gly Asn Thr Leu Thr Cys Tyr
2705                2710                2715                2720

Ile Lys Ala Arg Ala Ala Cys Arg Ala Ala Gly Leu Gln Asp Cys Thr
            2725                2730                2735

Met Leu Val Cys Gly Asp Asp Leu Val Val Ile Cys Glu Ser Ala Gly
            2740                2745                2750

Val Gln Glu Asp Ala Ala Ser Leu Arg Ala Phe Thr Glu Ala Met Thr
        2755                2760                2765

Arg Tyr Ser Ala Pro Pro Gly Asp Pro Pro Gln Pro Glu Tyr Asp Leu
```

|  |  |  |  |  |  |  |  |  |  |
|--|--|--|--|--|--|--|--|--|--|
| | | 2770 | | | 2775 | | | 2780 | |
| Glu | Leu | Ile | Thr | Ser | Cys | Ser | Ser | Asn | Val | Ser | Val | Ala | His | Asp | Gly |
| 2785 | | | | 2790 | | | | 2795 | | | | 2800 | | | |

Glu Leu Ile Thr Ser Cys Ser Ser Asn Val Ser Val Ala His Asp Gly
2785                2790                2795                2800

Ala Gly Lys Arg Val Tyr Tyr Leu Thr Arg Asp Pro Thr Thr Pro Leu
            2805                2810                2815

Ala Arg Ala Ala Trp Glu Thr Ala Arg His Thr Pro Val Asn Ser Trp
        2820                2825                2830

Leu Gly Asn Ile Ile Met Phe Ala Pro Thr Leu Trp Ala Arg Met Ile
            2835                2840                2845

Leu Met Thr His Phe Phe Ser Val Leu Ile Ala Arg Asp Gln Leu Glu
        2850                2855                2860

Gln Ala Leu Asn Cys Glu Ile Tyr Gly Ala Cys Tyr Ser Ile Glu Pro
2865                2870                2875                2880

Leu Asp Leu Pro Pro Ile Ile Gln Arg Leu His Gly Leu Ser Ala Phe
            2885                2890                2895

Ser Leu His Ser Tyr Ser Pro Gly Glu Ile Asn Arg Val Ala Ala Cys
        2900                2905                2910

Leu Arg Lys Leu Gly Val Pro Pro Leu Arg Ala Trp Arg His Arg Ala
        2915                2920                2925

Arg Ser Val Arg Ala Arg Leu Leu Ser Arg Gly Gly Arg Ala Ala Ile
        2930                2935                2940

Cys Gly Lys Tyr Leu Phe Asn Trp Ala Val Arg Thr Lys Leu Lys Leu
2945                2950                2955                2960

Thr Pro Ile Ala Ala Ala Gly Arg Leu Asp Leu Ser Gly Trp Phe Thr
            2965                2970                2975

Ala Gly Tyr Ser Gly Gly Asp Ile Tyr His Ser Val Ser His Ala Arg
        2980                2985                2990

Pro Arg Trp Phe Trp Phe Cys Leu Leu Leu Leu Ala Ala Gly Val Gly
        2995                3000                3005

Ile Tyr Leu Leu Pro Asn Arg
    3010                3015

<210> SEQ ID NO 7
<211> LENGTH: 9611
<212> TYPE: DNA
<213> ORGANISM: Hepatitis C virus

<400> SEQUENCE: 7
gccagccccc tgatggggc gacactccac catgaatcac tcccctgtga ggaactactg    60
tcttcacgca gaaagcgtct agccatggcg ttagtatgag tgtcgtgcag cctccaggac   120
cccccctccc gggagagcca tagtggtctg cggaaccggt gagtacaccg gaattgccag   180
gacgaccggg tcctttcttg gataaaccg ctcaatgcct ggagatttgg gcgtgccccc   240
gcaagactgc tagccgagta gtgttgggtc gcgaaaggcc ttgtggtact gcctgatagg   300
gtgcttgcga gtgccccggg aggtctcgta gaccgtgcac catgagcaca atcctaaac   360 ctcaaagaaa aaccaaaaga acaccaacc gtcgcccaca agacgttaag tttccgggcg   420
gcggccagat cgttggcgga gtatacttgt tgccgcgcag gggccccagg ttgggtgtgc   480
gcgcgacaag gaagacttcg gagcggtccc agccacgtgg aaggcgccag cccatcccta   540
aagatcggcg ctccactggc aaatcctggg gaaaccagg ataccctgg ccctatacg     600 ggaatgaggg actcggctgg gcaggatggc tcctgtcccc ccgaggttcc cgtccctctt   660
ggggccccaa tgaccccgg cataggtcgc gcaacgtggg taaggtcatc gatacccta    720

```
cgtgcggctt tgccgacctc atggggtaca tccctgtcgt gggcgccccg ctcggcggcg      780
tcgccagagc tctcgcgcat ggcgtgagag tcctggagga cggggttaat tttgcaacag      840
ggaacttacc cggttgctcc ttttctatct tcttgctggc cctgctgtcc tgcatcacca      900
ccccggtctc cgctgccgaa gtgaagaaca tcagtaccgg ctacatggtg actaacgact      960
gcaccaatga cagcattacc tggcagctcc aggctgctgt cctccacgtc ccgggtgcg      1020 tcccgtgcga gaaagtgggg aatgcatctc agtgctggat accggtctca ccgaatgtgg      1080
ccgtgcagcg gcccggcgcc ctcacgcagg gcttgcggac gcacatcgac atggttgtga      1140
tgtccgccac gctctgctct gccctctacg tgggggacct ctgcgtgggg gtgatgctcg      1200
cagcccaaat gttcattgtc tcgccgcagc accactggtt tgtccaagac tgcaattgct      1260
ccatctaccc tggtaccatc actggacacc gcatggcatg gacatgatg atgaactggt      1320 cgcccacggc taccatgatc ttggcgtacg cgatgcgtgt ccccgaggtc attatagaca      1380
tcattagcgg ggctcattgg ggcgtcatgt tcggcttggc ctacttctct atgcagggag      1440
cgtgggcgaa agtcgttgtc atccttctgt tggccgccgg ggtggacgcg cgcacccata      1500
ctgttggggg ttctgccgcg cagaccaccg ggcgcctcac cagcttattt gacatgggcc      1560 ccagcagaa aatccagctc gttaacacca atggcagctg gcacatcaac cgcaccgccc      1620
tgaactgcaa tgactccttg cacaccggct ttatcgcgtc tctgttctac acccacagct      1680
tcaactcgtc aggatgtccc gaacgcatgt ccgcctgccg cagtatcgag gccttccggg      1740
tgggatgggg cgccttgcaa tatgaggata atgtcaccaa tccagaggat atgagaccct      1800
attgctggca ctacccacca aggcagtgtg gcgtggtctc cgcgaagact gtgtgtggcc      1860
cagtgtactg tttcacccc agcccagtgg tagtgggcac gaccgacagg cttggagcgc      1920
ccacttacac gtgggggggag aatgagacag atgtcttcct attgaacagc actcgaccac      1980 cgctgggggtc atggttcggc tgcacgtgga tgaactcttc tggctacacc aagacttgcg      2040
gcgcaccacc ctgccgtact agagctgact tcaacgccag cacggacctg ttgtgcccca      2100
cggactgttt taggaagcat cctgatacca cttacctcaa atgcggctct gggccctggc      2160
tcacgccaag gtgcctgatc gactacccct acaggctctg gcattacccc tgcacagtta      2220
actataccat cttcaaaata aggatgtatg tgggaggggt tgagcacagg ctcacggctg      2280
catgcaattt cactcgtggg gatcgttgca acttggagga cagagacaga agtcaactgt      2340 ctccttgtt gcactccacc acggaatggg ccattttacc ttgctcttac tcggacctgc      2400
ccgccttgtc gactggtctt ctccacctcc accaaaacat cgtggacgta caattcatgt      2460
atggcctatc acctgccctc acaaaataca tcgtccgatg ggagtgggta atactcttat      2520
tcctgctctt agcggacgcc agggttttgcg cctgcttatg gatgctcatc ttgttgggcc      2580
aggccgaagc agcactagag aagctggtca tcttgcacgc tgcgagcgca gctagctgca      2640
atggcttcct atattttgtc atcttttccg tggctgcttg gtacatcaag ggtcgggtag      2700
tccccttagc tacctattcc ctcactggcc tgtggtcctt tagcctactg ctcctagcat      2760
tgccccaaca ggcatatgca ctggacacgg aggtggccgc gtcgtgtggc ggcgttgttc      2820
ttgtcgggtt aatggcgctg actctgtcgc catattacaa gcgctatatc agctggtgca      2880
tgtggtggct tcagtatttt ctgaccgaga tagaagcgca actgcacgtg tgggttcccc      2940
ccctcaacgt ccggggggggg cgcgatgccg tcatcttact catgtgtgta gtacacccga      3000
ccctggtatt tgcatcacc aaactactcc tggccatctt cggacccctt tggattcttc      3060
aagccagttt gcttaaagtc ccctacttcg tgcgcgttca aggccttctc cggatctgcg      3120
```

-continued

```
cgctagcgcg gaagatagcc ggaggtcatt acgtgcaaat ggccatcatc aagttagggg       3180
cgcttactgg cacctatgtg tataaccatc tcacccctct tcgagactgg gcgcacaacg       3240
gcctgcgaga tctggccgtg gctgtggaac cagtcgtctt ctcccgaatg gagaccaagc       3300
tcatcacgtg gggggcagat accgccgcgt gcggtgacat catcaacggc ttgcccgtct       3360
ctgcccgtag gggccaggag atactgcttg gccagccga cggaatggtc tccaaggggt       3420
ggaggttgct ggcgcccatc acggcgtacg cccagcagac gagaggcctc ctagggtgta       3480
taatcaccag cctgactggc cgggacaaaa accaagtgga gggtgaggtc cagatcgtgt       3540
caactgctac ccaaaccttc ctggcaacgt gcatcaatgg ggtatgctgg actgtctacc       3600
acggggccgg aacgaggacc atcgcatcac ccaagggtcc tgtcatccag atgtatacca       3660
atgtggacca agaccttgtg ggctggcccg ctcctcaagg ttcccgctca ttgacaccct       3720
gtacctgcgg ctcctcggac ctttacctgg tcacgaggca cgccgatgtc attcccgtgc       3780
gccggcgagg tgatagcagg ggtagcctgc tttcgccccg gcccatttcc tacttgaaag       3840
gctcctcggg gggtccgctg ttgtgccccg cgggacacgc cgtgggccta ttcagggccg       3900
cggtgtgcac ccgtggagtg gctaaagcgg tggactttat ccctgtggag aacctaggga       3960
caaccatgag atccccggtg ttcacggaca actcctctcc accagcagtg ccccagagct       4020
tccaggtggc ccacctgcat gctcccaccg gcagcggtaa gagcaccaag gtcccggctg       4080
cgtacgcagc ccagggctac aaggtgttgg tgctcaaccc ctctgttgct gcaacgctgg       4140
gctttggtgc ttacatgtcc aaggcccatg gggttgatcc taatatcagg accggggtga       4200
gaacaattac cactggcagc cccatcacgt actccaccta cggcaagttc cttgccgacg       4260
gcgggtgctc aggaggtgct tatgacataa taatttgtga cgagtgccac tccacggatg       4320
ccacatccat cttgggcatc ggcactgtcc ttgaccaagc agagactgcg ggggcgagac       4380
tggttgtgct cgccactgct accccctccg gctccgtcac tgtgtcccat cctaacatcg       4440
aggaggttgc tctgtccacc accggagaga tccccttta cggcaaggct atccccctcg       4500
aggtgatcaa gggggaaga catctcatct tctgccactc aaagaagaag tgcgacgagc       4560
tcgccgcgaa gctggtcgca ttgggcatca atgccgtggc ctactaccgc ggtcttgacg       4620
tgtctgtcat cccgaccagc ggcgatgttg tcgtcgtgtc gaccgatgct ctcatgactg       4680
gctttaccgg cgacttcgac tctgtgatag actgcaacac gtgtgtcact cagacagtcg       4740
atttcagcct tgaccctacc tttaccattg agacaaccac gctcccccag gatgctgtct       4800
ccaggactca acgccggggc aggactggca gggggaagcc aggcatctat agatttgtgg       4860
caccggggga gcgcccctcc ggcatgttcg actcgtccgt cctctgtgag tgctatgacg       4920
cgggctgtgc ttggtatgag ctcacgcccg ccgagactac agttaggcta cgagcgtaca       4980
tgaacacccc gggcttccc gtgtgccagg accatcttga attttgggag ggcgtctttta       5040
cgggcctcac tcatatagat gcccacttt tatcccagac aaagcagagt ggggagaact       5100
ttccttacct ggtagcgtac caagccaccg tgtgcgctag gctcaagcc cctcccccat       5160
cgtgggacca gatgtggaag tgtttgatcc gccttaaacc cacccctccat gggccaacac       5220
ccctgctata cagactgggc gctgttcaga atgaagtcac cctgacgcac ccaatcacca       5280
aatacatcat gacatgcatg tcggccgacc tggaggtcgt cacgagcacc tgggtgctcg       5340
ttggcggcgt cctggctgct ctggccgcgt attgcctgtc aacaggctgc gtggtcatag       5400
tgggcaggat cgtcttgtcc gggaagccgg caattatacc tgacagggag gttctctacc       5460
```

```
aggagttcga tgagatggaa gagtgctctc agcacttacc gtacatcgag caagggatga    5520
tgctcgctga gcagttcaag cagaaggccc tcggcctcct gcagaccgcg tcccgccatg    5580
cagaggttat cacccctgct gtccagacca actggcagaa actcgaggtc ttttgggcga    5640
agcacatgtg gaatttcatc agtgggatac aatacttggc gggcctgtca acgctgcctg    5700 gtaacccgc cattgcttca ttgatggctt ttacagctgc cgtcaccagc ccactaacca    5760
ctggccaaac cctcctcttc aacatattgg ggggtgggt ggctgccag ctcgccgccc    5820 ccggtgccgc tactgccttt gtgggtgctg gcctagctgg cgccgccatc ggcagcgttg    5880
gactggggaa ggtcctcgtg gacattcttg cagggtatgg cgcgggcgtg gcgggagctc    5940
ttgtagcatt caagatcatg agcggtgagg tcccctccac ggaggacctg gtcaatctgc    6000
tgcccgccat cctctcgcct ggagcccttg tagtcggtgt ggtctgcgca gcaatactgc    6060
gccggcacgt tggcccgggc gaggggggcag tgcaatggat gaaccggcta atagccttcg    6120
cctcccgggg gaaccatgtt tcccccacgc actacgtgcc ggagagcgat gcagccgccc    6180
gcgtcactgc catactcagc agcctcactg taacccagct cctgaggcga ctgcatcagt    6240
ggataagctc ggagtgtacc actccatgct ccggttcctg gctaagggac atctgggact    6300
ggatatgcga ggtgctgagc gactttaaga cctggctgaa agccaagctc atgccacaac    6360
tgcctgggat tcccttttgtg tcctgccagc gcgggtatag ggggtctgg cgaggagacg    6420 gcattatgca cactcgctgc cactgtggag ctgagatcac tggacatgtc aaaaacggga    6480
cgatgaggat cgtcggtcct aggacctgca ggaacatgtg gagtgggacg ttccccatta    6540
acgcctacac cacgggcccc tgtactcccc ttcctgcgcc gaactataag ttcgcgctgt    6600
ggagggtgtc tgcagaggaa tacgtggaga taaggcgggt ggggggacttc cactacgtat    6660 cgggtatgac tactgacaat cttaaatgcc cgtgccagat cccatcgccc gaattttca    6720 cagaattgga cggggtgcgc ctacacaggt ttgcgccccc ttgcaagccc ttgctgcggg    6780
aggaggtatc attcagagta ggactccacg agtacccggt ggggtcgcaa ttaccttgcg    6840
agcccgaacc ggacgtagcc gtgttgacgt ccatgctcac tgatccctcc catataacag    6900
cagaggcggc cgggagaagg ttggcgagag ggtcacccc ttctatggcc agctcctcgg    6960
ctagccagct gtccgctcca tctctcaagg caacttgcac cgccaaccat gactcccctg    7020
acgccgagct catagaggct aacctcctgt ggaggcagga gatgggcggc aacatcacca    7080
gggttgagtc agagaacaaa gtggtgattc tggactcctt cgatccgctt gtggcagagg    7140
aggatgagcg ggaggtctcc gtacctgcag aaattctgcg gaagtctcgg agattcgccc    7200
gggccctgcc cgtctgggcg cggccggact acaacccccc gctagtagag acgtggaaaa    7260
agcctgacta cgaaccacct gtggtccatg gctgcccgct accacctcca cggtcccctc    7320
ctgtgcctcc gcctcggaaa aagcgtacgg tggtcctcac cgaatcaacc ctatctactg    7380
ccttggccga gcttgccacc aaaagttttg gcagctcctc aacttccggc attacgggcg    7440
acaatacgac aacatcctct gagcccgccc cttctggctg cccccccgac tccgacgttg    7500
agtcctattc ttccatgccc ccctggagg gggagcctgg ggatccggat ctcagcgacg    7560
ggtcatggtc gacggtcagt agtgggggccg acacggaaga tgtcgtgtgc tgctcaatgt    7620
cttattcctg gacaggcgca ctcgtcaccc cgtgcgctgc ggaagaacaa aaactgccca    7680
tcaacgcact gagcaactcg ttgctacgcc atcacaatct ggtgtattcc accacttcac    7740
gcagtgcttg ccaaaggcag aagaaagtca catttgacag actgcaagtt ctggacagcc    7800
attaccagga cgtgctcaag gaggtcaaag cagcggcgtc aaaagtgaag gctaacttgc    7860
```

-continued

```
tatccgtaga ggaagcttgc agcctgacgc ccccacattc agccaaatcc aagtttggct    7920
atggggcaaa agacgtccgt tgccatgcca gaaaggccgt agcccacatc aactccgtgt    7980
ggaaagacct tctggaagac agtgtaacac aatagacac taccatcatg gccaagaacg    8040
aggttttctg cgttcagcct gagaaggggg gtcgtaagcc agctcgtctc atcgtgttcc    8100
ccgacctggg cgtgcgcgtg tgcgagaaga tggccctgta cgacgtggtt agcaagctcc    8160
ccctggccgt gatgggaagc tcctacggat tccaatactc accaggacag cgggttgaat    8220
tcctcgtgca agcgtggaag tccaagaaga ccccgatggg gttctcgtat gatacccgct    8280
gttttgactc cacagtcact gagagcgaca tccgtacgga ggaggcaatt taccaatgtt    8340
gtgacctgga cccccaagcc cgcgtggcca tcaagtccct cactgagagg ctttatgttg    8400
ggggccctct taccaattca agggggaaa actgcggcta ccgcaggtgc cgcgcgagcg    8460
gcgtactgac aactagctgt ggtaacaccc tcacttgcta catcaaggcc cgggcagcct    8520
gtcgagccgc agggctccag gactgcacca tgctcgtgtg tggcgacgac ttagtcgtta    8580
tctgtgaaag tgcgggggtc caggaggacg cggcgagcct gagagccttc acggaggcta    8640
tgaccaggta ctccgccccc ccggggacc ccccacaacc agaatacgac ttggagctta    8700
taacatcatg ctcctccaac gtgtcagtcg cccacgacgg cgctggaaag agggtctact    8760
accttacccg tgaccctaca accccctcg cgagagccgc gtgggagaca gcaagacaca    8820
ctccagtcaa ttcctggcta ggcaacataa tcatgtttgc ccccacactg tgggcgagga    8880
tgatactgat gacccatttc tttagcgtcc tcatagccag ggatcagctt gaacaggctc    8940
ttaactgtga gatctacgga gcctgctact ccatagaacc actggatcta cctccaatca    9000
ttcaaagact ccatggcctc agcgcatttt cactccacac ttactctcca ggtgaaatca    9060
atagggtggc cgcatgcctc agaaaacttg gggtcccgcc cttgcgagct tggagacacc    9120
gggcccggag cgtccgcgct aggcttctgt ccagaggagg cagggctgct atatgtggca    9180
agtacctctt caactgggca gtaagaacaa agctcaaact cactccaata gcggccgctg    9240
gccggctgga cttgtccggt tggttcacgg ctggctacag cggggagac atttatcaca    9300 gcgtgtctca tgcccggccc cgctggttct ggttttgcct actcctgctc gctgcagggg    9360
taggcatcta cctcctcccc aaccgatgaa ggttggggta acactccgg cctcttaagc    9420 catttcctgt ttttttttt tttttttttt ttttttcttt tttttttttttc tttcctttcc   9480 ttcttttttt cctttctttt tccttctttt aatggtggct ccatcttagc cctagtcacg    9540
gctagctgtg aaaggtccgt gagccgcatg actgcagaga gtgctgatac tggcctctct    9600
gcagatcatg t                                                          9611
```

<210> SEQ ID NO 8
<211> LENGTH: 3015
<212> TYPE: PRT
<213> ORGANISM: Hepatitis C virus

<400> SEQUENCE: 8

Met Ser Thr Asn Pro Lys Pro Gln Arg Lys Thr Lys Arg Asn Thr Asn
 1               5                  10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Ar

```
                50                  55                  60
Ile Pro Lys Asp Arg Arg Ser Thr Gly Lys Ser Trp Gly Lys Pro Gly
 65                  70                  75                  80

Tyr Pro Trp Pro Leu Tyr Gly Asn Glu Gly Leu Gly Trp Ala Gly Trp
                 85                  90                  95

Leu Leu Ser Pro Arg Gly Ser Arg Pro Ser Trp Gly Pro Asn Asp Pro
                100                 105                 110

Arg His Arg Ser Arg Asn Val Gly Lys Val Ile Asp Thr Leu Thr Cys
                115                 120                 125

Gly Phe Ala Asp Leu Met Gly Tyr Ile Pro Val Val Gly Ala Pro Leu
130                 135                 140

Gly Gly Val Ala Arg Ala Leu Ala His Gly Val Arg Val Leu Glu Asp
145                 150                 155                 160

Gly Val Asn Phe Ala Thr Gly Asn Leu Pro Gly Cys Ser Phe Ser Ile
                165                 170                 175

Phe Leu Leu Ala Leu Leu Ser Cys Ile Thr Thr Pro Val Ser Ala Ala
                180                 185                 190

Glu Val Lys Asn Ile Ser Thr Gly Tyr Met Val Thr Asn Asp Cys Thr
                195                 200                 205

Asn Asp Ser Ile Thr Trp Gln Leu Gln Ala Ala Val Leu His Val Pro
210                 215                 220

Gly Cys Val Pro Cys Glu Lys Val Gly Asn Ala Ser Gln Cys Trp Ile
225                 230                 235                 240

Pro Val Ser Pro Asn Val Ala Val Gln Arg Pro Gly Ala Leu Thr Gln
                245                 250                 255

Gly Leu Arg Thr His Ile Asp Met Val Val Met Ser Ala Thr Leu Cys
                260                 265                 270

Ser Ala Leu Tyr Val Gly Asp Leu Cys Gly Gly Val Met Leu Ala Ala
                275                 280                 285

Gln Met Phe Ile Val Ser Pro Gln His His Trp Phe Val Gln Asp Cys
                290                 295                 300

Asn Cys Ser Ile Tyr Pro Gly Thr Ile Thr Gly His Arg Met Ala Trp
305                 310                 315                 320

Asp Met Met Met Asn Trp Ser Pro Thr Ala Thr Met Ile Leu Ala Tyr
                325                 330                 335

Ala Met Arg Val Pro Glu Val Ile Ile Asp Ile Ile Ser Gly Ala His
                340                 345                 350

Trp Gly Val Met Phe Gly Leu Ala Tyr Phe Ser Met Gln Gly Ala Trp
                355                 360                 365

Ala Lys Val Val Val Ile Leu Leu Leu Ala Ala Gly Val Asp Ala Arg
                370                 375                 380

Thr His Thr Val Gly Gly Ser Ala Ala Gln Thr Thr Gly Arg Leu Thr
385                 390                 395                 400

Ser Leu Phe Asp Met Gly Pro Arg Gln Lys Ile Gln Leu Val Asn Thr
                405                 410                 415

Asn Gly Ser Trp His Ile Asn Arg Thr Ala Leu Asn Cys Asn Asp Ser
                420                 425                 430

Leu His Thr Gly Phe Ile Ala Ser Leu Phe Tyr Thr His Ser Phe Asn
                435                 440                 445

Ser Ser Gly Cys Pro Glu Arg Met Ser Ala Cys Arg Ser Ile Glu Ala
                450                 455                 460

Phe Arg Val Gly Trp Gly Ala Leu Gln Tyr Glu Asp Asn Val Thr Asn
465                 470                 475                 480
```

```
Pro Glu Asp Met Arg Pro Tyr Cys Trp His Tyr Pro Pro Arg Gln Cys
            485                 490                 495
Gly Val Val Ser Ala Lys Thr Val Cys Gly Pro Val Tyr Cys Phe Thr
                500                 505                 510
Pro Ser Pro Val Val Gly Thr Thr Asp Arg Leu Gly Ala Pro Thr
            515                 520                 525
Tyr Thr Trp Gly Glu Asn Glu Thr Asp Val Phe Leu Leu Asn Ser Thr
    530                 535                 540
Arg Pro Pro Leu Gly Ser Trp Phe Gly Cys Thr Trp Met Asn Ser Ser
545                 550                 555                 560
Gly Tyr Thr Lys Thr Cys Gly Ala Pro Pro Cys Arg Thr Arg Ala Asp
                565                 570                 575
Phe Asn Ala Ser Thr Asp Leu Leu Cys Pro Thr Asp Cys Phe Arg Lys
            580                 585                 590
His Pro Asp Thr Thr Tyr Leu Lys Cys Gly Ser Gly Pro Trp Leu Thr
            595                 600                 605
Pro Arg Cys Leu Ile Asp Tyr Pro Tyr Arg Leu Trp His Tyr Pro Cys
        610                 615                 620
Thr Val Asn Tyr Thr Ile Phe Lys Ile Arg Met Tyr Val Gly Gly Val
625                 630                 635                 640
Glu His Arg Leu Thr Ala Ala Cys Asn Phe Thr Arg Gly Asp Arg Cys
                645                 650                 655
Asn Leu Glu Asp Arg Asp Arg Ser Gln Leu Ser Pro Leu Leu His Ser
            660                 665                 670
Thr Thr Glu Trp Ala Ile Leu Pro Cys Ser Tyr Ser Asp Leu Pro Ala
        675                 680                 685
Leu Ser Thr Gly Leu Leu His Leu His Gln Asn Ile Val Asp Val Gln
        690                 695                 700
Phe Met Tyr Gly Leu Ser Pro Ala Leu Thr Lys Tyr Ile Val Arg Trp
705                 710                 715                 720
Glu Trp Val Ile Leu Leu Phe Leu Leu Leu Ala Asp Ala Arg Val Cys
                725                 730                 735
Ala Cys Leu Trp Met Leu Ile Leu Leu Gly Gln Ala Glu Ala Ala Leu
            740                 745                 750
Glu Lys Leu Val Ile Leu His Ala Ala Ser Ala Ala Ser Cys Asn Gly
            755                 760                 765
Phe Leu Tyr Phe Val Ile Phe Phe Val Ala Ala Trp Tyr Ile Lys Gly
            770                 775                 780
Arg Val Val Pro Leu Ala Thr Tyr Ser Leu Thr Gly Leu Trp Ser Phe
785                 790                 795                 800
Ser Leu Leu Leu Leu Ala Leu Pro Gln Gln Ala Tyr Ala Leu Asp Thr
                805                 810                 815
Glu Val Ala Ala Ser Cys Gly Gly Val Val Leu Val Gly Leu Met Ala
            820                 825                 830
Leu Thr Leu Ser Pro Tyr Tyr Lys Arg Tyr Ile Ser Trp Cys Met Trp
            835                 840                 845
Trp Leu Gln Tyr Phe Leu Thr Arg Val Glu Ala Gln Leu His Val Trp
        850                 855                 860
Val Pro Pro Leu Asn Val Arg Gly Gly Arg Asp Ala Val Ile Leu Leu
865                 870                 875                 880
Met Cys Val Val His Pro Thr Leu Val Phe Asp Ile Thr Lys Leu Leu
                885                 890                 895
```

-continued

Leu Ala Ile Phe Gly Pro Leu Trp Ile Leu Gln Ala Ser Leu Leu Lys
        900                 905                 910

Val Pro Tyr Phe Val Arg Val Gln Gly Leu Leu Arg Ile Cys Ala Leu
        915                 920                 925

Ala Arg Lys Ile Ala Gly Gly His Tyr Val Gln Met Ala Ile Ile Lys
        930                 935                 940

Leu Gly Ala Leu Thr Gly Thr Tyr Val Tyr Asn His Leu Thr Pro Leu
945                 950                 955                 960

Arg Asp Trp Ala His Asn Gly Leu Arg Asp Leu Ala Val Ala Val Glu
                965                 970                 975

Pro Val Val Phe Ser Arg Met Glu Thr Lys Leu Ile Thr Trp Gly Ala
        980                 985                 990

Asp Thr Ala Ala Cys Gly Asp Ile Ile Asn Gly Leu Pro Val Ser Ala
        995                 1000                1005

Arg Arg Gly Gln Glu Ile Leu Leu Gly Pro Ala Asp Gly Met Val Ser
    1010                1015                1020

Lys Gly Trp Arg Leu Leu Ala Pro Ile Thr Ala Tyr Ala Gln Gln Thr
1025                1030                1035                1040

Arg Gly Leu Leu Gly Cys Ile Ile Thr Ser Leu Thr Gly Arg Asp Lys
            1045                1050                1055

Asn Gln Val Glu Gly Glu Val Gln Ile Val Ser Thr Ala Thr Gln Thr
            1060                1065                1070

Phe Leu Ala Thr Cys Ile Asn Gly Val Cys Trp Thr Val Tyr His Gly
        1075                1080                1085

Ala Gly Thr Arg Thr Ile Ala Ser Pro Lys Gly Pro Val Ile Gln Met
    1090                1095                1100

Tyr Thr Asn Val Asp Gln Asp Leu Val Gly Trp Pro Ala Pro Gln Gly
1105                1110                1115                1120

Ser Arg Ser Leu Thr Pro Cys Thr Cys Gly Ser Ser Asp Leu Tyr Leu
            1125                1130                1135

Val Thr Arg His Ala Asp Val Ile Pro Val Arg Arg Arg Gly Asp Ser
            1140                1145                1150

Arg Gly Ser Leu Leu Ser Pro Arg Pro Ile Ser Tyr Leu Lys Gly Ser
        1155                1160                1165

Ser Gly Gly Pro Leu Leu Cys Pro Ala Gly His Ala Val Gly Leu Phe
    1170                1175                1180

Arg Ala Ala Val Cys Thr Arg Gly Val Ala Lys Ala Val Asp Phe Ile
1185                1190                1195                1200

Pro Val Glu Asn Leu Gly Thr Thr Met Arg Ser Pro Val Phe Thr Asp
            1205                1210                1215

Asn Ser Ser Pro Pro Ala Val Pro Gln Ser Phe Gln Val Ala His Leu
        1220                1225                1230

His Ala Pro Thr Gly Ser Gly Lys Ser Thr Lys Val Pro Ala Ala Tyr
        1235                1240                1245

Ala Ala Gln Gly Tyr Lys Val Leu Val Leu Asn Pro Ser Val Ala Ala
    1250                1255                1260

Thr Leu Gly Phe Gly Ala Tyr Met Ser Lys Ala His Gly Val Asp Pro
1265                1270                1275                1280

Asn Ile Arg Thr Gly Val Arg Thr Ile Thr Thr Gly Ser Pro Ile Thr
            1285                1290                1295

Tyr Ser Thr Tyr Gly Lys Phe Leu Ala Asp Gly Gly Cys Ser Gly Gly
        1300                1305                1310

Ala Tyr Asp Ile Ile Ile Cys Asp Glu Cys His Ser Thr Asp Ala Thr

-continued

```
            1315                1320                1325
Ser Ile Leu Gly Ile Gly Thr Val Leu Asp Gln Ala Glu Thr Ala Gly
    1330                1335                1340
Ala Arg Leu Val Val Leu Ala Thr Ala Thr Pro Pro Gly Ser Val Thr
1345                1350                1355                1360
Val Ser His Pro Asn Ile Glu Glu Val Ala Leu Ser Thr Thr Gly Glu
            1365                1370                1375
Ile Pro Phe Tyr Gly Lys Ala Ile Pro Leu Glu Val Ile Lys Gly Gly
            1380                1385                1390
Arg His Leu Ile Phe Cys His Ser Lys Lys Cys Asp Glu Leu Ala
        1395                1400                1405
Ala Lys Leu Val Ala Leu Gly Ile Asn Ala Val Ala Tyr Tyr Arg Gly
    1410                1415                1420
Leu Asp Val Ser Val Ile Pro Thr Ser Gly Asp Val Val Val Ser
1425                1430                1435                1440
Thr Asp Ala Leu Met Thr Gly Phe Thr Gly Asp Phe Asp Ser Val Ile
            1445                1450                1455
Asp Cys Asn Thr Cys Val Thr Gln Thr Val Asp Phe Ser Leu Asp Pro
            1460                1465                1470
Thr Phe Thr Ile Glu Thr Thr Thr Leu Pro Gln Asp Ala Val Ser Arg
            1475                1480                1485
Thr Gln Arg Arg Gly Arg Thr Gly Arg Gly Lys Pro Gly Ile Tyr Arg
    1490                1495                1500
Phe Val Ala Pro Gly Glu Arg Pro Ser Gly Met Phe Asp Ser Ser Val
1505                1510                1515                1520
Leu Cys Glu Cys Tyr Asp Ala Gly Cys Ala Trp Tyr Glu Leu Thr Pro
            1525                1530                1535
Ala Glu Thr Thr Val Arg Leu Arg Ala Tyr Met Asn Thr Pro Gly Leu
            1540                1545                1550
Pro Val Cys Gln Asp His Leu Glu Phe Trp Glu Gly Val Phe Thr Gly
            1555                1560                1565
Leu Thr His Ile Asp Ala His Phe Leu Ser Gln Thr Lys Gln Ser Gly
    1570                1575                1580
Glu Asn Phe Pro Tyr Leu Val Ala Tyr Gln Ala Thr Val Cys Ala Arg
1585                1590                1595                1600
Ala Gln Ala Pro Pro Pro Ser Trp Asp Gln Met Trp Lys Cys Leu Ile
            1605                1610                1615
Arg Leu Lys Pro Thr Leu His Gly Pro Thr Pro Leu Leu Tyr Arg Leu
            1620                1625                1630
Gly Ala Val Gln Asn Glu Val Thr Leu Thr His Pro Ile Thr Lys Tyr
        1635                1640                1645
Ile Met Thr Cys Met Ser Ala Asp Leu Glu Val Val Thr Ser Thr Trp
    1650                1655                1660
Val Leu Val Gly Gly Val Leu Ala Ala Leu Ala Ala Tyr Cys Leu Ser
1665                1670                1675                1680
Thr Gly Cys Val Val Ile Val Gly Arg Ile Val Leu Ser Gly Lys Pro
            1685                1690                1695
Ala Ile Ile Pro Asp Arg Glu Val Leu Tyr Gln Glu Phe Asp Glu Met
            1700                1705                1710
Glu Glu Cys Ser Gln His Leu Pro Tyr Ile Glu Gln Gly Met Met Leu
        1715                1720                1725
Ala Glu Gln Phe Lys Gln Lys Ala Leu Gly Leu Leu Gln Thr Ala Ser
    1730                1735                1740
```

```
Arg His Ala Glu Val Ile Thr Pro Ala Val Gln Thr Asn Trp Gln Lys
1745                1750                1755                1760

Leu Glu Val Phe Trp Ala Lys His Met Trp Asn Phe Ile Ser Gly Ile
                1765                1770                1775

Gln Tyr Leu Ala Gly Leu Ser Thr Leu Pro Gly Asn Pro Ala Ile Ala
            1780                1785                1790

Ser Leu Met Ala Phe Thr Ala Ala Val Thr Ser Pro Leu Thr Thr Gly
        1795                1800                1805

Gln Thr Leu Leu Phe Asn Ile Leu Gly Gly Trp Val Ala Ala Gln Leu
    1810                1815                1820

Ala Ala Pro Gly Ala Ala Thr Ala Phe Val Gly Ala Gly Leu Ala Gly
1825                1830                1835                1840

Ala Ala Ile Gly Ser Val Gly Leu Gly Lys Val Leu Val Asp Ile Leu
                1845                1850                1855

Ala Gly Tyr Gly Ala Gly Val Ala Gly Ala Leu Val Ala Phe Lys Ile
            1860                1865                1870

Met Ser Gly Glu Val Pro Ser Thr Glu Asp Leu Val Asn Leu Leu Pro
        1875                1880                1885

Ala Ile Leu Ser Pro Gly Ala Leu Val Val Gly Val Val Cys Ala Ala
    1890                1895                1900

Ile Leu Arg Arg His Val Gly Pro Gly Glu Gly Ala Val Gln Trp Met
1905                1910                1915                1920

Asn Arg Leu Ile Ala Phe Ala Ser Arg Gly Asn His Val Ser Pro Thr
                1925                1930                1935

His Tyr Val Pro Glu Ser Asp Ala Ala Ala Arg Val Thr Ala Ile Leu
            1940                1945                1950

Ser Ser Leu Thr Val Thr Gln Leu Leu Arg Arg Leu His Gln Trp Ile
        1955                1960                1965

Ser Ser Glu Cys Thr Thr Pro Cys Ser Gly Ser Trp Leu Arg Asp Ile
    1970                1975                1980

Trp Asp Trp Ile Cys Glu Val Leu Ser Asp Phe Lys Thr Trp Leu Lys
1985                1990                1995                2000

Ala Lys Leu Met Pro Gln Leu Pro Gly Ile Pro Phe Val Ser Cys Gln
                2005                2010                2015

Arg Gly Tyr Arg Gly Val Trp Arg Gly Asp Gly Ile Met His Thr Arg
            2020                2025                2030

Cys His Cys Gly Ala Glu Ile Thr Gly His Val Lys Asn Gly Thr Met
        2035                2040                2045

Arg Ile Val Gly Pro Arg Thr Cys Arg Asn Met Trp Ser Gly Thr Phe
    2050                2055                2060

Pro Ile Asn Ala Tyr Thr Thr Gly Pro Cys Thr Pro Leu Pro Ala Pro
2065                2070                2075                2080

Asn Tyr Lys Phe Ala Leu Trp Arg Val Ser Ala Glu Glu Tyr Val Glu
                2085                2090                2095

Ile Arg Arg Val Gly Asp Phe His Tyr Val Ser Gly Met Thr Thr Asp
            2100                2105                2110

Asn Leu Lys Cys Pro Cys Gln Ile Pro Ser Pro Glu Phe Phe Thr Glu
        2115                2120                2125

Leu Asp Gly Val Arg Leu His Arg Phe Ala Pro Pro Cys Lys Pro Leu
    2130                2135                2140

Leu Arg Glu Glu Val Ser Phe Arg Val Gly Leu His Glu Tyr Pro Val
2145                2150                2155                2160
```

-continued

```
Gly Ser Gln Leu Pro Cys Glu Pro Glu Pro Asp Val Ala Val Leu Thr
            2165                2170                2175
Ser Met Leu Thr Asp Pro Ser His Ile Thr Ala Glu Ala Ala Gly Arg
            2180                2185                2190
Arg Leu Ala Arg Gly Ser Pro Ser Met Ala Ser Ser Ala Ser
            2195                2200                2205
Gln Leu Ser Ala Pro Ser Leu Lys Ala Thr Cys Thr Ala Asn His Asp
            2210                2215                2220
Ser Pro Asp Ala Glu Leu Ile Glu Ala Asn Leu Leu Trp Arg Gln Glu
2225                2230                2235                2240
Met Gly Gly Asn Ile Thr Arg Val Glu Ser Glu Asn Lys Val Val Ile
            2245                2250                2255
Leu Asp Ser Phe Asp Pro Leu Val Ala Glu Glu Asp Glu Arg Glu Val
            2260                2265                2270
Ser Val Pro Ala Glu Ile Leu Arg Lys Ser Arg Arg Phe Ala Arg Ala
            2275                2280                2285
Leu Pro Val Trp Ala Arg Pro Asp Tyr Asn Pro Pro Leu Val Glu Thr
            2290                2295                2300
Trp Lys Lys Pro Asp Tyr Glu Pro Pro Val Val His Gly Cys Pro Leu
2305                2310                2315                2320
Pro Pro Pro Arg Ser Pro Pro Val Pro Pro Arg Lys Lys Arg Thr
            2325                2330                2335
Val Val Leu Thr Glu Ser Thr Leu Ser Thr Ala Leu Ala Glu Leu Ala
            2340                2345                2350
Thr Lys Ser Phe Gly Ser Ser Ser Thr Ser Gly Ile Thr Gly Asp Asn
            2355                2360                2365
Thr Thr Thr Ser Ser Glu Pro Ala Pro Ser Gly Cys Pro Pro Asp Ser
            2370                2375                2380
Asp Val Glu Ser Tyr Ser Ser Met Pro Pro Leu Glu Gly Glu Pro Gly
2385                2390                2395                2400
Asp Pro Asp Leu Ser Asp Gly Ser Trp Ser Thr Val Ser Ser Gly Ala
            2405                2410                2415
Asp Thr Glu Asp Val Val Cys Cys Ser Met Ser Tyr Ser Trp Thr Gly
            2420                2425                2430
Ala Leu Val Thr Pro Cys Ala Ala Glu Glu Gln Lys Leu Pro Ile Asn
            2435                2440                2445
Ala Leu Ser Asn Ser Leu Leu Arg His His Asn Leu Val Tyr Ser Thr
            2450                2455                2460
Thr Ser Arg Ser Ala Cys Gln Arg Gln Lys Lys Val Thr Phe Asp Arg
2465                2470                2475                2480
Leu Gln Val Leu Asp Ser His Tyr Gln Asp Val Leu Lys Glu Val Lys
            2485                2490                2495
Ala Ala Ala Ser Lys Val Lys Ala Asn Leu Leu Ser Val Glu Glu Ala
            2500                2505                2510
Cys Ser Leu Thr Pro Pro His Ser Ala Lys Ser Lys Phe Gly Tyr Gly
            2515                2520                2525
Ala Lys Asp Val Arg Cys His Ala Arg Lys Ala Val Ala His Ile Asn
            2530                2535                2540
Ser Val Trp Lys Asp Leu Leu Glu Asp Ser Val Thr Pro Ile Asp Thr
2545                2550                2555                2560
Thr Ile Met Ala Lys Asn Glu Val Phe Cys Val Gln Pro Glu Lys Gly
            2565                2570                2575
Gly Arg Lys Pro Ala Arg Leu Ile Val Phe Pro Asp Leu Gly Val Arg
```

-continued

```
                 2580              2585              2590
Val Cys Glu Lys Met Ala Leu Tyr Asp Val Val Ser Lys Leu Pro Leu
    2595              2600              2605
Ala Val Met Gly Ser Ser Tyr Gly Phe Gln Tyr Ser Pro Gly Gln Arg
    2610              2615              2620
Val Glu Phe Leu Val Gln Ala Trp Lys Ser Lys Lys Thr Pro Met Gly
2625              2630              2635              2640
Phe Ser Tyr Asp Thr Arg Cys Phe Asp Ser Thr Val Thr Glu Ser Asp
            2645              2650              2655
Ile Arg Thr Glu Glu Ala Ile Tyr Gln Cys Cys Asp Leu Asp Pro Gln
        2660              2665              2670
Ala Arg Val Ala Ile Lys Ser Leu Thr Glu Arg Leu Tyr Val Gly Gly
        2675              2680              2685
Pro Leu Thr Asn Ser Arg Gly Glu Asn Cys Gly Tyr Arg Arg Cys Arg
        2690              2695              2700
Ala Ser Gly Val Leu Thr Thr Ser Cys Gly Asn Thr Leu Thr Cys Tyr
2705              2710              2715              2720
Ile Lys Ala Arg Ala Ala Cys Arg Ala Ala Gly Leu Gln Asp Cys Thr
            2725              2730              2735
Met Leu Val Cys Gly Asp Asp Leu Val Val Ile Cys Glu Ser Ala Gly
        2740              2745              2750
Val Gln Glu Asp Ala Ala Ser Leu Arg Ala Phe Thr Glu Ala Met Thr
        2755              2760              2765
Arg Tyr Ser Ala Pro Pro Gly Asp Pro Pro Gln Pro Glu Tyr Asp Leu
    2770              2775              2780
Glu Leu Ile Thr Ser Cys Ser Ser Asn Val Ser Val Ala His Asp Gly
2785              2790              2795              2800
Ala Gly Lys Arg Val Tyr Tyr Leu Thr Arg Asp Pro Thr Thr Pro Leu
            2805              2810              2815
Ala Arg Ala Ala Trp Glu Thr Ala Arg His Thr Pro Val Asn Ser Trp
        2820              2825              2830
Leu Gly Asn Ile Ile Met Phe Ala Pro Thr Leu Trp Ala Arg Met Ile
        2835              2840              2845
Leu Met Thr His Phe Phe Ser Val Leu Ile Ala Arg Asp Gln Leu Glu
    2850              2855              2860
Gln Ala Leu Asn Cys Glu Ile Tyr Gly Ala Cys Tyr Ser Ile Glu Pro
2865              2870              2875              2880
Leu Asp Leu Pro Pro Ile Ile Gln Arg Leu His Gly Leu Ser Ala Phe
            2885              2890              2895
Ser Leu His Ser Tyr Ser Pro Gly Glu Ile Asn Arg Val Ala Ala Cys
            2900              2905              2910
Leu Arg Lys Leu Gly Val Pro Pro Leu Arg Ala Trp Arg His Arg Ala
        2915              2920              2925
Arg Ser Val Arg Ala Arg Leu Leu Ser Arg Gly Gly Arg Ala Ala Ile
    2930              2935              2940
Cys Gly Lys Tyr Leu Phe Asn Trp Ala Val Arg Thr Lys Leu Lys Leu
2945              2950              2955              2960
Thr Pro Ile Ala Ala Ala Gly Arg Leu Asp Leu Ser Gly Trp Phe Thr
            2965              2970              2975
Ala Gly Tyr Ser Gly Gly Asp Ile Tyr His Ser Val Ser His Ala Arg
        2980              2985              2990
Pro Arg Trp Phe Trp Phe Cys Leu Leu Leu Leu Ala Ala Gly Val Gly
    2995              3000              3005
```

Ile Tyr Leu Leu Pro Asn Arg
    3010              3015

<210> SEQ ID NO 9
<211> LENGTH: 9611
<212> TYPE: DNA
<213> ORGANISM: Hepatitis C virus

<400> SEQUENCE: 9

| | | | | | |
|---|---|---|---|---|---|
| gccagccccc | tgatggggc | gacactccac | catgaatcac | tccctgtga | ggaactactg | 60 |
| tcttcacgca | gaaagcgtct | agccatggcg | ttagtatgag | tgtcgtgcag | cctccaggac | 120 |
| ccccctccc | gggagagcca | tagtggtctg | cggaaccggt | gagtacaccg | gaattgccag | 180 |
| gacgaccggg | tcctttcttg | gataaaccg | ctcaatgcct | ggagatttgg | gcgtgccccc | 240 |
| gcaagactgc | tagccgagta | gtgttgggtc | gcgaaaggcc | ttgtggtact | gcctgatagg | 300 |
| gtgcttgcga | gtgccccggg | aggtctcgta | gaccgtgcac | catgagcaca | aatcctaaac | 360 |
| ctcaaagaaa | aaccaaaaga | aacaccaacc | gtcgcccaca | agacgttaag | tttccgggcg | 420 |
| gcggccagat | cgttggcgga | gtatacttgt | tgccgcgcag | gggccccagg | ttgggtgtgc | 480 |
| gcgcgacaag | gaagacttcg | gagcggtccc | agccacgtgg | aaggcgccag | cccatcccta | 540 |
| aagatcggcg | ctccactggc | aaatcctggg | gaaaaccagg | ataccctgg | ccctatacg | 600 |
| ggaatgaggg | actcggctgg | gcaggatggc | tcctgtcccc | ccgaggttcc | cgtccctctt | 660 |
| ggggccccaa | tgaccccgg | cataggtcgc | gcaacgtggg | taaggtcatc | gatacctaa | 720 |
| cgtgcggctt | tgccgacctc | atgggtaca | tccctgtcgt | gggcgccccg | ctcggcggcg | 780 |
| tcgccagagc | tctcgcgcat | ggcgtgagag | tcctggagga | cggggttaat | tttgcaacag | 840 |
| ggaacttacc | cggttgctcc | ttttctatct | tcttgctggc | cctgctgtcc | tgcatcacca | 900 |
| ccccggtctc | cgctgccgaa | gtgaagaaca | tcagtaccgg | ctacatggtg | actaacgact | 960 |
| gcaccaatga | cagcattacc | tggcagctcc | aggctgctgt | cctccacgtc | cccgggtgcg | 1020 |
| tcccgtgcga | gaaagtgggg | aatgcatctc | agtgctggat | accggtctca | ccgaatgtgg | 1080 |
| ccgtgcagcg | gcccggcgcc | ctcacgcagg | gcttgcggac | gcacatcgac | atggttgtga | 1140 |
| tgtccgccac | gctctgctct | gccctctacg | tgggggacct | ctgcggtggg | gtgatgctcg | 1200 |
| cagcccaaat | gttcattgtc | tcgccgcagc | accactggtt | tgtccaagac | tgcaattgct | 1260 |
| ccatctaccc | tggtaccatc | actggacacc | gcatggcatg | ggacatgatg | atgaactggt | 1320 |
| cgcccacggc | taccatgatc | ttggcgtacg | cgatgcgtgt | ccccgaggtc | attatagaca | 1380 |
| tcattagcgg | ggctcattgg | ggcgtcatgt | tcggcttggc | ctacttctct | atgcagggag | 1440 |
| cgtgggcgaa | agtcgttgtc | atccttctgt | tggccgccgg | ggtggacgcg | cgcacccata | 1500 |
| ctgttggggg | ttctgccgcg | cagaccaccg | ggcgcctcac | cagcttattt | gacatgggcc | 1560 |
| ccaggcagaa | aatccagctc | gttaacacca | atggcagctg | gcacatcaac | cgcaccgccc | 1620 |
| tgaactgcaa | tgactccttg | cacaccggct | ttatcgcgtc | tctgttctac | acccacagct | 1680 |
| tcaactcgtc | aggatgtccc | gaacgcatgt | ccgcctgccg | cagtatcgag | gccttccggg | 1740 |
| tgggatgggg | cgccttgcaa | tatgaggata | atgtcaccaa | tccagaggat | atgagaccct | 1800 |
| attgctggca | ctaccacca | aggcagtgtg | gcgtggtctc | cgcgaagact | gtgtgtggcc | 1860 |
| cagtgtactg | tttcaccccc | agcccagtgg | tagtgggcac | gaccgacagg | cttggagcgc | 1920 |
| ccacttacac | gtgggggag | aatgagacag | atgtcttcct | attgaacagc | actgaccac | 1980 |
| cgctggggtc | atggttcggc | tgcacgtgga | tgaactcttc | tggctacacc | aagacttgcg | 2040 |

```
gcgcaccacc ctgccgtact agagctgact tcaacgccag cacggacctg ttgtgcccca    2100
cggactgttt taggaagcat cctgatacca cttacctcaa atgcggctct gggccctggc    2160
tcacgccaag gtgcctgatc gactacccct acaggctctg cattacccc tgcacagtta    2220
actataccat cttcaaaata aggatgtatg tgggaggggt tgagcacagg ctcacggctg    2280
catgcaattt cactcgtggg gatcgttgca acttggagga cagagacaga agtcaactgt    2340
ctcctttgtt gcactccacc acggaatggg ccattttacc ttgctcttac tcggacctgc    2400
ccgccttgtc gactggtctt ctccacctcc accaaaacat cgtggacgta caattcatgt    2460
atggcctatc acctgccctc acaaaataca tcgtccgatg ggagtgggta atactcttat    2520
tcctgctctt agcggacgcc agggtttgcg cctgcttatg gatgctcatc ttgttgggcc    2580
aggccgaagc agctttggag aacctcgtaa tactcaatgc agcatccctg gccgggacgc    2640
acggtcttgt gtccttcctc gtgttcttct gctttgcgtg gtatctgaag ggtaggtggg    2700
tgcccggagc ggtctacgcc ctctacggga tgtggcctct cctcctgctc ctgctggcgt    2760
tgcctcagcg ggcatatgca ctggacacgg aggtggccgc gtcgtgtggc ggcgttgttc    2820
ttgtcgggtt aatggcgctg actctgtcgc catattacaa gcgctatatc agctggtgca    2880
tgtggtggct tcagtatttt ctgaccagag tagaagcgca actgcacgtg tgggttcccc    2940
ccctcaacgt ccggggggg cgcgatgccg tcatcttact catgtgtgta gtacacccga    3000
ccctggtatt tgacatcacc aaactactcc tggccatctt cggaccccctt tggattcttc    3060
aagccagttt gcttaaagtc ccctacttcg tgcgcgttca aggccttctc cggatctgcg    3120
cgctagcgcg gaagatagcc ggaggtcatt acgtgcaaat ggccatcatc aagttagggg    3180
cgcttactgg cacctatgtg tataaccatc tcacccctct tcgagactgg gcgcacaacg    3240
gcctgcgaga tctggccgtg gctgtggaac cagtcgtctt ctcccgaatg gagaccaagc    3300
tcatcacgtg ggggggcagat accgccgcgt gcggtgacat catcaacggc ttgcccgtct    3360
ctgcccgtag gggccaggag atactgcttg gccagccga cggaatggtc tccaagggtt    3420
ggaggttgct ggcgcccatc acggcgtacg cccagcagac gagaggcctc ctagggtgta    3480
taatcaccag cctgactggc cgggacaaaa accaagtgga gggtgaggtc cagatcgtgt    3540
caactgctac ccaaaccttc ctggcaacgt gcatcaatgg ggtatgctgg actgtctacc    3600
acgggggccgg aacgaggacc atcgcatcac ccaagggtcc tgtcatccag atgtatacca    3660
atgtggacca agaccttgtg ggctggcccg ctcctcaagg ttcccgctca ttgacaccct    3720
gtacctgcgg ctcctcggac ctttacctgg tcacgaggca cgccgatgtc attcccgtgc    3780
gccggcgagg tgatagcagg ggtagcctgc tttcgccccg gcccatttcc tacttgaaag    3840
gctcctcggg gggtccgctg ttgtgccccg cgggacacgc cgtgggccta ttcagggccg    3900
cggtgtgcac ccgtggagtg gctaaagcgg tggactttat ccctgtggag aacctaggga    3960
caaccatgag atccccggtg ttcacggaca actcctctcc accagcagtg ccccagagct    4020
tccaggtggc ccacctgcat gctcccaccg gcagcggtaa gagcaccaag gtcccggctg    4080
cgtacgcagc ccagggctac aaggtgttgg tgctcaaccc ctctgttgct gcaacgctgg    4140
gctttggtgc ttacatgtcc aaggcccatg gggttgatcc taatatcagg accggggtga    4200
gaacaattac cactggcagc cccatcacgt actccaccta cggcaagttc cttgccgacg    4260
gcgggtgctc aggaggtgct tatgacataa taatttgtga cgagtgccac tccacggatg    4320
ccacatccat cttgggcatc ggcactgtcc ttgaccaagc agagactgcg ggggcgagac    4380
```

-continued

```
tggttgtgct cgccactgct acccctccgg gctccgtcac tgtgtcccat cctaacatcg    4440
aggaggttgc tctgtccacc accggagaga tcccctttta cggcaaggct atcccccctcg  4500
aggtgatcaa gggggggaaga catctcatct tctgccactc aaagaagaag tgcgacgagc  4560
tcgccgcgaa gctggtcgca ttgggcatca atgccgtggc ctactaccgc ggtcttgacg   4620
tgtctgtcat cccgaccagc ggcgatgttg tcgtcgtgtc gaccgatgct ctcatgactg   4680
gctttaccgg cgacttcgac tctgtgatag actgcaacac gtgtgtcact cagacagtcg   4740
atttcagcct tgaccctacc tttaccattg agacaaccac gctcccccag gatgctgtct   4800
ccaggactca acgccggggc aggactggca gggggaagcc aggcatctat agatttgtgg   4860
caccgggggga gcgcccctcc ggcatgttcg actcgtccgt cctctgtgag tgctatgacg  4920
cgggctgtgc ttggtatgag ctcacgcccg ccgagactac agttaggcta cgagcgtaca   4980
tgaacacccc ggggcttccc gtgtgccagg accatcttga attttgggag ggcgtcttta   5040
cgggcctcac tcatatagat gcccactttt tatcccagac aaagcagagt ggggagaact   5100
ttccttacct ggtagcgtac caagccaccg tgtgcgctag ggctcaagcc cctcccccat   5160
cgtgggacca gatgtggaag tgtttgatcc gccttaaacc caccctccat gggccaacac   5220
ccctgctata cagactgggc gctgttcaga atgaagtcac cctgacgcac ccaatcacca   5280
aatacatcat gacatgcatg tcggccgacc tggaggtcgt cacgagcacc tgggtgctcg   5340
ttggcggcgt cctggctgct ctggccgcgt attgcctgtc aacaggctgc gtggtcatag   5400
tgggcaggat cgtcttgtcc gggaagccgg caattatacc tgacagggag gttctctacc   5460
aggagttcga tgagatggaa gagtgctctc agcacttacc gtacatcgag caagggatga   5520
tgctcgctga gcagttcaag cagaaggccc tcggcctcct gcagaccgcg tcccgccatg   5580
cagaggttat cacccctgct gtccagacca actggcagaa actcgaggtc ttttgggcga   5640
agcacatgtg gaatttcatc agtgggatac aatacttggc gggcctgtca acgctgcctg   5700
gtaaccccgc cattgcttca ttgatggctt ttacagctgc cgtcaccagc ccactaacca   5760
ctggccaaac cctcctcttc aacatattgg ggggtgggt ggctgcccag ctcgccgccc    5820
ccggtgccgc tactgccttt gtgggtgctg gcctagctgg cgccgccatc ggcagcgttg   5880
gactggggaa ggtcctcgtg gacattcttg cagggtatgg cgcggggcgtg gcgggagctc   5940
ttgtagcatt caagatcatg agcggtgagg tcccctccac ggaggacctg gtcaatctgc   6000
tgcccgccat cctctcgcct ggagcccttg tagtcggtgt ggtctgcgca gcaatactgc   6060
gccggcacgt tgggcccggc gagggggcag tgcaatggat gaaccggcta atagccttcg   6120
cctcccgggg gaaccatgtt tcccccacgc actacgtgcc ggagagcgat gcagccgccc   6180
gcgtcactgc catactcagc agcctcactg taacccagcc cctgaggcga ctgcatcagt   6240
ggataagctc ggagtgtacc actccatgct ccggttcctg gctaagggac atctgggact   6300
ggatatgcga ggtgctgagc gactttaaga cctggctgaa agccaagctc atgccacaac   6360
tgcctgggat tccctttgtg tcctgccagc gcgggtatag gggggtctgg cgaggagacg   6420
gcattatgca cactcgctgc cactgtggag ctgagtacac tggacatgtc aaaaacggga   6480
cgatgaggat cgtcggtcct aggacctgca ggaacatgtg gagtgggacg ttccccatta   6540
acgcctacac cacgggcccc tgtactcccc ttcctgcgcc gaactataag ttcgcgctgt   6600
ggagggtgtc tgcagaggaa tacgtggaga taaggcgggt gggggacttc cactacgtat   6660
cgggtatgac tactgacaat cttaaatgcc cgtgccagat cccatcgccc gaatttttca   6720
cagaattgga cggggtgcgc ctacacaggt ttgcgccccc ttgcaagccc ttgctgcggg   6780
```

-continued

```
aggaggtatc attcagagta ggactccacg agtacccggt ggggtcgcaa ttaccttgcg    6840
agcccgaacc ggacgtagcc gtgttgacgt ccatgctcac tgatccctcc catataacag    6900
cagaggcggc cggagaagg ttggcgagag ggtcaccccc ttctatggcc agctcctcgg     6960
ctagccagct gtccgctcca tctctcaagg caacttgcac cgccaaccat gactcccctg    7020
acgccgagct catagaggct aacctcctgt ggaggcagga gatgggcggc aacatcacca    7080
gggttgagtc agagaacaaa gtggtgattc tggactcctt cgatccgctt gtggcagagg    7140
aggatgagcg ggaggtctcc gtacctgcag aaattctgcg gaagtctcgg agattcgccc    7200
gggccctgcc cgtctgggcg cggccggact acaaccccc gctagtagag acgtggaaaa    7260
agcctgacta cgaaccacct gtggtccatg gctgcccgct accacctcca cggtcccctc    7320
ctgtgcctcc gcctcggaaa aagcgtacgg tggtcctcac cgaatcaacc ctatctactg    7380
ccttggccga gcttgccacc aaaagttttg gcagctcctc aacttccggc attacgggcg    7440
acaatacgac aacatcctct gagcccgccc cttctggctg ccccccgac tccgacgttg     7500 agtcctattc ttccatgccc ccctggagg gggagcctgg ggatccggat ctcagcgacg     7560
ggtcatggtc gacggtcagt agtggggccg acacggaaga tgtcgtgtgc tgctcaatgt    7620
cttattcctg gacaggcgca ctcgtcaccc cgtgcgctgc ggaagaacaa aaactgccca    7680
tcaacgcact gagcaactcg ttgctacgcc atcacaatct ggtgtattcc accacttcac    7740
gcagtgcttg ccaaaggcag aagaaagtca catttgacag actgcaagtt ctggacagcc    7800
attaccagga cgtgctcaag gaggtcaaag cagcggcgtc aaaagtgaag gctaacttgc    7860
tatccgtaga ggaagcttgc agcctgacgc ccccacattc agccaaatcc aagtttggct    7920
atggggcaaa agacgtccgt tgccatgcca gaaaggccgt agcccacatc aactccgtgt    7980
ggaaagacct tctggaagac agtgtaacac caatagacac taccatcatg gccaagaacg    8040
aggttttctg cgttcagcct gagaagggg gtcgtaagcc agctcgtctc atcgtgttcc     8100
ccgacctggg cgtgcgcgtg tgcgagaaga tggccctgta cgacgtggtt agcaagctcc    8160
ccctggccgt gatgggaagc tcctacggat tccaatactc accaggacag cgggttgaat    8220
tcctcgtgca agcgtggaag tccaagaaga ccccgatggg gttctcgtat gatacccgct    8280
gttttgactc cacagtcact gagagcgaca tccgtacgga ggaggcaatt taccaatgtt    8340
gtgacctgga ccccaagcc cgcgtggcca tcaagtccct cactgagagg ctttatgttg     8400
ggggccctct taccaattca agggggaaa actgcggcta ccgcaggtgc cgcgcgagcg     8460
gcgtactgac aactagctgt ggtaacaccc tcacttgcta catcaaggcc cgggcagcct    8520
gtcgagccgc agggctccag gactgcacca tgctcgtgtg tggcgacgac ttagtcgtta    8580
tctgtgaaag tgcggggtc caggaggacg cggcgagcct gagagccttc acggaggcta    8640
tgaccaggta ctccgcccc ccggggacc ccccacaacc agaatacgac ttggagctta     8700
taacatcatg ctcctccaac gtgtcagtcg cccacgacgg cgctggaaag agggtctact    8760
accttacccg tgaccctaca ccccctcg cgagagccgc gtgggagaca gcaagacaca     8820
ctccagtcaa ttcctggcta ggcaacataa tcatgtttgc ccccacactg tgggcgagga    8880
tgatactgat gacccattc tttagcgtcc tcatagccag ggatcagctt gaacaggctc     8940
ttaactgtga gatctacgga gcctgctact ccatagaacc actggatcta cctccaatca    9000
ttcaaagact ccatgcctc agcgcatttt cactccacag ttactctcca ggtgaaatca    9060 ataggggtggc cgcatgcctc agaaaacttg gggtcccgcc cttgcgagct ggagacaccc    9120
```

-continued

```
gggcccggag cgtccgcgct aggcttctgt ccagaggagg cagggctgct atatgtggca    9180
agtacctctt caactgggca gtaagaacaa agctcaaact cactccaata gcggccgctg    9240
gccggctgga cttgtccggt tggttcacgg ctggctacag cggggagac atttatcaca     9300 gcgtgtctca tgcccggccc cgctggttct ggttttgcct actcctgctc gctgcagggg    9360
taggcatcta cctcctcccc aaccgatgaa ggttggggta acactccgg cctcttaagc     9420 catttcctgt tttttttttt tttttttttt tttttttctt tttttttttc tttcctttcc    9480
ttcttttttt cctttctttt tcccttcttt aatggtggct ccatcttagc cctagtcacg    9540
gctagctgtg aaaggtccgt gagccgcatg actgcagaga gtgctgatac tggcctctct    9600
gcagatcatg t                                                         9611
```

<210> SEQ ID NO 10
<211> LENGTH: 3015
<212> TYPE: PRT
<213> ORGANISM: Hepatitis C virus

<400> SEQUENCE: 10

```
Met Ser Thr Asn Pro Lys Pro Gln Arg Lys Thr Lys Arg Asn Thr Asn
 1               5                  10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Asn Asp Pro
            100                 105                 110

Arg His Arg Ser Arg Asn Val Gly Lys Val Ile Asp Thr Leu Thr Cys
        115                 120                 125

Gly Phe Ala Asp Leu Met Gly Tyr Ile Pro Val Val Gly Ala Pro Leu
    130                 135                 140

Gly Gly Val Ala Arg Ala Leu Ala His Gly Val Arg Val Leu Glu Asp
145                 150                 155                 160

Gly Val Asn Phe Ala Thr Gly Asn Leu Pro Gly Cys Ser Phe Ser Ile
                165                 170                 175

Phe Leu Leu Ala Leu Leu Ser Cys Ile Thr Thr Pro Val Ser Ala Ala
            180                 185                 190

Glu Val Lys Asn Ile Ser Thr Gly Tyr Met Val Thr Asn Asp Cys Thr
        195                 200                 205

Asn Asp Ser Ile Thr Trp Gln Leu Gln Ala Ala Val Leu His Val Pro
    210                 215                 220

Gly Cys Val Pro Cys Glu Lys Val Gly Asn Ala Ser Gln Cys Trp Ile
225                 230                 235                 240

Pro Val Ser Pro Asn Val Ala Val Gln Arg Pro Gly Ala Leu Thr Gln
                245                 250                 255

Gly Leu Arg Thr His Ile Asp Met Val Val Met Ser Ala Thr Leu Cys
            260                 265                 270

Ser Ala Leu Tyr Val Gly Asp Leu Cys Gly Gly Val Met Leu Ala Ala
        275                 280                 285
```

-continued

```
Gln Met Phe Ile Val Ser Pro Gln His His Trp Phe Val Gln Asp Cys
    290                 295                 300
Asn Cys Ser Ile Tyr Pro Gly Thr Ile Thr Gly His Arg Met Ala Trp
305                 310                 315                 320
Asp Met Met Met Asn Trp Ser Pro Thr Ala Thr Met Ile Leu Ala Tyr
                    325                 330                 335
Ala Met Arg Val Pro Glu Val Ile Ile Asp Ile Ile Ser Gly Ala His
            340                 345                 350
Trp Gly Val Met Phe Gly Leu Ala Tyr Phe Ser Met Gln Gly Ala Trp
        355                 360                 365
Ala Lys Val Val Ile Leu Leu Ala Ala Gly Val Asp Ala Arg
370                 375                 380
Thr His Thr Val Gly Ser Ala Ala Gln Thr Thr Gly Arg Leu Thr
385                 390                 395                 400
Ser Leu Phe Asp Met Gly Pro Arg Gln Lys Ile Gln Leu Val Asn Thr
                405                 410                 415
Asn Gly Ser Trp His Ile Asn Arg Thr Ala Leu Asn Cys Asn Asp Ser
            420                 425                 430
Leu His Thr Gly Phe Ile Ala Ser Leu Phe Tyr Thr His Ser Phe Asn
        435                 440                 445
Ser Ser Gly Cys Pro Glu Arg Met Ser Ala Cys Arg Ser Ile Glu Ala
450                 455                 460
Phe Arg Val Gly Trp Gly Ala Leu Gln Tyr Glu Asp Asn Val Thr Asn
465                 470                 475                 480
Pro Glu Asp Met Arg Pro Tyr Cys Trp His Tyr Pro Arg Gln Cys
                485                 490                 495
Gly Val Val Ser Ala Lys Thr Val Cys Gly Pro Val Tyr Cys Phe Thr
            500                 505                 510
Pro Ser Pro Val Val Gly Thr Thr Asp Arg Leu Gly Ala Pro Thr
        515                 520                 525
Tyr Thr Trp Gly Glu Asn Glu Thr Asp Val Phe Leu Leu Asn Ser Thr
        530                 535                 540
Arg Pro Pro Leu Gly Ser Trp Phe Gly Cys Thr Trp Met Asn Ser Ser
545                 550                 555                 560
Gly Tyr Thr Lys Thr Cys Gly Ala Pro Pro Cys Arg Thr Arg Ala Asp
                565                 570                 575
Phe Asn Ala Ser Thr Asp Leu Leu Cys Pro Thr Asp Cys Phe Arg Lys
            580                 585                 590
His Pro Asp Thr Thr Tyr Leu Lys Cys Gly Ser Gly Pro Trp Leu Thr
        595                 600                 605
Pro Arg Cys Leu Ile Asp Tyr Pro Tyr Arg Leu Trp His Tyr Pro Cys
        610                 615                 620
Thr Val Asn Tyr Thr Ile Phe Lys Ile Arg Met Tyr Val Gly Gly Val
625                 630                 635                 640
Glu His Arg Leu Thr Ala Ala Cys Asn Phe Thr Arg Gly Asp Arg Cys
                645                 650                 655
Asn Leu Glu Asp Arg Asp Arg Ser Gln Leu Ser Pro Leu Leu His Ser
            660                 665                 670
Thr Thr Glu Trp Ala Ile Leu Pro Cys Ser Tyr Ser Asp Leu Pro Ala
        675                 680                 685
Leu Ser Thr Gly Leu Leu His Leu His Gln Asn Ile Val Asp Val Gln
        690                 695                 700
```

```
                                                    -continued

Phe Met Tyr Gly Leu Ser Pro Ala Leu Thr Lys Tyr Ile Val Arg Trp
705                 710                 715                 720

Glu Trp Val Ile Leu Leu Phe Leu Leu Leu Ala Asp Ala Arg Val Cys
            725                 730                 735

Ala Cys Leu Trp Met Leu Ile Leu Leu Gly Gln Ala Glu Ala Ala Leu
        740                 745                 750

Glu Asn Leu Val Ile Leu Asn Ala Ala Ser Leu Ala Gly Thr His Gly
    755                 760                 765

Leu Val Ser Phe Leu Val Phe Phe Cys Phe Ala Trp Tyr Leu Lys Gly
770                 775                 780

Arg Trp Val Pro Gly Ala Val Tyr Ala Leu Tyr Gly Met Trp Pro Leu
785                 790                 795                 800

Leu Leu Leu Leu Leu Ala Leu Pro Gln Arg Ala Tyr Ala Leu Asp Thr
            805                 810                 815

Glu Val Ala Ala Ser Cys Gly Val Val Leu Val Gly Leu Met Ala
        820                 825                 830

Leu Thr Leu Ser Pro Tyr Tyr Lys Arg Tyr Ile Ser Trp Cys Met Trp
    835                 840                 845

Trp Leu Gln Tyr Phe Leu Thr Arg Val Glu Ala Gln Leu His Val Trp
850                 855                 860

Val Pro Pro Leu Asn Val Arg Gly Gly Arg Asp Ala Val Ile Leu Leu
865                 870                 875                 880

Met Cys Val Val His Pro Thr Leu Val Phe Asp Ile Thr Lys Leu Leu
            885                 890                 895

Leu Ala Ile Phe Gly Pro Leu Trp Ile Leu Gln Ala Ser Leu Leu Lys
        900                 905                 910

Val Pro Tyr Phe Val Arg Val Gln Gly Leu Leu Arg Ile Cys Ala Leu
    915                 920                 925

Ala Arg Lys Ile Ala Gly Gly His Tyr Val Gln Met Ala Ile Ile Lys
930                 935                 940

Leu Gly Ala Leu Thr Gly Thr Tyr Val Tyr Asn His Leu Thr Pro Leu
945                 950                 955                 960

Arg Asp Trp Ala His Asn Gly Leu Arg Asp Leu Ala Val Ala Val Glu
            965                 970                 975

Pro Val Val Phe Ser Arg Met Glu Thr Lys Leu Ile Thr Trp Gly Ala
        980                 985                 990

Asp Thr Ala Ala Cys Gly Asp Ile Ile Asn Gly Leu Pro Val Ser Ala
    995                 1000                1005

Arg Arg Gly Gln Glu Ile Leu Leu Gly Pro Ala Asp Gly Met Val Ser
    1010                1015                1020

Lys Gly Trp Arg Leu Leu Ala Pro Ile Thr Ala Tyr Ala Gln Gln Thr
1025                1030                1035                1040

Arg Gly Leu Leu Gly Cys Ile Ile Thr Ser Leu Thr Gly Arg Asp Lys
            1045                1050                1055

Asn Gln Val Glu Gly Glu Val Gln Ile Val Ser Thr Ala Thr Gln Thr
        1060                1065                1070

Phe Leu Ala Thr Cys Ile Asn Gly Val Cys Trp Thr Val Tyr His Gly
    1075                1080                1085

Ala Gly Thr Arg Thr Ile Ala Ser Pro Lys Gly Pro Val Ile Gln Met
    1090                1095                1100

Tyr Thr Asn Val Asp Gln Asp Leu Val Gly Trp Pro Ala Pro Gln Gly
1105                1110                1115                1120

Ser Arg Ser Leu Thr Pro Cys Thr Cys Gly Ser Ser Asp Leu Tyr Leu
```

-continued

```
                1125                1130                1135
Val Thr Arg His Ala Asp Val Ile Pro Val Arg Arg Gly Asp Ser
            1140                1145                1150
Arg Gly Ser Leu Leu Ser Pro Arg Pro Ile Ser Tyr Leu Lys Gly Ser
            1155                1160                1165
Ser Gly Gly Pro Leu Leu Cys Pro Ala Gly His Ala Val Gly Leu Phe
            1170                1175                1180
Arg Ala Ala Val Cys Thr Arg Gly Val Ala Lys Ala Val Asp Phe Ile
1185                1190                1195                1200
Pro Val Glu Asn Leu Gly Thr Thr Met Arg Ser Pro Val Phe Thr Asp
            1205                1210                1215
Asn Ser Ser Pro Pro Ala Val Pro Gln Ser Phe Gln Val Ala His Leu
            1220                1225                1230
His Ala Pro Thr Gly Ser Gly Lys Ser Thr Lys Val Pro Ala Ala Tyr
            1235                1240                1245
Ala Ala Gln Gly Tyr Lys Val Leu Val Leu Asn Pro Ser Val Ala Ala
            1250                1255                1260
Thr Leu Gly Phe Gly Ala Tyr Met Ser Lys Ala His Gly Val Asp Pro
1265                1270                1275                1280
Asn Ile Arg Thr Gly Val Arg Thr Ile Thr Thr Gly Ser Pro Ile Thr
            1285                1290                1295
Tyr Ser Thr Tyr Gly Lys Phe Leu Ala Asp Gly Gly Cys Ser Gly Gly
            1300                1305                1310
Ala Tyr Asp Ile Ile Ile Cys Asp Glu Cys His Ser Thr Asp Ala Thr
            1315                1320                1325
Ser Ile Leu Gly Ile Gly Thr Val Leu Asp Gln Ala Glu Thr Ala Gly
            1330                1335                1340
Ala Arg Leu Val Val Leu Ala Thr Ala Thr Pro Pro Gly Ser Val Thr
1345                1350                1355                1360
Val Ser His Pro Asn Ile Glu Glu Val Ala Leu Ser Thr Thr Gly Glu
            1365                1370                1375
Ile Pro Phe Tyr Gly Lys Ala Ile Pro Leu Glu Val Ile Lys Gly Gly
            1380                1385                1390
Arg His Leu Ile Phe Cys His Ser Lys Lys Lys Cys Asp Glu Leu Ala
            1395                1400                1405
Ala Lys Leu Val Ala Leu Gly Ile Asn Ala Val Ala Tyr Tyr Arg Gly
            1410                1415                1420
Leu Asp Val Ser Val Ile Pro Thr Ser Gly Asp Val Val Val Val Ser
1425                1430                1435                1440
Thr Asp Ala Leu Met Thr Gly Phe Thr Gly Asp Phe Asp Ser Val Ile
            1445                1450                1455
Asp Cys Asn Thr Cys Val Thr Gln Thr Val Asp Phe Ser Leu Asp Pro
            1460                1465                1470
Thr Phe Thr Ile Glu Thr Thr Thr Leu Pro Gln Asp Ala Val Ser Arg
            1475                1480                1485
Thr Gln Arg Arg Gly Arg Thr Gly Arg Gly Lys Pro Gly Ile Tyr Arg
            1490                1495                1500
Phe Val Ala Pro Gly Glu Arg Pro Ser Gly Met Phe Asp Ser Ser Val
1505                1510                1515                1520
Leu Cys Glu Cys Tyr Asp Ala Gly Cys Ala Trp Tyr Glu Leu Thr Pro
            1525                1530                1535
Ala Glu Thr Thr Val Arg Leu Arg Ala Tyr Met Asn Thr Pro Gly Leu
            1540                1545                1550
```

-continued

```
Pro Val Cys Gln Asp His Leu Glu Phe Trp Glu Gly Val Phe Thr Gly
            1555                1560                1565

Leu Thr His Ile Asp Ala His Phe Leu Ser Gln Thr Lys Gln Ser Gly
            1570                1575            1580

Glu Asn Phe Pro Tyr Leu Val Ala Tyr Gln Ala Thr Val Cys Ala Arg
1585                1590                1595                1600

Ala Gln Ala Pro Pro Ser Trp Asp Gln Met Trp Lys Cys Leu Ile
                1605                1610                1615

Arg Leu Lys Pro Thr Leu His Gly Pro Thr Pro Leu Leu Tyr Arg Leu
            1620                1625                1630

Gly Ala Val Gln Asn Glu Val Thr Leu Thr His Pro Ile Thr Lys Tyr
            1635                1640                1645

Ile Met Thr Cys Met Ser Ala Asp Leu Glu Val Val Thr Ser Thr Trp
            1650                1655                1660

Val Leu Val Gly Gly Val Leu Ala Ala Leu Ala Ala Tyr Cys Leu Ser
1665                1670                1675                1680

Thr Gly Cys Val Val Ile Val Gly Arg Ile Val Leu Ser Gly Lys Pro
            1685                1690                1695

Ala Ile Ile Pro Asp Arg Glu Val Leu Tyr Gln Glu Phe Asp Glu Met
            1700                1705                1710

Glu Glu Cys Ser Gln His Leu Pro Tyr Ile Glu Gln Gly Met Met Leu
            1715                1720                1725

Ala Glu Gln Phe Lys Gln Lys Ala Leu Gly Leu Leu Gln Thr Ala Ser
            1730                1735                1740

Arg His Ala Glu Val Ile Thr Pro Ala Val Gln Thr Asn Trp Gln Lys
1745                1750                1755                1760

Leu Glu Val Phe Trp Ala Lys His Met Trp Asn Phe Ile Ser Gly Ile
                1765                1770                1775

Gln Tyr Leu Ala Gly Leu Ser Thr Leu Pro Gly Asn Pro Ala Ile Ala
            1780                1785                1790

Ser Leu Met Ala Phe Thr Ala Ala Val Thr Ser Pro Leu Thr Thr Gly
            1795                1800                1805

Gln Thr Leu Leu Phe Asn Ile Leu Gly Gly Trp Val Ala Ala Gln Leu
            1810                1815                1820

Ala Ala Pro Gly Ala Ala Thr Ala Phe Val Gly Ala Gly Leu Ala Gly
1825                1830                1835                1840

Ala Ala Ile Gly Ser Val Gly Leu Gly Lys Val Leu Val Asp Ile Leu
                1845                1850                1855

Ala Gly Tyr Gly Ala Gly Val Ala Gly Ala Leu Val Ala Phe Lys Ile
            1860                1865                1870

Met Ser Gly Glu Val Pro Ser Thr Glu Asp Leu Val Asn Leu Leu Pro
            1875                1880                1885

Ala Ile Leu Ser Pro Gly Ala Leu Val Val Gly Val Val Cys Ala Ala
            1890                1895                1900

Ile Leu Arg Arg His Val Gly Pro Gly Glu Gly Ala Val Gln Trp Met
1905                1910                1915                1920

Asn Arg Leu Ile Ala Phe Ala Ser Arg Gly Asn His Val Ser Pro Thr
                1925                1930                1935

His Tyr Val Pro Glu Ser Asp Ala Ala Ala Arg Val Thr Ala Ile Leu
            1940                1945                1950

Ser Ser Leu Thr Val Thr Gln Leu Leu Arg Arg Leu His Gln Trp Ile
            1955                1960                1965
```

```
Ser Ser Glu Cys Thr Thr Pro Cys Ser Gly Ser Trp Leu Arg Asp Ile
    1970                1975                1980

Trp Asp Trp Ile Cys Glu Val Leu Ser Asp Phe Lys Thr Trp Leu Lys
1985            1990                1995                2000

Ala Lys Leu Met Pro Gln Leu Pro Gly Ile Pro Phe Val Ser Cys Gln
                2005                2010                2015

Arg Gly Tyr Arg Gly Val Trp Arg Gly Asp Gly Ile Met His Thr Arg
            2020                2025                2030

Cys His Cys Gly Ala Glu Ile Thr Gly His Val Lys Asn Gly Thr Met
        2035                2040                2045

Arg Ile Val Gly Pro Arg Thr Cys Arg Asn Met Trp Ser Gly Thr Phe
    2050                2055                2060

Pro Ile Asn Ala Tyr Thr Thr Gly Pro Cys Thr Pro Leu Pro Ala Pro
2065                2070                2075                2080

Asn Tyr Lys Phe Ala Leu Trp Arg Val Ser Ala Glu Glu Tyr Val Glu
                2085                2090                2095

Ile Arg Arg Val Gly Asp Phe His Tyr Val Ser Gly Met Thr Thr Asp
            2100                2105                2110

Asn Leu Lys Cys Pro Cys Gln Ile Pro Ser Pro Glu Phe Phe Thr Glu
        2115                2120                2125

Leu Asp Gly Val Arg Leu His Arg Phe Ala Pro Pro Cys Lys Pro Leu
    2130                2135                2140

Leu Arg Glu Glu Val Ser Phe Arg Val Gly Leu His Glu Tyr Pro Val
2145                2150                2155                2160

Gly Ser Gln Leu Pro Cys Glu Pro Glu Pro Asp Val Ala Val Leu Thr
                2165                2170                2175

Ser Met Leu Thr Asp Pro Ser His Ile Thr Ala Glu Ala Ala Gly Arg
            2180                2185                2190

Arg Leu Ala Arg Gly Ser Pro Pro Ser Met Ala Ser Ser Ser Ala Ser
        2195                2200                2205

Gln Leu Ser Ala Pro Ser Leu Lys Ala Thr Cys Thr Ala Asn His Asp
    2210                2215                2220

Ser Pro Asp Ala Glu Leu Ile Glu Ala Asn Leu Leu Trp Arg Gln Glu
2225                2230                2235                2240

Met Gly Gly Asn Ile Thr Arg Val Glu Ser Glu Asn Lys Val Val Ile
                2245                2250                2255

Leu Asp Ser Phe Asp Pro Leu Val Ala Glu Glu Asp Glu Arg Glu Val
            2260                2265                2270

Ser Val Pro Ala Glu Ile Leu Arg Lys Ser Arg Arg Phe Ala Arg Ala
        2275                2280                2285

Leu Pro Val Trp Ala Arg Pro Asp Tyr Asn Pro Pro Leu Val Glu Thr
    2290                2295                2300

Trp Lys Lys Pro Asp Tyr Glu Pro Pro Val Val His Gly Cys Pro Leu
2305                2310                2315                2320

Pro Pro Pro Arg Ser Pro Pro Val Pro Pro Pro Arg Lys Lys Arg Thr
                2325                2330                2335

Val Val Leu Thr Glu Ser Thr Leu Ser Thr Ala Leu Ala Glu Leu Ala
            2340                2345                2350

Thr Lys Ser Phe Gly Ser Ser Ser Thr Ser Gly Ile Thr Gly Asp Asn
        2355                2360                2365

Thr Thr Thr Ser Ser Glu Pro Ala Pro Ser Gly Cys Pro Pro Asp Ser
    2370                2375                2380

Asp Val Glu Ser Tyr Ser Ser Met Pro Pro Leu Glu Gly Glu Pro Gly
```

-continued

```
            2385                2390                2395                2400
Asp Pro Asp Leu Ser Asp Gly Ser Trp Ser Thr Val Ser Ser Gly Ala
                2405                2410                2415
Asp Thr Glu Asp Val Val Cys Cys Ser Met Ser Tyr Ser Trp Thr Gly
                2420                2425                2430
Ala Leu Val Thr Pro Cys Ala Ala Glu Glu Gln Lys Leu Pro Ile Asn
                2435                2440                2445
Ala Leu Ser Asn Ser Leu Leu Arg His His Asn Leu Val Tyr Ser Thr
                2450                2455                2460
Thr Ser Arg Ser Ala Cys Gln Arg Gln Lys Lys Val Thr Phe Asp Arg
2465                2470                2475                2480
Leu Gln Val Leu Asp Ser His Tyr Gln Asp Val Leu Lys Glu Val Lys
                2485                2490                2495
Ala Ala Ala Ser Lys Val Lys Ala Asn Leu Leu Ser Val Glu Glu Ala
                2500                2505                2510
Cys Ser Leu Thr Pro Pro His Ser Ala Lys Ser Lys Phe Gly Tyr Gly
                2515                2520                2525
Ala Lys Asp Val Arg Cys His Ala Arg Lys Ala Val Ala His Ile Asn
                2530                2535                2540
Ser Val Trp Lys Asp Leu Leu Glu Asp Ser Val Thr Pro Ile Asp Thr
2545                2550                2555                2560
Thr Ile Met Ala Lys Asn Glu Val Phe Cys Val Gln Pro Glu Lys Gly
                2565                2570                2575
Gly Arg Lys Pro Ala Arg Leu Ile Val Phe Pro Asp Leu Gly Val Arg
                2580                2585                2590
Val Cys Glu Lys Met Ala Leu Tyr Asp Val Val Ser Lys Leu Pro Leu
                2595                2600                2605
Ala Val Met Gly Ser Ser Tyr Gly Phe Gln Tyr Ser Pro Gly Gln Arg
                2610                2615                2620
Val Glu Phe Leu Val Gln Ala Trp Lys Ser Lys Lys Thr Pro Met Gly
2625                2630                2635                2640
Phe Ser Tyr Asp Thr Arg Cys Phe Asp Ser Thr Val Thr Glu Ser Asp
                2645                2650                2655
Ile Arg Thr Glu Glu Ala Ile Tyr Gln Cys Cys Asp Leu Asp Pro Gln
                2660                2665                2670
Ala Arg Val Ala Ile Lys Ser Leu Thr Glu Arg Leu Tyr Val Gly Gly
                2675                2680                2685
Pro Leu Thr Asn Ser Arg Gly Glu Asn Cys Gly Tyr Arg Arg Cys Arg
                2690                2695                2700
Ala Ser Gly Val Leu Thr Thr Ser Cys Gly Asn Thr Leu Thr Cys Tyr
2705                2710                2715                2720
Ile Lys Ala Arg Ala Ala Cys Arg Ala Ala Gly Leu Gln Asp Cys Thr
                2725                2730                2735
Met Leu Val Cys Gly Asp Asp Leu Val Val Ile Cys Glu Ser Ala Gly
                2740                2745                2750
Val Gln Glu Asp Ala Ala Ser Leu Arg Ala Phe Thr Glu Ala Met Thr
                2755                2760                2765
Arg Tyr Ser Ala Pro Pro Gly Asp Pro Pro Gln Pro Glu Tyr Asp Leu
                2770                2775                2780
Glu Leu Ile Thr Ser Cys Ser Ser Asn Val Ser Val Ala His Asp Gly
2785                2790                2795                2800
Ala Gly Lys Arg Val Tyr Tyr Leu Thr Arg Asp Pro Thr Thr Pro Leu
                2805                2810                2815
```

Ala Arg Ala Ala Trp Glu Thr Ala Arg His Thr Pro Val Asn Ser Trp
         2820                2825                2830

Leu Gly Asn Ile Ile Met Phe Ala Pro Thr Leu Trp Ala Arg Met Ile
         2835                2840                2845

Leu Met Thr His Phe Phe Ser Val Leu Ile Ala Arg Asp Gln Leu Glu
         2850                2855                2860

Gln Ala Leu Asn Cys Glu Ile Tyr Gly Ala Cys Tyr Ser Ile Glu Pro
2865                2870                2875                2880

Leu Asp Leu Pro Pro Ile Ile Gln Arg Leu His Gly Leu Ser Ala Phe
             2885                2890                2895

Ser Leu His Ser Tyr Ser Pro Gly Glu Ile Asn Arg Val Ala Ala Cys
             2900                2905                2910

Leu Arg Lys Leu Gly Val Pro Pro Leu Arg Ala Trp Arg His Arg Ala
             2915                2920                2925

Arg Ser Val Arg Ala Arg Leu Leu Ser Arg Gly Gly Arg Ala Ala Ile
             2930                2935                2940

Cys Gly Lys Tyr Leu Phe Asn Trp Ala Val Arg Thr Lys Leu Lys Leu
2945                2950                2955                2960

Thr Pro Ile Ala Ala Ala Gly Arg Leu Asp Leu Ser Gly Trp Phe Thr
             2965                2970                2975

Ala Gly Tyr Ser Gly Gly Asp Ile Tyr His Ser Val Ser His Ala Arg
             2980                2985                2990

Pro Arg Trp Phe Trp Phe Cys Leu Leu Leu Ala Ala Gly Val Gly
             2995                3000                3005

Ile Tyr Leu Leu Pro Asn Arg
    3010                3015

<210> SEQ ID NO 11
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 11
actggacacg gaggtggccg cgtc                                          24

<210> SEQ ID NO 12
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 12
ttgttcttgt cgggttaatg gcgc                                          24

<210> SEQ ID NO 13
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 13
gggtgtacta cacacatgag taag                                          24

<210> SEQ ID NO 14
<211> LENGTH: 22

-continued

```
<212> TYPE: DNA
<213> ORGANISM: Artificial Sequence
<220> FEATURE:
<223> OTHER INFORMATION: synthetic oligonucleotide

<400> SEQUENCE: 14
aagcgcccct aacttgatga tg                                              22

<210> SEQ ID NO 15
<211> LENGTH: 40
<212> TYPE: DNA
<213> ORGANISM: Artificial Sequence
<220> FEATURE:
<223> OTHER INFORMATION: synthetic oligonucleotide

<400> SEQUENCE: 15
cgtcatcgat acctcagcgg gcatatgcac tggacacgga                           40

<210> SEQ ID NO 16
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 16
gtccagtgca tatgcccgct gagg                                            24

<210> SEQ ID NO 17
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 17
catgcaccag ctgatatagc gcttgtaata tg                                   32

<210> SEQ ID NO 18
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 18
tccgtagagg aagcttgcag cctgacgccc                                      30

<210> SEQ ID NO 19
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 19
cagaggaggc agggctgcta tatgtggcaa gtac                                 34

<210> SEQ ID NO 20
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 20
```

-continued

```
gtacttgcca catatagcag ccctgcctcc tctg                              34
```

<210> SEQ ID NO 21
<211> LENGTH: 43
<212> TYPE: DNA
<213> ORGANISM: Artificial Sequence
<220> FEATURE:
<223> OTHER INFORMATION: synthetic oligonucleotide

<400> SEQUENCE: 21

```
cgtctctaga caggaaatgg cttaagaggc cggagtgttt acc                    43
```

<210> SEQ ID NO 22
<211> LENGTH: 65
<212> TYPE: DNA
<213> ORGANISM: Artificial Sequence
<220> FEATURE:
<223> OTHER INFORMATION: synthetic oligonucleotide

<400> SEQUENCE: 22

```
ttatggatgc tcatcttgtt gggccaggcc gaagcagctt tggagaacct cgtaatactc  60
aatgc                                                              65
```

<210> SEQ ID NO 23
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 23

```
aggatttgtg ctcatggtgc acggtctacg ag                                32
```

<210> SEQ ID NO 24
<211> LENGTH: 50
<212> TYPE: DNA
<213> ORGANISM: Artificial Sequence
<220> FEATURE:
<223> OTHER INFORMATION: synthetic oligonucleotide

<400> SEQUENCE: 24

```
ttttttttgc ggccgctaat acgactcact atagacccgc ccctaatagg             50
```

<210> SEQ ID NO 25
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 25

```
ccgtgcacca tgagcacaaa tcctaaacct c                                 31
```

<210> SEQ ID NO 26
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 26

```
ggatgtaccc catgaggtcg gcaaag                                       26
```

<210> SEQ ID NO 27
<211> LENGTH: 30

```
<212> TYPE: DNA
<213> ORGANISM: Artificial Sequence
<220> FEATURE:
<223> OTHER INFORMATION: synthetic oligonucleotide

<400> SEQUENCE: 27
gtttgcgcct gcttatggat gctcatcttg                                    30

<210> SEQ ID NO 28
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 28
gcgtcataag catatgcctg ttgggg                                        26

<210> SEQ ID NO 29
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 29
ccctcagcac tggagtacat ctg                                           23

<210> SEQ ID NO 30
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 30
cgtcatgcat acccctaggg cggctctcat tgaagaggg                          39

<210> SEQ ID NO 31
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 31
cgtcccctct tcaatgagag ccgctctaga                                    30

<210> SEQ ID NO 32
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 32
gcggtgaaga ccaagctcaa actcactc                                      28

<210> SEQ ID NO 33
<211> LENGTH: 41
<212> TYPE: DNA
<213> ORGANISM: Artificial Sequence
<220> FEATURE:
<223> OTHER INFORMATION: synthetic oligonucleotide

<400> SEQUENCE: 33
```

```
aatctagaag gcgcgcttcc ggcaatggag tgagtttgag c                           41
```

<210> SEQ ID NO 34
<211> LENGTH: 38
<212> TYPE: DNA
<213> ORGANISM: Artificial Sequence
<220> FEATURE:
<223> OTHER INFORMATION: synthetic oligonucleotide

<400> SEQUENCE: 34

```
cgtctctaga ggataaatcc aggaggcgcg cttccggc                              38
```

<210> SEQ ID NO 35
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 35

```
tacttttttgt aggggtaggc cttttcc                                         27
```

<210> SEQ ID NO 36
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 36

```
cgtctctaga gtgtagctaa tgtgtgccgc tcta                                  34
```

<210> SEQ ID NO 37
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 37

```
ctatggagtg tagctaatgt gtgc                                             24
```

<210> SEQ ID NO 38
<211> LENGTH: 107
<212> TYPE: DNA
<213> ORGANISM: Artificial Sequence
<220> FEATURE:
<223> OTHER INFORMATION: synthetic oligonucleotide

<400> SEQUENCE: 38

```
cgtctctaga catgatctgc agagagacca gttacggcac tctctgcagt catgcggctc      60
acggaccttt cacagctagc cgtgactagg gctaagatgg agccacc                   107
```

<210> SEQ ID NO 39
<211> LENGTH: 45
<212> TYPE: PRT
<213> ORGANISM: Hepatitis C virus

<400> SEQUENCE: 39

```
Leu Leu Leu Ala Ala Gly Val Asp Ala Arg Thr His Thr Val Gly Gly
 1               5                  10                  15

Ser Ala Ala Gln Thr Thr Gly Arg Leu Thr Ser Leu Phe Asp Met Gly
                20                  25                  30

Pro Arg Gln Lys Ile Gln Leu Val Asn Thr Asn Gly Ser
```

```
                  35                  40                  45

<210> SEQ ID NO 40
<211> LENGTH: 45
<212> TYPE: PRT
<213> ORGANISM: Hepatitis c virus

<400> SEQUENCE: 40

Leu Leu Leu Ala Ala Gly Val Asp Ala Arg Thr His Thr Val Gly Gly
 1               5                  10                  15

Ser Ala Ala Gln Thr Thr Gly Arg Leu Thr Ser Leu Phe Asp Met Gly
            20                  25                  30

Pro Arg Gln Lys Ile Gln Leu Val Asn Thr Asn Gly Ser
        35                  40                  45

<210> SEQ ID NO 41
<211> LENGTH: 45
<212> TYPE: PRT
<213> ORGANISM: Hepatitis C virus

<400> SEQUENCE: 41

Leu Leu Leu Ala Ala Gly Val Asp Ala Arg Thr His Thr Val Gly Gly
 1               5                  10                  15

Ser Ala Ala Gln Thr Thr Gly Arg Leu Thr Ser Leu Phe Asp Met Gly
            20                  25                  30

Pro Arg Gln Lys Ile Gln Leu Val Asn Thr Asn Gly Ser
        35                  40                  45

<210> SEQ ID NO 42
<211> LENGTH: 45
<212> TYPE: PRT
<213> ORGANISM: Hepatitis C virus

<400> SEQUENCE: 42

Leu Leu Leu Ala Ala Gly Val Asp Ala Arg Thr His Thr Val Gly Gly
 1               5                  10                  15

Ser Ala Ala Gln Thr Thr Gly Arg Leu Thr Ser Leu Phe Asp Met Gly
            20                  25                  30

Pro Arg Gln Lys Ile Gln Leu Val Asn Thr Asn Gly Ser
        35                  40                  45

<210> SEQ ID NO 43
<211> LENGTH: 45
<212> TYPE: PRT
<213> ORGANISM: Hepatitis C virus

<400> SEQUENCE: 43

Leu Leu Leu Ala Ala Gly Val Asp Ala Arg Thr His Thr Val Gly Gly
 1               5                  10                  15

Ser Ala Ala Gln Thr Thr Gly Arg Leu Thr Ser Leu Phe Asp Met Gly
            20                  25                  30

Pro Arg Gln Lys Ile Gln Leu Val Asn Thr Asn Gly Ser
        35                  40                  45

<210> SEQ ID NO 44
<211> LENGTH: 45
<212> TYPE: PRT
<213> ORGANISM: Hepatitis C virus

<400> SEQUENCE: 44

Leu Leu Leu Ala Ala Gly Val Asp Ala Arg Thr His Thr Val Gly Gly
```

```
                1               5                  10                 15
Ser Ala Ala Gln Thr Thr Gly Arg Leu Thr Ser Leu Phe Asp Met Gly
            20                  25                 30

Pro Arg Gln Lys Ile Gln Leu Val Asn Thr Asn Gly Ser
            35                  40              45

<210> SEQ ID NO 45
<211> LENGTH: 45
<212> TYPE: PRT
<213> ORGANISM: Hepatitis C virus

<400> SEQUENCE: 45

Leu Leu Leu Ala Ala Gly Val Asp Ala Arg Thr His Thr Val Gly Gly
 1               5                  10                 15

Ser Ala Ala Gln Thr Thr Gly Arg Leu Thr Ser Leu Phe Asp Met Gly
            20                  25                 30

Pro Arg Gln Lys Ile Gln Leu Val Asn Thr Asn Gly Ser
            35                  40              45

<210> SEQ ID NO 46
<211> LENGTH: 45
<212> TYPE: PRT
<213> ORGANISM: Hepatitis C virus

<400> SEQUENCE: 46

Leu Leu Leu Ala Ala Gly Val Asp Ala Gln Thr His Thr Val Gly Gly
 1               5                  10                 15

Ser Ala Ala Gln Thr Thr Gly Arg Leu Thr Ser Leu Phe Asp Met Gly
            20                  25                 30

Pro Arg Gln Lys Ile Gln Leu Ile Asn Thr Asn Gly Ser
            35                  40              45

<210> SEQ ID NO 47
<211> LENGTH: 45
<212> TYPE: PRT
<213> ORGANISM: Artificial Sequence
<220> FEATURE:
<223> OTHER INFORMATION: consensus sequence

<400> SEQUENCE: 47

Leu Leu Leu Ala Ala Gly Val Asp Ala Arg Thr His Thr Val Gly Gly
 1               5                  10                 15

Ser Ala Ala Gln Thr Thr Gly Arg Leu Thr Ser Leu Phe Asp Met Gly
            20                  25                 30

Pro Arg Gln Lys Ile Gln Leu Val Asn Thr Asn Gly Ser
            35                  40              45

<210> SEQ ID NO 48
<211> LENGTH: 45
<212> TYPE: PRT
<213> ORGANISM: Hepatitis C virus

<400> SEQUENCE: 48

Leu Leu Leu Ala Ala Gly Val Asp Ala Gln Thr His Thr Val Gly Gly
 1               5                  10                 15

Ser Thr Ala His Asn Ala Arg Thr Leu Thr Gly Met Phe Ser Leu Gly
            20                  25                 30

Ala Arg Gln Lys Ile Gln Leu Ile Asn Thr Asn Gly Ser
            35                  40              45
```

```
<210> SEQ ID NO 49
<211> LENGTH: 360
<212> TYPE: DNA
<213> ORGANISM: Hepatitis C virus

<400> SEQUENCE: 49
gccagccccc tgatggggc gacactccac catgaatcac tcccctgtga ggaactactg      60
tcttcacgca gaaagcgtct agccatggcg ttagtatgag tgtcgtgcag cctccaggac     120 ccccctccc gggagagcca tagtggtctg cggaaccggt gagtacaccg gaattgccag      180
gacgaccggg tcctttcttg gataaacccg ctcaatgcct ggagatttgg gcgtgccccc    240
gcaagactgc tagccgagta tgttgggtc gcgaaaggcc ttgtggtact gcctgatagg      300
gtgcttgcga gtgccccggg aggtctcgta gaccgtgcac catgagcacg aatcctaaac    360

<210> SEQ ID NO 50
<211> LENGTH: 360
<212> TYPE: DNA
<213> ORGANISM: Hepatitis C virus

<400> SEQUENCE: 50
gccagccccc tgatggggc gacactccac catgaatcac tcccctgtga ggaactactg      60
tcttcacgca gaaagcgtct agccatggcg ttagtatgag tgtcgtgcag cctccaggac     120 ccccctccc gggagagcca tagtggtctg cggaaccggt gagtacaccg gaattgccgg      180
gaagactggg tcctttcttg gataaacccg ctctatgccc ggccatttgg gcgtgccccc    240
gcaagactgc tagccgagta gcgttgggtt gcgaaaggcc ttgtggtact gcctgatagg     300
gtgcttgcga gtgccccggg aggtctcgta gaccgtgcac catgagcaca aatcctaaac    360

<210> SEQ ID NO 51
<211> LENGTH: 360
<212> TYPE: DNA
<213> ORGANISM: Hepatitis C virus

<400> SEQUENCE: 51
gccagccccc tgatggggc gacactccac catgaatcac tcccctgtga ggaactactg      60
tcttcacgca gaaagcgtct agccatggcg ttagtatgag tgtcgtgcag cctccaggac     120 ccccctccc gggagagcca tagtggtctg cggaaccggt gagtacaccg gaattgccgg      180
gaagactggg tcctttcttg gataaacccg ctctatgccc ggccatttgg gcgtgccccc    240
gcaagactgc tagccgagta gcgttgggtt gcgaaaggcc ttgtggtact gcctgatagg     300
gtgcttgcga gtgccccggg aggtctcgta gaccgtgcac catgagcaca aatcctaaac    360

<210> SEQ ID NO 52
<211> LENGTH: 360
<212> TYPE: DNA
<213> ORGANISM: Hepatitis C virus

<400> SEQUENCE: 52
gccagccccc tgatggggc gacactccac catgaatcac tcccctgtga ggaactactg      60
tcttcacgca gaaagcgtct agccatggcg ttagtatgag tgtcgtgcag cctccaggac     120 ccccctccc gggagagcca tagtggtctg cggaaccggt gagtacaccg gaattgccag      180
gacgaccggg tcctttcttg gataaacccg ctcaatgcct ggagatttgg gcgtgccccc    240
gcaagactgc tagccgagta tgttgggtc gcgaaaggcc ttgtggtact gcctgatagg      300
gtgcttgcga gtgccccggg aggtctcgta gaccgtgcac catgagcaca aatcctaaac    360
```

<210> SEQ ID NO 53
<211> LENGTH: 360
<212> TYPE: DNA
<213> ORGANISM: Hepatitis C virus

<400> SEQUENCE: 53

```
gccagccccc tgatggggc gacactccac catgaatcac tccctgtga ggaactactg      60
tcttcacgca gaaagcgtct agccatggcg ttagtatgag tgtcgtgcag cctccaggac    120
ccccctccc gggagagcca tagtggtctg cggaaccggt gagtacaccg gaattgccag     180
gacgaccggg tcctttcttg gataaacccg ctcaatgcct ggagatttgg gcgtgccccc    240
gcaagactgc tagccgagta gtgttgggtc gcgaaaggcc ttgtggtact gcctgatagg    300
gtgcttgcga gtgccccggg aggtctcgta gaccgtgcac catgagcaca atcctaaac     360
```

<210> SEQ ID NO 54
<211> LENGTH: 359
<212> TYPE: DNA
<213> ORGANISM: Hepatitis C virus

<400> SEQUENCE: 54

```
acccgcccct aatagggcg acactccgcc atgaatcact cccctgtgag gaactactgt     60
cttcacgcag aaagcgtcta gccatggcgt tagtatgagt gtcgtacagc ctccaggccc    120
ccccctcccg ggagagccat agtggtctgc ggaaccggtg agtacaccgg aattgccggg    180
aagactgggt cctttcttgg ataaacccgc tctatgcccg ccatttgggc cgtgcccccg    240
caagactgct agccgagtag cgttggggttg cgaaaggcct tgtggtactg cctgataggt   300
tgcttgcgag tgccccggga ggtctcgtag accgtgcacc atgagcacaa atcctaaac    359
```

<210> SEQ ID NO 55
<211> LENGTH: 225
<212> TYPE: DNA
<213> ORGANISM: Hepatitis C virus

<400> SEQUENCE: 55

```
tgaaggttgg ggtaaacact ccggcctctt aagccatttc ctgyyyyyyy yyyyyyyyyy     60
yyyyyyyyyy yyyyyyyyyy yyyyyyyyyy yyyyyyyyyy yyyyyyyyyy yyyyyyyyyy    120
yyyyaatggt ggctccatct tagccctagt cacggctagc tgtgaaaggt ccgtgagccg    180
catgactgca gagagtgctg atactggcct ctctgcagat catgt                    225
```

<210> SEQ ID NO 56
<211> LENGTH: 225
<212> TYPE: DNA
<213> ORGANISM: Hepatitis C virus

<400> SEQUENCE: 56

```
tgaaggttgg ggtaaacact ccggcctctt aagccatttc ctgyyyyyyy yyyyyyyyyy     60
yyyyyy yyyyyyyyyy yyyyyyyyyy yyyyyyyyyy yyyyyyyyyy yyyyyyyyyy       120
yyyyaatggt ggctccatct tagccctagt cacggctagc tgtgaaaggt ccgtgagccg    180
catgactgca gagagtgctg atactggcct ctctgcagat catgt                    225
```

<210> SEQ ID NO 57
<211> LENGTH: 225
<212> TYPE: DNA
<213> ORGANISM: Hepatitis C virus

<400> SEQUENCE: 57

```
tgaaggttgg ggtaaacact ccggcctctt aagccatttc ctgyyyyyyy yyyyyyyyyy      60
yyyyyyyyyy yyyyyyyyyy yyyyyyyyyy yyyyyyyyyy yyyyyyyyyy yyyyyyyyyy     120
yyyyaatggt ggctccatct tagccctagt cacggctagc tgtgaaaggt ccgtgagccg     180
catgactgca gagagtgctg atactggcct ctctgcagat catgt                     225
```

<210> SEQ ID NO 58
<211> LENGTH: 225
<212> TYPE: DNA
<213> ORGANISM: Hepatitis C virus

<400> SEQUENCE: 58

```
tgaaggttgg ggtaaacact ccggcctctt aagccatttc ctgyyyyyyy yyyyyyyyyy      60
yyyyyyyyyy yyyyyyyyyy yyyyyyyyyy yyyyyyyyyy yyyyyyyyyy yyyyyyyyyy     120
yyyyaatggt ggctccatct tagccctagt cacggctagc tgtgaaaggt ccgtgagccg     180
catgactgca gagagtgctg atactggcct ctctgcagat catgt                     225
```

<210> SEQ ID NO 59
<211> LENGTH: 225
<212> TYPE: DNA
<213> ORGANISM: Hepatitis C virus

<400> SEQUENCE: 59

```
tgaaggttgg ggtaaacact ccggcctctt aagccatttc ctgyyyyyyy yyyyyyyyyy      60
yyyyyyyyyy yyyyyyyyyy yyyyyyyyyy yyyyyyyyyy yyyyyyyyyy yyyyyyyyyy     120
yyyyaatggt ggctccatct tagccctagt cacggctagc tgtgaaaggt ccgtgagccg     180
catgactgca gagagtgctg atactggcct ctctgcagat catgt                     225
```

<210> SEQ ID NO 60
<211> LENGTH: 272
<212> TYPE: DNA
<213> ORGANISM: hepatitis C virus

<400> SEQUENCE: 60

```
tagagcggca cacattagct acactccata gctaactgtc ccyyyyyyyy yyyyyyyyyy      60
yyyyyyyyyy yyyyyyyyyy yyyyyyyyyy yyyyyyyyyy yyyyyyyyyy yyyyyyyyyy     120
yyyyyyyyyy yyyyyyyyyy yyyyyyyyyy yyyyyyyyyy yyyyyyyyyy yyyyggtggc     180
tccatcttag ccctagtcac ggctagctgt gaaaggtccg tgagccgcat gactgcagag     240
agtgccgtaa ctggtctctc tgcagatcat gt                                   272
```

<210> SEQ ID NO 61
<211> LENGTH: 96
<212> TYPE: PRT
<213> ORGANISM: Hepatitis C virus

<400> SEQUENCE: 61

```
Arg Val Cys Ser Cys Leu Trp Met Met Leu Leu Ile Ser Gln Ala Glu
 1               5                  10                  15

Ala Ala Leu Glu Asn Leu Val Ile Leu Asn Ala Ala Ser Leu Ala Gly
             20                  25                  30

Thr His Gly Leu Val Ser Phe Leu Val Phe Phe Cys Phe Ala Trp Tyr
         35                  40                  45

Leu Lys Gly Arg Trp Val Pro Gly Ala Val Tyr Ala Leu Tyr Gly Met
     50                  55                  60
```

-continued

Trp Pro Leu Leu Leu Leu Leu Ala Leu Pro Gln Arg Ala Tyr Ala
65                  70                  75                  80

Leu Asp Thr Glu Val Ala Ala Ser Cys Gly Gly Val Val Leu Val Gly
                85                  90                  95

<210> SEQ ID NO 62
<211> LENGTH: 96
<212> TYPE: PRT
<213> ORGANISM: Hepatitis C virus

<400> SEQUENCE: 62

Arg Val Cys Ala Cys Leu Trp Met Leu Ile Leu Leu Gly Gln Ala Glu
1               5                   10                  15

Ala Ala Leu Glu Lys Leu Val Ile Leu His Ala Ala Ser Ala Ala Ser
                20                  25                  30

Cys Asn Gly Phe Leu Tyr Phe Val Ile Phe Phe Val Ala Ala Trp Tyr
                35                  40                  45

Ile Lys Gly Arg Val Val Pro Leu Ala Thr Tyr Ser Leu Thr Gly Leu
            50                  55                  60

Trp Ser Phe Ser Leu Leu Leu Leu Ala Leu Pro Gln Gln Ala Tyr Ala
65                  70                  75                  80

Leu Asp Thr Glu Val Ala Ala Ser Cys Gly Gly Val Val Leu Val Gly
                85                  90                  95

<210> SEQ ID NO 63
<211> LENGTH: 96
<212> TYPE: PRT
<213> ORGANISM: Hepatitis C virus

<400> SEQUENCE: 63

Arg Val Cys Ala Cys Leu Trp Met Leu Ile Leu Leu Gly Gln Ala Glu
1               5                   10                  15

Ala Ala Leu Glu Asn Leu Val Ile Leu Asn Ala Ala Ser Leu Ala Gly
                20                  25                  30

Thr His Gly Leu Val Ser Phe Leu Val Phe Phe Cys Phe Ala Trp Tyr
                35                  40                  45

Leu Lys Gly Arg Trp Val Pro Gly Ala Val Tyr Ala Leu Tyr Gly Met
            50                  55                  60

Trp Pro Leu Leu Leu Leu Leu Ala Leu Pro Gln Arg Ala Tyr Ala
65                  70                  75                  80

Leu Asp Thr Glu Val Ala Ala Ser Cys Gly Gly Val Val Leu Val Gly
                85                  90                  95

<210> SEQ ID NO 64
<211> LENGTH: 96
<212> TYPE: PRT
<213> ORGANISM: Hepatitis C virus

<400> SEQUENCE: 64

Arg Val Cys Ala Cys Leu Trp Met Leu Ile Leu Leu Gly Gln Ala Glu
1               5                   10                  15

Ala Ala Leu Glu Lys Leu Val Ile Leu His Ala Ala Ser Ala Ala Ser
                20                  25                  30

Cys Asn Gly Phe Leu Tyr Phe Val Ile Phe Phe Val Ala Ala Trp Tyr
                35                  40                  45

Ile Lys Gly Arg Val Val Pro Leu Ala Thr Tyr Ser Leu Thr Gly Leu
            50                  55                  60

Trp Ser Phe Ser Leu Leu Leu Leu Ala Leu Pro Gln Gln Ala Tyr Ala

```
                65                  70                  75                  80
Leu Asp Thr Glu Val Ala Ala Ser Cys Gly Gly Val Val Leu Val Gly
                        85                  90                  95
```

<210> SEQ ID NO 65
<211> LENGTH: 96
<212> TYPE: PRT
<213> ORGANISM: Hepatitis C virus

<400> SEQUENCE: 65

```
Arg Val Cys Ala Cys Leu Trp Met Leu Ile Leu Leu Gly Gln Ala Glu
 1               5                  10                  15

Ala Ala Leu Glu Asn Leu Val Ile Leu Asn Ala Ala Ser Leu Ala Gly
                20                  25                  30

Thr His Gly Leu Val Ser Phe Leu Val Phe Phe Cys Phe Ala Trp Tyr
            35                  40                  45

Leu Lys Gly Arg Trp Val Pro Gly Ala Val Tyr Ala Leu Tyr Gly Met
        50                  55                  60

Trp Pro Leu Leu Leu Leu Leu Leu Ala Leu Pro Gln Arg Ala Tyr Ala
65                  70                  75                  80

Leu Asp Thr Glu Val Ala Ala Ser Cys Gly Gly Val Val Leu Val Gly
                85                  90                  95
```

<210> SEQ ID NO 66
<211> LENGTH: 96
<212> TYPE: PRT
<213> ORGANISM: Hepatitis C virus

<400> SEQUENCE: 66

```
Arg Val Cys Ala Cys Leu Trp Met Leu Ile Leu Leu Gly Gln Ala Glu
 1               5                  10                  15

Ala Ala Leu Glu Lys Leu Val Ile Leu His Ala Ala Ser Ala Ala Ser
                20                  25                  30

Cys Asn Gly Phe Leu Tyr Phe Val Ile Phe Phe Val Ala Ala Trp Tyr
            35                  40                  45

Ile Lys Gly Arg Val Val Pro Leu Ala Thr Tyr Ser Leu Thr Gly Leu
        50                  55                  60

Trp Ser Phe Ser Leu Leu Leu Leu Ala Leu Pro Gln Gln Ala Tyr Ala
65                  70                  75                  80

Tyr Asp Ala Ser Val His Gly Gln Ile Gly Ala Ala Leu Leu Val Met
                85                  90                  95
```

<210> SEQ ID NO 67
<211> LENGTH: 9599
<212> TYPE: DNA
<213> ORGANISM: Hepatitis C virus

<400> SEQUENCE: 67

```
gccagccccc tgatgggggc gacactccac catgaatcac tcccctgtga ggaactactg    60
tcttcacgca gaaagcgtct agccatggcg ttagtatgag tgtcgtgcag cctccaggac   120 ccccctccc gggagagcca tagtggtctg cggaaccggt gagtacaccg gaattgccag   180
gacgaccggg tctttcttg gataaacccg ctcaatgcct ggagatttgg gcgtgccccc   240
gcaagactgc tagccgagta gtgttgggtc gcgaaaggcc ttgtggtact gcctgatagg   300
gtgcttgcga gtgccccggg aggtctcgta gaccgtgcac catgagcacg aatcctaaac   360
ctcaaagaaa aaccaaacgt aacaccaacc gtcgcccaca ggacgtcaag ttcccgggtg   420
```

```
gcggtcagat cgttggtgga gtttacttgt tgccgcgcag gggccctaga ttgggtgtgc    480
gcgcgacgag gaagacttcc gagcggtcgc aacctcgagg tagacgtcag cctatcccca    540
aggcacgtcg gcccgagggc aggacctggg ctcagcccgg gtaccttggg ccctctatg     600 gcaatgaggg ttgcgggtgg gcgggatggc tcctgtctcc ccgtggctct cggcctagct    660
ggggccccac agaccccgg cgtaggtcgc gcaatttggg taaggtcatc gatacccta      720 cgtgcggctt cgccgacctc atgggtaca taccgctcgt cggcgcccct cttggaggcg     780
ctgccagggc cctggcgcat ggcgtccggg ttctggaaga cggcgtgaac tatgcaacag    840
ggaaccttcc tggttgctct ttctctatct tccttctggc cctgctctct tgcctgactg    900
tgcccgcttc agcctaccaa gtgcgcaatt cctcggggct ttaccatgtc accaatgatt    960
gccctaactc gagtattgtg tacgaggcgg ccgatgccat cctgcacact ccggggtgtg   1020
tcccttgcgt tcgcgagggt aacgcctcga ggtgttgggt ggcggtgacc cccacggtgg   1080
ccaccaggga cggcaaactc cccacaacgc agcttcgacg tcatatcgat ctgcttgtcg   1140
ggagcgccac cctctgctcg gccctctacg tgggggacct gtgcgggtct gtctttcttg   1200
ttggtcaact gtttaccttc tctcccaggc gccactggac gacgcaagac tgcaattgtt   1260
ctatctatcc cggccatata acgggtcatc gcatggcatg ggatatgatg atgaactggt   1320
cccctacggc agcgttggtg gtagctcagc tgctccggat cccacaagcc atcatggaca   1380
tgatcgctgg tgctcactgg ggagtcctgg cgggcatagc gtatttctcc atggtgggga   1440
actgggcgaa ggtcctggta gtgctgctgc tatttgccgg cgtcgacgcg gaaacccacg   1500
tcaccggggg aaatgccggc cgcaccacgg ctgggcttgt tggtctcctt acaccaggcg   1560
ccaagcagaa catccaactg atcaacacca acggcagttg gcacatcaat agcacggcct   1620
tgaattgcaa tgaaagcctt aacaccggct ggttagcagg gctcttctat caacacaaat   1680
tcaactcttc aggctgtcct gagaggttgg ccagctgccg acgccttacc gattttgccc   1740
agggctgggg tcctatcagt tatgccaacg gaagcggcct cgacgaacgc ccctactgct   1800
ggcactaccc tccaagacct tgtggcattg tgcccgcaaa gagcgtgtgt ggcccggtat   1860
attgcttcac tcccagcccc gtggtggtgg gaacgaccga caggtcgggc gcgcctacct   1920
acagctgggg tgcaaatgat acggatgtct tcgtccttaa caacaccagg ccaccgctgg   1980
gcaattggtt cggttgtacc tggatgaact caactggatt caccaaagtg tgcggagcgc   2040 cccccttgtgt catcggaggg gtgggcaaca acaccttgct ctgccccact gattgcttcc   2100
gcaaacatcc ggaagccaca tactctcggt gcggctccgg tcctggatt acacccaggt    2160 gcatggtcga ctacccgtat aggctttggc actatccttg taccatcaat tacaccatat   2220
tcaaagtcag gatgtacgtg ggaggggtcg agcacaggct ggaagcggcc tgcaactgga   2280
cgcggggcga acgctgtgat ctggaagaca gggacaggtc cgagctcagc ccgttgctgc   2340
tgtccaccac acagtggcag gtccttccgt gttctttcac gaccctgcca gccttgtcca   2400
ccggcctcat ccacctccac cagaacattg tggacgtgca gtacttgtac ggggtagggt   2460
caagcatcgc gtcctgggcc attaagtggg agtacgtcgt tctcctgttc cttctgcttg   2520
cagacgcgcg cgtctgctcc tgcttgtgga tgatgttact catatcccaa gcggaggcgg   2580
ctttggagaa cctcgtaata ctcaatgcag catccctggc cggacgcac ggtcttgtgt    2640 ccttcctcgt gttcttctgc tttgcgtggt atctgaaggg taggtgggtg cccggagcgg   2700
tctacgccct ctacggatg tggcctctcc tcctgctcct gctggcgttg cctcagcggg    2760
catacgcact ggacacggag gtggccgcgt cgtgtggcgg cgttgttctt gtcgggttaa   2820
```

-continued

```
tggcgctgac tctgtcgcca tattacaagc gctatatcag ctggtgcatg tggtggcttc    2880
agtattttct gaccagagta gaagcgcaac tgcacgtgtg ggttccccccc ctcaacgtcc   2940
gggggggggcg cgatgccgtc atcttactca tgtgtgtagt acacccgacc ctggtatttg   3000
acatcaccaa actactcctg gccatcttcg gacccctttg gattcttcaa gccagtttgc   3060
ttaaagtccc ctacttcgtg cgcgttcaag gccttctccg gatctgcgcg ctagcgcgga   3120
agatagccgg aggtcattac gtgcaaatgg ccatcatcaa gttagggggcg cttactggca   3180
cctatgtgta taaccatctc accccctcttc gagactgggc gcacaacggc ctgcgagatc   3240
tggccgtggc tgtggaacca gtcgtcttct cccgaatgga gaccaagctc atcacgtggg   3300
gggcagatac cgccgcgtgc ggtgacatca tcaacggctt gcccgtctct gcccgtaggg   3360
gccaggagat actgcttggg ccagccgacg gaatggtctc caagggggtgg aggttgctgg   3420
cgcccatcac ggcgtacgcc cagcagacga gaggcctcct agggtgtata atcaccagcc   3480
tgactggccg ggacaaaaac caagtggagg gtgaggtcca gatcgtgtca actgctaccc   3540
aaaccttcct ggcaacgtgc atcaatgggg tatgctggac tgtctaccac ggggccggaa   3600
cgaggaccat cgcatcaccc aagggtcctg tcatccagat gtataccaat gtggaccaag   3660
accttgtggg ctggcccgct cctcaaggtt cccgctcatt gacaccctgt acctgcggct   3720
cctcggacct ttacctggtc acgaggcacg ccgatgtcat tcccgtgcgc cggcgaggtg   3780
atagcagggg tagcctgctt tcgccccggc ccatttccta cttgaaaggc tcctcggggg   3840
gtccgctgtt gtgccccgcg gacacgccg tgggcctatt cagggccgcg gtgtgcaccc   3900
gtggagtggc taaagcggtg gactttatcc ctgtggagaa cctagggaca accatgagat   3960
cccccggtgtt cacggacaac tcctctccac cagcagtgcc ccagagcttc caggtggccc   4020
acctgcatgc tcccaccggc agcggtaaga gcaccaaggt cccggctgcg tacgcagccc   4080
agggctacaa ggtgttggtg ctcaacccct ctgttgctgc aacgctgggc tttggtgctt   4140
acatgtccaa ggcccatggg gttgatccta atatcaggac cggggtgaga acaattacca   4200
ctggcagccc catcacgtac tccacctacg gcaagttcct tgccgacggc gggtgctcag   4260
gaggtgctta tgacataata atttgtgacg agtgccactc cacggatgcc acatccatct   4320
tgggcatcgg cactgtcctt gaccaagcag agactgcggg ggcgagactg gttgtgctcg   4380
ccactgctac ccctccgggc tccgtcactg tgtcccatcc taacatcgag gaggttgctc   4440
tgtccaccac cggagagatc ccctttttacg gcaaggctat ccccctcgag gtgatcaagg   4500
ggggaagaca tctcatcttc tgccactcaa agaagaagtg cgacgagctc gccgcgaagc   4560
tggtcgcatt gggcatcaat gccgtggcct actaccgcgg tcttgacgtg tctgtcatcc   4620
cgaccagcgg cgatgttgtc gtcgtgtcga ccgatgctct catgactggc tttaccggcg   4680
acttcgactc tgtgatagac tgcaacacgt gtgtcactca gacagtcgat ttcagccttg   4740
accctacctt taccattgag acaaccacgc tcccccagga tgctgtctcc aggactcaac   4800
gccggggcag gactggcagg gggaagccag gcatctatag atttgtggca ccggggggagc   4860
gccccctccgg catgttcgac tcgtccgtcc tctgtgagtg ctatgacgcg ggctgtgctt   4920
ggtatgagct cacgcccgcc gagactacag ttaggctacg agcgtacatg aacacccgg    4980
ggcttcccgt gtgccaggac catcttgaat tttgggaggg cgtctttacg ggcctcactc   5040
atatagatgc ccacttttta tcccagacaa agcagagtgg ggagaacttt ccttacctgg   5100
tagcgtacca agccaccgtg tgcgctaggg ctcaagcccc tccccccatcg tgggaccaga   5160
```

-continued

```
tgtggaagtg tttgatccgc cttaaaccca ccctccatgg gccaacaccc ctgctataca    5220
gactgggcgc tgttcagaat gaagtcaccc tgacgcaccc aatcaccaaa tacatcatga    5280
catgcatgtc ggccgacctg gaggtcgtca cgagcacctg ggtgctcgtt ggcggcgtcc    5340
tggctgctct ggccgcgtat tgcctgtcaa caggctgcgt ggtcatagtg ggcaggatcg    5400
tcttgtccgg gaagccggca attatacctg acagggaggt tctctaccag gagttcgatg    5460
agatggaaga gtgctctcag cacttaccgt acatcgagca agggatgatg ctcgctgagc    5520
agttcaagca gaaggccctc ggcctcctgc agaccgcgtc ccgccatgca gaggttatca    5580
cccctgctgt ccagaccaac tggcagaaac tcgaggtctt ttgggcgaag cacatgtgga    5640
atttcatcag tgggatacaa tacttggcgg gcctgtcaac gctgcctggt aaccccgcca    5700
ttgcttcatt gatggctttt acagctgccg tcaccagccc actaaccact ggccaaaccc    5760
tcctcttcaa catattgggg gggtgggtgg ctgcccagct cgccgccccc ggtgccgcta    5820
ctgcctttgt gggtgctggc ctagctggcg ccgccatcgg cagcgttgga ctggggaagg    5880
tcctcgtgga cattcttgca gggtatggcg cgggcgtggc gggagctctt gtagcattca    5940
agatcatgag cggtgaggtc ccctccacgg aggacctggt caatctgctg cccgccatcc    6000
tctcgcctgg agcccttgta gtcggtgtgg tctgcgcagc aatactgcgc cggcacgttg    6060
gcccgggcga gggggcagtg caatggatga accggctaat agccttcgcc tcccggggga    6120
accatgtttc ccccacgcac tacgtgccgg agagcgatgc agccgcccgc gtcactgcca    6180
tactcagcag cctcactgta acccagctcc tgaggcgact gcatcagtgg ataagctcgg    6240
agtgtaccac tccatgctcc ggttcctggc taagggacat ctgggactgg atatgcgagg    6300
tgctgagcga ctttaagacc tggctgaaag ccaagctcat gccacaactg cctgggattc    6360
cctttgtgtc ctgccagcgc gggtataggg gggtctggcg aggagacggc attatgcaca    6420
ctcgctgcca ctgtggagct gagatcactg gacatgtcaa aaacgggacg atgaggatcg    6480
tcggtcctag gacctgcagg aacatgtgga gtgggacgtt ccccattaac gcctacacca    6540
cgggcccctg tactccccct cctgcgccga actataagtt cgcgctgtgg agggtgtctg    6600
cagaggaata cgtggagata aggcgggtgg gggacttcca ctacgtatcg ggtatgacta    6660
ctgacaatct taaatgcccg tgccagatcc catcgcccga atttttcaca gaattggacg    6720
gggtgcgcct acacaggttt gcgccccctt gcaagcccct gctgcgggag gaggtatcat    6780
tcagagtagg actccacgag tacccggtgg ggtcgcaatt accttgcgag cccgaaccgg    6840
acgtagccgt gttgacgtcc atgctcactg atccctccca tataacagca gaggcggccg    6900
ggagaaggtt ggcgagaggg tcacccccctt ctatggccag ctcctcggct agccagctgt    6960
ccgctccatc tctcaaggca acttgcaccg ccaaccatga ctcccctgac gccgagctca    7020
tagaggctaa cctcctgtgg aggcaggaga tgggcggcaa catcaccagg gttgagtcag    7080
agaacaaagt ggtgattctg gactccttcg atccgcttgt ggcagaggag gatgagcggg    7140
aggtctccgt acctgcagaa attctgcgga gtctcggag attcgcccgg ccctgcccg    7200 tctgggcgcg gccggactac aaccccccgc tagtagagac gtggaaaaag cctgactacg    7260
aaccacctgt ggtccatggc tgccgctac cacctccacg gtcccctcct gtgcctccgc    7320
ctcggaaaaa gcgtacggtg gtcctcaccg aatcaaccct atctactgcc ttggccgagc    7380
ttgccaccaa aagttttggc agctcctcaa cttccggcat tacgggcgac aatacgacaa    7440
catcctctga gccgcccct tctgctgcc ccccgactc cgacgttgag tcctattctt    7500
ccatgccccc cctggagggg gagcctgggg atccggatct cagcgacggg tcatggtcga    7560
```

-continued

```
cggtcagtag tggggccgac acggaagatg tcgtgtgctg ctcaatgtct tattcctgga    7620
caggcgcact cgtcaccccg tgcgctgcgg aagaacaaaa actgcccatc aacgcactga    7680
gcaactcgtt gctacgccat cacaatctgg tgtattccac cacttcacgc agtgcttgcc    7740
aaaggcagaa gaaagtcaca tttgacagac tgcaagttct ggacagccat taccaggacg    7800
tgctcaagga ggtcaaagca gcggcgtcaa aagtgaaggc taacttgcta tccgtagagg    7860
aagcttgcag cctgacgccc ccacattcag ccaaatccaa gtttggctat ggggcaaaag    7920
acgtccgttg ccatgccaga aaggccgtag cccacatcaa ctccgtgtgg aaagaccttc    7980
tggaagacag tgtaacacca atagacacta ccatcatggc caagaacgag gttttctgcg    8040
ttcagcctga aagggggggt cgtaagccag ctcgtctcat cgtgttcccc gacctgggcg    8100
tgcgcgtgtg cgagaagatg gccctgtacg acgtggttag caagctcccc ctggccgtga    8160
tgggaagctc ctacggattc caatactcac caggacagcg ggttgaattc ctcgtgcaag    8220
cgtggaagtc caagaagacc ccgatgggt tctcgtatga tacccgctgt tttgactcca    8280
cagtcactga gagcgacatc cgtacggagg aggcaattta ccaatgttgt gacctggacc    8340
cccaagcccg cgtggccatc aagtccctca ctgagaggct ttatgttggg ggccctctta    8400
ccaattcaag gggggaaaac tgcggctacc gcaggtgccg cgcgagcggc gtactgacaa    8460
ctagctgtgg taacaccctc acttgctaca tcaaggcccg gcagcctgt cgagccgcag    8520
ggctccagga ctgcaccatg ctcgtgtgtg gcgacgactt agtcgttatc tgtgaaagtg    8580
cggggggtcca ggaggacgcg gcgagcctga gagccttcac ggaggctatg accaggtact    8640
ccgccccccc cggggacccc ccacaaccag aatacgactt ggagcttata acatcatgct    8700
cctccaacgt gtcagtcgcc cacgacgcg ctggaaagag ggtctactac cttacccgtg    8760
accctacaac ccccctcgcg agagccgcgt gggagacagc aagacacact ccagtcaatt    8820
cctggctagg caacataatc atgtttgccc ccacactgtg ggcgaggatg atactgatga    8880
cccatttctt tagcgtcctc atagccaggg atcagcttga acaggctctt aactgtgaga    8940
tctacggagc ctgctactcc atagaaccac tggatctacc tccaatcatt caaagactcc    9000
atggcctcag cgcatttca ctccacagtt actctccagg tgaaatcaat agggtggccg    9060
catgcctcag aaaacttggg gtcccgcct tgcgagcttg gagacaccgg cccggagcg    9120
tccgcgctag gcttctgtcc agaggaggca gggctgccat atgtggcaag tacctcttca    9180
actgggcagt aagaacaaag ctcaaactca ctccaataagc ggccgctggc cggctggact    9240
tgtccggttg gttcacggct ggctacagcg ggggagacat ttatcacagc gtgtctcatg    9300
cccgggcccg ctggttctgg tttttgcctac tcctgctcgc tgcagggta ggcatctacc    9360
tcctcccaa ccgatgaagg ttggggtaaaa cactccggcc tcttaagcca tttcctgttt    9420
tttttttttt tttttttttt tttttcttt tttttttcct tccttctt cttttttcc        9480
ttttctttttc ccttctttaa tggtggctcc atcttagccc tagtcacggc tagctgtgaa    9540
aggtccgtga ccgcatgac tgcagagagt gctgatactg gcctctctgc agatcatgt     9599
```

<210> SEQ ID NO 68
<211> LENGTH: 3011
<212> TYPE: PRT
<213> ORGANISM: Hepatitis C Virus

<400> SEQUENCE: 68

Met Ser Thr Asn Pro Lys Pro Gln Arg Lys Thr Lys Arg Asn Thr Asn
 1               5                  10                  15

```
Arg Arg Pro Gln Asp Val Lys Phe Pro Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
        50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Ser Gly Leu Tyr His Val Thr Asn Asp Cys Pro
            195                 200                 205

Asn Ser Ser Ile Val Tyr Glu Ala Ala Asp Ala Ile Leu His Thr Pro
210                 215                 220

Gly Cys Val Pro Cys Val Arg Glu Gly Asn Ala Ser Arg Cys Trp Val
225                 230                 235                 240

Ala Val Thr Pro Thr Val Ala Thr Arg Asp Gly Lys Leu Pro Thr Thr
                245                 250                 255

Gln Leu Arg Arg His Ile Asp Leu Leu Val Gly Ser Ala Thr Leu Cys
            260                 265                 270

Ser Ala Leu Tyr Val Gly Asp Leu Cys Gly Ser Val Phe Leu Val Gly
            275                 280                 285

Gln Leu Phe Thr Phe Ser Pro Arg Arg His Trp Thr Thr Gln Asp Cys
    290                 295                 300

Asn Cys Ser Ile Tyr Pro Gly His Ile Thr Gly His Arg Met Ala Trp
305                 310                 315                 320

Asp Met Met Met Asn Trp Ser Pro Thr Ala Ala Leu Val Val Ala Gln
                325                 330                 335

Leu Leu Arg Ile Pro Gln Ala Ile Met Asp Met Ile Ala Gly Ala His
            340                 345                 350

Trp Gly Val Leu Ala Gly Ile Ala Tyr Phe Ser Met Val Gly Asn Trp
            355                 360                 365

Ala Lys Val Leu Val Val Leu Leu Leu Phe Ala Gly Val Asp Ala Glu
    370                 375                 380

Thr His Val Thr Gly Gly Asn Ala Gly Arg Thr Thr Ala Gly Leu Val
385                 390                 395                 400

Gly Leu Leu Thr Pro Gly Ala Lys Gln Asn Ile Gln Leu Ile Asn Thr
                405                 410                 415

Asn Gly Ser Trp His Ile Asn Ser Thr Ala Leu Asn Cys Asn Glu Ser
            420                 425                 430
```

```
Leu Asn Thr Gly Trp Leu Ala Gly Leu Phe Tyr Gln His Lys Phe Asn
        435                 440                 445

Ser Ser Gly Cys Pro Glu Arg Leu Ala Ser Cys Arg Arg Leu Thr Asp
        450                 455                 460

Phe Ala Gln Gly Trp Gly Pro Ile Ser Tyr Ala Asn Gly Ser Gly Leu
465                 470                 475                 480

Asp Glu Arg Pro Tyr Cys Trp His Tyr Pro Arg Pro Cys Gly Ile
                485                 490                 495

Val Pro Ala Lys Ser Val Cys Gly Pro Val Tyr Cys Phe Thr Pro Ser
            500                 505                 510

Pro Val Val Gly Thr Thr Asp Arg Ser Gly Ala Pro Thr Tyr Ser
            515                 520                 525

Trp Gly Ala Asn Asp Thr Asp Val Phe Val Leu Asn Asn Thr Arg Pro
    530                 535                 540

Pro Leu Gly Asn Trp Phe Gly Cys Thr Trp Met Asn Ser Thr Gly Phe
545                 550                 555                 560

Thr Lys Val Cys Gly Ala Pro Pro Cys Val Ile Gly Val Gly Asn
            565                 570                 575

Asn Thr Leu Leu Cys Pro Thr Asp Cys Phe Arg Lys His Pro Glu Ala
            580                 585                 590

Thr Tyr Ser Arg Cys Gly Ser Gly Pro Trp Ile Thr Pro Arg Cys Met
            595                 600                 605

Val Asp Tyr Pro Tyr Arg Leu Trp His Tyr Pro Cys Thr Ile Asn Tyr
    610                 615                 620

Thr Ile Phe Lys Val Arg Met Tyr Val Gly Gly Val Glu His Arg Leu
625                 630                 635                 640

Glu Ala Ala Cys Asn Trp Thr Arg Gly Glu Arg Cys Asp Leu Glu Asp
            645                 650                 655

Arg Asp Arg Ser Glu Leu Ser Pro Leu Leu Leu Ser Thr Thr Gln Trp
            660                 665                 670

Gln Val Leu Pro Cys Ser Phe Thr Thr Leu Pro Ala Leu Ser Thr Gly
            675                 680                 685

Leu Ile His Leu His Gln Asn Ile Val Asp Val Gln Tyr Leu Tyr Gly
        690                 695                 700

Val Gly Ser Ser Ile Ala Ser Trp Ala Ile Lys Trp Glu Tyr Val Val
705                 710                 715                 720

Leu Leu Phe Leu Leu Leu Ala Asp Ala Arg Val Cys Ser Cys Leu Trp
            725                 730                 735

Met Met Leu Leu Ile Ser Gln Ala Glu Ala Ala Leu Glu Asn Leu Val
            740                 745                 750

Ile Leu Asn Ala Ala Ser Leu Ala Gly Thr His Gly Leu Val Ser Phe
            755                 760                 765

Leu Val Phe Phe Cys Phe Ala Trp Tyr Leu Lys Gly Arg Trp Val Pro
770                 775                 780

Gly Ala Val Tyr Ala Leu Tyr Gly Met Trp Pro Leu Leu Leu Leu Leu
785                 790                 795                 800

Leu Ala Leu Pro Gln Arg Ala Tyr Ala Leu Asp Thr Glu Val Ala Ala
            805                 810                 815

Ser Cys Gly Gly Val Val Leu Val Gly Leu Met Ala Leu Thr Leu Ser
            820                 825                 830

Pro Tyr Tyr Lys Arg Tyr Ile Ser Trp Cys Met Trp Trp Leu Gln Tyr
            835                 840                 845

Phe Leu Thr Arg Val Glu Ala Gln Leu His Val Trp Val Pro Pro Leu
```

-continued

```
                        850                 855                 860
Asn Val Arg Gly Gly Arg Asp Ala Val Ile Leu Leu Met Cys Val Val
865                 870                 875                 880

His Pro Thr Leu Val Phe Asp Ile Thr Lys Leu Leu Ala Ile Phe
                    885                 890                 895

Gly Pro Leu Trp Ile Leu Gln Ala Ser Leu Leu Lys Val Pro Tyr Phe
                900                 905                 910

Val Arg Val Gln Gly Leu Leu Arg Ile Cys Ala Leu Ala Arg Lys Ile
                915                 920                 925

Ala Gly Gly His Tyr Val Gln Met Ala Ile Ile Lys Leu Gly Ala Leu
930                 935                 940

Thr Gly Thr Tyr Val Tyr Asn His Leu Thr Pro Leu Arg Asp Trp Ala
945                 950                 955                 960

His Asn Gly Leu Arg Asp Leu Ala Val Ala Val Glu Pro Val Val Phe
                    965                 970                 975

Ser Arg Met Glu Thr Lys Leu Ile Thr Trp Gly Ala Asp Thr Ala Ala
                980                 985                 990

Cys Gly Asp Ile Ile Asn Gly Leu Pro Val Ser Ala Arg Arg Gly Gln
                995                 1000                1005

Glu Ile Leu Leu Gly Pro Ala Asp Gly Met Val Ser Lys Gly Trp Arg
                1010                1015                1020

Leu Leu Ala Pro Ile Thr Ala Tyr Ala Gln Gln Thr Arg Gly Leu Leu
1025                1030                1035                1040

Gly Cys Ile Ile Thr Ser Leu Thr Gly Arg Asp Lys Asn Gln Val Glu
                    1045                1050                1055

Gly Glu Val Gln Ile Val Ser Thr Ala Thr Gln Thr Phe Leu Ala Thr
                    1060                1065                1070

Cys Ile Asn Gly Val Cys Trp Thr Val Tyr His Gly Ala Gly Thr Arg
                1075                1080                1085

Thr Ile Ala Ser Pro Lys Gly Pro Val Ile Gln Met Tyr Thr Asn Val
                    1090                1095                1100

Asp Gln Asp Leu Val Gly Trp Pro Ala Pro Gln Gly Ser Arg Ser Leu
1105                1110                1115                1120

Thr Pro Cys Thr Cys Gly Ser Ser Asp Leu Tyr Leu Val Thr Arg His
                    1125                1130                1135

Ala Asp Val Ile Pro Val Arg Arg Arg Gly Asp Ser Arg Gly Ser Leu
                    1140                1145                1150

Leu Ser Pro Arg Pro Ile Ser Tyr Leu Lys Gly Ser Ser Gly Gly Pro
                1155                1160                1165

Leu Leu Cys Pro Ala Gly His Ala Val Gly Leu Phe Arg Ala Ala Val
                1170                1175                1180

Cys Thr Arg Gly Val Ala Lys Ala Val Asp Phe Ile Pro Val Glu Asn
1185                1190                1195                1200

Leu Gly Thr Thr Met Arg Ser Pro Val Phe Thr Asp Asn Ser Ser Pro
                    1205                1210                1215

Pro Ala Val Pro Gln Ser Phe Gln Val Ala His Leu His Ala Pro Thr
                    1220                1225                1230

Gly Ser Gly Lys Ser Thr Lys Val Pro Ala Ala Tyr Ala Ala Gln Gly
                1235                1240                1245

Tyr Lys Val Leu Val Leu Asn Pro Ser Val Ala Ala Thr Leu Gly Phe
1250                1255                1260

Gly Ala Tyr Met Ser Lys Ala His Gly Val Asp Pro Asn Ile Arg Thr
1265                1270                1275                1280
```

-continued

Gly Val Arg Thr Ile Thr Thr Gly Ser Pro Ile Thr Tyr Ser Thr Tyr
            1285                1290                1295

Gly Lys Phe Leu Ala Asp Gly Gly Cys Ser Gly Gly Ala Tyr Asp Ile
            1300                1305                1310

Ile Ile Cys Asp Glu Cys His Ser Thr Asp Ala Thr Ser Ile Leu Gly
            1315                1320                1325

Ile Gly Thr Val Leu Asp Gln Ala Glu Thr Ala Gly Ala Arg Leu Val
            1330                1335                1340

Val Leu Ala Thr Ala Thr Pro Pro Gly Ser Val Thr Val Ser His Pro
1345                1350                1355                1360

Asn Ile Glu Glu Val Ala Leu Ser Thr Thr Gly Glu Ile Pro Phe Tyr
            1365                1370                1375

Gly Lys Ala Ile Pro Leu Glu Val Ile Lys Gly Arg His Leu Ile
            1380                1385                1390

Phe Cys His Ser Lys Lys Lys Cys Asp Glu Leu Ala Ala Lys Leu Val
            1395                1400                1405

Ala Leu Gly Ile Asn Ala Val Ala Tyr Tyr Arg Gly Leu Asp Val Ser
            1410                1415                1420

Val Ile Pro Thr Ser Gly Asp Val Val Val Ser Thr Asp Ala Leu
1425                1430                1435                1440

Met Thr Gly Phe Thr Gly Asp Phe Asp Ser Val Ile Asp Cys Asn Thr
            1445                1450                1455

Cys Val Thr Gln Thr Val Asp Phe Ser Leu Asp Pro Thr Phe Thr Ile
            1460                1465                1470

Glu Thr Thr Thr Leu Pro Gln Asp Ala Val Ser Arg Thr Gln Arg Arg
            1475                1480                1485

Gly Arg Thr Gly Arg Gly Lys Pro Gly Ile Tyr Arg Phe Val Ala Pro
            1490                1495                1500

Gly Glu Arg Pro Ser Gly Met Phe Asp Ser Ser Val Leu Cys Glu Cys
1505                1510                1515                1520

Tyr Asp Ala Gly Cys Ala Trp Tyr Glu Leu Thr Pro Ala Glu Thr Thr
            1525                1530                1535

Val Arg Leu Arg Ala Tyr Met Asn Thr Pro Gly Leu Pro Val Cys Gln
            1540                1545                1550

Asp His Leu Glu Phe Trp Glu Gly Val Phe Thr Gly Leu Thr His Ile
            1555                1560                1565

Asp Ala His Phe Leu Ser Gln Thr Lys Gln Ser Gly Glu Asn Phe Pro
            1570                1575                1580

Tyr Leu Val Ala Tyr Gln Ala Thr Val Cys Ala Arg Ala Gln Ala Pro
1585                1590                1595                1600

Pro Pro Ser Trp Asp Gln Met Trp Lys Cys Leu Ile Arg Leu Lys Pro
            1605                1610                1615

Thr Leu His Gly Pro Thr Pro Leu Leu Tyr Arg Leu Gly Ala Val Gln
            1620                1625                1630

Asn Glu Val Thr Leu Thr His Pro Ile Thr Lys Tyr Ile Met Thr Cys
            1635                1640                1645

Met Ser Ala Asp Leu Glu Val Val Thr Ser Thr Trp Val Leu Val Gly
            1650                1655                1660

Gly Val Leu Ala Ala Leu Ala Ala Tyr Cys Leu Ser Thr Gly Cys Val
1665                1670                1675                1680

Val Ile Val Gly Arg Ile Val Leu Ser Gly Lys Pro Ala Ile Ile Pro
            1685                1690                1695

-continued

```
Asp Arg Glu Val Leu Tyr Gln Glu Phe Asp Glu Met Glu Glu Cys Ser
        1700                1705                1710

Gln His Leu Pro Tyr Ile Glu Gln Gly Met Met Leu Ala Glu Gln Phe
        1715                1720                1725

Lys Gln Lys Ala Leu Gly Leu Leu Gln Thr Ala Ser Arg His Ala Glu
        1730                1735                1740

Val Ile Thr Pro Ala Val Gln Thr Asn Trp Gln Lys Leu Glu Val Phe
1745                1750                1755                1760

Trp Ala Lys His Met Trp Asn Phe Ile Ser Gly Ile Gln Tyr Leu Ala
                1765                1770                1775

Gly Leu Ser Thr Leu Pro Gly Asn Pro Ala Ile Ala Ser Leu Met Ala
                1780                1785                1790

Phe Thr Ala Ala Val Thr Ser Pro Leu Thr Thr Gly Gln Thr Leu Leu
                1795                1800                1805

Phe Asn Ile Leu Gly Gly Trp Val Ala Ala Gln Leu Ala Ala Pro Gly
        1810                1815                1820

Ala Ala Thr Ala Phe Val Gly Ala Gly Leu Ala Gly Ala Ala Ile Gly
1825                1830                1835                1840

Ser Val Gly Leu Gly Lys Val Leu Val Asp Ile Leu Ala Gly Tyr Gly
                1845                1850                1855

Ala Gly Val Ala Gly Ala Leu Val Ala Phe Lys Ile Met Ser Gly Glu
                1860                1865                1870

Val Pro Ser Thr Glu Asp Leu Val Asn Leu Leu Pro Ala Ile Leu Ser
                1875                1880                1885

Pro Gly Ala Leu Val Val Gly Val Val Cys Ala Ala Ile Leu Arg Arg
        1890                1895                1900

His Val Gly Pro Gly Glu Gly Ala Val Gln Trp Met Asn Arg Leu Ile
1905                1910                1915                1920

Ala Phe Ala Ser Arg Gly Asn His Val Ser Pro Thr His Tyr Val Pro
                1925                1930                1935

Glu Ser Asp Ala Ala Ala Arg Val Thr Ala Ile Leu Ser Ser Leu Thr
                1940                1945                1950

Val Thr Gln Leu Leu Arg Arg Leu His Gln Trp Ile Ser Ser Glu Cys
                1955                1960                1965

Thr Thr Pro Cys Ser Gly Ser Trp Leu Arg Asp Ile Trp Asp Trp Ile
        1970                1975                1980

Cys Glu Val Leu Ser Asp Phe Lys Thr Trp Leu Lys Ala Lys Leu Met
1985                1990                1995                2000

Pro Gln Leu Pro Gly Ile Pro Phe Val Ser Cys Gln Arg Gly Tyr Arg
                2005                2010                2015

Gly Val Trp Arg Gly Asp Gly Ile Met His Thr Arg Cys His Cys Gly
                2020                2025                2030

Ala Glu Ile Thr Gly His Val Lys Asn Gly Thr Met Arg Ile Val Gly
                2035                2040                2045

Pro Arg Thr Cys Arg Asn Met Trp Ser Gly Thr Phe Pro Ile Asn Ala
        2050                2055                2060

Tyr Thr Thr Gly Pro Cys Thr Pro Leu Pro Ala Pro Asn Tyr Lys Phe
2065                2070                2075                2080

Ala Leu Trp Arg Val Ser Ala Glu Glu Tyr Val Glu Ile Arg Arg Val
                2085                2090                2095

Gly Asp Phe His Tyr Val Ser Gly Met Thr Thr Asp Asn Leu Lys Cys
                2100                2105                2110

Pro Cys Gln Ile Pro Ser Pro Glu Phe Phe Thr Glu Leu Asp Gly Val
```

```
                2115                2120                2125
Arg Leu His Arg Phe Ala Pro Pro Cys Lys Pro Leu Leu Arg Glu Glu
        2130                2135                2140
Val Ser Phe Arg Val Gly Leu His Glu Tyr Pro Val Gly Ser Gln Leu
2145                2150                2155                2160
Pro Cys Glu Pro Glu Pro Asp Val Ala Val Leu Thr Ser Met Leu Thr
                2165                2170                2175
Asp Pro Ser His Ile Thr Ala Glu Ala Ala Gly Arg Arg Leu Ala Arg
        2180                2185                2190
Gly Ser Pro Pro Ser Met Ala Ser Ser Ala Ser Gln Leu Ser Ala
        2195                2200                2205
Pro Ser Leu Lys Ala Thr Cys Thr Ala Asn His Asp Ser Pro Asp Ala
        2210                2215                2220
Glu Leu Ile Glu Ala Asn Leu Leu Trp Arg Gln Glu Met Gly Gly Asn
2225                2230                2235                2240
Ile Thr Arg Val Glu Ser Glu Asn Lys Val Val Ile Leu Asp Ser Phe
                2245                2250                2255
Asp Pro Leu Val Ala Glu Glu Asp Glu Arg Glu Val Ser Val Pro Ala
        2260                2265                2270
Glu Ile Leu Arg Lys Ser Arg Arg Phe Ala Arg Ala Leu Pro Val Trp
        2275                2280                2285
Ala Arg Pro Asp Tyr Asn Pro Pro Leu Val Glu Thr Trp Lys Lys Pro
        2290                2295                2300
Asp Tyr Glu Pro Pro Val Val His Gly Cys Pro Leu Pro Pro Arg
2305                2310                2315                2320
Ser Pro Pro Val Pro Pro Arg Lys Lys Arg Thr Val Val Leu Thr
                2325                2330                2335
Glu Ser Thr Leu Ser Thr Ala Leu Ala Glu Leu Ala Thr Lys Ser Phe
                2340                2345                2350
Gly Ser Ser Ser Thr Ser Gly Ile Thr Gly Asp Asn Thr Thr Thr Ser
        2355                2360                2365
Ser Glu Pro Ala Pro Ser Gly Cys Pro Pro Asp Ser Asp Val Glu Ser
        2370                2375                2380
Tyr Ser Ser Met Pro Pro Leu Glu Gly Glu Pro Gly Asp Pro Asp Leu
2385                2390                2395                2400
Ser Asp Gly Ser Trp Ser Thr Val Ser Ser Gly Ala Asp Thr Glu Asp
                2405                2410                2415
Val Val Cys Cys Ser Met Ser Tyr Ser Trp Thr Gly Ala Leu Val Thr
                2420                2425                2430
Pro Cys Ala Ala Glu Glu Gln Lys Leu Pro Ile Asn Ala Leu Ser Asn
        2435                2440                2445
Ser Leu Leu Arg His His Asn Leu Val Tyr Ser Thr Thr Ser Arg Ser
2450                2455                2460
Ala Cys Gln Arg Gln Lys Lys Val Thr Phe Asp Arg Leu Gln Val Leu
2465                2470                2475                2480
Asp Ser His Tyr Gln Asp Val Leu Lys Glu Val Lys Ala Ala Ser
                2485                2490                2495
Lys Val Lys Ala Asn Leu Leu Ser Val Glu Glu Ala Cys Ser Leu Thr
                2500                2505                2510
Pro Pro His Ser Ala Lys Ser Lys Phe Gly Tyr Gly Ala Lys Asp Val
        2515                2520                2525
Arg Cys His Ala Arg Lys Ala Val Ala His Ile Asn Ser Val Trp Lys
        2530                2535                2540
```

```
Asp Leu Leu Glu Asp Ser Val Thr Pro Ile Asp Thr Thr Ile Met Ala
2545                2550                2555                2560

Lys Asn Glu Val Phe Cys Val Gln Pro Glu Lys Gly Gly Arg Lys Pro
                2565                2570                2575

Ala Arg Leu Ile Val Phe Pro Asp Leu Gly Val Arg Val Cys Glu Lys
            2580                2585                2590

Met Ala Leu Tyr Asp Val Val Ser Lys Leu Pro Leu Ala Val Met Gly
        2595                2600                2605

Ser Ser Tyr Gly Phe Gln Tyr Ser Pro Gly Gln Arg Val Glu Phe Leu
    2610                2615                2620

Val Gln Ala Trp Lys Ser Lys Thr Pro Met Gly Phe Ser Tyr Asp
2625                2630                2635                2640

Thr Arg Cys Phe Asp Ser Thr Val Thr Glu Ser Asp Ile Arg Thr Glu
                2645                2650                2655

Glu Ala Ile Tyr Gln Cys Cys Asp Leu Asp Pro Gln Ala Arg Val Ala
            2660                2665                2670

Ile Lys Ser Leu Thr Glu Arg Leu Tyr Val Gly Gly Pro Leu Thr Asn
        2675                2680                2685

Ser Arg Gly Glu Asn Cys Gly Tyr Arg Arg Cys Arg Ala Ser Gly Val
    2690                2695                2700

Leu Thr Thr Ser Cys Gly Asn Thr Leu Thr Cys Tyr Ile Lys Ala Arg
2705                2710                2715                2720

Ala Ala Cys Arg Ala Ala Gly Leu Gln Asp Cys Thr Met Leu Val Cys
                2725                2730                2735

Gly Asp Asp Leu Val Val Ile Cys Glu Ser Ala Gly Val Gln Glu Asp
            2740                2745                2750

Ala Ala Ser Leu Arg Ala Phe Thr Glu Ala Met Thr Arg Tyr Ser Ala
        2755                2760                2765

Pro Pro Gly Asp Pro Pro Gln Pro Glu Tyr Asp Leu Glu Leu Ile Thr
    2770                2775                2780

Ser Cys Ser Ser Asn Val Ser Val Ala His Asp Gly Ala Gly Lys Arg
2785                2790                2795                2800

Val Tyr Tyr Leu Thr Arg Asp Pro Thr Thr Pro Leu Ala Arg Ala Ala
                2805                2810                2815

Trp Glu Thr Ala Arg His Thr Pro Val Asn Ser Trp Leu Gly Asn Ile
            2820                2825                2830

Ile Met Phe Ala Pro Thr Leu Trp Ala Arg Met Ile Leu Met Thr His
        2835                2840                2845

Phe Phe Ser Val Leu Ile Ala Arg Asp Gln Leu Glu Gln Ala Leu Asn
    2850                2855                2860

Cys Glu Ile Tyr Gly Ala Cys Tyr Ser Ile Glu Pro Leu Asp Leu Pro
2865                2870                2875                2880

Pro Ile Ile Gln Arg Leu His Gly Leu Ser Ala Phe Ser Leu His Ser
                2885                2890                2895

Tyr Ser Pro Gly Glu Ile Asn Arg Val Ala Ala Cys Leu Arg Lys Leu
            2900                2905                2910

Gly Val Pro Pro Leu Arg Ala Trp Arg His Arg Ala Arg Ser Val Arg
        2915                2920                2925

Ala Arg Leu Leu Ser Arg Gly Gly Arg Ala Ala Ile Cys Gly Lys Tyr
    2930                2935                2940

Leu Phe Asn Trp Ala Val Arg Thr Lys Leu Lys Leu Thr Pro Ile Ala
2945                2950                2955                2960
```

```
Ala Ala Gly Arg Leu Asp Leu Ser Gly Trp Phe Thr Ala Gly Tyr Ser
            2965                2970                2975

Gly Gly Asp Ile Tyr His Ser Val Ser His Ala Arg Pro Arg Trp Phe
        2980                2985                2990

Trp Phe Cys Leu Leu Leu Leu Ala Ala Gly Val Gly Ile Tyr Leu Leu
    2995                3000                3005

Pro Asn Arg
    3010

<210> SEQ ID NO 69
<211> LENGTH: 9596
<212> TYPE: DNA
<213> ORGANISM: Hepatitis C virus

<400> SEQUENCE: 69
```

| | | | | | |
|---|---|---|---|---|---|
| gccagccccc | tgatggggc | gacactccac | catgaatcac | tccctgtga | ggaactactg | 60 |
| tcttcacgca | gaaagcgtct | agccatggcg | ttagtatgag | tgtcgtgcag | cctccaggac | 120 |
| ccccctccc | gggagagcca | tagtggtctg | cggaaccggt | gagtacaccg | gaattgccag | 180 |
| gacgaccggg | tcctttcttg | gatcaaaccc | gctcaatgcc | tggagatttg | ggcgtgcccc | 240 |
| cgcgagactg | ctagccgagt | agtgttgggt | cgcgaaaggc | cttgtggtac | tgcctgatag | 300 |
| ggtgcttgcg | agtgccccgg | gaggtctcgt | agaccgtgca | ccatgagcac | gaatcctaaa | 360 |
| cctcaaagaa | aaaccaaacg | taacaccaac | cgccgcccac | aggacgtcaa | gttcccgggc | 420 |
| ggtggtcaaa | tcgttggtgg | agtttacctg | ttgccgcgca | ggggccccag | gttgggtgtg | 480 |
| cgcgcgacta | ggaagacttc | cgagcggtcg | caacctcgtg | gaaggcgaca | acctatccca | 540 |
| aaggctcgcc | gacccgaggg | cagggcctgg | gctcagcccg | ggtaccttg | cccctctat | 600 |
| ggcaatgagg | gcttggggtg | gcaggatgg | ctcctgtcac | cccgcggctc | ccggcctagt | 660 |
| tggggcccca | cggaccccg | gcgtaggtcg | cgtaacttgg | gtaaggtcat | cgataccctt | 720 |
| acatgcggct | tcgccgatct | catggggtac | attccgctcg | tcggcgcccc | cctaggggc | 780 |
| gctgccaggg | ccttggcaca | cggtgtccgg | gttctggag | acggcgtgaa | ctatgcaaca | 840 |
| gggaacttgc | ccggttgctc | tttctctatc | ttcctcttgg | ctctgctgtc | ctgtttgacc | 900 |
| atcccagctt | ccgcttatga | agtgcgcaac | gtgtccggga | tataccatgt | cacgaacgac | 960 |
| tgctccaact | caagcattgt | gtatgaggca | gcggacgtga | tcatgcatac | tcccgggtgc | 1020 |
| gtgccctgtg | ttcgggaggg | caacagctcc | cgttgctggg | tagcgctcac | tcccacgctc | 1080 |
| gcggccagag | atgccagcgt | ccccactacg | acaatacgac | gccacgtcga | cttgctcgtt | 1140 |
| gggacggctg | ctttctgctc | cgctatgtac | gtgggggatc | tctgcggatc | tattttcctc | 1200 |
| gtctcccagc | tgttcacctt | ctcgcctcgc | cggcatgaga | cagtgcagga | ctgcaactgc | 1260 |
| tcaatctatc | ccggccatgt | atcaggtcac | cgcatggctt | gggatatgat | gatgaactgg | 1320 |
| tcacctacaa | cagccctagt | ggtgtcgcag | ttgctccgga | tcccacaagc | tgtcgtggac | 1380 |
| atggtggcgg | gggcccactg | gggagtcctg | gcgggccttg | cctactattc | catggtaggg | 1440 |
| aactgggcta | aggttctgat | tgtggcgcta | ctctttgccg | gcgttgacgg | ggagaccac | 1500 |
| acgacgggga | gggtggtcgg | ccgcaccacc | tccgggttta | cgtccctttt | ctcatctggg | 1560 |
| gcgtctcaga | aaatccagct | tgtgaatacc | aacggcagct | ggcacatcaa | caggactgct | 1620 |
| ctaaattgca | atgactccct | ccagactggg | ttccttgccg | cgctgttcta | cacacacaag | 1680 |
| ttcaactcgc | ccgggtgccc | ggagcgcatg | gcagctgcc | gcccattga | ctggttcgcc | 1740 |
| cagggggtggg | gccccatcac | ctatactgag | cctaacagct | cggatcagag | gccttattgc | 1800 |

```
tggcattacg cgcctcgacc gtgtggtatc gtacccgcgt cgcaggtgtg tggtccagtg    1860
tattgtttca cccccaagccc tgttgtggtg gggaccaccg atcgttccgg tgtccctacg    1920
tatagctggg gggagaatga gacagacgtg atgctcctga acaacacgcg tccgccacaa    1980
ggcaactggt tcggctgtac atggatgaat agtactgggt tcactaagac gtgcggaggc    2040
cccccgtgta acatcggggg ggtcggtaac cgcaccttga tctgccccac ggactgcttc    2100
cggaagcacc ccgaggctac ttacacaaaa tgtggctcgg ggccctggtt gacacctagg    2160
tgcctagtag actacccata caggctctgg cactacccct gcaccctcaa tttttccatc    2220
tttaaggtta ggatgtatgt gggggcgtg gagcacaggc tcaatgccgc atgcaattgg     2280
actcgaggag agcgctgtaa cttggaggac agggataggc agaactcag cccgctgctg     2340 ctgtctacaa cagagtggca gatactgccc tgtgccttca ccaccctacc ggctttatcc    2400
actggtttga tccatctcca tcagaacatc gtggacgtgc aatacctgta cggtgtaggg    2460
tcagcgtttg tctcctttgc aatcaaatgg gagtacatcc tgttgctttt ccttctcctg    2520
gcagacgcgc gagtgtgtgc ctgcttgtgg atgatgctgc tgatagccca ggctgaggcc    2580
gccttagaga acttggtggt cctcaatgcg gcgtccgtgg ccggagcgca tggtattctc    2640
tcctttcttg tgttcttctg cgccgcctgg tacattaagg gcaggctggc tcctggggcg    2700
gcgtatgctt tttatggcgt atggccgctg ctcctgctcc tactgcgtt accaccacga     2760 gcttacgcct tggaccggga gatggctgca tcgtgcgggg gtgcggttct tgtaggtctg    2820
gtattcttga cctatcacc atactacaaa gtgtttctca ctaggctcat atggtggtta    2880
caatacttta tcaccagagc cgaggcgcac atgcaagtgt gggtccccc cctcaacgtt    2940 cggggaggcc gcgatgccat catcctcctc acgtgtgcgg ttcatccaga gttaattttt    3000
gacatcacca aactcctgct cgccatactc ggcccgctca tggtgctcca ggctggcata    3060
acgagagtgc cgtacttcgt gcgcgctcaa gggctcattc gtgcatgcat gttagtgcga    3120
aaagtcgccg ggggtcatta tgtccaaatg gccttcatga agctgggcgc gctgacaggt    3180
acgtacgttt ataaccatct tacccccactg cgggactggg cccacgcggg cctacgagac    3240
cttgcggtgg cggtagagcc cgtcgtcttc tccgccatgg agaccaaggt catcacctgg    3300
ggagcagaca ccgctgcgtg tgggacatc atcttgggtc tacccgtctc cgcccgaagg     3360
gggaaggaga tatttttggg accggctgat agtctcgaag ggcaagggtg gcgactcctt    3420
gcgcccatca cggcctactc ccaacaaacg cggggcgtac ttggttgcgt catcactagc    3480
ctcacaggcc gggacaagaa ccaggtcgaa ggggaggttc aagtggtttc taccgcaaca    3540
caatctttcc tggcgacctg catcaacggc gtgtgctgga ctgtctacca tggcgctggc    3600
tcaaagaccc tagccggtcc aaaaggtcca atcacccaaa tgtacaccaa tgtagacctg    3660
gacctcgtcg gctggcaggc gccccccggg gcgcgctcca tgacaccatg cagctgtggc    3720
agctcggacc tttacttggt cacgagacat gctgatgtca tcccggtgcg ccggcgaggc    3780
gacagcaggg ggagtctact ctcccccagg cccgtctcct acctgaaggg ctcctcgggt    3840
ggtcctttgc tttgccctt ggggcacgtc gtgggcgtct tccgggctgc tgtgtgcacc    3900 cgggggggtcg cgaaggcggt ggacttcata cccgttgagt ctatggaaac taccatgcgg    3960
tctccggtct tcacagacaa ctcatccccc ccggctgtac cgcagacatt ccaagtggca    4020
catctgcacg ctcctactgg cagcggcaag agcaccaaag tgccggctgc gtatgcagcc    4080
caagggtaca aggtgctcgt cctgaatccg tccgttgccg ccaccttagg gtttgggcg    4140
```

```
tatatgtcca aggcacacgg tatcgaccct aacatcagaa ctggggtaag gaccattacc   4200
acgggcggct ccattacgta ctccacctat ggcaagttcc ttgccgacgg tggctgctcc   4260
gggggcgcct atgacatcat aatatgtgat gagtgccact caactgactc gactaccatc   4320
ttgggcattg gcacagtcct ggaccaagcg gagacggctg gagcgcggct tgtcgtgctc   4380
gccaccgcta cacctccggg atcggttacc gtgccacacc ccaatatcga ggaaataggc   4440
ctgtccaaca atgagagat ccccttctat ggcaaagcca tccccattga ggccatcaag   4500
gggggaggc atctcatttt ctgccattcc aagaagaaat gtgacgagct cgccgcaaag   4560
ctgacaggcc tcggactgaa cgctgtagca tattaccggg gccttgatgt gtccgtcata   4620
ccgcctatcg gagacgtcgt tgtcgtggca acagacgctc taatgacggg tttcaccggc   4680
gattttgact cagtgatcga ctgcaataca tgtgtcactc agacagtcga cttcagcttg   4740
gatcccacct tcaccattga gacgacgacc gtgccccaag acgcggtgtc gcgctcgcaa   4800
cggcgaggta gaactggcag gggtaggagt ggcatctaca ggtttgtgac tccaggagaa   4860
cggccctcgg gcatgttcga ttcttcggtc ctgtgtgagt gctatgacgc gggctgtgct   4920
tggcatgagc tcacgcccgc tgagacctcg gttaggttgc gggcttacct aaatacacca   4980
ggattgcccg tctgccagga ccatctggag ttctgggaga gcgtcttcac aggcctcacc   5040
cacatagatg cccacttcct gtcccagact aaacaggcag gagacaactt tccttacctg   5100
gtggcatatc aagctacagt gtgcgccagg gctcaagctc cacctccatc gtgggaccaa   5160
atgtggaagt gtctcatacg gctgaaacct acactgcacg ggccaacacc cctgctgtat   5220
aggctaggag ccgtccaaaa tgaggtcatc ctcacacacc ccataactaa atacatcatg   5280
gcatgcatgt cggctgacct ggaggtcgtc actagcacct gggtgctggt gggcggagtc   5340
cttgcagctt tggccgcata ctgcctgacg acaggcagtg tggtcattgt gggcaggatc   5400
atcttgtccg ggaagccagc tgtcgttccc gacaggaag tcctctacca ggagttcgat   5460
gagatggaag agtgtgcctc acaacttcct tacatcgagc agggaatgca gctcgccgag   5520
caatttaagc agaaggcgct cggattgttg caaacggcca ccaagcaagc ggaggctgct   5580
gctcccgtgg tggagtccaa gtggcgagcc ctcgagacct tctggcgaa gcacatgtgg   5640
aatttcatca gcggaataca gtacctagca ggcttatcca ctctgcctgg aaaccccgcg   5700
atagcatcat tgatggcatt tacagcttct atcactagcc cgctcaccac ccaaaacacc   5760
ctcctgttta acatcttggg gggatggtg gctgcccaac tcgctcctcc cagcgctgcg   5820
tcagctttcg tgggcgccgg catcgccgga gcggctgttg gcagcatagg ccttgggaag   5880
gtgctcgtgg acatcctggc gggctatggg gcgggggtag ccggcgcact cgtggccttt   5940
aaggtcatga gcggcgaggt gccctccacc gaggacctgg tcaacttact ccctgccatc   6000
ctctctcctg gtgccctggt cgtcggggtc gtgtgcgcag caatactgcg ccggcacgtg   6060
ggcccgggag aggggctgt gcagtggatg aaccggctga tagcgttcgc ttcgcggggt   6120
aaccacgtct cccccacgca ctatgtgcct gagagcgacg ctgcagcacg tgtcactcag   6180
atcctcccta gccttaccat cactcaactg ctgaagcggc ttcaccagtg gattaatgag   6240
gactgctcta cgccatgctc cggctcgtgg ctaagggatg tttgggattg gatatgcacg   6300
gtgttgactg acttcaagac ctggctccag tccaagctcc tgccgcggtt accgggagtc   6360
ccttttcctgt catgccaacg cgggtacaag ggagtctggc gggggacgg catcatgcaa   6420
accacctgcc catgtggagc acagatcgcc ggacatgtca aaaacggttc catgaggatc   6480
gtagggccta ggacctgcag caacacgtgg cacggaacgt tccccatcaa cgcatacacc   6540
```

-continued

```
acgggacctt gcacaccttc cccggcgccc aactattcca gggcgctatg gcgggtggct    6600
gctgaggagt acgtggaggt tacgcgtgtg ggggatttcc actacgtgac gggcatgacc    6660
actgacaacg taaagtgccc atgccaggtt ccggcccccg aattcttcac ggaggtggat    6720
ggagtgcggt tgcacaggta cgctccggcg tgcagacctc tcctacggga ggacgtcacg    6780
ttccaggtcg ggctcaacca atacttggtc ggtcgcagc tcccatgcga gcccgaaccg     6840
gacgtaacag tgcttacttc catgctcacc gatccctccc acattacagc agagacggct    6900
aagcgtaggc tggctagagg gtctccccc tctttagcca gctcatcagc tagccagttg     6960
tctgcgcctt ctttgaaggc gacatgcact acccaccatg actccccgga cgctgacctc    7020
atcgaggcca acctcttgtg gcggcaggag atgggcggaa acatcactcg cgtggagtca    7080
gagaataagg tagtaattct ggactctttc gaaccgcttc acgcggaggg ggatgagagg    7140
gagatatccg tcgcggcgga gatcctgcga aaatccagga agttcccctc agcgttgccc    7200
atatgggcac gcccggacta caatcctcca ctgttagagt cctggaagga cccggactac    7260
gtccctccgg tggtacacgg atgcccattg ccacctacca aggctcctcc aataccacct    7320
ccacggagaa agaggacggt tgtcctgaca gaatccaatg tgtcttctgc cttggcggag    7380
ctcgccacta agaccttcgg tagctccgga tcgtcggccg tcgatagcgg cacggcgacc    7440
gcccttcctg acctggcctc cgacgacggt gacaaaggat ccgacgttga gtcgcactcc    7500
tccatgcccc cccttgaagg ggagccgggg gaccccgatc tcagcgacgg gtcttggtct    7560
accgtgagtg aggaggctag tgaggacgtc gtctgctgct caatgtccta tacgtggaca    7620
ggcgccctga tcacgccatg cgctgcggag gaaagtaagc tgcccatcaa cccgttgagc    7680
aactctttgc tgcgtcacca caacatggtc tacgccacaa catcccgcag cgcaagcctc    7740
cggcagaaga aggtcacctt tgacagattg caagtcctgg acgaccatta ccgggacgtg    7800
ctcaaggaga tgaaggcgaa ggcgtccaca gttaaggcta agcttctatc tatagaggag    7860
gcctgcaagc tgacgccccc acattcggcc aaatccaaat ttggctatgg ggcaaaggac    7920
gtccggaacc tatccagcag ggccgttaac cacatccgct ccgtgtggga ggacttgctg    7980
gaagacactg aaacaccaat tgacaccacc atcatggcaa aaagtgaggt tttctgcgtc    8040
caaccagaga agggaggccg caagccagct cgccttatcg tattcccaga cctgggagtt    8100
cgtgtatgcg agaagatggc cctttacgac gtggtctcca cccttcctca ggccgtgatg    8160
ggctcctcat acggatttca atactccccc aagcagcggg tcgagttcct ggtgaatacc    8220
tggaaatcaa agaaatgccc tatgggcttc tcatatgaca ctcgctgttt tgactcaacg    8280
gtcaccgaga gtgacattcg tgttgaggag tcaatttacc aatgttgtga cttggccccc    8340
gaggccagac aggccataag gtcgctcaca gagcggcttt acatcggggg tcccctgact    8400
aactcaaaag gcagaactg cggttatcgc cggtgccgcg caagtggcgt gctgacgact     8460
agctgcggta ataccctcac atgttacttg aaggccactg cggcctgtcg agctgcaaag    8520
ctccaggact gcacgatgct cgtgaacgga gacgaccttg tcgttatctg tgaaagcgcg    8580
ggaacccagg aggatgcggc ggccctacga gccttcacgg aggctatgac taggtattcc    8640
gcccccccg gggatccgcc ccaaccagaa tacgacctgg agctgataac atcatgttcc    8700
tccaatgtgt cagtcgcgca cgatgcatcc ggcaaaaggg tatactacct cacccgtgac    8760
cccaccaccc cccttgcacg ggctgcgtgg gagacagcta gacacactcc aatcaactct    8820
tggctaggca atatcatcat gtatgcgccc acccctatggg caaggatgat tctgatgact    8880
```

-continued

```
cacttttcct ccatccttct agctcaagag caacttgaaa agccctggga ttgtcagatc      8940
tacgggcttt gctactccat tgagccactt gacctacctc agatcattga acgactccat      9000
ggtcttagcg catttacact ccacagttac tctccaggtg agatcaatag ggtggcttca      9060
tgcctcagga aacttggggt accacccttg cgaacctgga gacatcgggc cagaagtgtc      9120
cgcgctaagc tactgtccca ggggggagg gccgccactt gtggcagata cctctttaac      9180
tgggcagtaa ggaccaagct taaactcact ccaatcccgg ccgcgtccca gctggacttg      9240
tctggctggt tcgtcgctgg ttacagcggg ggagacatat atcacagcct gtctcgtgcc      9300
cgaccccgct ggtttccgtt gtgcctactc ctactttctg taggggtagg catttacctg      9360
ctccccaacc gatgaacggg gagctaacca ctccaggcct taagccattt cctgtttttt      9420
tttttttttt ttttttttttt ttcttttttt ttttcttttcc tttccttctt tttttccttt      9480 cttttttccct tctttaatgg tggctccatc ttagccctag tcacggctag ctgtgaaagg      9540
tccgtgagcc gcatgactgc agagagtgct gatactggcc tctctgcaga tcatgt         9596
```

<210> SEQ ID NO 70
<211> LENGTH: 3010
<212> TYPE: PRT
<213> ORGANISM: Hepatitis C virus

<400> SEQUENCE: 70

```
Met Ser Thr Asn Pro Lys Pro Gln Arg Lys Thr Lys Arg Asn Thr Asn
1               5                  10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Ala Trp Ala Gln Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala Tyr
            180                 185                 190

Glu Val Arg Asn Val Ser Gly Ile Tyr His Val Thr Asn Asp Cys Ser
        195                 200                 205

Asn Ser Ser Ile Val Tyr Glu Ala Ala Asp Val Ile Met His Thr Pro
    210                 215                 220

Gly Cys Val Pro Cys Val Arg Glu Gly Asn Ser Ser Arg Cys Trp Val
225                 230                 235                 240

Ala Leu Thr Pro Thr Leu Ala Ala Arg Asp Ala Ser Val Pro Thr Thr
                245                 250                 255
```

```
Thr Ile Arg Arg His Val Asp Leu Leu Val Gly Thr Ala Ala Phe Cys
            260                 265                 270

Ser Ala Met Tyr Val Gly Asp Leu Cys Gly Ser Ile Phe Leu Val Ser
            275                 280                 285

Gln Leu Phe Thr Phe Ser Pro Arg Arg His Glu Thr Val Gln Asp Cys
            290                 295                 300

Asn Cys Ser Ile Tyr Pro Gly His Val Ser Gly His Arg Met Ala Trp
305                 310                 315                 320

Asp Met Met Met Asn Trp Ser Pro Thr Thr Ala Leu Val Val Ser Gln
                    325                 330                 335

Leu Leu Arg Ile Pro Gln Ala Val Val Asp Met Val Ala Gly Ala His
            340                 345                 350

Trp Gly Val Leu Ala Gly Leu Ala Tyr Tyr Ser Met Val Gly Asn Trp
            355                 360                 365

Ala Lys Val Leu Ile Val Ala Leu Leu Phe Ala Gly Val Asp Gly Glu
            370                 375                 380

Thr His Thr Thr Gly Arg Val Val Gly Arg Thr Thr Ser Gly Phe Thr
385                 390                 395                 400

Ser Leu Phe Ser Ser Gly Ala Ser Gln Lys Ile Gln Leu Val Asn Thr
                    405                 410                 415

Asn Gly Ser Trp His Ile Asn Arg Thr Ala Leu Asn Cys Asn Asp Ser
            420                 425                 430

Leu Gln Thr Gly Phe Leu Ala Ala Leu Phe Tyr Thr His Lys Phe Asn
            435                 440                 445

Ser Pro Gly Cys Pro Glu Arg Met Ala Ser Cys Arg Pro Ile Asp Trp
            450                 455                 460

Phe Ala Gln Gly Trp Gly Pro Ile Thr Tyr Thr Glu Pro Asn Ser Ser
465                 470                 475                 480

Asp Gln Arg Pro Tyr Cys Trp His Tyr Ala Pro Arg Pro Cys Gly Ile
                    485                 490                 495

Val Pro Ala Ser Gln Val Cys Gly Pro Val Tyr Cys Phe Thr Pro Ser
            500                 505                 510

Pro Val Val Val Gly Thr Thr Asp Arg Ser Gly Val Pro Thr Tyr Ser
            515                 520                 525

Trp Gly Glu Asn Glu Thr Asp Val Met Leu Leu Asn Asn Thr Arg Pro
            530                 535                 540

Pro Gln Gly Asn Trp Phe Gly Cys Thr Trp Met Asn Ser Thr Gly Phe
545                 550                 555                 560

Thr Lys Thr Cys Gly Gly Pro Pro Cys Asn Ile Gly Gly Val Gly Asn
                    565                 570                 575

Arg Thr Leu Ile Cys Pro Thr Asp Cys Phe Arg Lys His Pro Glu Ala
            580                 585                 590

Thr Tyr Thr Lys Cys Gly Ser Gly Pro Trp Leu Thr Pro Arg Cys Leu
            595                 600                 605

Val Asp Tyr Pro Tyr Arg Leu Trp His Tyr Pro Cys Thr Leu Asn Phe
            610                 615                 620

Ser Ile Phe Lys Val Arg Met Tyr Val Gly Gly Val Glu His Arg Leu
625                 630                 635                 640

Asn Ala Ala Cys Asn Trp Thr Arg Gly Glu Arg Cys Asn Leu Glu Asp
                    645                 650                 655

Arg Asp Arg Ser Glu Leu Ser Pro Leu Leu Leu Ser Thr Thr Glu Trp
            660                 665                 670
```

```
Gln Ile Leu Pro Cys Ala Phe Thr Thr Leu Pro Ala Leu Ser Thr Gly
        675                 680                 685

Leu Ile His Leu His Gln Asn Ile Val Asp Val Gln Tyr Leu Tyr Gly
        690                 695                 700

Val Gly Ser Ala Phe Val Ser Phe Ala Ile Lys Trp Glu Tyr Ile Leu
705                 710                 715                 720

Leu Leu Phe Leu Leu Leu Ala Asp Ala Arg Val Cys Ala Cys Leu Trp
                725                 730                 735

Met Met Leu Leu Ile Ala Gln Ala Glu Ala Ala Leu Glu Asn Leu Val
            740                 745                 750

Val Leu Asn Ala Ala Ser Val Ala Gly Ala His Gly Ile Leu Ser Phe
        755                 760                 765

Leu Val Phe Phe Cys Ala Ala Trp Tyr Ile Lys Gly Arg Leu Ala Pro
770                 775                 780

Gly Ala Ala Tyr Ala Phe Tyr Gly Val Trp Pro Leu Leu Leu Leu Leu
785                 790                 795                 800

Leu Ala Leu Pro Pro Arg Ala Tyr Ala Leu Asp Arg Glu Met Ala Ala
                805                 810                 815

Ser Cys Gly Gly Ala Val Leu Val Gly Leu Val Phe Leu Thr Leu Ser
            820                 825                 830

Pro Tyr Tyr Lys Val Phe Leu Thr Arg Leu Ile Trp Trp Leu Gln Tyr
        835                 840                 845

Phe Ile Thr Arg Ala Glu Ala His Met Gln Val Trp Val Pro Pro Leu
850                 855                 860

Asn Val Arg Gly Gly Arg Asp Ala Ile Ile Leu Leu Thr Cys Ala Val
865                 870                 875                 880

His Pro Glu Leu Ile Phe Asp Ile Thr Lys Leu Leu Leu Ala Ile Leu
                885                 890                 895

Gly Pro Leu Met Val Leu Gln Ala Gly Ile Thr Arg Val Pro Tyr Phe
            900                 905                 910

Val Arg Ala Gln Gly Leu Ile Arg Ala Cys Met Leu Val Arg Lys Val
        915                 920                 925

Ala Gly Gly His Tyr Val Gln Met Ala Phe Met Lys Leu Gly Ala Leu
930                 935                 940

Thr Gly Thr Tyr Val Tyr Asn His Leu Thr Pro Leu Arg Asp Trp Ala
945                 950                 955                 960

His Ala Gly Leu Arg Asp Leu Ala Val Ala Val Glu Pro Val Phe
                965                 970                 975

Ser Ala Met Glu Thr Lys Val Ile Thr Trp Gly Ala Asp Thr Ala Ala
            980                 985                 990

Cys Gly Asp Ile Ile Leu Gly Leu Pro Val Ser Ala Arg Arg Gly Lys
        995                 1000                1005

Glu Ile Phe Leu Gly Pro Ala Asp Ser Leu Glu Gly Gln Gly Trp Arg
    1010                1015                1020

Leu Leu Ala Pro Ile Thr Ala Tyr Ser Gln Gln Thr Arg Gly Val Leu
1025                1030                1035                1040

Gly Cys Val Ile Thr Ser Leu Thr Gly Arg Asp Lys Asn Gln Val Glu
                1045                1050                1055

Gly Glu Val Gln Val Val Ser Thr Ala Thr Gln Ser Phe Leu Ala Thr
            1060                1065                1070

Cys Ile Asn Gly Val Cys Trp Thr Val Tyr His Gly Ala Gly Ser Lys
        1075                1080                1085

Thr Leu Ala Gly Pro Lys Gly Pro Ile Thr Gln Met Tyr Thr Asn Val
```

```
                1090                1095                1100
Asp Leu Asp Leu Val Gly Trp Gln Ala Pro Pro Gly Ala Arg Ser Met
1105                1110                1115                1120

Thr Pro Cys Ser Cys Gly Ser Ser Asp Leu Tyr Leu Val Thr Arg His
                1125                1130                1135

Ala Asp Val Ile Pro Val Arg Arg Gly Asp Ser Arg Gly Ser Leu
                1140            1145                1150

Leu Ser Pro Arg Pro Val Ser Tyr Leu Lys Gly Ser Gly Gly Pro
            1155                1160                1165

Leu Leu Cys Pro Ser Gly His Val Val Gly Val Phe Arg Ala Val
        1170                1175                1180

Cys Thr Arg Gly Val Ala Lys Ala Val Asp Phe Ile Pro Val Glu Ser
1185                1190                1195                1200

Met Glu Thr Thr Met Arg Ser Pro Val Phe Thr Asp Asn Ser Ser Pro
                1205                1210                1215

Pro Ala Val Pro Gln Thr Phe Gln Val Ala His Leu His Ala Pro Thr
                1220                1225                1230

Gly Ser Gly Lys Ser Thr Lys Val Pro Ala Ala Tyr Ala Ala Gln Gly
            1235                1240                1245

Tyr Lys Val Leu Val Leu Asn Pro Ser Val Ala Ala Thr Leu Gly Phe
            1250                1255                1260

Gly Ala Tyr Met Ser Lys Ala His Gly Ile Asp Pro Asn Ile Arg Thr
1265                1270                1275                1280

Gly Val Arg Thr Ile Thr Thr Gly Gly Ser Ile Thr Tyr Ser Thr Tyr
                1285                1290                1295

Gly Lys Phe Leu Ala Asp Gly Gly Cys Ser Gly Gly Ala Tyr Asp Ile
            1300                1305                1310

Ile Ile Cys Asp Glu Cys His Ser Thr Asp Ser Thr Thr Ile Leu Gly
            1315                1320                1325

Ile Gly Thr Val Leu Asp Gln Ala Glu Thr Ala Gly Ala Arg Leu Val
        1330                1335                1340

Val Leu Ala Thr Ala Thr Pro Pro Gly Ser Val Thr Val Pro His Pro
1345                1350                1355                1360

Asn Ile Glu Glu Ile Gly Leu Ser Asn Asn Gly Glu Ile Pro Phe Tyr
                1365                1370                1375

Gly Lys Ala Ile Pro Ile Glu Ala Ile Lys Gly Gly Arg His Leu Ile
            1380                1385                1390

Phe Cys His Ser Lys Lys Cys Asp Glu Leu Ala Ala Lys Leu Thr
            1395                1400                1405

Gly Leu Gly Leu Asn Ala Val Ala Tyr Tyr Arg Gly Leu Asp Val Ser
        1410                1415                1420

Val Ile Pro Pro Ile Gly Asp Val Val Val Ala Thr Asp Ala Leu
1425                1430                1435                1440

Met Thr Gly Phe Thr Gly Asp Phe Asp Ser Val Ile Asp Cys Asn Thr
                1445                1450                1455

Cys Val Thr Gln Thr Val Asp Phe Ser Leu Asp Pro Thr Phe Thr Ile
                1460                1465                1470

Glu Thr Thr Thr Val Pro Gln Asp Ala Val Ser Arg Ser Gln Arg Arg
            1475                1480                1485

Gly Arg Thr Gly Arg Gly Arg Ser Gly Ile Tyr Arg Phe Val Thr Pro
        1490                1495                1500

Gly Glu Arg Pro Ser Gly Met Phe Asp Ser Ser Val Leu Cys Glu Cys
1505                1510                1515                1520
```

```
Tyr Asp Ala Gly Cys Ala Trp His Glu Leu Thr Pro Ala Glu Thr Ser
            1525                1530                1535

Val Arg Leu Arg Ala Tyr Leu Asn Thr Pro Gly Leu Pro Val Cys Gln
            1540                1545                1550

Asp His Leu Glu Phe Trp Ser Val Phe Thr Gly Leu Thr His Ile
            1555                1560                1565

Asp Ala His Phe Leu Ser Gln Thr Lys Gln Ala Gly Asp Asn Phe Pro
            1570                1575                1580

Tyr Leu Val Ala Tyr Gln Ala Thr Val Cys Ala Arg Ala Gln Ala Pro
1585                1590                1595                1600

Pro Pro Ser Trp Asp Gln Met Trp Lys Cys Leu Ile Arg Leu Lys Pro
            1605                1610                1615

Thr Leu His Gly Pro Thr Pro Leu Leu Tyr Arg Leu Gly Ala Val Gln
            1620                1625                1630

Asn Glu Val Ile Leu Thr His Pro Ile Thr Lys Tyr Ile Met Ala Cys
            1635                1640                1645

Met Ser Ala Asp Leu Glu Val Val Thr Ser Thr Trp Val Leu Val Gly
            1650                1655                1660

Gly Val Leu Ala Ala Leu Ala Ala Tyr Cys Leu Thr Thr Gly Ser Val
1665                1670                1675                1680

Val Ile Val Gly Arg Ile Ile Leu Ser Gly Lys Pro Ala Val Val Pro
            1685                1690                1695

Asp Arg Glu Val Leu Tyr Gln Glu Phe Asp Glu Met Glu Glu Cys Ala
            1700                1705                1710

Ser Gln Leu Pro Tyr Ile Glu Gln Gly Met Gln Leu Ala Glu Gln Phe
            1715                1720                1725

Lys Gln Lys Ala Leu Gly Leu Leu Gln Thr Ala Thr Lys Gln Ala Glu
            1730                1735                1740

Ala Ala Ala Pro Val Val Glu Ser Lys Trp Arg Ala Leu Glu Thr Phe
1745                1750                1755                1760

Trp Ala Lys His Met Trp Asn Phe Ile Ser Gly Ile Gln Tyr Leu Ala
            1765                1770                1775

Gly Leu Ser Thr Leu Pro Gly Asn Pro Ala Ile Ala Ser Leu Met Ala
            1780                1785                1790

Phe Thr Ala Ser Ile Thr Ser Pro Leu Thr Thr Gln Asn Thr Leu Leu
            1795                1800                1805

Phe Asn Ile Leu Gly Gly Trp Val Ala Ala Gln Leu Ala Pro Pro Ser
            1810                1815                1820

Ala Ala Ser Ala Phe Val Gly Ala Gly Ile Ala Gly Ala Ala Val Gly
1825                1830                1835                1840

Ser Ile Gly Leu Gly Lys Val Leu Val Asp Ile Leu Ala Gly Tyr Gly
            1845                1850                1855

Ala Gly Val Ala Gly Ala Leu Val Ala Phe Lys Val Met Ser Gly Glu
            1860                1865                1870

Val Pro Ser Thr Glu Asp Leu Val Asn Leu Leu Pro Ala Ile Leu Ser
            1875                1880                1885

Pro Gly Ala Leu Val Val Gly Val Val Cys Ala Ala Ile Leu Arg Arg
            1890                1895                1900

His Val Gly Pro Gly Glu Gly Ala Val Gln Trp Met Asn Arg Leu Ile
1905                1910                1915                1920

Ala Phe Ala Ser Arg Gly Asn His Val Ser Pro Thr His Tyr Val Pro
            1925                1930                1935
```

```
Glu Ser Asp Ala Ala Arg Val Thr Gln Ile Leu Pro Ser Leu Thr
            1940                1945                1950

Ile Thr Gln Leu Leu Lys Arg Leu His Gln Trp Ile Asn Glu Asp Cys
        1955                1960                1965

Ser Thr Pro Cys Ser Gly Ser Trp Leu Arg Asp Val Trp Asp Trp Ile
            1970                1975                1980

Cys Thr Val Leu Thr Asp Phe Lys Thr Trp Leu Gln Ser Lys Leu Leu
1985                1990                1995                2000

Pro Arg Leu Pro Gly Val Pro Phe Leu Ser Cys Gln Arg Gly Tyr Lys
            2005                2010                2015

Gly Val Trp Arg Gly Asp Gly Ile Met Gln Thr Thr Cys Pro Cys Gly
            2020                2025                2030

Ala Gln Ile Ala Gly His Val Lys Asn Gly Ser Met Arg Ile Val Gly
            2035                2040                2045

Pro Arg Thr Cys Ser Asn Thr Trp His Gly Thr Phe Pro Ile Asn Ala
            2050                2055                2060

Tyr Thr Thr Gly Pro Cys Thr Pro Ser Pro Ala Pro Asn Tyr Ser Arg
2065                2070                2075                2080

Ala Leu Trp Arg Val Ala Ala Glu Glu Tyr Val Glu Val Thr Arg Val
            2085                2090                2095

Gly Asp Phe His Tyr Val Thr Gly Met Thr Thr Asp Asn Val Lys Cys
            2100                2105                2110

Pro Cys Gln Val Pro Ala Pro Glu Phe Phe Thr Glu Val Asp Gly Val
            2115                2120                2125

Arg Leu His Arg Tyr Ala Pro Ala Cys Arg Pro Leu Leu Arg Glu Asp
            2130                2135                2140

Val Thr Phe Gln Val Gly Leu Asn Gln Tyr Leu Val Gly Ser Gln Leu
2145                2150                2155                2160

Pro Cys Glu Pro Glu Pro Asp Val Thr Val Leu Thr Ser Met Leu Thr
            2165                2170                2175

Asp Pro Ser His Ile Thr Ala Glu Thr Ala Lys Arg Arg Leu Ala Arg
            2180                2185                2190

Gly Ser Pro Pro Ser Leu Ala Ser Ser Ser Ala Ser Gln Leu Ser Ala
            2195                2200                2205

Pro Ser Leu Lys Ala Thr Cys Thr Thr His His Asp Ser Pro Asp Ala
            2210                2215                2220

Asp Leu Ile Glu Ala Asn Leu Leu Trp Arg Gln Glu Met Gly Gly Asn
2225                2230                2235                2240

Ile Thr Arg Val Glu Ser Glu Asn Lys Val Val Ile Leu Asp Ser Phe
            2245                2250                2255

Glu Pro Leu His Ala Glu Gly Asp Glu Arg Glu Ile Ser Val Ala Ala
            2260                2265                2270

Glu Ile Leu Arg Lys Ser Arg Lys Phe Pro Ser Ala Leu Pro Ile Trp
            2275                2280                2285

Ala Arg Pro Asp Tyr Asn Pro Pro Leu Leu Glu Ser Trp Lys Asp Pro
            2290                2295                2300

Asp Tyr Val Pro Pro Val Val His Gly Cys Pro Leu Pro Pro Thr Lys
2305                2310                2315                2320

Ala Pro Pro Ile Pro Pro Pro Arg Arg Lys Arg Thr Val Val Leu Thr
            2325                2330                2335

Glu Ser Asn Val Ser Ser Ala Leu Ala Glu Leu Ala Thr Lys Thr Phe
            2340                2345                2350

Gly Ser Ser Gly Ser Ser Ala Val Asp Ser Gly Thr Ala Thr Ala Leu
```

-continued

```
            2355                2360                2365
Pro Asp Leu Ala Ser Asp Asp Gly Asp Lys Gly Ser Asp Val Glu Ser
    2370                2375                2380
His Ser Ser Met Pro Pro Leu Glu Gly Glu Pro Gly Asp Pro Asp Leu
2385                2390                2395                2400
Ser Asp Gly Ser Trp Ser Thr Val Ser Glu Glu Ala Ser Glu Asp Val
            2405                2410                2415
Val Cys Cys Ser Met Ser Tyr Thr Trp Thr Gly Ala Leu Ile Thr Pro
            2420                2425                2430
Cys Ala Ala Glu Glu Ser Lys Leu Pro Ile Asn Pro Leu Ser Asn Ser
            2435                2440                2445
Leu Leu Arg His His Asn Met Val Tyr Ala Thr Thr Ser Arg Ser Ala
            2450                2455                2460
Ser Leu Arg Gln Lys Lys Val Thr Phe Asp Arg Leu Gln Val Leu Asp
2465                2470                2475                2480
Asp His Tyr Arg Asp Val Leu Lys Glu Met Lys Ala Lys Ala Ser Thr
            2485                2490                2495
Val Lys Ala Lys Leu Leu Ser Ile Glu Glu Ala Cys Lys Leu Thr Pro
            2500                2505                2510
Pro His Ser Ala Lys Ser Lys Phe Gly Tyr Gly Ala Lys Asp Val Arg
            2515                2520                2525
Asn Leu Ser Ser Arg Ala Val Asn His Ile Arg Ser Val Trp Glu Asp
            2530                2535                2540
Leu Leu Glu Asp Thr Glu Thr Pro Ile Asp Thr Thr Ile Met Ala Lys
2545                2550                2555                2560
Ser Glu Val Phe Cys Val Gln Pro Glu Lys Gly Gly Arg Lys Pro Ala
            2565                2570                2575
Arg Leu Ile Val Phe Pro Asp Leu Gly Val Arg Val Cys Glu Lys Met
            2580                2585                2590
Ala Leu Tyr Asp Val Val Ser Thr Leu Pro Gln Ala Val Met Gly Ser
            2595                2600                2605
Ser Tyr Gly Phe Gln Tyr Ser Pro Lys Gln Arg Val Glu Phe Leu Val
            2610                2615                2620
Asn Thr Trp Lys Ser Lys Lys Cys Pro Met Gly Phe Ser Tyr Asp Thr
2625                2630                2635                2640
Arg Cys Phe Asp Ser Thr Val Thr Glu Ser Asp Ile Arg Val Glu Glu
            2645                2650                2655
Ser Ile Tyr Gln Cys Cys Asp Leu Ala Pro Glu Ala Arg Gln Ala Ile
            2660                2665                2670
Arg Ser Leu Thr Glu Arg Leu Tyr Ile Gly Gly Pro Leu Thr Asn Ser
            2675                2680                2685
Lys Gly Gln Asn Cys Gly Tyr Arg Arg Cys Arg Ala Ser Gly Val Leu
            2690                2695                2700
Thr Thr Ser Cys Gly Asn Thr Leu Thr Cys Tyr Leu Lys Ala Thr Ala
2705                2710                2715                2720
Ala Cys Arg Ala Ala Lys Leu Gln Asp Cys Thr Met Leu Val Asn Gly
            2725                2730                2735
Asp Asp Leu Val Val Ile Cys Glu Ser Ala Gly Thr Gln Glu Asp Ala
            2740                2745                2750
Ala Ala Leu Arg Ala Phe Thr Glu Ala Met Thr Arg Tyr Ser Ala Pro
            2755                2760                2765
Pro Gly Asp Pro Pro Gln Pro Glu Tyr Asp Leu Glu Leu Ile Thr Ser
            2770                2775                2780
```

```
Cys Ser Ser Asn Val Ser Val Ala His Asp Ala Ser Gly Lys Arg Val
2785            2790            2795            2800

Tyr Tyr Leu Thr Arg Asp Pro Thr Thr Pro Leu Ala Arg Ala Ala Trp
            2805            2810            2815

Glu Thr Ala Arg His Thr Pro Ile Asn Ser Trp Leu Gly Asn Ile Ile
            2820            2825            2830

Met Tyr Ala Pro Thr Leu Trp Ala Arg Met Ile Leu Met Thr His Phe
            2835            2840            2845

Phe Ser Ile Leu Leu Ala Gln Glu Gln Leu Glu Lys Ala Leu Asp Cys
    2850            2855            2860

Gln Ile Tyr Gly Ala Cys Tyr Ser Ile Glu Pro Leu Asp Leu Pro Gln
2865            2870            2875            2880

Ile Ile Glu Arg Leu His Gly Leu Ser Ala Phe Thr Leu His Ser Tyr
            2885            2890            2895

Ser Pro Gly Glu Ile Asn Arg Val Ala Ser Cys Leu Arg Lys Leu Gly
            2900            2905            2910

Val Pro Pro Leu Arg Thr Trp Arg His Arg Ala Arg Ser Val Arg Ala
            2915            2920            2925

Lys Leu Leu Ser Gln Gly Gly Arg Ala Ala Thr Cys Gly Arg Tyr Leu
    2930            2935            2940

Phe Asn Trp Ala Val Arg Thr Lys Leu Lys Leu Thr Pro Ile Pro Ala
2945            2950            2955            2960

Ala Ser Gln Leu Asp Leu Ser Gly Trp Phe Val Ala Gly Tyr Ser Gly
            2965            2970            2975

Gly Asp Ile Tyr His Ser Leu Ser Arg Ala Arg Pro Arg Trp Phe Pro
            2980            2985            2990

Leu Cys Leu Leu Leu Leu Ser Val Gly Val Gly Ile Tyr Leu Leu Pro
    2995            3000            3005

Asn Arg
    3010
```